United States Patent
Utsumi et al.

(10) Patent No.: US 9,097,971 B2
(45) Date of Patent: Aug. 4, 2015

(54) COMPOUND, RADICAL POLYMERIZATION INITIATOR, METHOD FOR PRODUCING COMPOUND, POLYMER, RESIST COMPOSITION, AND METHOD FOR FORMING RESIST PATTERN

(75) Inventors: Yoshiyuki Utsumi, Kawasaki (JP); Takahiro Dazai, Kawasaki (JP); Jun Iwashita, Kawasaki (JP); Kenri Konno, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 14/126,535

(22) PCT Filed: Jun. 15, 2012

(86) PCT No.: PCT/JP2012/065389
§ 371 (c)(1),
(2), (4) Date: Dec. 16, 2013

(87) PCT Pub. No.: WO2012/173235
PCT Pub. Date: Dec. 20, 2012

(65) Prior Publication Data
US 2014/0141373 A1    May 22, 2014

(30) Foreign Application Priority Data

Jun. 17, 2011 (JP) ................. 2011-135672
Oct. 4, 2011 (JP) ................. 2011-220101

(51) Int. Cl.
| | |
|---|---|
| G03F 7/004 | (2006.01) |
| G03F 7/038 | (2006.01) |
| C08F 4/04 | (2006.01) |
| G03F 7/039 | (2006.01) |
| C07C 309/12 | (2006.01) |
| C07C 381/12 | (2006.01) |
| C07C 25/18 | (2006.01) |

(52) U.S. Cl.
CPC ............... *G03F 7/038* (2013.01); *C07C 25/18* (2013.01); *C07C 309/12* (2013.01); *C07C 381/12* (2013.01); *C08F 4/04* (2013.01); *G03F 7/0045* (2013.01); *G03F 7/0046* (2013.01); *G03F 7/0397* (2013.01); *C07C 2101/14* (2013.01); *C07C 2103/74* (2013.01)

(58) Field of Classification Search
None
See application file for complete search history.

(56) References Cited

U.S. PATENT DOCUMENTS

| | | | |
|---|---|---|---|
| 3,956,269 A * | 5/1976 | Sheppard et al. | 534/886 |
| 5,945,517 A | 8/1999 | Nitta et al. | |
| 6,153,733 A | 11/2000 | Yukawa et al. | |
| 6,949,325 B2 | 9/2005 | Li et al. | |
| 2001/0049073 A1 | 12/2001 | Hada et al. | |
| 2002/0055124 A1 | 5/2002 | Janda et al. | |
| 2004/0110085 A1 | 6/2004 | Iwai et al. | |
| 2007/0231708 A1 | 10/2007 | Matsumaru et al. | |
| 2008/0187860 A1 | 8/2008 | Tsubaki et al. | |
| 2009/0280433 A1* | 11/2009 | Matsumura et al. | 430/270.1 |
| 2009/0317743 A1 | 12/2009 | Shiono et al. | |
| 2010/0055608 A1 | 3/2010 | Ohashi et al. | |
| 2011/0177453 A1 | 7/2011 | Masubuchi et al. | |
| 2011/0244392 A1 | 10/2011 | Hirano et al. | |

(Continued)

FOREIGN PATENT DOCUMENTS

| | | |
|---|---|---|
| GB | 916782 A | 1/1963 |
| JP | A-06-065310 | 3/1994 |

(Continued)

OTHER PUBLICATIONS

Sedlak et al., "Synthesis and Characterization of New Surface Active Azo Initiators for Radical Reactions," Molecules (Electronic Publication) vol. 5, No. 5, pp. 730-736, 2000.*

(Continued)

*Primary Examiner* — Cynthia Hamilton
(74) *Attorney, Agent, or Firm* — Knobbe Martens Olson & Bear LLP

(57) ABSTRACT

A compound represented by formula (I). In the formula, $R^1$ represents a hydrocarbon group of 1 to 10 carbon atoms; Z represents a hydrocarbon group of 1 to 10 carbon atoms or a cyano group; provided that $R^1$ and Z may be mutually bonded to form a ring; X represents a divalent linking group having any one selected from —O—C(=O)—, —NH—C(=O)— and —NH—C(=NH)— on a terminal that comes into contact with Q; p represents an integer of 1 to 3; Q represents a hydrocarbon group having a valency of (p+1), provided that, when p is 1, Q may be a single bond; $R^2$ represents a single bond, an alkylene group which may have a substituent or an arylene group which may have a substituent; q represents 0 or 1; r represents an integer of 0 to 8; and $A^+$ represents a metal cation or an organic cation.

[Chemical Formula 1]

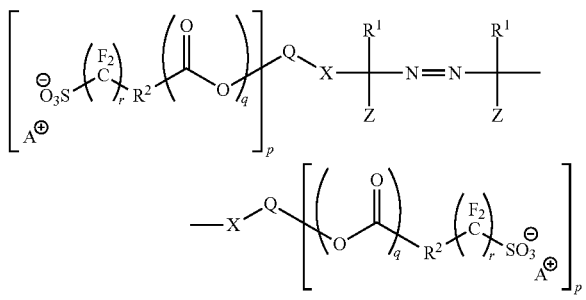

4 Claims, No Drawings

(56) References Cited

U.S. PATENT DOCUMENTS

| | | | |
|---|---|---|---|
| 2012/0237876 A1 | 9/2012 | Maruyama et al. | |
| 2013/0022911 A1* | 1/2013 | Utsumi et al. | 430/270.1 |
| 2013/0045443 A1* | 2/2013 | Utsumi et al. | 430/270.1 |
| 2013/0065183 A1 | 3/2013 | Kobayashi et al. | |

FOREIGN PATENT DOCUMENTS

| | | |
|---|---|---|
| JP | A-09-208554 | 8/1997 |
| JP | A-11-035551 | 2/1999 |
| JP | A-11-035552 | 2/1999 |
| JP | A-11-035573 | 2/1999 |
| JP | A-11-322707 | 11/1999 |
| JP | A-2000-206694 | 7/2000 |
| JP | A-2003-241385 | 8/2003 |
| JP | A-2005-336452 | 12/2005 |
| JP | A-2006-045311 | 2/2006 |
| JP | A-2006-259582 | 9/2006 |
| JP | A-2006-317803 | 11/2006 |
| JP | A-2008-292975 | 12/2008 |
| JP | A-2009-025723 | 2/2009 |
| JP | A-2010-002870 | 1/2010 |
| JP | A-2010-037528 | 2/2010 |
| JP | A-2010-077404 | 4/2010 |
| JP | A-2010-095643 | 4/2010 |
| JP | A-2011-158879 | 8/2011 |
| JP | A-2013-057836 | 3/2013 |
| WO | WO 2004/074242 A2 | 9/2004 |
| WO | WO 2011/070947 A1 | 6/2011 |

OTHER PUBLICATIONS

Imroz et al., "Comparing emulsion polymerization of methacrylate-monomers with different hydrophilicity," Polymer, vol. 46, No. 4, pp. 1017-1023, 2005.*

English translation of JP, 2010-077404 A (2010) from machine translation from AIPN Japan Patent Office National Center for Industrial Property Information and Training, generated Sep. 11, 2014, pp. 1-57 and pp. 1-36.*

Office Action in Japanese Patent Application No. 2011-220101, mailed on Oct. 7, 2014.

Aslamazova et al., "On the colloidal stability of poly(methyl methacrylate) and polystyrene particles prepared with surface-active initiators," Colloids and Surfaces, A: Physiochemical and Engineering Aspects, vol. 300, No. 3, pp. 260-267, 2007.

International Search Report mailed on Sep. 4, 2012 in International Application No. PCT/JP2012/065389.

* cited by examiner

COMPOUND, RADICAL POLYMERIZATION INITIATOR, METHOD FOR PRODUCING COMPOUND, POLYMER, RESIST COMPOSITION, AND METHOD FOR FORMING RESIST PATTERN

This application is the U.S. National Phase under 35 U.S.C. §371 of International Application No. PCT/JP2012/065389, filed Jun. 15, 2012, designating the U.S., and published in Japanese as WO 2012/173235 on Dec. 20, 2012, which claims priority to Japanese Patent Application No. 2011-135672, filed Jun. 17, 2011; and Japanese Patent Application No. 2011-220101, filed Oct. 4, 2011, the entire contents of which are incorporated herein by reference.

TECHNICAL FIELD

The present invention relates to a new compound useful as a radical polymerization initiator, a radical polymerization initiator containing the compound, a method of producing the compound, a new polymeric compound useful for a resist composition, a resist composition containing the polymeric compound, and a method of forming a resist pattern using the resist composition.

Priority is claimed on Japanese Patent Application No. 2011-135672, filed Jun. 17, 2011, and Japanese Patent Application No. 2011-220101, filed Oct. 4, 2011, the contents of which are incorporated herein by reference.

DESCRIPTION OF RELATED ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

A resist material in which the exposed portions become soluble in a developing solution is called a positive-type, and a resist material in which the exposed portions become insoluble in a developing solution is called a negative-type.

In recent years, in the production of semiconductor elements and liquid crystal display elements, advances in lithography techniques have led to rapid progress in the field of pattern miniaturization.

Typically, these miniaturization techniques involve shortening the wavelength (increasing the energy) of the exposure light source. Conventionally, ultraviolet radiation typified by g-line and i-line radiation has been used, but nowadays KrF excimer lasers and ArF excimer lasers are starting to be introduced in mass production of the semiconductor elements. Furthermore, research is also being conducted into lithography techniques that use an exposure light source having a wavelength shorter (energy higher) than these excimer lasers, such as electron beam, extreme ultraviolet radiation (EUV), and X ray.

Resist materials for use with these types of exposure light sources require lithography properties such as a high resolution capable of reproducing patterns of minute dimensions, and a high level of sensitivity to these types of exposure light sources.

As a resist material that satisfies these conditions, a chemically amplified resist composition is used, which includes a base component that exhibits a changed solubility in a developing solution under the action of acid and an acid generator component that generates acid upon exposure.

For example, in the case where the developing solution is an alkali developing solution (alkali developing process), a chemically amplified positive resist which contains, as a base component (base resin), a resin which exhibits increased solubility in an alkali developing solution under action of acid, and an acid generator is typically used. If the resist film formed using the resist composition is selectively exposed during formation of a resist pattern, then within the exposed portions, acid is generated from the acid generator component, and the action of this acid causes an increase in the solubility of the resin component in an alkali developing solution, making the exposed portions soluble in the alkali developing solution. In this manner, the unexposed portions remain to form a positive resist pattern. The base resin used exhibits increased polarity by the action of acid, thereby exhibiting increased solubility in an alkali developing solution, whereas the solubility in an organic solvent is decreased. Therefore, when such a base resin is applied to a process using a developing solution containing an organic solvent (organic developing solution) (hereafter, this process is referred to as "solvent developing process" or "negative tone-developing process") instead of an alkali developing process, the solubility of the exposed portions in an organic developing solution is decreased. As a result, in the solvent developing process, the unexposed portions of the resist film are dissolved and removed by the organic developing solution, and a negative resist pattern in which the exposed portions are remaining is formed. The negative tone-developing process is proposed, for example, in Patent Document 1. Patent Document 2 proposes a negative tone-developing process and a resist composition used for the process.

Currently, resins that contain structural units derived from (meth)acrylate esters within the main chain (acrylic resins) are now widely used as base resins for resist compositions that use ArF excimer laser lithography, as they exhibit excellent transparency in the vicinity of 193 nm (for example, see Patent Document 3).

In recent years, base resins that include a structural unit which functions as an acid generator have also been used (see for example, Patent Documents 4 and 5).

In general, A polymer used for a base resin is produced by radical polymerization using monomers having various functions. As a polymerization initiator used in radical polymerization, an azo-type polymerization initiator such as azobisisobutyronitrile (AIBN) or dimethyl-2,2-azobis(2-methylpropionate) is generally used.

An azo-type polymerization initiator is decomposed by heat or light and generates nitrogen gas and a radical, the radical proceeds addition polymerization with monomers, thereby obtaining a polymer. Therefore, at the terminal of the resulting polymer, a partial structure of the azo-type polymerization initiator is introduced.

In recent years, the partial structure derived from a polymerization initiator to be introduced at the terminal of polymer has been attracting attention, and a polymerization initiator containing a base dissociable group (which is a functional group) as a partial structure, and a polymeric compound obtained by using the polymerization initiator are disclosed (see Patent Document 6).

DOCUMENTS OF RELATED ART

Patent Document

[Patent Document 1] Japanese Unexamined Patent Application, First Publication No. 2008-292975

[Patent Document 2] Japanese Unexamined Patent Application, First Publication No. 2009-025723

[Patent Document 3] Japanese Unexamined Patent Application, First Publication No. 2003-241385

[Patent Document 4] Japanese Unexamined Patent Application, First Publication No. 2006-045311

[Patent Document 5] Japanese Unexamined Patent Application, First Publication No. 2011-158879

[Patent Document 6] Japanese Unexamined Patent Application, First Publication No. 2010-37528

SUMMARY OF THE INVENTION

Problems to be Solved by the Invention

As further progress is expected to be made in lithography techniques and the application field for lithography techniques is expected to expand, development of a novel material for use in lithography will be desired. For example, as miniaturization of resist patterns progress, further improvement will be demanded for resist materials with respect to various lithography properties such as resolution, roughness (LWR (line width roughness: non-uniformity of the line width) and the like in the case of a line pattern, and circularity in the case of a hole pattern), MEF (mask reproducibility) and EL margin (exposure latitude), and pattern shape, as well as sensitivity and resolution. However, when the base resins as those disclosed in Patent Documents 3 and 6 were used, there was still room for improvement in lithography properties and resist pattern shape.

The present invention takes the above circumstances into consideration, with an object of providing a resist composition which exhibits excellent lithography properties an pattern shape, a new polymeric compound useful for the resist composition, a new compound useful as a radical polymerization initiator which is used in production of the polymeric compound, a method of producing the compound, a radical polymerization initiator containing the compound, and a method of forming a resist pattern using the resist composition.

For solving the above-mentioned problems, the present invention employs the following aspects.

A first aspect of the present invention is a compound represented by general formula (1) shown below.

[Chemical Formula 1]

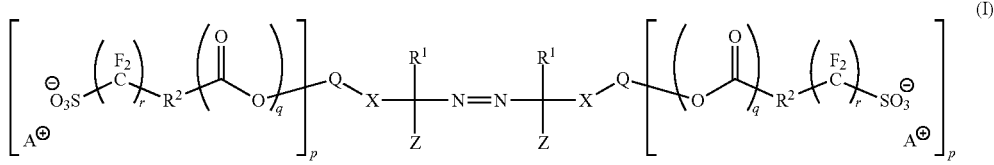
(I)

In the formula, $R^1$ represents a hydrocarbon group of 1 to 10 carbon atoms; Z represents a hydrocarbon group of 1 to 10 carbon atoms or a cyano group; provided that $R^1$ and Z may be mutually bonded to form a ring; X represents a divalent linking group having any one selected from —O—C(=O)—, —NH—C(=O)— and —NH—C(=NH)— on a terminal that comes into contact with Q; p represents an integer of 1 to 3;

Q represents a hydrocarbon group having a valency of (p+1), provided that, when p is 1, Q may be a single bond;

$R^2$ represents a single bond, an alkylene group which may have a substituent or an aromatic group which may have a substituent; q represents 0 or 1; r represents an integer of 0 to 8; $A^+$ represents a metal cation or an organic cation; and the plurality of $R^1$, Z, X, p, Q, $R^2$, q, r and $A^+$ may be the same or different from each other.

A second aspect of the present invention is a radical polymerization initiator containing the compound of the first aspect.

A third aspect of the present invention is a method of producing a compound of the first aspect, including reacting a compound represented by general formula (i-1) shown below with a compound represented by general formula (i-2) shown below.

[Chemical Formula 2]

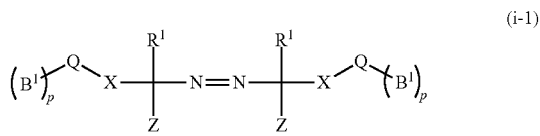
(i-1)

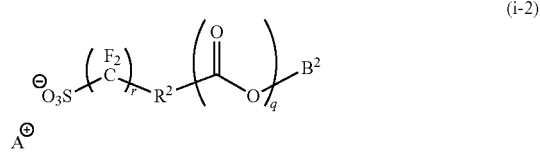
(i-2)

In the formulae, $R^1$, Z, X, Q, p, q, $R^2$, r and $A^+$ are the same as defined above; $B^1$ and $B^2$ each independently represents H or OH; and the plurality of $R^1$, Z, X, p, Q and $B^1$ may be the same or different from each other.

A fourth aspect of the present invention is a polymeric compound having a group represented by general formula (I-1) shown below on at least one terminal of the main chain thereof.

[Chemical Formula 3]

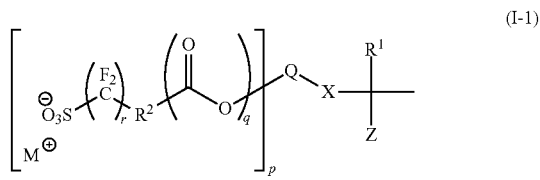
(I-1)

In the formula, $R^1$ represents a hydrocarbon group of 1 to 10 carbon atoms; Z represents a hydrocarbon group of 1 to 10 carbon atoms or a cyano group; provided that $R^1$ and Z may be mutually bonded to form a ring; X represents a divalent linking group having any one selected from —O—C(=O)—, —NH—C(=O)— and —NH—C(=NH)— on a terminal that comes into contact with Q; p represents an integer of 1 to 3;

Q represents a hydrocarbon group having a valency of (p+1), provided that, when p is 1, Q may be a single bond; and $R^2$ represents a single bond, an alkylene group which may have a substituent or an aromatic group which may have a substituent; q represents 0 or 1; r represents an integer of 0 to 8; and $M^+$ represents an organic cation.

A fifth aspect of the present invention is a resist composition including a polymeric compound of the fourth aspect.

A sixth aspect of the present invention is a method of forming a resist pattern, including: forming a resist film on a substrate using a resist composition of the fifth aspect; conducting exposure of the resist film; and developing the resist film to form a resist pattern.

A seventh aspect of the present invention is a resist composition including: a base component (A) which exhibits changed solubility in a developing solution under action of acid and generates acid upon exposure; an acid generator component (C) which generates acid having a pKa of at least 0 upon exposure, provided that the base component (A) is excluded from the component (C); and an acid generator component (B) which generates acid upon exposure, provided that, the base component (A) and the acid generator component (C) are excluded from the component (B); the base component (A) including a polymeric compound (A1) having an anion portion on at least one terminal of a main chain thereof, and the anion portion generating acid upon exposure.

A eighth aspect of the present invention is a method of forming a resist pattern, including: forming a resist film on a substrate using a resist composition according to the seventh aspect; conducting exposure of the resist film; and developing the resist film to form a resist pattern.

In the present description and claims, the term "aliphatic" is a relative concept used in relation to the term "aromatic", and defines a group or compound that has no aromaticity.

The term "alkyl group" includes linear, branched or cyclic, monovalent saturated hydrocarbon, unless otherwise specified.

The term "alkylene group" includes linear, branched or cyclic, divalent saturated hydrocarbon, unless otherwise specified. The same applies for the alkyl group within an alkoxy group.

A "halogenated alkyl group" is a group in which part or all of the hydrogen atoms of an alkyl group are substituted with a halogen atom, and a "halogenated alkylene group" is a group in which part or all of the hydrogen atoms of an alkylene group are substituted with a halogen atom. Examples of the halogen atom include a fluorine atom, a chlorine atom, a bromine atom and an iodine atom.

A "fluorinated alkyl group" or a "fluorinated alkylene group" is a group in which part or all of the hydrogen atoms of an alkyl group or an alkylene group have been substituted with fluorine atom(s).

The term "structural unit" refers to a monomer unit that contributes to the formation of a polymeric compound (resin, polymer, copolymer).

An "acrylate ester" refers to a compound in which the terminal hydrogen atom of the carboxy group of acrylic acid ($CH_2$=CH—COOH) has been substituted with an organic group.

A "structural unit derived from an acrylate ester" refers to a structural unit that is formed by the cleavage of the ethylenic double bond of an acrylate ester.

Examples of the substituent bonded to the carbon atom on the α-position in the "acrylate ester which may have the hydrogen atom bonded to the carbon atom on the α-position substituted with a substituent" include a halogen atom, an alkyl group of 1 to 5 carbon atoms, a halogenated alkyl group of 1 to 5 carbon atoms and a hydroxyalkyl group. With respect to the "structural unit derived from an acrylate ester", the "α-position (the carbon atom on the α-position)" refers to the carbon atom having the carbonyl group bonded thereto, unless specified otherwise.

Examples of the halogen atom as the substituent which may be bonded to the carbon atom on the α-position include a fluorine atom, a chlorine atom, a bromine atom and an iodine atom.

Specific examples of the alkyl group of 1 to 5 carbon atoms for the substituent which may be bonded to the carbon atom on the α-position include linear or branched alkyl groups such as a methyl group, an ethyl group, a propyl group, an isopropyl group, an n-butyl group, an isobutyl group, a tert-butyl group, a pentyl group, an isopentyl group and a neopentyl group.

Specific examples of the halogenated alkyl group of 1 to 5 carbon atoms for the substituent include groups in which part or all of the hydrogen atoms of the aforementioned "alkyl group of 1 to 5 carbon atoms for the substituent" are substituted with halogen atoms. Examples of the halogen atom include a fluorine atom, a chlorine atom, a bromine atom and an iodine atom, and a fluorine atom is particularly desirable.

Specific examples of the hydroxyalkyl group of 1 to 5 carbon atoms for the substituent include groups in which part or all of the hydrogen atoms of the aforementioned "alkyl group of 1 to 5 carbon atoms for the substituent" are substituted with hydroxy groups.

In the present invention, it is preferable that a hydrogen atom, an alkyl group of 1 to 5 carbon atoms or a halogenated alkyl group of 1 to 5 carbon atoms is bonded to the carbon atom on the α-position, a hydrogen atom, an alkyl group of 1 to 5 carbon atoms or a fluorinated alkyl group of 1 to 5 carbon atoms is more preferable, and in terms of industrial availability, a hydrogen atom or a methyl group is the most desirable.

The term "exposure" is used as a general concept that includes irradiation with any form of radiation.

Advantageous Effect of the Invention

According to the present invention, there are provided a resist composition which exhibits excellent lithography properties an pattern shape, a new polymeric compound useful for the resist composition, a new compound useful as a radical polymerization initiator which is used in production of the polymeric compound, a method of producing the compound, a radical polymerization initiator containing the compound, and a method of forming a resist pattern using the resist composition.

DETAILED DESCRIPTION OF THE INVENTION

<<Compound>>

The compound according to the first aspect of the present invention is a compound represented by general formula (I) shown below (hereafter, this compound is frequently referred to as "compound (I)").

[Chemical Formula 4]

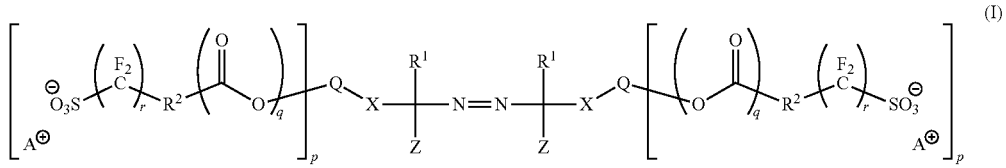

(I)

In the formula, $R^1$ represents a hydrocarbon group of 1 to 10 carbon atoms; Z represents a hydrocarbon group of 1 to 10 carbon atoms or a cyano group; provided that $R^1$ and Z may be mutually bonded to form a ring; X represents a divalent linking group having any one selected from —O—C(═O)—, —NH—C(═O)— and —NH—C(═NH)— on a terminal that comes into contact with Q; p represents an integer of 1 to 3;

Q represents a hydrocarbon group having a valency of (p+1), provided that, when p is 1, Q may be a single bond; and $R^2$ represents a single bond, an alkylene group which may have a substituent or an aromatic group which may have a substituent; q represents 0 or 1; r represents an integer of 0 to 8; $A^+$ represents a metal cation or an organic cation; and the plurality of $R^1$, Z, X, p, Q, $R^2$, q, r and $A^+$ may be the same or different from each other.

In general formula (I) above, $R^1$ represents a hydrocarbon group of 1 to 10 carbon atoms. The hydrocarbon group of 1 to 10 carbon atoms may be either an aliphatic hydrocarbon group or an aromatic hydrocarbon group, an aliphatic hydrocarbon group is preferable, and a monovalent saturated aliphatic hydrocarbon group (i.e., alkyl group) is more preferable.

As specific examples of the alkyl group, a linear or branched aliphatic hydrocarbon group, and an aliphatic hydrocarbon group containing a ring in the structure thereof can be given.

The linear alkyl group preferably has 1 to 8 carbon atoms, more preferably 1 to 5, and most preferably 1 to 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 5 carbon atoms. Specific examples of such branched alkyl groups include an isopropyl group, an isobutyl group, a tert-butyl group, an isopentyl group and a neopentyl group, and an isopropyl group or a tert-butyl group is particularly desirable.

As examples of the hydrocarbon group containing a ring in the structure thereof, a cyclic aliphatic hydrocarbon group (a group in which one hydrogen atom has been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 8 carbon atoms, and more preferably 4 to 6 carbon atoms. Specific examples include groups in which one or more hydrogen atoms have been removed from a monocycloalkane such as cyclopentane or cyclohexane.

The cyclic aliphatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (═O).

In general formula (I) above, Z represents a hydrocarbon group of 1 to 10 carbon atoms or a cyano group (—CN).

As the hydrocarbon group of 1 to 10 carbon atoms for Z, the same hydrocarbon groups of 1 to 10 carbon atoms as those described above for $R^1$ can be used.

In the present invention, $R^1$ and Z each independently represents a linear or branched alkyl group, wherein the terminal of $R^1$ may be mutually bonded to the terminal of Z to form a ring. As the formed ring, a ring having 3 to 8 carbon atoms is preferable, and preferable examples thereof includes cyclopentane, cyclohexane, cycloheptane and cyclooctane.

Among these, as the combination of $R^1$ and Z in the present invention, a combination of a methyl group and a methyl group; a combination of an ethyl group and an ethyl group; a combination of a methyl group and a cyano group; a combination of an ethyl group and a cyano group; and a group in which two carbon atoms have been removed from cyclopentane which is formed by $R^1$ and Z mutually bonded, are preferable, and it is particularly preferable that $R^1$ is a methyl group and Z is a cyano group.

In general formula (I) above, the plurality of $R^1$ and Z may be the same or different from each other, and are preferably the same in terms of industry.

In general formula (I) above, X represents a divalent linking group having any one selected from —O—C(═O)—, —NH—C(═O)— and —NH—C(═NH)— on a terminal that comes into contact with Q. When Q is a single bond, the terminal that comes into contact with Q is a terminal that comes into contact with —(C(═O)—O)$_q$—, $R^2$, —CF$_2$— or SO$_3^-$ in the general formula (I). The divalent linking group for X may consist of —O—C(═O)—, —NH—C(═O)— or —NH—C(═NH)—. X may contain —O—C(═O)—, —NH—C(═O)— or —NH—C(═NH)— in addition to the group at the terminal thereof which is bonded to Q.

Examples of the divalent linking group for X include a group consisting of —O—C(═O)—, —NH—C(═O)— or —NH—C(═NH)—; a combination of a divalent hydrocarbon group which may have a substituent or a divalent linking group containing a hetero atom, with any one of —O—C(═O)—, —NH—C(═O)— or —NH—C(═NH)—.

(Divalent Hydrocarbon Group which May have a Substituent)

In the present invention, a hydrocarbon "has a substituent" means that part or all of the hydrogen atoms within the hydrocarbon group is substituted with groups or atoms other than hydrogen atom.

The divalent hydrocarbon group which may have a substituent may be either an aliphatic hydrocarbon group or an aromatic hydrocarbon group. An "aliphatic hydrocarbon group" refers to a hydrocarbon group that has no aromaticity.

The aliphatic hydrocarbon group may be saturated or unsaturated. In general, the aliphatic hydrocarbon group is preferably saturated.

As specific examples of the aliphatic hydrocarbon group for the divalent hydrocarbon group, a linear or branched aliphatic hydrocarbon group, and an aliphatic hydrocarbon group having a ring in the structure thereof can be given.

The linear or branched aliphatic hydrocarbon group preferably has 1 to 10 carbon atoms, more preferably 1 to 8, still more preferably 1 to 5, and most preferably 1 or 2.

As the linear aliphatic hydrocarbon group, a linear alkylene group is preferable, and specific examples include a methylene group [—CH$_2$—], an ethylene group [—(CH$_2$)$_2$—], a trimethylene group [—(CH$_2$)$_3$—], a tetramethylene group [—(CH$_2$)$_4$—] and a pentamethylene group [—(CH$_2$)$_5$—].

As the branched aliphatic hydrocarbon group, a branched alkylene group is preferable, and specific examples include alkylalkylene groups, e.g., alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)—, and —C(CH$_2$CH$_3$)$_2$—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$—, and —C(CH$_2$CH$_3$)$_2$—CH$_2$—; alkyltrimethylene groups such as —CH(CH$_3$)CH$_2$CH$_2$—, and —CH$_2$CH(CH$_3$)CH$_2$—; and alkyltetramethylene groups such as —CH(CH$_3$)CH$_2$CH$_2$CH$_2$—, and —CH$_2$CH(CH$_3$)CH$_2$CH$_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated alkyl group of 1 to 5 carbon atoms, and an oxygen atom (═O).

As examples of the aliphatic hydrocarbon group containing a ring in the structure thereof, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (═O).

Examples of the aforementioned aromatic hydrocarbon group for the divalent hydrocarbon group include a divalent aromatic hydrocarbon group in which one hydrogen atom has been removed from a benzene ring of a monovalent aromatic hydrocarbon group such as a phenyl group, a biphenyl group, a fluorenyl group, a naphthyl group, an anthryl group or a phenanthryl group; an aromatic hydrocarbon group in which part of the carbon atoms constituting the ring of the aforementioned divalent aromatic hydrocarbon group has been substituted with a hetero atom such as an oxygen atom, a sulfur atom or a nitrogen atom; and an aromatic hydrocarbon group in which one hydrogen atom has been removed from a benzene ring of an arylalkyl group such as a benzyl group, a phenethyl group, a 1-naphthylmethyl group, a 2-naphthylmethyl group, a 1-naphthylethyl group or a 2-naphthylethyl group.

The aromatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (═O).

(Divalent Linking Group Containing a Hetero Atom)

Examples of the divalent linking group containing a hetero atom include —O—, —C(═O)—O—, —C(═O)—, —O—C(═O)—O—, —C(═O)—NH—, —NH—, —NH—C(═NH)— (H may be substituted with a substituent such as an alkyl group or an acyl group), —S—, —S(═O)$_2$—, —S(═O)$_2$—O—, "-A-O—B— (wherein O is an oxygen atom, and each of A and B independently represents a divalent hydrocarbon group which may have a substituent)" and a combination of a divalent hydrocarbon group which may have a substituent with a divalent linking group containing a hetero atom. As examples of the divalent hydrocarbon group which may have a substituent, the same groups as those described above for the hydrocarbon group which may have a substituent can be given, and a linear or branched aliphatic hydrocarbon group or an aliphatic hydrocarbon group containing a ring in the structure thereof is preferable.

When the H in the divalent linking group —NH— is replaced with a substituent such as an alkyl group or an acyl group, the substituent preferably has 1 to 10 carbon atoms, more preferably 1 to 8 carbon atoms, and most preferably 1 to 5 carbon atoms.

When the divalent linking group is "A-O—B", each of A and B independently represents a divalent hydrocarbon group which may have a substituent.

The hydrocarbon group for A may be either an aliphatic hydrocarbon group, or an aromatic hydrocarbon group. An "aliphatic hydrocarbon group" refers to a hydrocarbon group that has no aromaticity.

The aliphatic hydrocarbon group for A may be either saturated or unsaturated. In general, the aliphatic hydrocarbon group is preferably saturated.

As specific examples of the aliphatic hydrocarbon group for A, a linear or branched aliphatic hydrocarbon group, and an aliphatic hydrocarbon group having a ring in the structure thereof can be given. These are the same as defined above.

Among these, as A, a linear aliphatic hydrocarbon group is preferable, more preferably a linear alkylene group, still more preferably a linear alkylene group of 2 to 5 carbon atoms, and most preferably an ethylene group.

As the hydrocarbon group for B, the same divalent hydrocarbon groups as those described above for A can be used.

As B, a linear or branched aliphatic hydrocarbon group is preferable, and a methylene group or an alkylmethylene group is particularly desirable.

The alkyl group within the alkyl methylene group is preferably a linear alkyl group of 1 to 5 carbon atoms, more preferably a linear alkyl group of 1 to 3 carbon atoms, and most preferably a methyl group.

When X in the present invention consists of —O—C(═O)—, —NH—C(═O)— or —NH—C(═NH)—, X is preferably —O—C(═O)— or —NH—C(═O)—. Here, the carbon atom (C) within —O—C(═O)— or the carbon atom (C) within —NH—C(═O)— is preferably bonded directly to the carbon atom which is bonded to R$^1$ and Z.

In the case where X is a combination of the divalent group as described above with any one of —O—C(═O)—, —NH—C(═O)— or —NH—C(═NH)—, X is preferably a combination of a linear or branched aliphatic hydrocarbon group of 1 to 5 carbon atoms or a divalent linking group containing a hetero atom, with any one of —O—C(═O)—, —NH—C(═O)— or —NH—C(═NH)—; more preferably a combination of at least one linking group selected from a methylene group, an ethylene group and a divalent linking group containing —NH—, with any one of —O—C(═O)—, —NH—C(═O)— or —NH—C(═NH)—; and particularly preferably a combination of two or more groups selected from an ethylene group, —O—C(═O)— and —NH—C(═O)—.

In general formula (I) above, the plurality of X may be the same or different from each other, and are preferably the same in terms of industry.

In general formula (I) above, p represents an integer of 1 to 3. When p is 2 or 3, the ratio of SO$_3^-$ in one molecule can be enhanced. Therefore, in a polymeric compound which is obtained when the compound is used as a radical polymerization initiator, the ratio of the sulfonic acid portion (SO$_3^-$) which acts as acid or is generated as acid can be enhanced, and a function of generating acid can be improved.

In the present invention, p is preferably 1.

In general formula (I) above, the plurality of p may be the same or different from each other, and are preferably the same in terms of industry.

In general formula (I) above, Q represents a hydrocarbon group having a valency of (p+1), provided that, when p is 1, Q may be a single bond.

When p is 1, Q represents a single bond or a divalent hydrocarbon group. Examples of the divalent hydrocarbon group include the same groups as those described above as the "divalent hydrocarbon group which may have a substituent" for X and which has no substituent. In the case where p is 1, as Q, a single bond, or a divalent aliphatic hydrocarbon group is preferable; a single bond, or a linear or branched alkylene group is more preferable; a single bond, a methylene group or an ethylene group is still more preferable; and a single bond or an ethylene group is particularly preferable.

When p is 2, Q represents a trivalent hydrocarbon group, and when p is 3, Q represents a tetravalent hydrocarbon group. Examples of the trivalent hydrocarbon group and tetravalent hydrocarbon group include groups in which one or two hydrogen atoms have been removed from the "divalent hydrocarbon group which may have a substituent" for X and which has no substituent. In particular, a trivalent aliphatic hydrocarbon group and tetravalent aliphatic hydrocarbon group are preferable.

Specific examples of the hydrocarbon group having a valency of (p+1) for Q are shown below.

In general formula (I) above, the plurality of Q may be the same or different from each other, and are preferably the same in terms of industry.

[Chemical Formula 5]

[Chemical Formula 6]

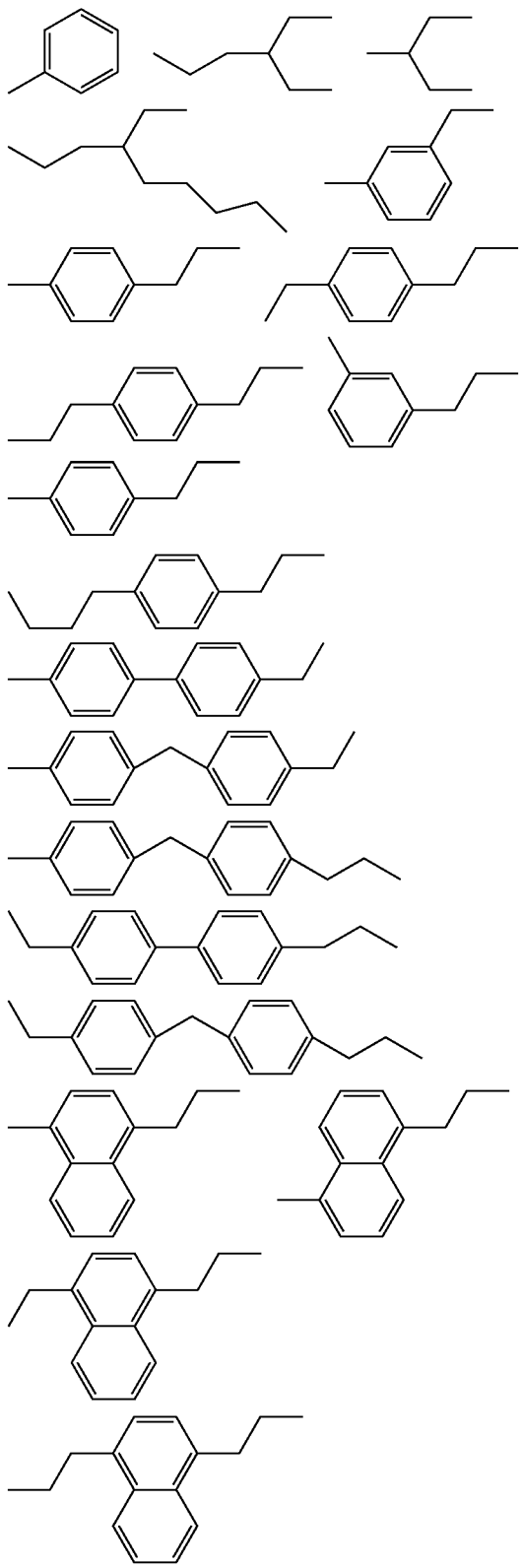

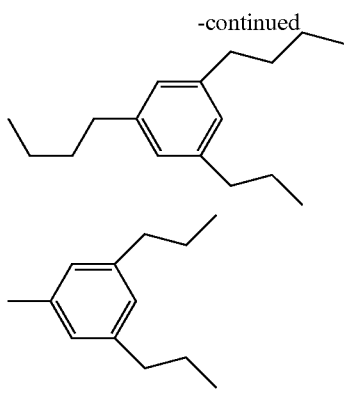

In general formula (I) above, q represents 0 or 1. When q is 0, it means that —(C(=O)—O)$_q$— is a single bond.

In the present invention, in the case where the divalent linking group for X does not contain —O—C(=O)—, q is preferably 1, and in the case where the divalent linking group for X contains —O—C(=O)—, q is preferably 0.

In general formula (I) above, the plurality of q may be the same or different from each other, and are preferably the same in terms of industry.

In general formula (I) above, R$^2$ represents a single bond, an alkylene group which may have a substituent, or an aromatic group which may have a substituent.

The alkylene group for R$^2$ may be chain-like or cyclic. Specific examples of the alkylene group include the same "linear or branched aliphatic hydrocarbon groups" and "aliphatic hydrocarbon group containing a ring in the structure thereof" as those described above for the "divalent hydrocarbon group which may have a substituent" for X. Among these, as the alkylene group for R$^2$, a linear alkylene group having 1 to 10 carbon atoms is preferable, and a methylene group or an ethylene group is more preferable.

The aromatic group of for R$^2$ which may have a substituent may be either an aromatic hydrocarbon group or an aromatic group which contains an atom other than carbon atoms in the ring structure thereof (i.e., heterocyclic compound).

As the aromatic hydrocarbon group, the same group as those described above for the "aromatic hydrocarbon group" in relation to the divalent hydrocarbon group for X which may have a substituent can be given. As the aromatic hydrocarbon group for R$^2$, a group in which one or more hydrogen atoms have been removed from a phenyl group or a naphthyl group is preferable. The aromatic hydrocarbon group for R$^2$ may be a group in which part or all of the hydrogen atoms of the aromatic hydrocarbon group have been substituted with an alkyl group of 1 to 5 carbon atoms, a fluorine atom, a fluorinated alkyl group of 1 to 5 carbon atoms, or an oxygen atom (=O), and preferably a group in which part or all of the hydrogen atoms of the aromatic hydrocarbon group have been substituted with a fluorine atom.

As the aromatic group containing an atom other than carbon atom in the ring structure thereof, a group in which two or more hydrogen atoms have been removed from a heterocycle such as quinoline, pyridine, oxole and imidazole is preferably used.

Among these, as R$^2$, a single bond or an aromatic group which may have a substituent is preferable.

In general formula (I) above, the plurality of R$^2$ may be the same or different from each other, and are preferably the same in terms of industry.

In general formula (I) above, r represents an integer of 0 to 8, and preferably 0 or 1. When r is 0, it means that —(CF$_2$)$_r$— is a single bond.

In the present invention, in the case where R$^2$ is a single bond or an alkylene group which may have a substituent, r is preferably an integer of 1 to 8, more preferably an integer of 1 to 4, still more preferably 1 or 2, and particularly preferably 1. In the case where R$^2$ is an aromatic group which may have a substituent, r is preferably 0.

In general formula (I) above, the plurality of r may be the same or different from each other, and are preferably the same in terms of industry.

As the compound (I), compounds represented by general formulae (I1) to (I5) shown below are preferable.

[Chemical Formula 7]

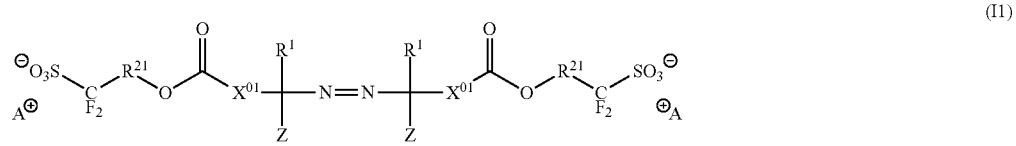
(I1)

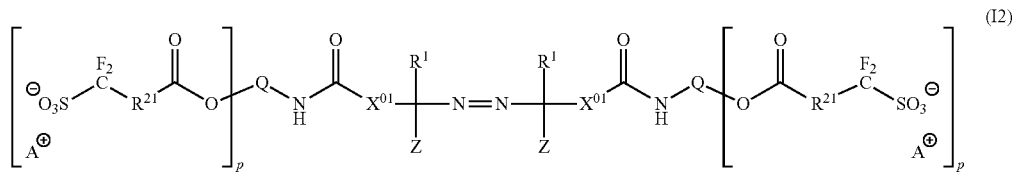
(I2)

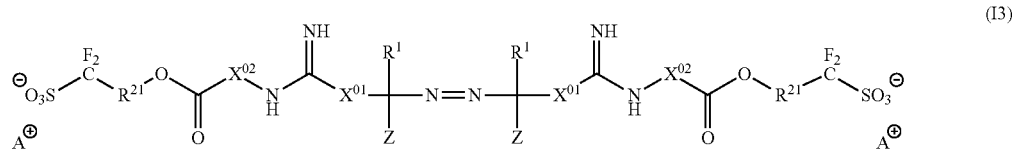
(I3)

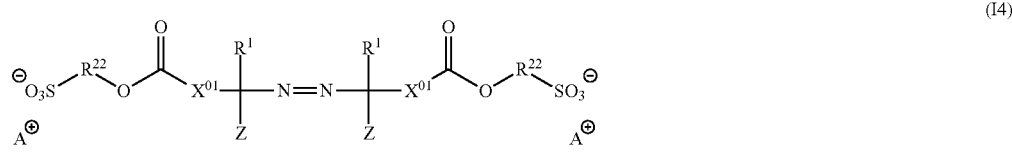
(I4)

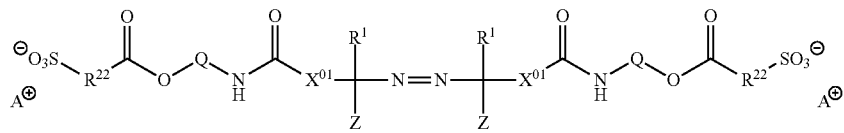

In the formulae, $R^1$, Z, Q, p and $A^+$ are the same as defined above; $X^{01}$ represents a single bond or an alkylene group which may have a substituent; $R^{21}$ represents a single bond or an alkylene group which may have a substituent; $X^{02}$ represents an alkylene group which may have a substituent; and $R^{22}$ represents an aromatic group which may have a substituent. the plurality of $R^1$, Z, Q, p, $A^+$, $X^{01}$, $R^{21}$, $X^{02}$ and $R^{22}$ may be the same or different from each other.

In the formulae (I1) to (I5), $R^1$, Z, Q, p and $A^+$ are the same as defined above.

In the formulae (I1) to (I5), $X^{01}$ represents a single bond or an alkylene group which may have a substituent. Specific examples of the alkylene group which may have a substituent include the same "linear or branched aliphatic hydrocarbon groups" and "aliphatic hydrocarbon group containing a ring in the structure thereof" as those described above for the "divalent hydrocarbon group which may have a substituent" for X.

As $X^{01}$, a single bond or an ethylene group is particularly desirable.

In the formulae (I1) to (I3), $R^{21}$ represents a single bond or an alkylene group which may have a substituent. The alkylene group for $R^{21}$ which may have a substituent is the same groups as those described above for $R^2$.

As $R^{21}$, a single bond or a methylene group is particularly desirable.

In the formula (I3), $X^{02}$ represents an alkylene group which may have a substituent, and specific examples thereof include the same "linear or branched aliphatic hydrocarbon groups" and "aliphatic hydrocarbon group containing a ring in the structure thereof" as those described above for the "divalent hydrocarbon group which may have a substituent" for X.

As $X^{02}$, an ethylene group is particularly desirable.

In the formulae (I4) and (I5), $R^{22}$ represents an aromatic group which may have a substituent. The aromatic group for $R^{22}$ which may have a substituent is the same groups as those described above for $R^2$.

As $R^{22}$, a group in which one or more hydrogen atoms have been removed from a phenyl group or a naphthyl group, or a group in which two or more hydrogen atoms have been removed from quinoline is particularly preferable.

Specific examples of a compounds represented by the formulae (I1) to (I5) are shown below. In the formulae, $A^+$ is the same as defined above, and will be described in detail later.

[Chemical Formula 8]

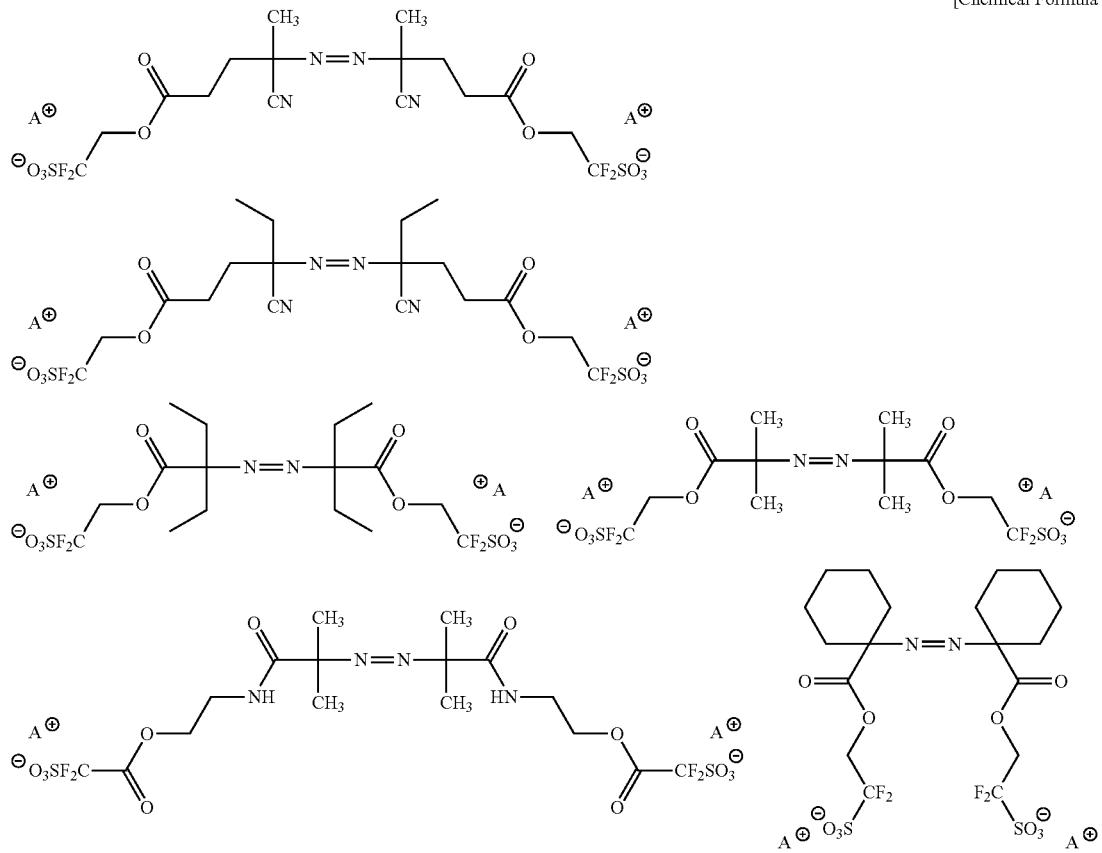

-continued
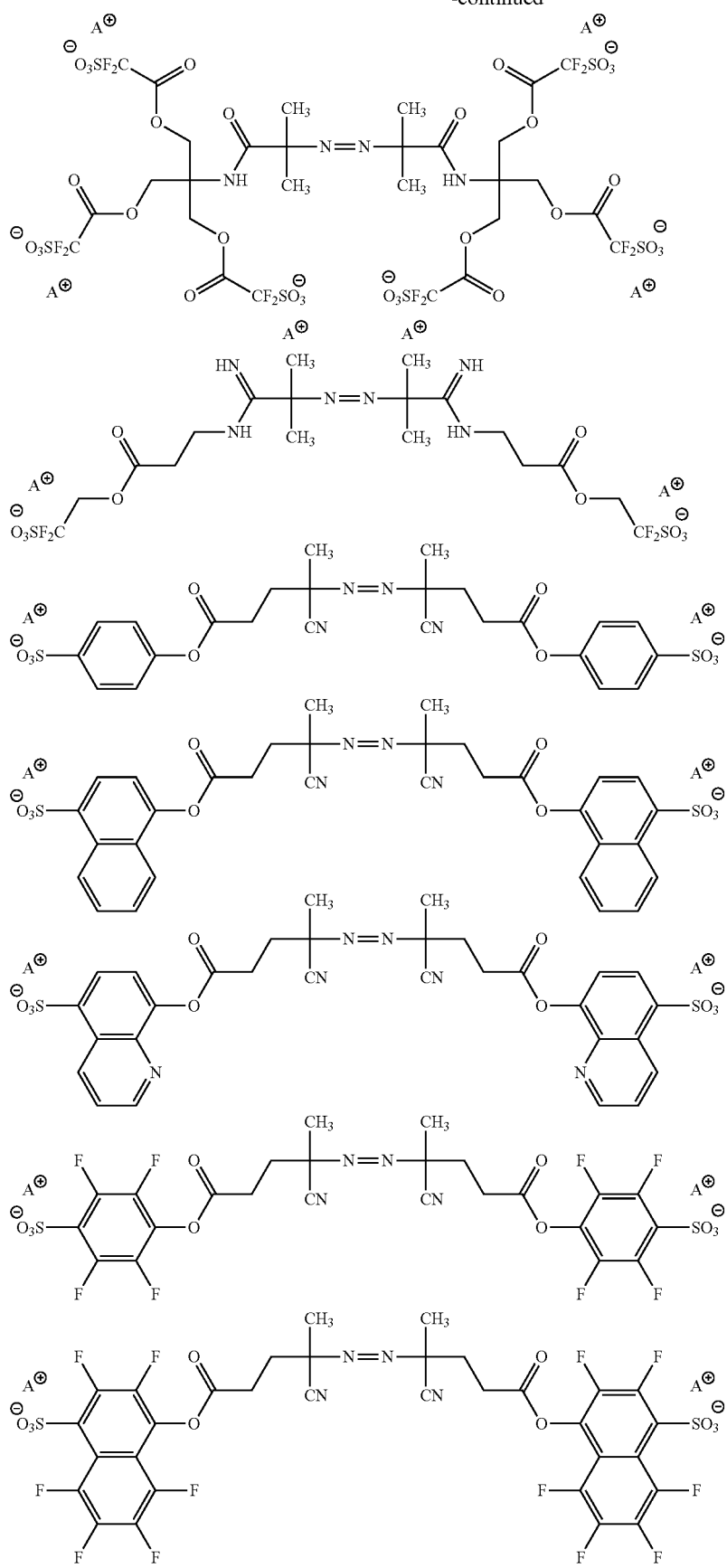
[Chemical Formula 9]

-continued

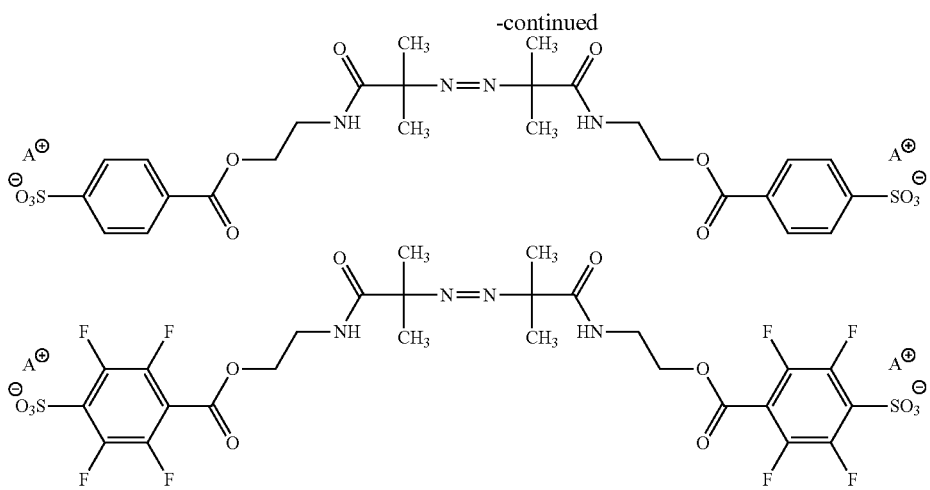

In general formula (I) above, A⁺ represents a metal cation or an organic cation.

When A⁺ is an organic cation, the compound (I) exhibits a function of generating acid upon exposure. When the compound is used as a radical polymerization initiator, the compound can impart a function of generating acid to the resulting polymeric compound. As described later, such a polymeric compound can be used for a resist composition.

When A⁺ is a metal cation, the compound (I) can be used as an intermediate compound for producing a compound useful as a radical polymerization initiator which can impart a function of generating acid to the resulting polymeric compound.

(Metal Cation)

The metal cation for A⁺ is not particularly limited, and is preferably an alkali metal ion. Specific examples of alkali metal ions include a sodium ion, a lithium ion and a potassium ion, and a sodium ion or a lithium ion is more preferable.

(Organic Cation)

The organic cation for A⁺ is not particularly limited, and an organic cation conventionally known as the cation moiety of a photo decomposable base used as a quencher for a resist composition or the cation moiety of an onium salt acid generator for a resist composition can be used.

As the organic cation for A⁺, for example, a cation moiety represented by general formula (c-1) or (c-2) shown below can be used.

[Chemical Formula 10]

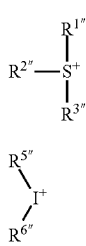

In the formulae, each of $R^{1\prime\prime}$ to $R^{3\prime\prime}$, $R^{5\prime\prime}$ and $R^{6\prime\prime}$ independently represents an aryl group or an alkyl group, provided that, in formula (c-1), two of $R^{1\prime\prime}$ to $R^{3\prime\prime}$ may be mutually bonded to form a ring with the sulfur atom.

In formula (c-1), $R^{1\prime\prime}$ to $R^{3\prime\prime}$ each independently represents an aryl group or an alkyl group. In formula (c-1), two of $R^{1\prime\prime}$ to $R^{3\prime\prime}$ may be bonded to each other to form a ring with the sulfur atom.

Further, among $R^{1\prime\prime}$ to $R^{3\prime\prime}$, it is preferable that at least one group represent an aryl group. Among $R^{1\prime\prime}$ to $R^{3\prime\prime}$, it is more preferable that two or more groups are aryl groups, and it is particularly desirable that all of $R^{1\prime\prime}$ to $R^{3\prime\prime}$ are aryl groups.

The aryl group for $R^{1\prime\prime}$ to $R^{3\prime\prime}$ is not particularly limited. For example, an aryl group having 6 to 20 carbon atoms may be used in which part or all of the hydrogen atoms of the aryl group may or may not be substituted with alkyl groups, alkoxy groups, halogen atoms or hydroxyl groups.

The aryl group is preferably an aryl group having 6 to 10 carbon atoms because it can be synthesized at a low cost. Specific examples thereof include a phenyl group and a naphthyl group.

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

The halogen atom, with which hydrogen atoms of the aryl group may be substituted, is preferably a fluorine atom.

The alkyl group for $R^{1\prime\prime}$ to $R^{3\prime\prime}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decyl group, and a methyl group is most preferable because it is excellent in resolution and can be synthesized at a low cost.

When two of $R^{1\prime\prime}$ to $R^{3\prime\prime}$ in formula (c-1) are bonded to each other to form a ring with the sulfur atom, it is preferable that the two of $R^{1\prime\prime}$ to $R^{3\prime\prime}$ form a 3- to 10-membered ring including the sulfur atom, and it is particularly desirable that the two of $R^{1\prime\prime}$ to $R^{3\prime\prime}$ form a 5- to 7-membered ring including the sulfur atom.

When two of $R^{1\prime\prime}$ to $R^{3\prime\prime}$ in formula (c-1) are bonded to each other to form a ring with the sulfur atom, the remaining one of $R^{1\prime\prime}$ to $R^{3\prime\prime}$ is preferably an aryl group. As examples of the aryl group, the same aryl groups as those described above for $R^{1\prime\prime}$ to $R^{3\prime\prime}$ can be used.

As preferable examples of the cation moiety represented by general formula (c-1), those represented by formulas (I-1-1) to (I-1-32) shown below can be given.

[Chemical Formula 11]
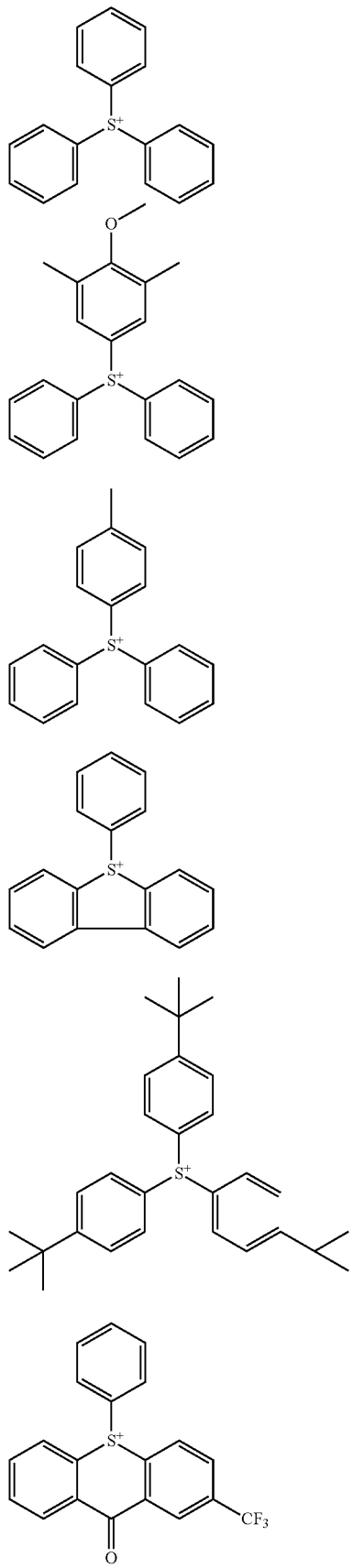
(I-1-1)
(I-1-2)
(I-1-3)
(I-1-4)
(I-1-5)
(I-1-6)
-continued
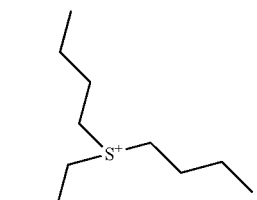
(I-1-7)
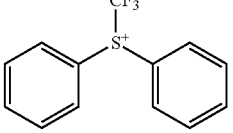
(I-1-8)
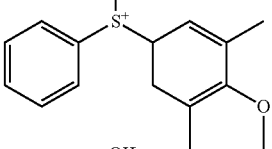
(I-1-9)
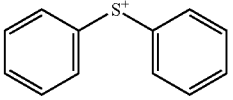
(I-1-10)
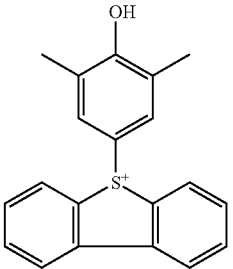
(I-1-11)
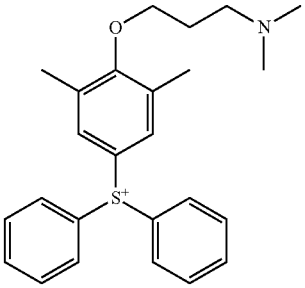
(I-1-12)
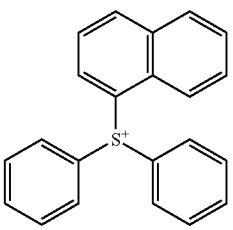
(I-1-13)

[Chemical Formula 12]
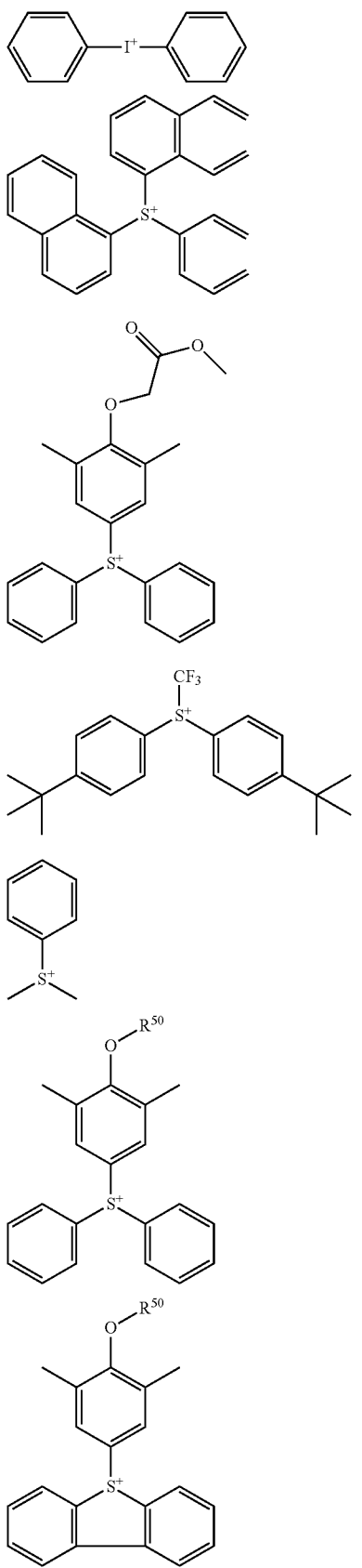
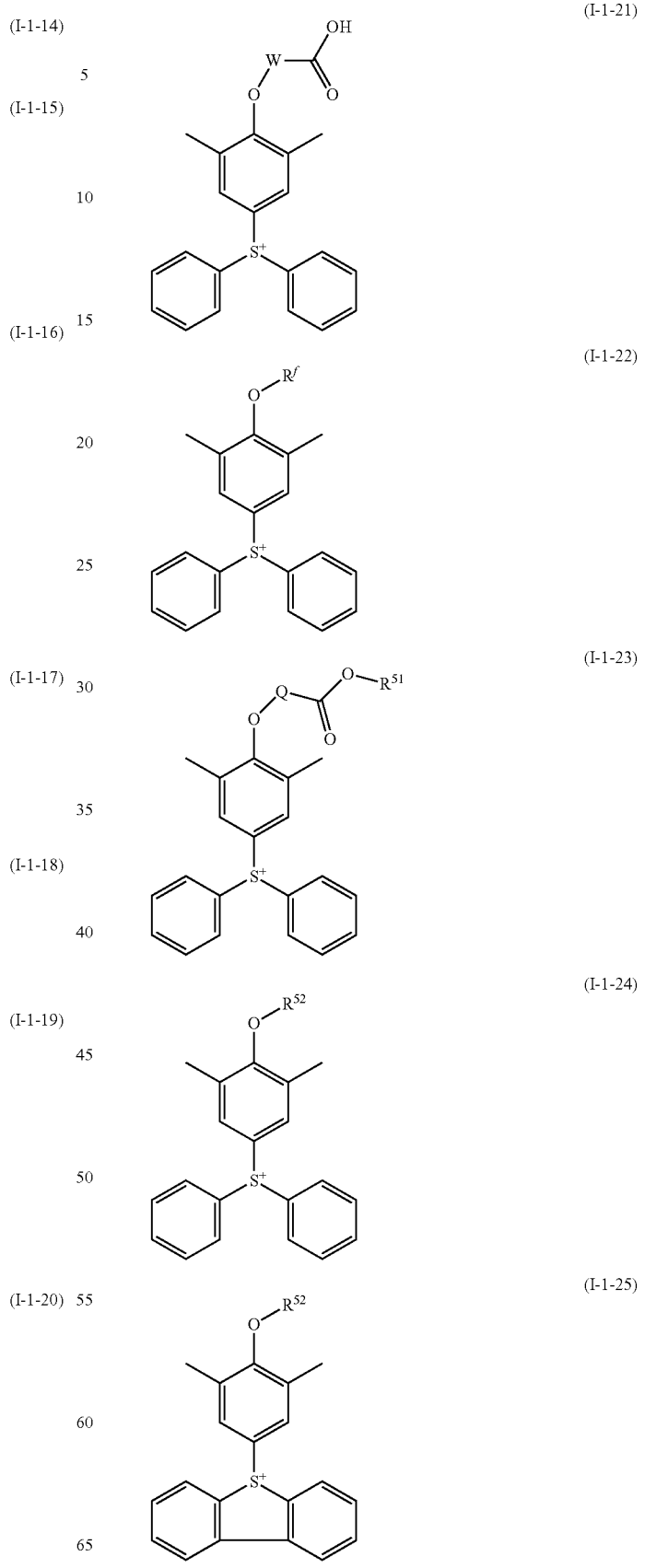

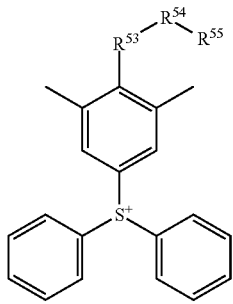
(I-1-26)

[Chemical Formula 13]

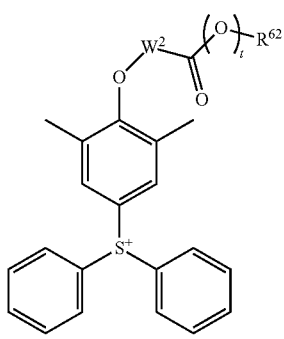
(I-1-27)

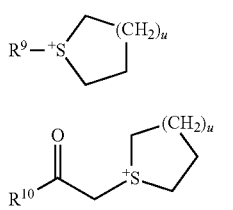
(I-1-28)

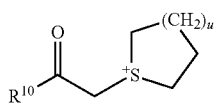
(I-1-29)

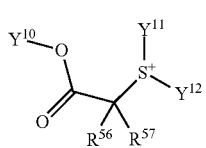
(I-1-30)

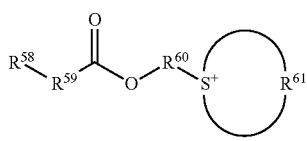
(I-1-31)

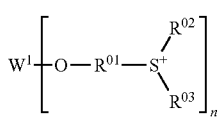
(I-1-32)

In formulae (I-1-19) and (I-1-20), $R^{50}$ represents a group containing an acid dissociable, dissolution inhibiting group, and is preferably a group represented by the formula (p1), (p1-1) or (p2) described later, or a group in which a group represented by the formula (1-1) to (1-9) or (2-1) to (2-6) described later is bonded to the oxygen atom of —$R^{91}$—C(=O)—O—. $R^{91}$ represents a single bond or a linear or branched alkylene group, and the alkylene group preferably has 1 to 5 carbon atoms.

In formula (I-1-21), W represents a divalent linking group, and examples thereof include the same divalent linking groups as those described above for X in the aforementioned formula (I). Among these, a linear or branched alkylene group, a divalent aliphatic cyclic group or a divalent linking group containing a hetero atom is preferable, a linear or branched alkylene group is more preferable, and a linear alkylene group is still more preferable.

In formula (I-1-22), $R^f$ represents a fluorinated alkyl group, i.e., a group in which an unsubstituted alkyl group has part or all of the hydrogen atoms substituted with fluorine atoms. The unsubstituted alkyl group is preferably a linear or branched alkyl group, and more preferably a linear alkyl group.

In formula (I-1-23), Q represents a divalent linking group, and $R^{51}$ represents an organic group having a carbonyl group, an ester bond or a sulfonyl group.

Examples of the divalent linking group for Q include the same divalent linking groups as those described above for X in the formula (I). As Q, an alkylene group or a divalent linking group containing an ester bond is preferable, and an alkylene group or —$R^{92}$—C(=O)—O—$R^{93}$— [each of $R^{92}$ and $R^{93}$ independently represents an alkylene group] is more preferable.

The organic group having a carbonyl group, an ester bond or a sulfonyl group for $R^{51}$ may be either an aromatic hydrocarbon group or an aliphatic hydrocarbon group. Examples of the aromatic hydrocarbon group and the aliphatic hydrocarbon group include the same groups as those described above for $X^3$. Among these, as the organic group having a carbonyl group, an ester bond or a sulfonyl group for $R^{51}$, an aliphatic hydrocarbon group is preferable, a bulky aliphatic hydrocarbon group is more preferable, and a cyclic saturated hydrocarbon group is still more preferable. Preferable examples of $R^{51}$ include a group represented by any one of the aforementioned formulas (L1) to (L6) and (S1) to (S4), the same group as those described later for $X^3$, and a monocyclic or polycyclic group in which the hydrogen atoms bonded thereto have been substituted with an oxygen atom (=O).

In formulae (I-1-24) and (I-1-25), $R^{52}$ represents an alkyl group of 4 to 10 carbon atoms which is not an acid dissociable group. As $R^{52}$, a linear or branched alkyl group is preferable, and a linear alkyl group is more preferable.

In formula (I-1-26), $R^{53}$ represents a divalent group having a base dissociable portion, $R^{54}$ represents a divalent linking group, and $R^{55}$ represents a group having an acid dissociable group.

The base dissociable portion within $R^{53}$ refers to a portion which is dissociable by the action of an alkali developing solution (e.g., a 2.38% by weight aqueous solution of tetramethylammonium hydroxide (TMAH) at 23° C.). By the dissociation of the base dissociable portion, the solubility in an alkali developing solution is increased. The alkali developing solution may be any one of those generally used in the fields of lithography. It is preferable that the base dissociable portion is dissociated the action of a 2.38% by weight aqueous solution of tetramethylammonium hydroxide at 23° C.

The $R^{53}$ group may be either a group constituted of only a base dissociable portion, or a group in which a base dissociable portion is boned to a group or atom which is not base dissociable.

The base dissociable portion within the $R^{53}$ group is most preferably an ester group (—C(=O)—O—).

Examples of the group or atom which is not base dissociable for $R^{53}$ include the divalent linking groups described above for X in the formula (I) and combinations of the linking groups (provided that groups which are base dissociable are excluded). The "combination of the linking groups" refer to a divalent linking group constituted of divalent linking groups bonded together. As such a "combination of linking groups", a combination of an alkylene group with a divalent linking group containing a hetero atom is preferable. However, it is preferable that the hetero atom is not adjacent to the atom within the base dissociable portion which has its bond cleaved by the action of a base.

The alkylene group is the same as defined for the linear or branched alkylene group for X in the formula (I).

The hetero atom is most preferably an oxygen atom.

Among the above examples, $R^{53}$ is preferably a group in which a base dissociable portion is boned to a group or atom which is not base dissociable.

$R^{54}$ represents a divalent linking group, and examples thereof include the same divalent linking groups as those described above for X in the formula (I). Among these, an alkylene group or a divalent aliphatic cyclic group is preferable, and an alkylene group is particularly desirable.

$R^{55}$ represents a group having an acid dissociable group.

The acid dissociable group is an organic group which can be dissociated by the action of an acid. The acid dissociable group is not particularly limited, and any group which has been proposed as an acid dissociable, dissolution inhibiting group of a base resin for a chemically amplified resist can be used. Specific examples include the same acid dissociable, dissolution inhibiting groups as those described later for the structural unit (a1), such as a cyclic or chain-like tertiary alkyl ester-type acid dissociable group or an acetal-type acid dissociable group (e.g., an alkoxyalkyl group). Among these, a tertiary alkyl ester-type acid dissociable group is particularly desirable.

The group having an acid dissociable group may be either the acid dissociable group itself, or a group in which an acid dissociable group is bonded to a group or atom which is not acid dissociable (a group or atom which remains bonded to the acid generator even after the dissociation of the acid dissociable group). Examples of the group or atom which is not acid dissociable include the same divalent linking groups as those described above for X in the formula (I).

In formula (I-1-27), $W^2$ represents a single bond or a divalent linking group, t represents 0 or 1, and $R^{62}$ represents a group which is not dissociable by acid (hereafter, referred to as "acid non-dissociable group").

Examples of the divalent linking group for $W^2$ include the same divalent linking groups as those described above for X in the formula (I). Among these, as $W^2$, a single bond is preferable.

t is preferably 0.

The acid non-dissociable group for $R^{62}$ is not particularly limited as long as it is a group which is not dissociable by acid. The acid non-dissociable group is preferably an acid non-dissociable hydrocarbon group which may have a substituent, more preferably a cyclic hydrocarbon group which may have a substituent, and still more preferably a group in which one hydrogen atom has been removed from adamantane.

In formulae (I-1-28) and (I-1-29), each of $R^9$ and $R^{10}$ independently represents a phenyl group or naphthyl group which may have a substituent, an alkyl group of 1 to 5 carbon atoms, an alkoxy group or a hydroxy group; and u represents an integer of 1 to 3, most preferably 1 or 2.

In formula (I-1-30), $Y^{10}$ represents a cyclic hydrocarbon group of 5 or more carbon atoms which may have a substituent, and is an acid dissociable group which may be dissociated by the action of an acid; each of $R^{56}$ and $R^{57}$ independently represents a hydrogen atom, an alkyl group or an aryl group, provided that $R^{56}$ and $R^{57}$ may be mutually bonded to form a ring; each of $Y^{11}$ and $Y^{12}$ independently represents an alkyl group or an aryl group, provided that $Y^{11}$ and $Y^{12}$ may be mutually bonded to form a ring.

$Y^{10}$ represents a cyclic hydrocarbon group of 5 or more carbon atoms which may have a substituent, and is an acid dissociable group which may be dissociated by the action of an acid. By virtue of the $Y^{10}$ group being a cyclic hydrocarbon group of 5 or more carbon atoms which may have a substituent, and is an acid dissociable group which may be dissociated by the action of an acid, various lithography properties such as resolution, LWR, exposure latitude (EL margin) and resist pattern are improved.

Examples of $Y^{10}$ include groups which form a cyclic tertiary alkyl ester with —C($R^{56}$)($R^{57}$)—C(=O)—O—.

A "tertiary alkyl ester" refers to a structure in which a tertiary carbon atom within a cyclic hydrocarbon group of 5 or more carbon atoms is bonded to the terminal oxygen atom of —C($R^{56}$)($R^{57}$)—C(=O)—O—. In this tertiary alkyl ester, the action of acid causes cleavage of the bond between the oxygen atom and the tertiary carbon atom.

The cyclic hydrocarbon group may have a substituent, and the carbon atom(s) within the substituent is not included in the number of carbon atoms of the "carbon atom of 5 or more carbon atoms".

Examples of the "aliphatic cyclic group" include monocyclic groups or polycyclic groups which have no aromaticity, and polycyclic groups are preferable.

The "aliphatic cyclic group" may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

As such aliphatic cyclic groups, groups in which two or more hydrogen atoms have been removed from a monocycloalkane or a polycycloalkane such as a bicycloalkane, tricycloalkane or tetracycloalkane which may or may not be substituted with an alkyl group of 1 to 5 carbon atoms, a fluorine atom or a fluorinated alkyl group, may be used. Specific examples include groups in which two or more hydrogen atoms have been removed from a monocycloalkane such as cyclopentane and cyclohexane; and groups in which two or more hydrogen atoms have been removed from a polycycloalkane such as adamantane, norbornane, isobornane, tricyclodecane or tetracyclododecane.

Each of $R^{56}$ and $R^{57}$ independently represents a hydrogen atom, an alkyl group or an aryl group.

Examples of the alkyl group or aryl group for $R^{56}$ and $R^{57}$ include the same alkyl groups and aryl groups as those described above for $R^{1\prime\prime}$ to $R^{3\prime\prime}$. Further, $R^{56}$ to $R^{57}$ may be mutually bonded to form a ring, like in the case of the aforementioned $R^{1\prime\prime}$ to $R^{3\prime\prime}$.

Among the above-mentioned examples, it is particularly desirable that both $R^{56}$ and $R^{57}$ represent a hydrogen atom.

Each of $Y^{11}$ and $Y^{12}$ independently represents an alkyl group or an aryl group.

Examples of the alkyl group or aryl group for $Y^{11}$ and $Y^{12}$ include the same alkyl groups and aryl groups as those described above for $R^{1\prime\prime}$ to $R^{3\prime\prime}$.

It is particularly desirable that each of $Y^{11}$ and $Y^{12}$ represents a phenyl group or a naphthyl group. Further, $Y^{11}$ and $Y^{12}$ may be mutually bonded to form a ring, like in the case of the aforementioned $R^{1\prime\prime}$ to $R^{3\prime\prime}$.

In formula (I-1-31), $R^{58}$ represents an aliphatic cyclic group; $R^{59}$ represents a single bond or an alkylene group which may have a substituent; $R^{60}$ represents an arylene group which may have a substituent; and $R^{61}$ represents an alkylene group of 4 or 5 carbon atoms which may have a substituent.

The aliphatic cyclic group for $R^{58}$ may be either a monocyclic group or a polycyclic group, but is preferably a polycyclic group, more preferably a group in which one or more hydrogen atoms have been removed from a polycycloalkane, and most preferably a group in which one or more hydrogen atoms have been removed from adamantane.

The alkylene group for $R^{59}$ which may have a substituent is preferably a linear or branched alkylene group. As $R^{59}$, a single bond or an alkylene group of 1 to 3 carbon atoms is preferable.

The arylene group for $R^{60}$ preferably has 6 to 20 carbon atoms, more preferably 6 to 14 carbon atoms, and still more preferably 6 to 10 carbon atoms. Examples of the arylene group include a phenylene group, a biphenylene group, a fluorenylene group, a naphthylene group, an anthrylene group and a phenanthrene group. In terms of synthesis at low cost, a phenylene group or a naphthylene group is preferable.

In formula (I-1-32), $R^{01}$ represents an arylene group or an alkylene group; each of $R^{02}$ and $R^{03}$ independently represents an aryl group or an alkyl group, provided that $R^{02}$ and $R^{03}$ may be mutually bonded to form a ring with the sulfur atom, and at least one of $R^{01}$ to $R^{03}$ represents an arylene group or an aryl group; $W^1$ represents a linking group having a valency of n; and n represents 2 or 3.

The arylene group for $R^{01}$ is not particularly limited, and examples thereof include arylene groups of 6 to 20 carbon atoms in which part or all of the hydrogen atoms may be substituted. The alkylene group for $R^{01}$ is not particularly limited, and examples thereof include linear, branched or cyclic alkylene groups of 1 to 10 carbon atoms.

The aryl group for $R^{02}$ and $R^{03}$ is not particularly limited, and examples thereof include aryl groups of 6 to 20 carbon atoms in which part or all of the hydrogen atoms may be substituted. The alkyl group for $R^{02}$ and $R^{03}$ is not particularly limited, and examples thereof include linear, branched or cyclic alkyl groups of 1 to 10 carbon atoms.

Examples of the divalent linking group for $W^1$ include the same divalent linking groups as those described above for X in the formula (I). The divalent linking group may be linear, branched or cyclic, but is preferably cyclic. Among these, an arylene group having two carbonyl groups, each bonded to the both terminals thereof is preferable.

The trivalent linking group for $W^1$ is preferably an arylene group combined with three carbonyl groups.

In formula (c-2), $R^{5\prime\prime\prime}$ and $R^{6\prime\prime\prime}$ each independently represent an aryl group or alkyl group. At least one of $R^{5\prime\prime\prime}$ and $R^{6\prime\prime\prime}$ represents an aryl group. It is preferable that both of $R^{5\prime\prime\prime}$ and $R^{6\prime\prime\prime}$ represent an aryl group.

As the aryl group for $R^{5\prime\prime\prime}$ and $R^{6\prime\prime\prime}$, the same aryl groups as those described above for $R^{1\prime\prime\prime}$ to $R^{3\prime\prime\prime}$ can be used.

As the alkyl group for $R^{5\prime\prime\prime}$ and $R^{6\prime\prime\prime}$, the same alkyl groups as those described above for $R^{1\prime\prime\prime}$ to $R^{3\prime\prime\prime}$ can be used.

It is particularly desirable that both of $R^{5\prime}$ and $R^{6\prime\prime\prime}$ represents a phenyl group.

Further, as examples of the organic cation for $A^+$, organic cations represented by general formula (c-3) shown below can also be given.

[Chemical Formula 14]

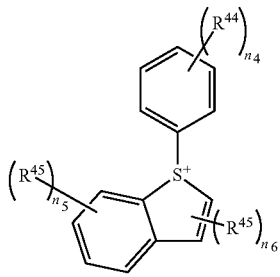

(c-3)

In formula, each of $R^{44}$ to $R^{46}$ independently represents an alkyl group, an acetyl group, an alkoxy group, a carboxy group, a hydroxyl group or a hydroxyalkyl group; each of $n_4$ and $n_5$ independently represents an integer of 0 to 3; and $n_6$ represents an integer of 0 to 2.

With respect to $R^{44}$ to $R^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert-butyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably a group in which one or more hydrogen atoms within the aforementioned alkyl group have been substituted with hydroxy groups, and examples thereof include a hydroxymethyl group, a hydroxyethyl group and a hydroxypropyl group.

If there are two or more of an individual $R^{44}$ to $R^{46}$ group, as indicated by the corresponding value of $n_1$ to $n_6$, then the two or more of the individual $R^{41}$ to $R^{46}$ group may be the same or different from each other.

$n_4$ is preferably 0 to 2, and more preferably 0 or 1.
$n_5$ is preferably 0 or 1, and more preferably 0.
$n_6$ is preferably 0 or 1, and more preferably 1.

In the present invention, as the compound (I), compounds represented by the formulae (I1) to (I5) are preferable, and the compound represented by the formula (I1) is particularly preferable. As the organic cation for $A^+$, organic cations represented by the aforementioned formulae (c-1) to (c-3) are preferable, and an organic cation represented by the aforementioned formula (c-1) is particularly preferable.

The production method of the compound (I) of the present invention is not particularly limited, and specific examples will be described later as in the third aspect.

<<Radial Polymerization Initiator>>

The radical polymerization initiator according to the second aspect of the present invention contains the compound represented by the general formula (I) (i.e., compound (I)) of the first aspect.

The radical polymerization initiator is useful as a polymerization initiator to polymerize monomers in radical polymerization reaction to synthesize a polymeric compound. The radical polymerization initiator of the present invention has acid generator ability in the case where $A^+$ in the general formula (I) is an organic cation, thereby imparting a function of generating acid to a compound to be obtained by polymerization. Therefore, the radical polymerization initiator of the present invention can be preferably used in radical polymerization for obtaining a polymeric compound which is used for a chemically amplified resist composition.

Monomers to be subjected to radical polymerization using the radical polymerization initiator may be any monomers polymerizable in radical polymerization reaction, and can be appropriately selected depending on a polymeric compound to be produced. As the monomers to be polymerized using the radical polymrization initiator of the present invention, acrylate ester-based monomers, vinyl-based monomers, styrene-based monomers are preferable, and acrylate ester-based monomers are particularly preferable. As the acrylate ester-based monomers, monomers which derive structural units (a1) to (a3) as described later can be mentioned.

<<Production Method of Compound>>

The third aspect of the present invention is a method of producing a compound represented by the general formula (I) (i.e., compound (I)) of the first aspect, including reacting a compound represented by general formula (i-1) shown below (hereafter, sometimes referred to as "compound (i-1)") with a compound represented by general formula (i-2) shown below (hereafter, sometimes referred to as "compound (i-2)").

[Chemical Formula 15]

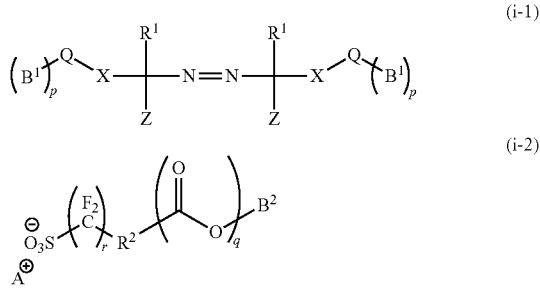

In the formulae, $R^1$, Z, X, Q, p, q, $R^2$, r and $A^+$ are the same as defined above; $B^1$ and $B^2$ each independently represents H or OH; and the plurality of $R^1$, Z, X, p, Q and $B^1$ may be the same or different from each other.

The production method of the compound of the present invention is not particularly limited, as long as it contains a step in which a compound (i-1) is reacted with a compound (i-2). For example, the compound (I) can be produced by reacting a compound (i-1) with a compound (i-2) under a suitable condition.

In the formula (i-1), $R^1$, Z, X, Q and p are the same as defined above, and $B^1$ represents H or OH.

In the case where Q has an oxygen atom on the terminal thereof which is bonded to $B^1$, or in the case where Q is a single bond and X has an oxygen atom on the terminal thereof which is bonded to $B^1$, $B^1$ is preferably H.

In the case where Q has no oxygen atom on the terminal thereof which is bonded to $B^1$, or in the case where Q is a single bond and X has no oxygen atom on the terminal thereof which is bonded to $B^1$, $B^1$ is preferably OH.

In the formula (i-2), q, $R^2$, r and $A^+$ are the same as defined above, and $B^2$ represents H and OH. When q is 1, $B^2$ is preferably H. On the other hand, when q is 0, $B^2$ is preferably OH.

As the compound (i-1) and the compound (i-2), commercially available compounds may be used, or the compounds may be synthesized.

The method for reacting the compound (i-1) with the compound (i-2) to obtain the compound (I) is not particularly limited, but can be performed, for example, by reacting the compound (i-1) with the compound (i-2) in an organic solvent in the presence of a condensation agent or a base, followed by washing and recovering the reaction mixture.

The condensation agent used in the reaction is not particularly limited. For example, a compound containing a carbodiimide group such as diisopropylcarbodiimide can be used, and one type may be used alone, or two or more types may be used in combination. The amount of the condensation agent is preferably 0.01 to 10 moles, per 1 mole of the compound (i-2).

The base used in the reaction is not particularly limited. Examples of the base include potassium carbonate, tertiary amines such as triethylamine, and aromatic amines such as pyridine. These bases may be used individually or in a combination of two or more. The amount of the base is preferably 0.01 to 10 moles, per 1 mole of the compound (i-2).

As the organic solvent used in the reaction, chlorinated hydrocarbon solvents such as dichloromethane are preferably used. The amount of the organic solvent is preferably 0.5 to 100 parts by weight, and more preferably 0.5 to 20 parts by weight, relative to the amount of the compound (i-2). As the solvent, one type may be used alone, or two or more types may be used in combination.

In general, in the case where p is 1, the amount of the compound (i-2) used in the above reaction is preferably 0.5 to 5 moles per 1 mole of the compound (i-1), and more preferably 0.8 to 4 moles per 1 mole of the compound (i-1).

The reaction time depends on the reactivity of the compounds (i-1) and (i-2), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

After the reaction, the compound (I) within the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

The structure of the compound (I) obtained in the above-described manner can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

<<Polymeric Compound (A1)>>

The resist composition of the seventh aspect of the present invention includes a polymeric compound (A1) having an anion portion which generates acid upon exposure, on at least one terminal of the main chain thereof. The polymeric compound (A1) can be obtained, for example, by a radical polymerization or an anion polymerization of the monomers corresponding with the structural units contained in the polymeric compound (A1) to be produced, using a radical polymerization initiator which contains an anion portion capable of generating acid upon exposure. As the monomers, commercially available monomers may be used, or the monomers may be synthesized by a conventional method.

The polymeric compound (A1) is preferably a radical polymeric compound (A1') of the fourth aspect of the present invention, obtainable by radical polymerization using a radical polymerization initiator containing a compound represented by the general formula (I), in terms of excellent lithography properties and pattern shape.

<<Polymeric Compound (A1')>>

The fourth aspect of the present invention is a polymeric compound (A1') having a group represented by general formula (I-1) shown below on at least one terminal of the main chain thereof

[Chemical Formula 16]

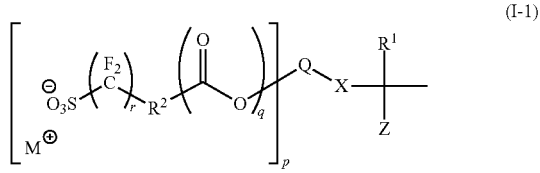

In the formula, $R^1$ represents a hydrocarbon group of 1 to 10 carbon atoms; Z represents a hydrocarbon group of 1 to 10 carbon atoms or a cyano group; provided that $R^1$ and Z may be mutually bonded to form a ring; X represents a divalent linking group having any one selected from —O—C(=O)—, —NH—C(=O)— and —NH—C(=NH)— on a terminal that comes into contact with Q; p represents an integer of 1 to 3;

Q represents a hydrocarbon group having a valency of (p+1), provided that, when p is 1, Q may be a single bond; and $R^2$ represents a single bond, an alkylene group which may have a substituent or an aromatic group which may have a substituent; q represents 0 or 1; r represents an integer of 0 to 8; $M^+$ represents an organic cation.

In the formula (I-1), $R^1$, Z, X, p, Q, $R^2$, q and r are respectively the same as defined for $R^1$, Z, X, p, Q, $R^2$, q and r in the formula (I) explained in the first aspect.

In the formula (I-1), $M^+$ represents an organic cation and is the same organic cation as those for $A^+$ in the formula (I) explained in the compound of the first aspect.

The polymeric compound (A1') of the fourth aspect of the present invention has a terminal group (I-1), thereby exhibiting a function of generating acid to generate acid upon exposure. That is, the terminal group (I-1) has a sulfonium salt portion at the terminal thereof, thereby generating sulfonic acid upon exposure.

In the fourth aspect of the present invention, a polymeric compound (A1') may be any polymeric compounds having a terminal group represented by general formula (I-1) shown below on at least one terminal of the main chain thereof. Other constituents (for example, structural unit constituting the polymeric compound) can be employed depending on the intended application of the polymeric compound.

The polymeric compound (A1') according to a fourth aspect of the present invention is useful for a resist composition. There are no particular limitations on the resist composition containing the polymeric compound of the present invention, although a chemically amplified resist composition including a base component that exhibits changed solubility in an alkali developing solution under the action of acid, and an acid generator component that generates acid upon exposure is ideal.

The polymeric compound (A1') according to a fourth aspect of the present invention is useful as either a base component for a chemically amplified resist composition, or an additive component which is optionally blended to the resist composition. It is particularly preferable to use as a base component. The constitutions of the polymeric compound useful as a base component will be described later in relation to the component (A1') contained in the resist composition of the fifth aspect of the present invention.

As the method of producing the polymeric compound (A1') which has a terminal group (I-1) on at least one terminal of the main chain thereof, the method of polymerizing desired monomers by radical polymerization using the radical polymerization initiator of the second aspect of the present invention can be preferably employed. That is, the polymeric compound of the fourth aspect of the present invention is preferably a radical polymeric compound obtainable by radical polymerization using the radical polymerization initiator of the second aspect of the present invention.

Monomers to be subjected to radical polymerization may be any monomers polymerizable in radical polymerization reaction, and monomers corresponding with the structural units constituting the polymeric compound can be appropriately selected depending on a polymeric compound to be produced.

The radical polymerization can be performed by a conventional method, except that the radical polymerization initiator of the present invention is used as a radical polymerization initiator.

In radical polymerization, as the radical polymerization initiator of the present invention, one type may be used, or two or more types may be used in combination.

In the case where the radical polymerization initiator of the present invention has a metal cation $A^+$ as a cation moiety, a salt exchange between the radical polymerization initiator and an onium salt having a desired organic cation is conducted in advance, thereby obtaining a radical polymerization initiator having an organic cation $M^+$. Salt exchange can be conducted by a normal method.

Production examples of the polymeric compound (A1') are shown below. A schematic diagram of a synthetic route in which a monomer represented by formula (a) (i.e., vinyl compound having a functional group such as an acid decomposable group; hereinafter, referred to as "monomer (a)") is subjected to radical polymerization using a radical polymerization initiator of a compound represented by formula (I) (hereafter, referred to as "radical polymerization initiator (I)") is shown in the production example below. The synthetic route of the polymeric compound is not limited the following production examples.

[Chemical Formula 17]

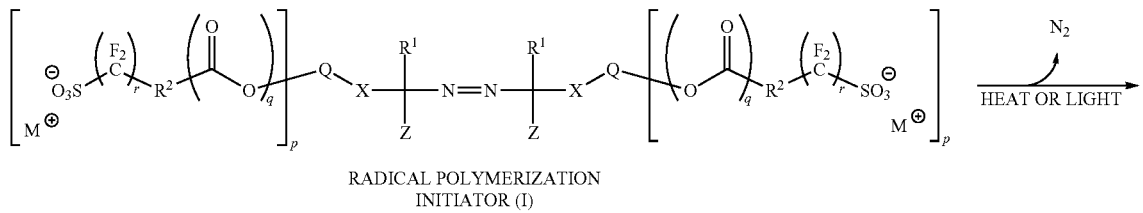

RADICAL POLYMERIZATION
INITIATOR (I)

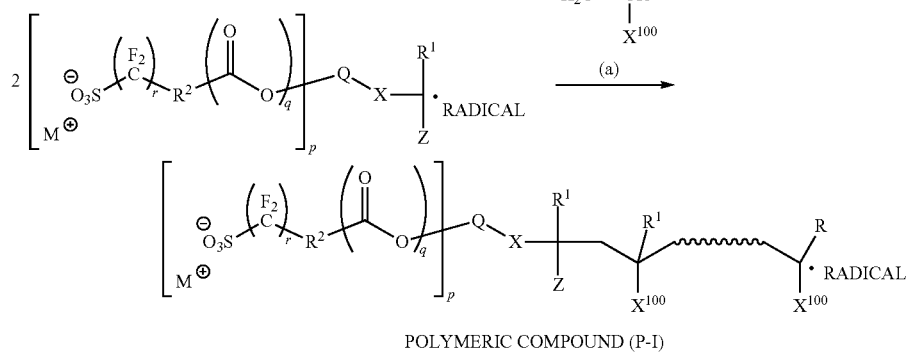

POLYMERIC COMPOUND (P-I)

In the formulae, $R^1$, Z, X, p, Q, $R^2$, q, r and $M^+$ are respectively the same as defined for $R^1$, Z, X, p, Q, $R^2$, q, r and $M^+$ in the aforementioned formula (I-1); and R represents a hydrogen atom, an alkyl group of 1 to 5 carbon atoms or a halogenated alkyl group of 1 to 5 carbon atoms; and $X^{100}$ represents an organic group containing a characteristic group.

In the synthetic route above, the radical polymerization initiator (I) is decomposed by the action of heat or light, thereby generating nitrogen gas ($N_2$) and a carbon radical.

Subsequently, the carbon radical acts on the monomer (a), and polymerization reaction between the monomers (a) proceeds, thereby obtaining the polymeric compound (P-I).

The resulting polymeric compound (P-I) has an anion portion which generates acid upon exposure, at one terminal of the main chain thereof. The "anion portion which generates acid upon exposure" is a residue derived from the radical polymerization initiator (I) (i.e., a terminal group (I-1) as described above).

As the radical polymerization initiator (I), compounds represented by general formulae (I1) to (I5) shown below are preferable.

[Chemical Formula 18]

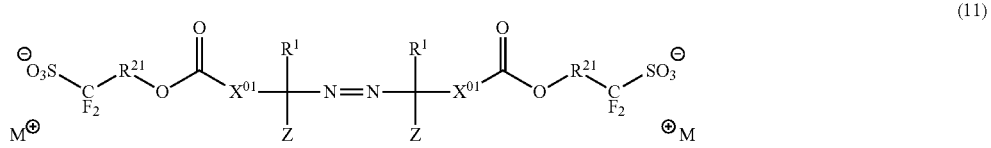
(I1)

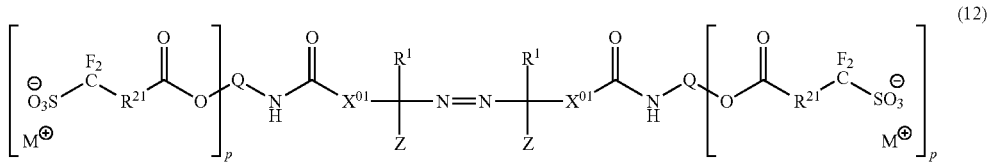
(I2)

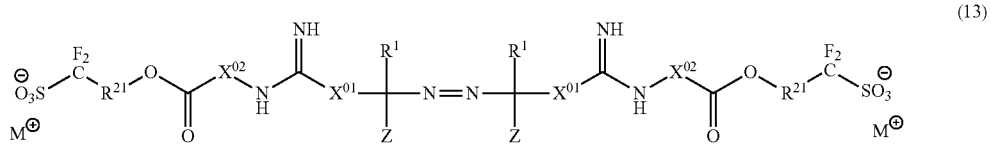
(I3)

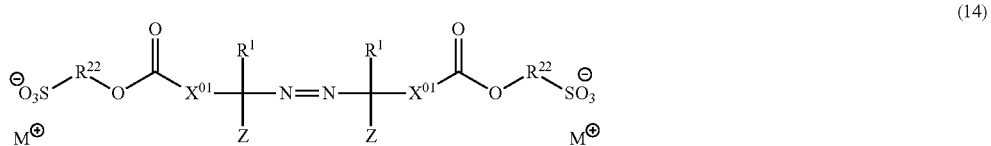
(I4)

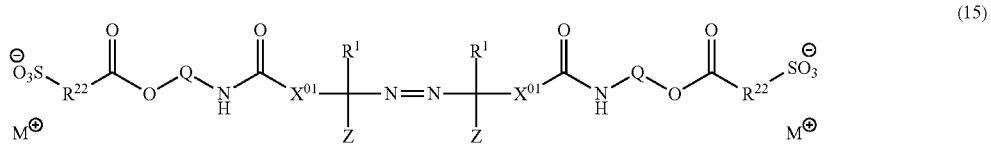
(I5)

In the formulae, $R^1$, Z, Q, p and $M^+$ are the same as defined above; $X^{01}$ represents a single bond or an alkylene group which may have a substituent; $R^{21}$ represents a single bond or an alkylene group which may have a substituent; $X^{02}$ represents an alkylene group which may have a substituent; and $R^{22}$ represents an aromatic group which may have a substituent; and the plurality of $R^1$, Z, Q, p, $M^+$, $X^{01}$, $R^{21}$, $X^{02}$ and $R^{22}$ may be the same or different from each other.

In the formulae (I1) to (I5), Z, $X^{01}$, Q, p and $M^+$ are the same as defined for $R^1$, Z, $X^{01}$, Q, p and $M^+$ in the formulae (I-1-1) to (I-1-5).

In the formulae (I1) to (I3), $R^{21}$ is the same as defined for $R^{21}$ in the formulae (I-1-1) to (I-1-3).

In the formula (I3), $X^{02}$ is the same as defined for $X^{02}$ in the formula (I-1-3).

In the formulae (I4) and (I5), $R^{22}$ is the same as defined for $R^{22}$ in the formulae (I-1-4) and (I-1-5).

Specific examples of a compounds represented by the formulae (I1) to (I5) are shown below. In the formulae, $M^+$ is the same as defined above.

[Chemical Formula 19]

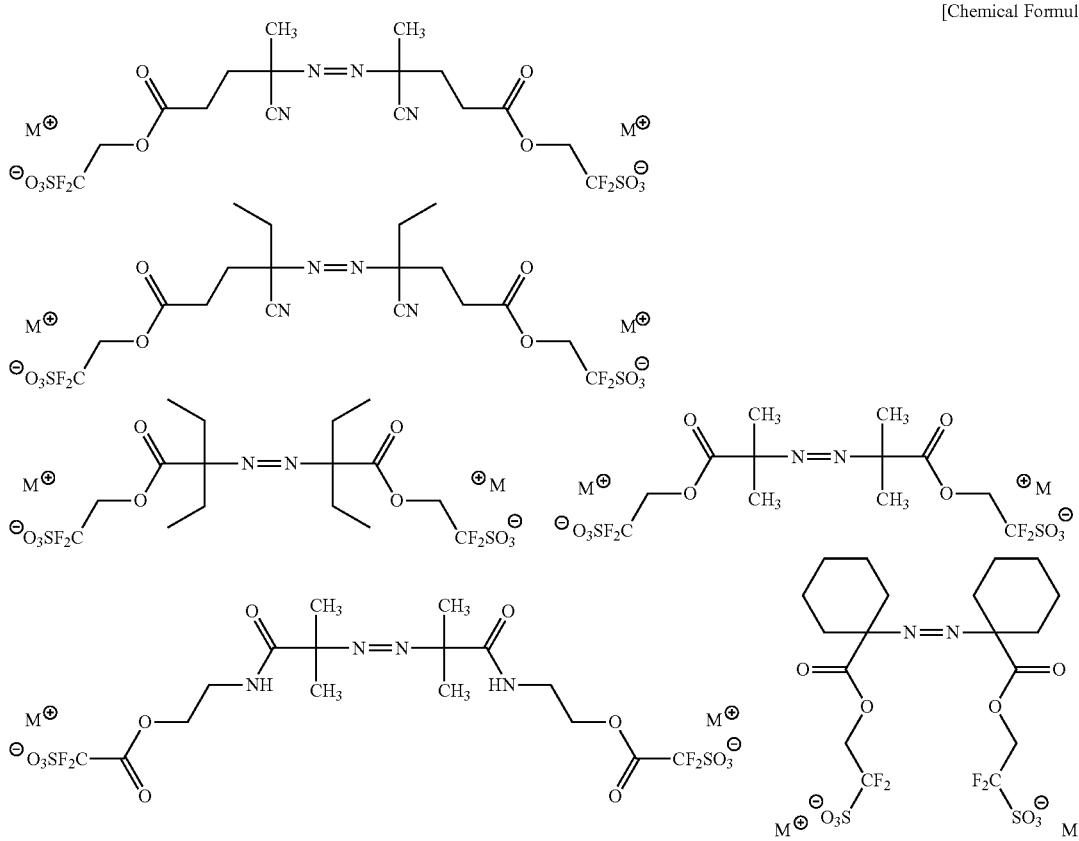

[Chemical Formula 20]

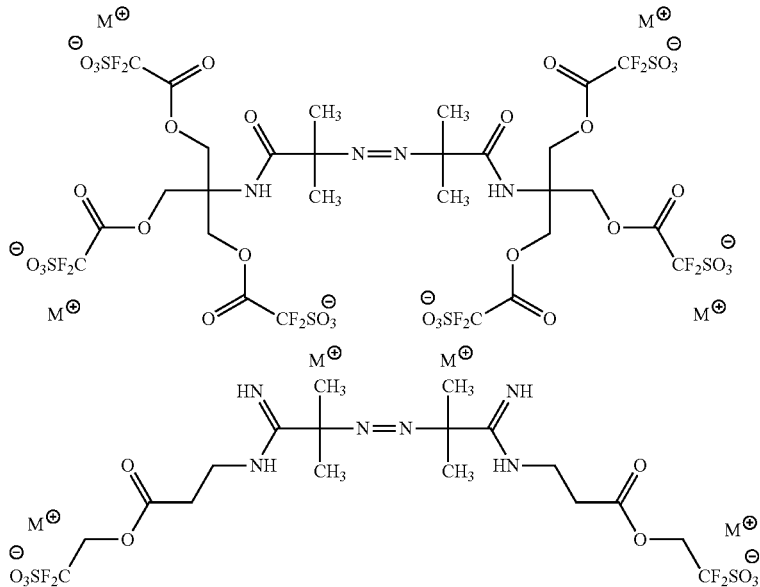

-continued
[Chemical Formula 21]
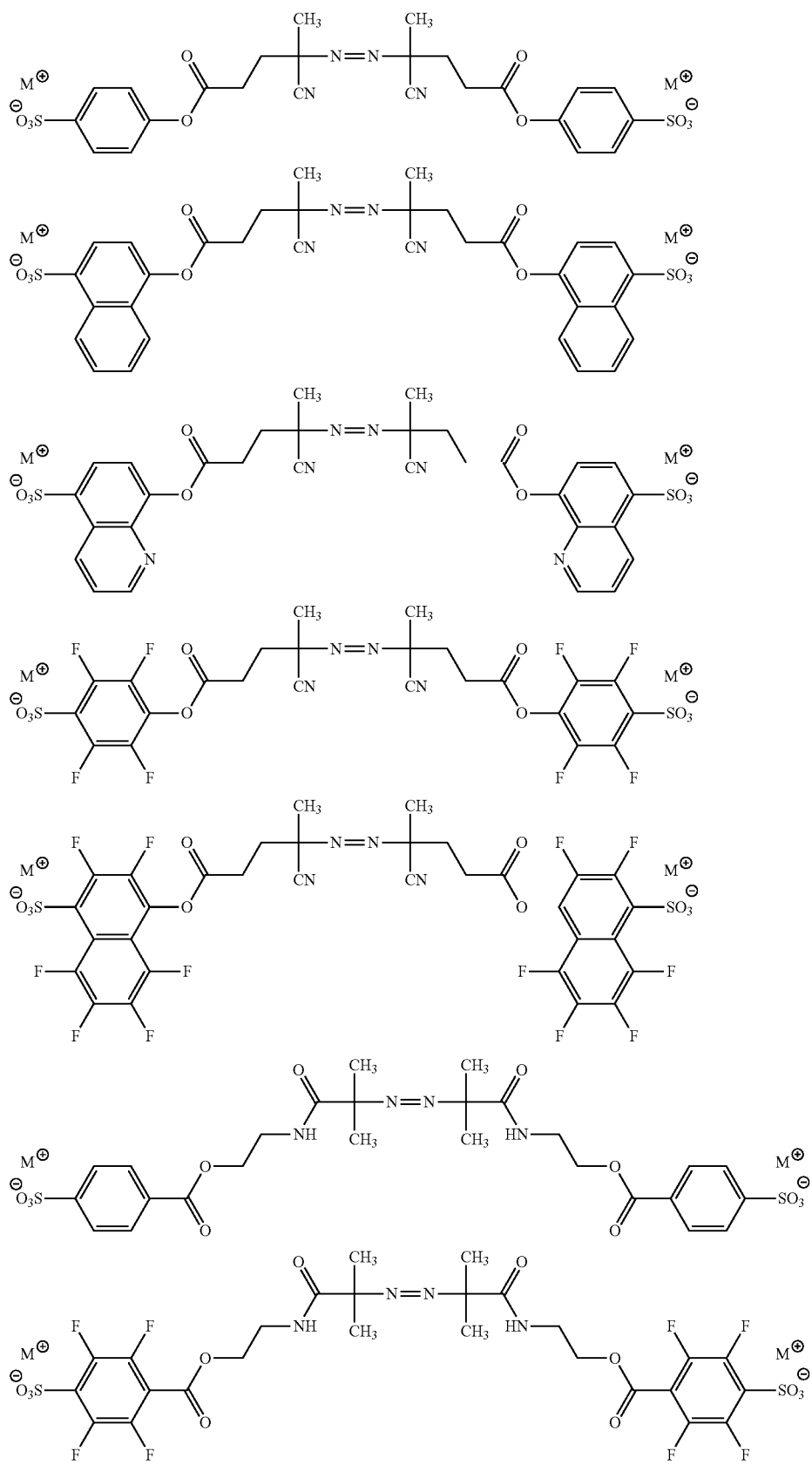

Among these, as the radical polymerization initiator (I), compounds represented by the formulae (I1) to (I5) are preferable, and the compound represented by the formula (I1) is particularly preferable.

As the organic cation for $M^+$, organic cations represented by the aforementioned formulae (c-1) to (c-3) are preferable, and an organic cation represented by the aforementioned formula (c-1) is particularly preferable.

As an another method of producing the polymeric compound of the present invention, a method in which by using a compound (I0) represented by general formula (I0) shown below as a radical polymerization initiator, a polymeric compound (polymeric compound precursor) which has a group represented by general formula (I-01) shown below on at least one terminal of the main chain, and thereby, a group "—$(OCO)_q$—$R^2$—$(CF_2)_r$—$SO_3^-A^+$" (wherein q, $R^2$, r and $A^+$ are the same as defined above) is introduced on the terminal of the main chain of the polymeric acid precursor (that is, the hydrogen atom on the terminal of the main chain is substituted with the aforementioned group).

As the compound (I0), a known compound can be used.

The introduction of the group "—$(OCO)_q$—$R^2$—$(CF_2)_r$—$SO_3^-A^+$" can be performed by a conventional method, and for example, can be conducted by reacting the polymeric compound precursor with a compound (i-02) represented by general formula (i-02) shown below. The reaction can be performed as in the method explained in relation to the method of producing a compound (I) of the third aspect.

[Chemical Formula 22]

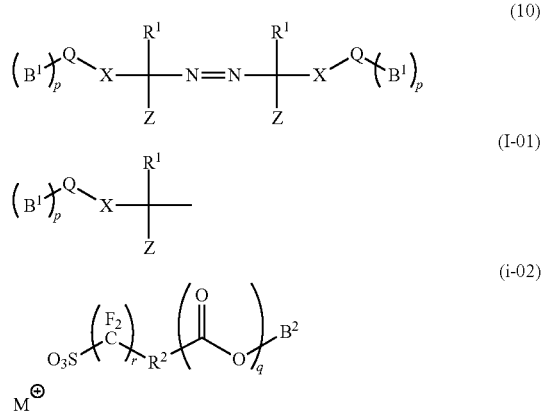

In the formulae, $R^1$, Z, X, Q, p, q, $R^2$, r, $M^+$, $B^1$ and $B^2$ are the same as defined above.

<<Resist Composition>>

The resist composition of the fifth aspect of the present invention includes a polymeric compound of the fourth aspect. By including the polymeric compound of the present invention, a resist film formed using the resist composition has an ability to generate acid upon exposure.

Therefore, by including the polymeric compound of the present invention, a resist film can form a pattern using a component which exhibits changed solubility by the action of acid, even when the resist film does not contain an acid generator. In the case where an acid generator is included in addition to the polymeric compound of the present invention, sensitivity can be improved, as compared to the case where the polymeric compound of the present invention is not included.

The resist composition of the present invention may be either a negative resist composition or a positive resist composition.

In the present specification, a resist composition which forms a positive pattern by dissolving and removing the exposed portions is called a positive resist composition, and a resist composition which forms a negative pattern by dissolving and removing the unexposed portions is called a negative resist composition.

The resist composition of the present invention can be used as a non-chemically amplified resist composition or a chemically amplified resist composition. In the present invention, it is particularly preferable to use the resist composition as a chemically amplified resist composition in terms of forming a resist pattern with high sensitivity and high resolution.

In general, a chemically amplified resist composition includes a base component which exhibits changed solubility in a developing solution under action of acid, and an acid generator component which generates acid upon exposure. When the resist composition is subjected to exposure, acid is generated from the acid generator component, and the action of that acid causes a change in the solubility of the base component in a developing solution. As a result, in the formation of a resist pattern, when a resist film obtained using the resist composition is subjected to selective exposure, the solubility in the developing solution of the exposed portions of the resist film changes (the solubility is increased in the case of positive tone, whereas the solubility is decreased in the case of negative tone) whereas the solubility in the developing solution of the unexposed portions remains unchanged. By developing the resist film, a resist pattern can be formed.

As described above, in a chemically amplified resist composition, a base component which exhibits changed solubility in a developing solution under action of acid is generally used.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed. The "organic compound having a molecular weight of 500 or more" which can be used as a base component is broadly classified into non-polymers and polymers. In general, as a non-polymer, any of those which have a molecular weight in the range of 500 to less than 4,000 is used. Hereafter, a non-polymer having a molecular weight in the range of 500 to less than 4,000 is referred to as a low molecular weight compound. As a polymer, any of those which have a molecular weight of 1,000 or more is generally used. Hereafter, a polymer having a molecular weight of 1,000 or more is referred to as a polymeric compound. With respect to a polymeric compound, the "molecular weight" is the weight average molecular weight in terms of the polystyrene equivalent value determined by gel permeation chromatography (GPC). Hereafter, a polymeric compound is frequently referred to simply as a "resin".

The resist composition of the fifth aspect of the present invention may include the polymeric compound of the fourth aspect of the present invention as a resin component which constitutes a base component that exhibits changed solubility in a developing solution by the action of acid, or may include the polymeric compound of the fourth aspect of the present invention in addition to a resin component which constitutes a base component. That is, the polymeric compound contained in the resist composition of the present invention may be a polymeric compound which exhibits changed solubility in a developing solution by the action of acid or may be a polymeric compound other than the aforementioned polymeric compound.

Among these, the polymeric compound contained in the resist composition of the present invention is preferably a polymeric compound which exhibits changed solubility in a developing solution by the action of acid and used as a base component.

The polymeric compound of the fourth aspect has a function of generating acid to generate sulfonic acid upon exposure, on the terminal thereof. In the case where the polymeric compound exhibits changed solubility in a developing solution by the action of acid, the acid generated upon exposure and portions (e.g., structural unit (a1) described later) of the polymeric compound, which contributes the change in solubility by the action of acid, are uniformly distributed within the resist film. At exposed portions, acid is generated uniformly from the polymeric compound, thereby changing the solubility of the polymeric compound thereof appropriately. As a result, excellent lithography properties can be obtained.

That is, the resist composition of the fifth aspect of the present invention preferably includes a base component (A) (hereafter, referred to as "component (A)") which exhibits changed solubility in a developing solution by the action of acid and generates acid upon exposure, and the component (A) preferably includes the polymeric compound of the fourth aspect of the present invention.

The resist composition of the seventh aspect of the present invention includes a base component (A) (hereafter, referred to as "component (A)") which exhibits changed solubility in a developing solution under action of acid and generates acid upon exposure; and an acid generator component (C) (hereafter referred to as "component (C)") which generates acid having a pKa of at least 0 upon exposure, provided that the base component (A) is excluded from the component (C); an acid generator component (B) (hereafter, referred to as "component (B)") which generates acid upon exposure, provided that the base component (A) and the acid generator component (C) are excluded from the component (B); the component (A) including a polymeric compound (A1) having an anion portion on at least one terminal of a main chain thereof, and the anion portion generating acid upon exposure.

With respect to a resist film formed using the resist composition, when a selective exposure is conducted during formation of a resist pattern, acid is generated from the terminal of the main chain of the component (A), the component (B) and the component (C), and the generated acid acts on the component (A) to change the solubility of the component (A) in a developing solution.

As a result, the solubility of the exposed portions in a developing solution is changed, whereas the solubility of the unexposed portions in a developing solution remains unchanged. Therefore, the exposed portions are dissolved and removed by developing in the case of a positive pattern, whereas unexposed portions are dissolved and removed in the case of a negative pattern, and hence, a resist pattern can be formed.

<Component (A)>

The component (A) is a base component which exhibits changed solubility in a developing solution under action of acid and generates acid upon exposure.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The "organic compound having a molecular weight of 500 or more" which can be used as a base component is broadly classified into non-polymers and polymers.

In general, as a non-polymer, any of those which have a molecular weight in the range of 500 to less than 4,000 is used. Hereafter, a non-polymer having a molecular weight in the range of 500 to less than 4,000 is referred to as a low molecular weight compound.

As a polymer, any of those which have a molecular weight of 1,000 or more is generally used. Hereafter, a polymer having a molecular weight of 1,000 or more is referred to as a polymeric compound. With respect to a polymeric compound, the "molecular weight" is the weight average molecular weight in terms of the polystyrene equivalent value determined by gel permeation chromatography (GPC). Hereafter, a polymeric compound is frequently referred to simply as a "resin".

When the resist composition of the present invention is a "negative resist composition for alkali developing process" which forms a negative pattern in an alkali developing process, for example, as the component (A), a base component that is soluble in an alkali developing solution is used, and a cross-linking agent is blended in the negative resist composition.

In the negative resist composition for alkali developing process, when acid is generated from the polymeric compound of the present invention, which is contained in component (A), upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (A) for a negative resist composition for alkali developing process, a resin that is soluble in an alkali developing solution (hereafter, referred to as "alkali-soluble resin") is used.

Examples of the alkali soluble resin include a resin having a structural unit derived from at least one of α-(hydroxyalkyl) acrylic acid and an alkyl ester of α-(hydroxyalkyl)acrylic acid (preferably an alkyl ester having 1 to 5 carbon atoms), as disclosed in Japanese Unexamined Patent Application, First Publication No. 2000-206694; an acrylic resin which has a sulfonamide group and may have the hydrogen atom bonded to the carbon atom on the α-position substituted with a substituent or polycycloolefin resin having a sulfoneamide group, as disclosed in U.S. Pat. No. 6,949,325; an acrylic resin which may have the hydrogen atom bonded to the carbon atom on the α-position substituted with a substituent and having a fluorinated alcohol, as disclosed in U.S. Pat. No. 6,949,325, Japanese Unexamined Patent Application, First Publication No. 2005-336452 or Japanese Unexamined Patent Application, First Publication No. 2006-317803; and a polycyclolefin resin having a fluorinated alcohol, as disclosed in Japanese Unexamined Patent Application, First Publication No. 2006-259582. These resins are preferable in that a resist pattern can be formed with minimal swelling.

Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group, or a melamine-based cross-linking agent is preferable, as it enables formation of a resist pattern with minimal swelling. The amount of the cross-linking agent added is preferably within a range from 1 to 50 parts by weight, relative to 100 parts by weight of the alkali-soluble resin.

In the case where the resist composition of the present invention is a resist composition which forms a positive pattern in an alkali developing process and a negative pattern in a solvent developing process, it is preferable to use a base component (A0) (hereafter, referred to as "component (A0)") which exhibits increased polarity by the action of acid. By using the component (A0), since the polarity of the base component changes prior to and after exposure, an excellent development contrast can be obtained not only in an alkali developing process, but also in a solvent developing process.

More specifically, in the case of applying an alkali developing process, the component (A0) is substantially insoluble in an alkali developing solution prior to exposure, but when acid is generated from the polymeric compound of the present invention, which is contained in component (A), upon exposure, the action of this acid causes an increase in the polarity of the base component, thereby increasing the solubility of the component (A0) in an alkali developing solution. Therefore, in the formation of a resist pattern, by conducting selective exposure of a resist film formed by applying the resist composition to a substrate, the exposed portions change from an insoluble state to a soluble state in an alkali developing solution, whereas the unexposed portions remain insoluble in an alkali developing solution, and hence, a positive resist pattern can be formed by alkali developing.

On the other hand, in the case of a solvent developing process, the component (A0) exhibits high solubility in an organic developing solution prior to exposure, and when acid is generated from the polymeric compound (A1') of the present invention, which is contained in component (A), upon exposure, the polarity of the component (A0) is increased by the action of the generated acid, thereby decreasing the solubility of the component (A0) in an organic developing solution. Therefore, in the formation of a resist pattern, by conducting selective exposure of a resist film formed by applying the resist composition to a substrate, the exposed portions changes from an soluble state to an insoluble state in an organic developing solution, whereas the unexposed portions remain soluble in an organic developing solution. As a result, by conducting development using an organic developing solution, a contrast can be made between the exposed portions and unexposed portions, thereby enabling the formation of a negative resist pattern.

In the resist composition of the present invention, the component (A) is preferably a base component which exhibits increased polarity by the action of acid (i.e., a component (A0)). That is, the resist composition of the present invention is preferably a chemically amplified resist composition which becomes a positive type in the case of an alkali developing process, and a negative type in the case of a solvent developing process.

In the resist composition of the fifth aspect of the present invention, the polymeric compound of the fourth aspect of the present invention, which is contained in component (A), is preferably a resin component which exhibits increased polarity by the action of acid. In the resist composition of the fifth aspect of the present invention, the component (A) preferably includes a polymeric compound (A1') of the present invention, which exhibits increased polarity by the action of acid (hereafter, sometimes referred to as "component (A1')").

In the resist composition of the seventh aspect of the present invention, the component (A) includes a polymeric compound (A1) having an anion portion which generates acid upon exposure, on at least one terminal of the main chain thereof (hereafter, sometimes referred to as "component (A1)"). The polymeric compound (A 1) is preferably a polymeric compound (A1') of the fourth aspect of the present invention.

[Polymeric Compound (A1)]

In the seventh aspect of the present invention, the component (A) includes a polymeric compound (A1) having an anion portion which generates acid upon exposure, on at least one terminal of the main chain thereof.

The terminals of the main chain of polymeric compound are a starting point and an end point of a molecular chain which grows by polymerization reaction such as radical polymerization or anion polymerization. A residue derived from a polymerization initiator, a chain transfer agent and a polymerization inhibitor is bonded to the terminal of the main chain of the polymeric compound. For example, in radical polymerization, the radical generated by decomposition of a radical polymerization initiator initiates polymerization of monomers. As a result, a residue derived from a radical polymerization initiator (that is, radical portion generated by decomposition) is bonded to the terminal of the main chain. In this point, the "at least one terminal of the main chain" is distinctly different from a terminal of the side chain which is branched from the main chain (that is, terminal of the structure constituting a structural unit).

That is, in the present invention, the "an anion portion which generates acid upon exposure" on at least one terminal of the main chain of the polymeric compound (A1) is not a structure derived from a monomer. The anion portion is preferably a residue derived from a polymerization initiator. The "residue derived from a polymerization initiator" will be described later in detail. Examples thereof include a residue derived from a polymerization initiator containing the anion portion; a group which can be formed by reacting a residue derived from a polymerization initiator that does not contains the anion portion with a compound containing the anion portion.

The polymeric compound (A1) has an anion portion, thereby exhibiting a function of generating acid to generate acid upon exposure.

Hereafter, the polymeric compound (A1) will be described in more detail.

[Anion Moiety]

As the "anion portion which generates acid upon exposure", an ionic partial structure of onium salt acid generators such as sulfonium salts or iodonium salts as an acid generator component which generates acid upon exposure and is used in a chemically amplified resist composition together with a base resin, can be preferably used. An onium salt acid generator is a salt of an acid anion and an onium ion as a countercation, and when it is decomposed upon exposure, an acid anion is generated to form acid. As the acid anion, a sulfonate anion, a carboxylate anion, a sulfonylimide anion, a bis(alkylsulfonyl)imide anion and a tris(alkylsulfonyl)methide anion are preferable. These acid anions are generated from the terminal of the main chain of the polymeric compound upon exposure.

As the acid anion, a sulfonate anion is preferable, and an alkylsulfonate anion or a fluorinated alkylsulfonate anion are more preferable. That is, as the "anion portion which generates acid upon exposure", an anion portion which generates a sulfonic acid is preferable, and an anion portion which generates an alkylsulfonic acid or a fluorinated alkylsulfonic acid is more preferable.

Among these, the anion portion preferably has a group represented by general formula (an 1) shown below. The group has an alkylsulfonate portion which may be fluorinated, and an alkylsulfonic acid which may be fluorinated is generated upon exposure. The alkylsulfonic acid can decompose an acid decomposable group in a structural unit (a1), satisfactorily.

[Chemical Formula 23]

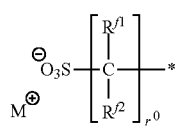

(an1)

In the formula, $R^{f1}$ and $R^{f2}$ each independently represents a hydrogen atom, an alkyl group, a fluorine atom or a fluorine alkyl group. $r^0$ represents an integer of 0 to 8; $M^+$ represents an organic cation ("*" in the formula represents a valence bond.)]

In the formula (an 1), the alkyl group for $R^{f1}$ and $R^{f2}$ is preferably an alkyl group of 1 to 5 carbon atoms, and specific examples thereof include a methyl group, an ethyl group, a propyl group, an isopropyl group, an n-butyl group, an isobutyl group, a tert-butyl group, a pentyl group, an isopentyl group and a neopentyl group.

The fluorinated alkyl group for $R^{f1}$ and $R^{f2}$ is preferably a group in which part or all of the hydrogen atoms within the aforementioned alkyl group for $R^{f1}$ and $R^{f2}$ have been substituted with a fluorine atom.

As $R^{f1}$ and $R^{f2}$, a fluorine atom or a fluorinated alkyl is preferable.

In the formula (an1), $r^0$ represents an integer of 1 to 4, and more preferably 1 or 2.

In the formula (an-1), $M^+$ represents an organic cation.

The organic cation for $M^+$ is not particularly limited, and an organic cation conventionally known as the cation moiety of a photo decomposable base used as a quencher for a resist composition or the cation moiety of an onium salt acid generator for a resist composition can be used.

As the organic cation for $M^+$, for example, a cation moiety represented by general formula (c-1) or (c-2) shown below can be used.

[Chemical Formula 24]

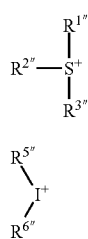

(c-1)

(c-2)

In the formulae, each of $R^{1'''}$ to $R^{3'''}$, $R^{5'''}$ and $R^{6'''}$ independently represents an aryl group or an alkyl group, provided that, in formula (c-1), two of $R^{1'''}$ to $R^{3'''}$ may be mutually bonded to form a ring with the sulfur atom.

In formula (c-1), $R^{1'''}$ to $R^{3'''}$ each independently represent an aryl group or alkyl group. In formula (c-1), two of $R^{1'''}$ to $R^{3'''}$ may be bonded to each other to form a ring with the sulfur atom.

It is preferable that at least one of $R^{1'''}$ to $R^{3'''}$ represent an aryl group. Among $R^{1'''}$ to $R^{3'''}$, it is more preferable that two or more groups are aryl groups, and it is particularly desirable that all of $R^{1'''}$ to $R^{3'''}$ are aryl groups.

The aryl group for $R^{1'''}$ to $R^{3'''}$ is not particularly limited. For example, an aryl group having 6 to 20 carbon atoms may be used in which part or all of the hydrogen atoms of the aryl group may or may not be substituted with alkyl groups, alkoxy groups, halogen atoms or hydroxyl groups.

The aryl group is preferably an aryl group having 6 to 10 carbon atoms because it can be synthesized at a low cost. Specific examples thereof include a phenyl group and a naphthyl group.

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

The halogen atom, with which hydrogen atoms of the aryl group may be substituted, is preferably a fluorine atom.

The alkyl group for $R^{1'''}$ to $R^{3'''}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decyl group, and a methyl group is most preferable because it is excellent in resolution and can be synthesized at a low cost.

When two of $R^{1'''}$ to $R^{3'''}$ in formula (c-1) are bonded to each other to form a ring with the sulfur atom, it is preferable that the two of $R^{1'''}$ to $R^{3'''}$ form a 3- to 10-membered ring including the sulfur atom, and it is particularly desirable that the two of $R^{1'''}$ to $R^{3'''}$ form a 5- to 7-membered ring including the sulfur atom.

When two of $R^{1'''}$ to $R^{3'''}$ in formula (c-1) are bonded to each other to form a ring with the sulfur atom, the remaining one of $R^{1'''}$ to $R^{3'''}$ is preferably an aryl group. As examples of the aryl group, the same aryl groups as those described above for $R^{1'''}$ to $R^{3'''}$ can be used.

As preferable examples of the cation moiety represented by general formula (c-1), those represented by formulas (c-1-1) to (c-1-32) shown below can be given.

[Chemical Formula 25]
(c-1-1) 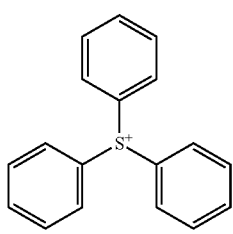
(c-1-2) 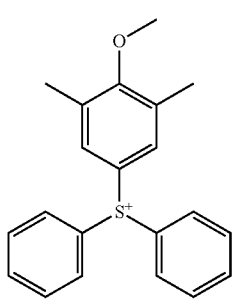
(c-1-3) 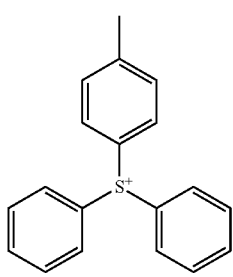 [SMILES: Cc1ccc([S+](c2ccccc2)c2ccccc2)cc1]
(c-1-4) 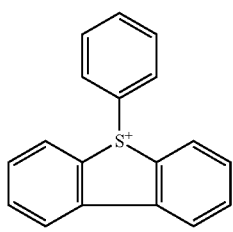
(c-1-5) 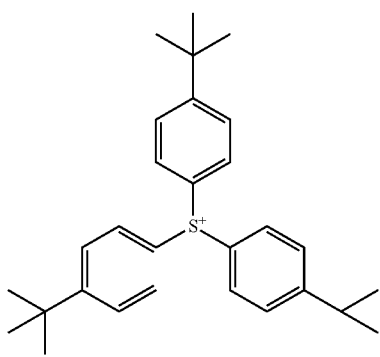 [SMILES: CC(C)(C)c1ccc([S+](c2ccc(C(C)(C)C)cc2)c2ccc(C(C)(C)C)cc2)cc1]
(c-1-6) 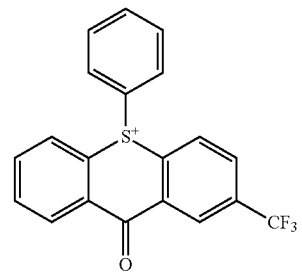
(c-1-7) 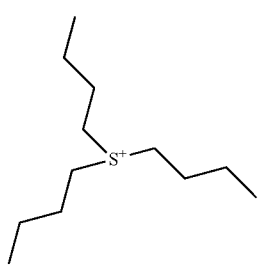
(c-1-8) 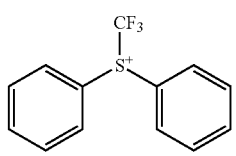
(c-1-9) 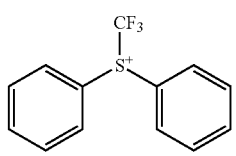
(c-1-10) 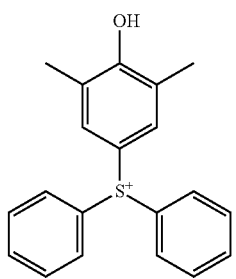
(c-1-11) 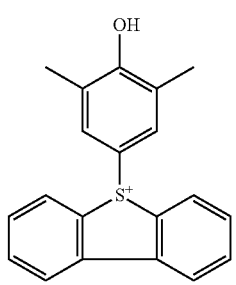

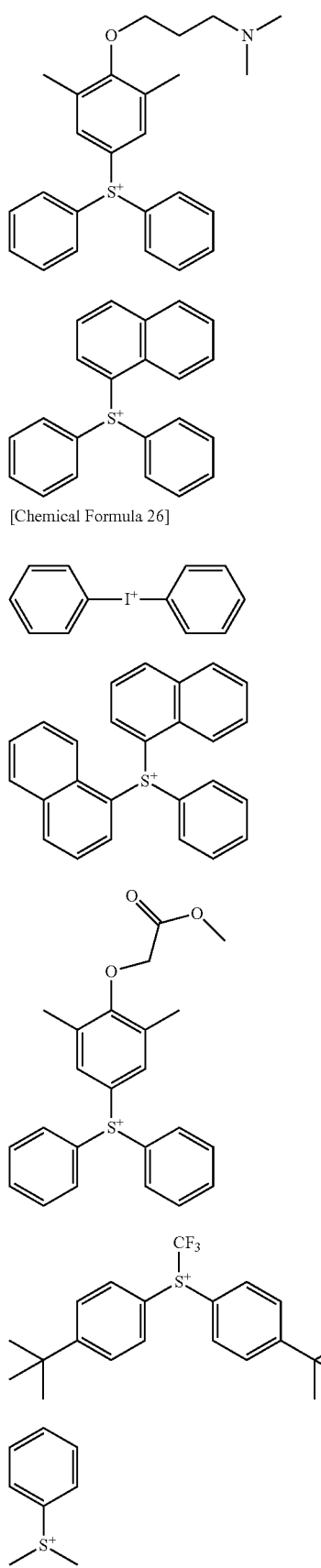
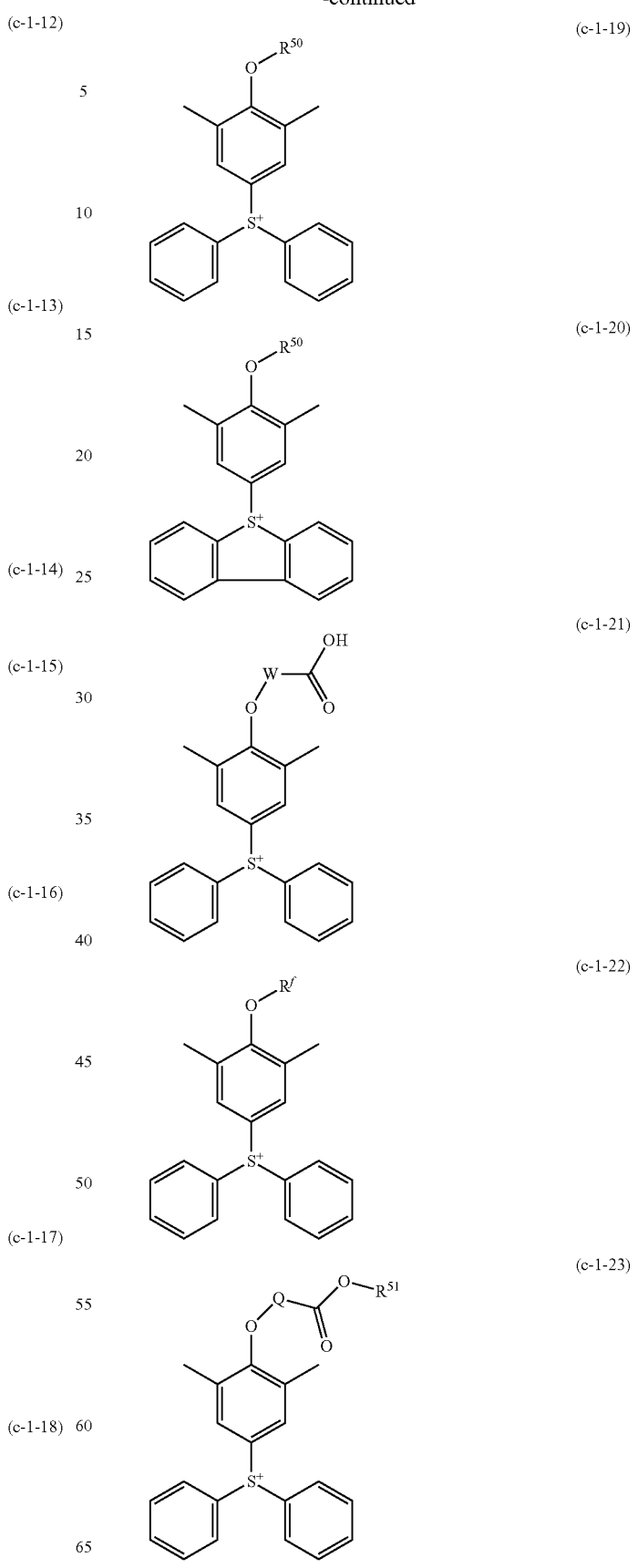

-continued (c-1-24)

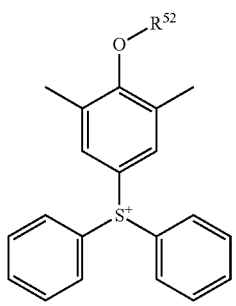

(c-1-25)

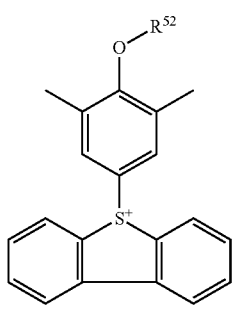

(c-1-26)

[Chemical Formula 27]

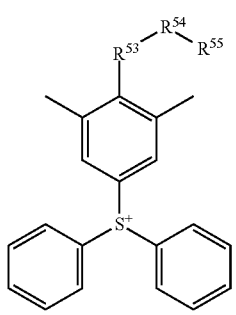

(c-1-27)

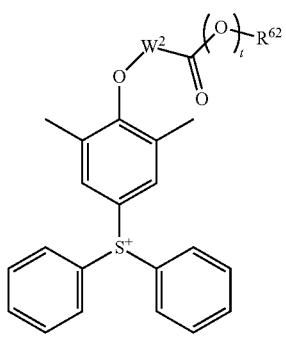

(c-1-28)

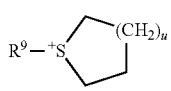

(c-1-29)

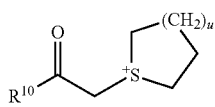

(c-1-30)

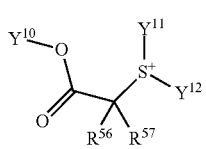

-continued (c-1-31)

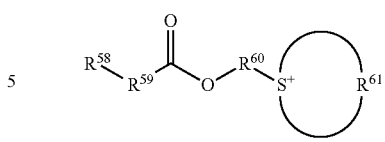

(c-1-32)

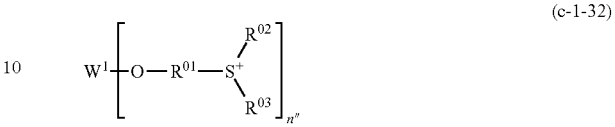

In formulae (c-1-19) and (c-1-20), $R^{50}$ represents a group containing an acid dissociable, dissolution inhibiting group, and is preferably a group represented by the formula (p1), (p1-1) or (p2) described later in the explanation of the structural unit (a1), or a group in which a group represented by the formula (1-1) to (1-9) or (2-1) to (2-6) described later in the explanation of the structural unit (a1) is bonded to the oxygen atom of $-R^{91}-C(=O)-O-$. $R^{91}$ represents a single bond or a linear or branched alkylene group, and the alkylene group preferably has 1 to 5 carbon atoms.

In general formula (c-1-21), W represents a divalent linking group.

The divalent linking group is not particularly limited, and preferable examples thereof include a divalent hydrocarbon group which may have a substituent and a divalent linking group containing a hetero atom.

(Divalent Hydrocarbon Group which May have a Substituent)

A hydrocarbon "has a substituent" means that part or all of the hydrogen atoms within the hydrocarbon group is substituted with a substituent (a group or an atom other than hydrogen).

The hydrocarbon group may be either an aliphatic hydrocarbon group or an aromatic hydrocarbon group.

An "aliphatic hydrocarbon group" refers to a hydrocarbon group that has no aromaticity. The aliphatic hydrocarbon group may be saturated or unsaturated. In general, the aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 8, and still more preferably 1 to 5.

As the linear aliphatic hydrocarbon group, a linear alkylene group is preferable, and specific examples include a methylene group [$-CH_2-$], an ethylene group [$-(CH_2)_2-$], a trimethylene group [$-(CH_2)_3-$], a tetramethylene group [$-(CH_2)_4-$] and a pentamethylene group [$-(CH_2)_5-$].

As the branched aliphatic hydrocarbon group, a branched alkylene group is preferable, and specific examples include alkylalkylene groups, e.g., alkylmethylene groups such as $-CH(CH_3)-$, $-CH(CH_2CH_3)-$, $-C(CH_3)_2-$, $-C(CH_3)(CH_2CH_3)-$, $-C(CH_3)(CH_2CH_2CH_3)-$, and $-C(CH_2CH_3)_2-$; alkylethylene groups such as $-CH(CH_3)CH_2-$, $-CH(CH_3)CH(CH_3)-$, $-C(CH_3)_2CH_2-$, $-CH(CH_2CH_3)CH_2-$, and $-C(CH_2CH_3)_2-CH_2$; alkyltrimethylene groups such as $-CH(CH_3)CH_2CH_2-$, and $-CH_2CH(CH_3)CH_2-$; and alkyltetramethylene groups such as $-CH(CH_3)CH_2CH_2CH_2-$, and $-CH_2CH(CH_3)CH_2CH_2-$. As the alkyl group within the alkylalkylene group, a linear alkyl group of 1 to 5 carbon atoms is preferable.

The linear or branched aliphatic hydrocarbon group may or may not have a substituent. Examples of the substituent include a fluorine atom, a fluorinated alkyl group of 1 to 5 carbon atoms, and an oxo group (=O).

As examples of the aliphatic hydrocarbon group containing a ring in the structure thereof, a cyclic aliphatic hydrocarbon group (a group in which two hydrogen atoms have been removed from an aliphatic hydrocarbon ring), a group in which the cyclic aliphatic hydrocarbon group is bonded to the terminal of a linear or branched aliphatic hydrocarbon group, and a group in which the cyclic aliphatic hydrocarbon group is interposed within a linear or branched aliphatic hydrocarbon group, can be given. As the linear or branched aliphatic hydrocarbon group, the same groups as those described above can be used.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic aliphatic hydrocarbon group, a group in which 2 hydrogen atoms have been removed from a monocycloalkane is preferable. The monocycloalkane preferably has 3 to 6 carbon atoms, and specific examples thereof include cyclopentane and cyclohexane. As the polycyclic aliphatic hydrocarbon group, a group in which two hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane.

The cyclic aliphatic hydrocarbon group may or may not have a substituent. Examples of the substituent include an alkyl group of 1 to 5 carbon atoms, a fluorine atom, a fluorinated alkyl group of 1 to 5 carbon atoms, and an oxo group (=O).

The aromatic hydrocarbon group is a hydrocarbon group having an aromatic ring.

The aromatic hydrocarbon group as the divalent hydrocarbon group for W preferably has 3 to 30 carbon atoms, more preferably 5 to 30, still more preferably 5 to 20, still more preferably 6 to 15, and most preferably 6 to 10. Here, the number of carbon atoms within a substituent(s) is not included in the number of carbon atoms of the aromatic hydrocarbon group.

Examples of the aromatic ring contained in the aromatic hydrocarbon group include aromatic hydrocarbon rings, such as benzene, biphenyl, fluorene, naphthalene, anthracene and phenanthrene; and aromatic hetero rings in which part of the carbon atoms constituting the aforementioned aromatic hydrocarbon rings has been substituted with a hetero atom. Examples of the hetero atom within the aromatic hetero rings include an oxygen atom, a sulfur atom and a nitrogen atom.

Specific examples of the aromatic hydrocarbon group include a group in which two hydrogen atoms have been removed from the aforementioned aromatic hydrocarbon ring or aromatic hetero ring (arylene group or heteroarlyene group); and a group in which one hydrogen atom has been removed from the aforementioned aromatic hydrocarbon ring or aromatic hetero ring (aryl group or heteroaryl group) and one hydrogen atom has been substituted with an alkylene group (for example, a group in which one hydrogen atom has been removed from an aryl group within an arylalkyl group such as a benzyl group, a phenethyl group, a 1-naphthylmethyl group, a 2-naphthylmethyl group, a 1-naphthylethyl group, or a 2-naphthylethyl group). The alkylene group which is bonded to the aforementioned aryl group or heteroaryl group preferably has 1 to 4 carbon atoms, more preferably 1 or 2 carbon atoms, and particularly preferably 1 carbon atom.

The aromatic hydrocarbon group may or may not have a substituent. For example, the hydrogen atom bonded to the aromatic hydrocarbon ring within the aromatic hydrocarbon group may be substituted with a substituent. Examples of substituents include an alkyl group, an alkoxy group, a halogen atom, a halogenated alkyl group, a hydroxyl group and an oxo group (=O).

The alkyl group as the substituent is preferably an alkyl group of 1 to 5 carbon atoms, and a methyl group, an ethyl group, a propyl group, an n-butyl group or a tert-butyl group is most desirable.

The alkoxy group as the substituent is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

(Divalent Linking Group Containing a Hetero Atom)

With respect to a divalent linking group containing a hetero atom, a hetero atom is an atom other than carbon and hydrogen, and examples thereof include an oxygen atom, a nitrogen atom, a sulfur atom and a halogen atom.

Specific examples of the divalent linking group containing a hetero atom include non-hydrocarbon linking groups such as —O—, —C(=O)—, —C(=O)—O—, —O—C(=O)—O—, —S—, —S(=O)$_2$—, —S(=O)$_2$—O—, —NH—, —NH—C(=O)—, —NH—C(=NH)— and =N—; and a combination of any one of these non-hydrocarbon linking groups with a divalent hydrocarbon group. As examples of the divalent hydrocarbon group, the same groups as those described above for the divalent hydrocarbon group which may have a substituent can be given, and a linear or branched aliphatic hydrocarbon group is preferable.

Among these, H of —NH— in —C(=O)—NH—, —NH—, or H of —NH— in —NH—C(=NH)— may be substituted with a substituent such as an alkyl group, an acyl group or the like. The substituent preferably has 1 to 10 carbon atoms, more preferably 1 to 8 carbon atoms, and particularly preferably 1 to 5 carbon atoms.

Examples of the divalent linking group which is a combination of a non-hydrocarbon linking group with a divalent hydrocarbon group include —Y$^{21}$—O—Y$^{22}$—, —[Y$^{21}$—C(=O)—O]$_{m'}$—Y$^{22}$—, —Y$^{21}$—O—C(=O)—Y$^{22}$— (provided that Y$^{21}$ and Y$^{22}$ each independently represents a divalent hydrocarbon group which may have a substituent; O represents an oxygen atom; and m' represents an integer of 0 to 3).

In the formula —Y$^{21}$—O—Y$^{22}$—, —[Y$^{21}$—C(=O)—O]$_{m'}$—Y$^{22}$— or —Y$^{21}$—O—C(=O)—Y$^{22}$—, Y$^{21}$ and Y$^{22}$ each independently represents a divalent hydrocarbon group which may have a substituent. Examples of the divalent hydrocarbon group include the same groups as those described above as the "divalent hydrocarbon group which may have a substituent".

As Y$^{21}$, a linear aliphatic hydrocarbon group is preferable, more preferably a linear alkylene group, still more preferably a linear alkylene group of 1 to 5 carbon atoms, and a methylene group or an ethylene group is particularly desirable.

As Y$^{22}$, a linear or branched aliphatic hydrocarbon group is preferable, and a methylene group, an ethylene group or an alkylmethylene group is more preferable. The alkyl group within the alkylmethylene group is preferably a linear alkyl group of 1 to 5 carbon atoms, more preferably a linear alkyl group of 1 to 3 carbon atoms, and most preferably a methyl group.

In the group represented by the formula —[$Y^{21}$—C(=O)—O]$_{m'}$—$Y^{22}$—, m' represents an integer of 0 to 3, preferably an integer of 0 to 2, more preferably 0 or 1, and particularly preferably 1. Namely, it is particularly desirable that the group represented by the formula —[$Y^{21}$—C(=O)—O]$_{m'}$—$Y^{22}$— is a group represented by the formula —$Y^{21}$—C(=O)—O—$Y^{22}$—. Among these, a group represented by the formula —(CH$_2$)$_{a'}$—C(=O)—O—(CH$_2$)$_{b'}$— is preferable. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

As the divalent linking group for W, a linear or branched alkylene group, a divalent aliphatic cyclic group or a divalent linking group containing a hetero atom is preferable, a linear or branched alkylene group is more preferable, and a linear alkylene group is still more preferable.

In formula (c-1-22), $R^f$ represents a fluorinated alkyl group, i.e., a group in which an unsubstituted alkyl group has part or all of the hydrogen atoms substituted with fluorine atoms. The unsubstituted alkyl group is preferably a linear or branched alkyl group, and more preferably a linear alkyl group.

In formula (c-1-23), Q represents a divalent linking group, and $R^{51}$ represents an organic group having a carbonyl group, an ester bond or a sulfonyl group.

Examples of the divalent linking group for Q include the same divalent linking groups as those described above for W in the formula (c-1-21). As Q, an alkylene group or a divalent linking group containing an ester bond is preferable, and an alkylene group or —$R^{92}$—C(=O)—O—$R^{93}$— [each of $R^{92}$ and $R^{93}$ independently represents an alkylene group] is more preferable.

The organic group having a carbonyl group, an ester bond or a sulfonyl group for $R^{51}$ may be either an aromatic hydrocarbon group or an aliphatic hydrocarbon group. Examples of the aromatic hydrocarbon group and the aliphatic hydrocarbon group include the same groups as those described above for $X^3$. Among these, as the organic group having a carbonyl group, an ester bond or a sulfonyl group for $R^{51}$, an aliphatic hydrocarbon group is preferable, a bulky aliphatic hydrocarbon group is more preferable, and a cyclic saturated hydrocarbon group is still more preferable. Preferable examples of $R^{51}$ include a group represented by any one of the aforementioned formulas (L1) to (L6) and (S1) to (S4), the same group as those described later for $X^3$, and a monocyclic or polycyclic group in which the hydrogen atoms bonded thereto have been substituted with an oxygen atom (=O).

In the formulae (c-1-24) and (c-1-25), $W^{52}$ represents an alkyl group of 4 to 10 that is not an acid dissociable group. As $R^{52}$, a linear or branched alkyl group is preferable, and a linear alkyl group is more preferable.

In formula (c-1-26), $R^{53}$ represents a divalent group having a base dissociable portion, $R^{54}$ represents a divalent linking group, and $R^{55}$ represents a group having an acid dissociable group.

The base dissociable portion within $R^{53}$ refers to a portion which is dissociable by the action of an alkali developing solution (e.g., a 2.38% by weight aqueous solution of tetramethylammonium hydroxide (TMAH) at 23° C.). By the dissociation of the base dissociable portion, the solubility in an alkali developing solution is increased. The alkali developing solution may be any one of those generally used in the fields of lithography. It is preferable that the base dissociable portion is dissociated the action of a 2.38% by weight aqueous solution of tetramethylammonium hydroxide at 23° C.

The $R^{53}$ group may be either a group constituted of only a base dissociable portion, or a group in which a base dissociable portion is boned to a group or atom which is not base dissociable.

The base dissociable portion within the $R^{53}$ group is most preferably an ester group (—C(=O)—O—).

Examples of the group or atom which is not base dissociable for $R^{53}$ include the divalent linking groups described above for W in the formula (c-1-21) and combinations of the linking groups (provided that groups which are base dissociable are excluded). The "combination of the linking groups" refers to a divalent linking group constituted of linking groups bonded together. As such a "combination of the linking groups", a combination of an alkylene group with a divalent linking group containing a hetero atom is preferable. However, it is preferable that the hetero atom is not adjacent to the atom within the base dissociable portion which has its bond cleaved by the action of a base.

The alkylene group is the same as defined for the linear or branched alkylene group for W in the formula (c-1-21).

The hetero atom is most preferably an oxygen atom.

Among the above examples, $R^{53}$ is preferably a group in which a base dissociable portion is boned to a group or atom which is not base dissociable.

$R^{54}$ represents a divalent linking group, and examples thereof include the same divalent linking groups as those described above for W in the formula (c-1-21). Among these, an alkylene group or a divalent aliphatic cyclic group is preferable, and an alkylene group is particularly desirable.

$R^{55}$ represents a group having an acid dissociable group.

The acid dissociable group is an organic group which can be dissociated by the action of an acid. The acid dissociable group is not particularly limited, and any group which has been proposed as an acid dissociable, dissolution inhibiting group of a base resin for a chemically amplified resist can be used. Specific examples include the same acid dissociable, dissolution inhibiting groups as those described later for the structural unit (a1), such as a cyclic or chain-like tertiary alkyl ester-type acid dissociable group or an acetal-type acid dissociable group (e.g., an alkoxyalkyl group). Among these, a tertiary alkyl ester-type acid dissociable group is particularly desirable.

The group having an acid dissociable group may be either the acid dissociable group itself, or a group in which an acid dissociable group is bonded to a group or atom which is not acid dissociable (a group or atom which remains bonded to the acid generator even after the dissociation of the acid dissociable group). Examples of the group or atom which is not acid dissociable include the same divalent linking groups as those described above for W in the formula (c-1-21).

In formula (c-1-27), $W^2$ represents a single bond or a divalent linking group, t represents 0 or 1, and $R^{62}$ represents a group which is not dissociable by acid (hereafter, referred to as "acid non-dissociable group").

Examples of the divalent linking group for $W^2$ include the same divalent linking groups as those described above for W in the formula (c-1-21). Among these, as $W^2$, a single bond is preferable.

t is preferably 0.

The acid non-dissociable group for $R^{62}$ is not particularly limited as long as it is a group which is not dissociable by acid. The acid non-dissociable group is preferably an acid non-dissociable hydrocarbon group which may have a substituent, more preferably a cyclic hydrocarbon group which may have a substituent, and still more preferably a group in which one hydrogen atom has been removed from adamantane.

In formulae (c-1-28) and (c-1-29), each of $R^9$ and $R^{10}$ independently represents a phenyl group or naphthyl group which may have a substituent, an alkyl group of 1 to 5 carbon atoms, an alkoxy group or a hydroxy group; and u represents an integer of 1 to 3, most preferably 1 or 2.

In formula (c-1-30), $Y^{10}$ represents a cyclic hydrocarbon group of 5 or more carbon atoms which may have a substituent, and is an acid dissociable group which may be dissociated by the action of an acid; each of $R^{56}$ and $R^{57}$ independently represents a hydrogen atom, an alkyl group or an aryl group, provided that $R^{56}$ and $R^{57}$ may be mutually bonded to form a ring; each of $Y^{11}$ and $Y^{12}$ independently represents an alkyl group or an aryl group, provided that $Y^{11}$ and $Y^{12}$ may be mutually bonded to form a ring.

$Y^{10}$ represents a cyclic hydrocarbon group of 5 or more carbon atoms which may have a substituent, and is an acid dissociable group which may be dissociated by the action of an acid. By virtue of the $Y^{10}$ group being a cyclic hydrocarbon group of 5 or more carbon atoms which may have a substituent, and is an acid dissociable group which may be dissociated by the action of an acid, various lithography properties such as resolution, LWR, exposure latitude (EL margin) and shape of a resist pattern are improved.

Examples of $Y^{10}$ include groups which form a cyclic tertiary alkyl ester with —C($R^{56}$)($R^{57}$)—C(=O)—O—.

A "tertiary alkyl ester" refers to a structure in which a tertiary carbon atom within a cyclic hydrocarbon group of 5 or more carbon atoms is bonded to the terminal oxygen atom of —C($R^{56}$)($R^{57}$)—C(=O)—O—. In this tertiary alkyl ester, the action of acid causes cleavage of the bond between the oxygen atom and the tertiary carbon atom.

The cyclic hydrocarbon group may have a substituent, and the carbon atom(s) within the substituent is not included in the number of carbon atoms of the "carbon atom of 5 or more carbon atoms".

The cyclic hydrocarbon group of 5 or more carbon atoms is preferably an aliphatic cyclic group.

Examples of the "aliphatic cyclic group" include monocyclic groups or polycyclic groups which have no aromaticity, and polycyclic groups are preferable.

The "aliphatic cyclic group" may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

As such aliphatic cyclic groups, groups in which two or more hydrogen atoms have been removed from a monocycloalkane or a polycycloalkane such as a bicycloalkane, tricycloalkane or tetracycloalkane which may or may not be substituted with an alkyl group of 1 to 5 carbon atoms, a fluorine atom or a fluorinated alkyl group, may be used. Specific examples include groups in which two or more hydrogen atoms have been removed from a monocycloalkane such as cyclopentane and cyclohexane; and groups in which two or more hydrogen atoms have been removed from a polycycloalkane such as adamantane, norbornane, isobornane, tricyclodecane or tetracyclododecane.

Each of $R^{56}$ and $R^{57}$ independently represents a hydrogen atom, an alkyl group or an aryl group.

Examples of the alkyl group or aryl group for $R^{56}$ and $R^{57}$ include the same alkyl groups and aryl groups as those described above for $R^{1'''}$ to $R^{3'''}$. Further, $R^{56}$ to $R^{57}$ may be mutually bonded to form a ring, like in the case of the aforementioned $R^{1'''}$ to $R^{3'''}$.

Among the above-mentioned examples, it is particularly desirable that both $R^{56}$ and $R^{57}$ represent a hydrogen atom.

Each of $Y^{11}$ and $Y^{12}$ independently represents an alkyl group or an aryl group.

Examples of the alkyl group or aryl group for $Y^{11}$ and $Y^{12}$ include the same alkyl groups and aryl groups as those described above for $R^{1'''}$ to $R^{3'''}$.

It is particularly desirable that each of $Y^{11}$ and $Y^{12}$ represents a phenyl group or a naphthyl group. Further, $Y^{11}$ and $Y^{12}$ may be mutually bonded to form a ring, like in the case of the aforementioned $R^{1'''}$ to $R^{3'''}$.

In formula (c-1-31), $R^{58}$ represents an aliphatic cyclic group; $R^{59}$ represents a single bond or an alkylene group which may have a substituent; $R^{60}$ represents an arylene group which may have a substituent; and $R^{61}$ represents an alkylene group of 4 or 5 carbon atoms which may have a substituent.

The aliphatic cyclic group for $R^{58}$ may be either a monocyclic group or a polycyclic group, but is preferably a polycyclic group, more preferably a group in which one or more hydrogen atoms have been removed from a polycycloalkane, and most preferably a group in which one or more hydrogen atoms have been removed from adamantane.

The alkylene group for $R^{59}$ which may have a substituent is preferably a linear or branched alkylene group. As $R^{59}$, a single bond or an alkylene group of 1 to 3 carbon atoms is preferable.

The arylene group for $R^{60}$ preferably has 6 to 20 carbon atoms, more preferably 6 to 14 carbon atoms, and still more preferably 6 to 10 carbon atoms. Examples of the arylene group include a phenylene group, a biphenylene group, a fluorenylene group, a naphthylene group, an anthrylene group and a phenanthrene group. In terms of synthesis at low cost, a phenylene group or a naphthylene group is preferable.

In formula (c-1-32), $R^{o1}$ represents an arylene group or an alkylene group; each of $R^{o2}$ and $R^{o3}$ independently represents an aryl group or an alkyl group, provided that $R^{o2}$ and $R^{o3}$ may be mutually bonded to form a ring with the sulfur atom, and at least one of $R^{o1}$ to $R^{o3}$ represents an arylene group or an aryl group; $W^1$ represents a linking group having a valency of n"; and n" represents 2 or 3.

The arylene group for $R^{o1}$ is not particularly limited, and examples thereof include arylene groups of 6 to 20 carbon atoms in which part or all of the hydrogen atoms may be substituted. The alkylene group for $R^{o1}$ is not particularly limited, and examples thereof include linear, branched or cyclic alkylene groups of 1 to 10 carbon atoms.

The aryl group for $R^{o2}$ and $R^{o3}$ is not particularly limited, and examples thereof include aryl groups of 6 to 20 carbon atoms in which part or all of the hydrogen atoms may be substituted. The alkyl group for $R^{o2}$ and $R^{o3}$ is not particularly limited, and examples thereof include linear, branched or cyclic alkyl groups of 1 to 10 carbon atoms.

Examples of the divalent linking group for $W^1$ include the same divalent linking groups as those described above for W in the formula (c-1-21). The divalent linking group may be linear, branched or cyclic, but is preferably cyclic. Among these, an arylene group having two carbonyl groups, each bonded to the both terminals thereof is preferable.

As the trivalent linking group for $W^1$, a group in which one hydrogen atom has been removed from the aforementioned divalent linking group and a group in which a hydrogen atom of the divalent linking group has been substituted with an another divalent linking group can be mentioned. Among these, a group in which an arylene group combined with three carbonyl groups is preferable.

In formula (c-2), $R^{5\prime\prime\prime}$ and $R^{6\prime\prime\prime}$ each independently represent an aryl group or alkyl group. Among $R^{5\prime\prime\prime}$ to $R^{6\prime\prime\prime}$, it is more preferable that at least one group is an aryl group, and it is particularly desirable that all of $R^{5\prime\prime\prime}$ to $R^{6\prime\prime\prime}$ are aryl groups.

As the aryl group for $R^{5\prime\prime\prime}$ and $R^{6\prime\prime\prime}$, the same aryl groups as those described above for $R^{1\prime\prime\prime}$ to $R^{3\prime\prime\prime}$ can be used.

As the alkyl group for $R^{5\prime\prime\prime}$ and $R^{6\prime\prime\prime}$, the same alkyl groups as those described above for $R^{1\prime\prime\prime}$ to $R^{3\prime\prime\prime}$ can be used.

It is particularly desirable that both of $R^{5\prime\prime\prime}$ and $R^{6\prime\prime\prime}$ represents a phenyl group.

Further, as examples of the organic cation for $M^+$, organic cations represented by general formula (c-3) shown below can also be given.

[Chemical Formula 28]

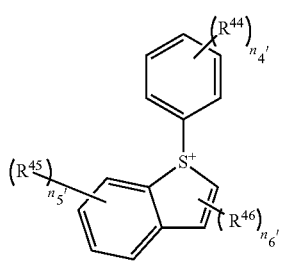

(c-3)

In formulae, each of $R^{44}$ to $R^{46}$ independently represents an alkyl group, an acetyl group, an alkoxy group, a carboxy group, a hydroxyl group or a hydroxyalkyl group; each of $n_4'$ and $n_5'$ independently represents an integer of 0 to 3; and $n_6'$ represents an integer of 0 to 2.

With respect to $R^{44}$ to $R^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert-butyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably a group in which one or more hydrogen atoms within the aforementioned alkyl group have been substituted with hydroxy groups, and examples thereof include a hydroxymethyl group, a hydroxyethyl group and a hydroxypropyl group.

If there are two or more of an individual $R^{44}$ to $R^{46}$ group, as indicated by the corresponding value of $n_4'$ to $n_6'$, then the two or more of the individual $R^{44}$ to $R^{46}$ group may be the same or different from each other.

$n_4'$ is preferably 0 to 2, and more preferably 0 or 1.

$n_5'$ is preferably 0 or 1, and more preferably 0.

$n_6'$ is preferably 0 or 1, and more preferably 1.

The polymeric compound (A1) preferably has a group represented by general formula (I-1) shown below (hereafter, sometimes referred to as "terminal group (I-1)") on at least one terminal of the main chain thereof, in terms of effect of improving the lithography properties.

[Chemical Formula 29]

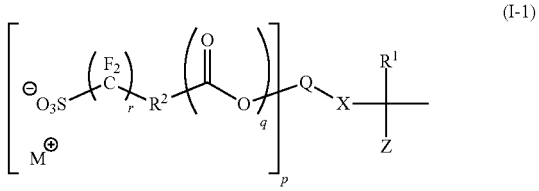

(I-1)

In the formula, $R^1$ represents a hydrocarbon group of 1 to 10 carbon atoms; Z represents a hydrocarbon group of 1 to 10 carbon atoms or a cyano group; provided that $R^1$ and Z may be mutually bonded to form a ring; X represents a divalent linking group having any one selected from —O—C(=O)—, —NH—C(=O)— and —NH—C(=NH)— on at least one terminal that comes into contact with Q; p represents an integer of 1 to 3;

Q represents a hydrocarbon group having a valency of (p+1), provided that, when p is 1, Q may be a single bond; and $R^2$ represents a single bond, an alkylene group which may have a substituent or an aromatic group which may have a substituent; q represents 0 or 1; r represents an integer of 0 to 8; and $M^+$ represents an organic cation.

In general formula (I-1) above, $M^+$ is the same as defined in the general formula (an1).

In general formula (I-1) above, $R^1$ represents a hydrocarbon group of 1 to 10 carbon atoms. The hydrocarbon group of 1 to 10 carbon atoms may be either an aliphatic hydrocarbon group or an aromatic hydrocarbon group, an aliphatic hydrocarbon group is preferable, and a monovalent saturated aliphatic hydrocarbon group (i.e., alkyl group) is more preferable.

As specific examples of the alkyl group, a linear or branched alkyl group, and an aliphatic hydrocarbon group containing a ring in the structure thereof can be given.

The linear alkyl group preferably has 1 to 8 carbon atoms, more preferably 1 to 5, and most preferably 1 to 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 5 carbon atoms. Specific examples of such branched alkyl groups include an isopropyl group, an isobutyl group, a tert-butyl group, an isopentyl group and a neopentyl group, and an isopropyl group or a tert-butyl group is particularly desirable.

As examples of the hydrocarbon group containing a ring in the structure thereof, a cyclic aliphatic hydrocarbon group (a group in which one hydrogen atom has been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 8 carbon atoms, and more preferably 4 to 6 carbon atoms. Specific examples include groups in which one or more hydrogen atoms have been removed from a monocycloalkane such as cyclopentane or cyclohexane.

The cyclic aliphatic hydrocarbon group may or may not have a substituent. Examples of the substituent include an alkyl group of 1 to 5 carbon atoms, a fluorine atom, a fluorinated alkyl group of 1 to 5 carbon atoms, and an oxygen atom (=O).

In general formula (I-1) above, Z represents a hydrocarbon group of 1 to 10 carbon atoms or a cyano group (—CN).

As the hydrocarbon group of 1 to 10 carbon atoms for Z, the same hydrocarbon groups of 1 to 10 carbon atoms as those described above for $R^1$ can be used.

$R^1$ and Z may be mutually bonded to form a ring. $R^1$ and Z each independently represents a linear or branched alkyl group, wherein the terminal of $R^1$ may be mutually bonded to the terminal of Z to form a ring. As the formed ring, a ring having 3 to 8 carbon atoms is preferable, and preferable examples thereof includes cyclopentane, cyclohexane, cycloheptane and cyclooctane.

Among these, as the combination of $R^1$ and Z in the present invention, a combination of a methyl group and a methyl group; a combination of an ethyl group and an ethyl group; a combination of a methyl group and a cyano group; a combination of an ethyl group and a cyano group; and a group in which two carbon atoms have been removed from cyclopentane formed by $R^1$ and Z mutually bonded, are preferable, and it is particularly preferable that $R^1$ is a methyl group and Z is a cyano group.

In general formula (I-1) above, X represents a divalent linking group having any one selected from —O—C(=O)—, —NH—C(=O)— and —NH—C(=NH)— on at least one terminal that comes into contact with Q.

When Q is a single bond, the terminal that comes into contact with Q is a terminal that comes into contact with —(C(=O)—O)$_q$—, $R^2$, —CF$_2$— or SO$_3^-$ in the general formula (I-1). The divalent linking group for X may consist of —O—C(=O)—, —NH—C(=O)—, or —NH—C(NH)—. X may contain another —O—C(=O)—, —NH—C(=O)—, or —NH—C(=NH)— in addition to the group at the terminal thereof which is bonded to Q.

Examples of the divalent linking group for X include a group consisting of —O—C(=O)—, —NH—C(=O)— or —NH—C(=NH)—; a combination of a divalent hydrocarbon group which may have a substituent or a divalent linking group containing a hetero atom, with any one of —O—C(=O)—, —NH—C(=O)— or —NH—C(=NH)—.

The divalent hydrocarbon group which may have a substituent and the divalent linking group containing a hetero atom are the same divalent linking groups as those described above for W in the aforementioned formula (c-1-21).

When X consists of —O—C(=O)—, —NH—C(=O)—, or —NH—C(=NH)—, X is preferably —O—C(=O)— or —NH—C(=O)—. Here, the carbon atom (C) within —O—C(=O)— or the carbon atom (C) within —NH—C(=O)— is preferably bonded directly to the carbon atom which is bonded to $R^1$ and Z.

In the case where X is a combination of the divalent group as described above with any one of —O—C(=O)—, —NH—C(=O)— or —NH—C(=NH)—, X is preferably a combination of a linear or branched aliphatic hydrocarbon group of 1 to 5 carbon atoms or a divalent linking group containing a hetero atom, with any one of —O—C(=O)—, —NH—C(=O)— or —NH—C(=NH)—; more preferably a combination of at least one linking group selected from a methylene group, an ethylene group and a divalent linking group containing —NH—, with any one of —O—C(=O)—, —NH—C(=O)— or —NH—C(=NH)—; and particularly preferably a combination of two or more groups selected from an ethylene group, —O—C(=O)— and —NH—C(=O)—.

In formula (I-1), p represents an integer of 1 to 3, preferably 1.

When p is 2 or 3, the ratio of SO$_3^-$ in one molecule can be enhanced.

Therefore, the ratio of the sulfonic acid portion (SO$_3^-$), which acts or is generated as acid, in a polymeric compound which is obtained when the compound is used as a radical polymerization initiator can be enhanced, and a function of generating acid can be improved.

In general formula (I-1) above, Q represents a hydrocarbon group having a valency of (p+1), provided that, when p is 1, Q may be a single bond.

When p is 1, Q represents a single bond or a divalent hydrocarbon group. Examples of the divalent hydrocarbon group include the same groups as those described above as the "divalent hydrocarbon group which may have a substituent" for X and which has no substituent. In the case where p is 1, as Q, a single bond, or a divalent aliphatic hydrocarbon group is preferable; a single bond, or a linear or branched alkylene group is more preferable; a single bond, a methylene group or an ethylene group is still more preferable; and a single bond or an ethylene group is particularly preferable.

When p is 2, Q represents a trivalent hydrocarbon group, and when p is 3, Q represents a tetravalent hydrocarbon group. Examples of the trivalent hydrocarbon group and tetravalent hydrocarbon group include groups in which one or two hydrogen atoms have been removed from the "divalent hydrocarbon group which may have a substituent" for X and which has no substituent. In particular, a trivalent aliphatic hydrocarbon group and tetravalent aliphatic hydrocarbon group are preferable.

Specific examples of the hydrocarbon group having a valency of (p+1) for Q are shown below.

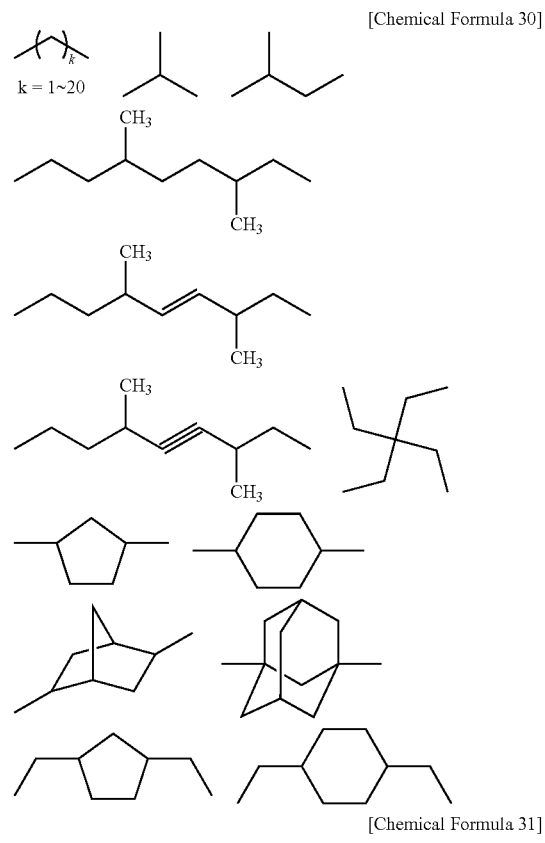

[Chemical Formula 30]

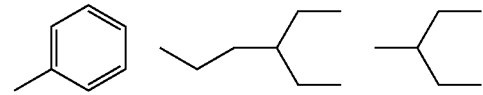

[Chemical Formula 31]

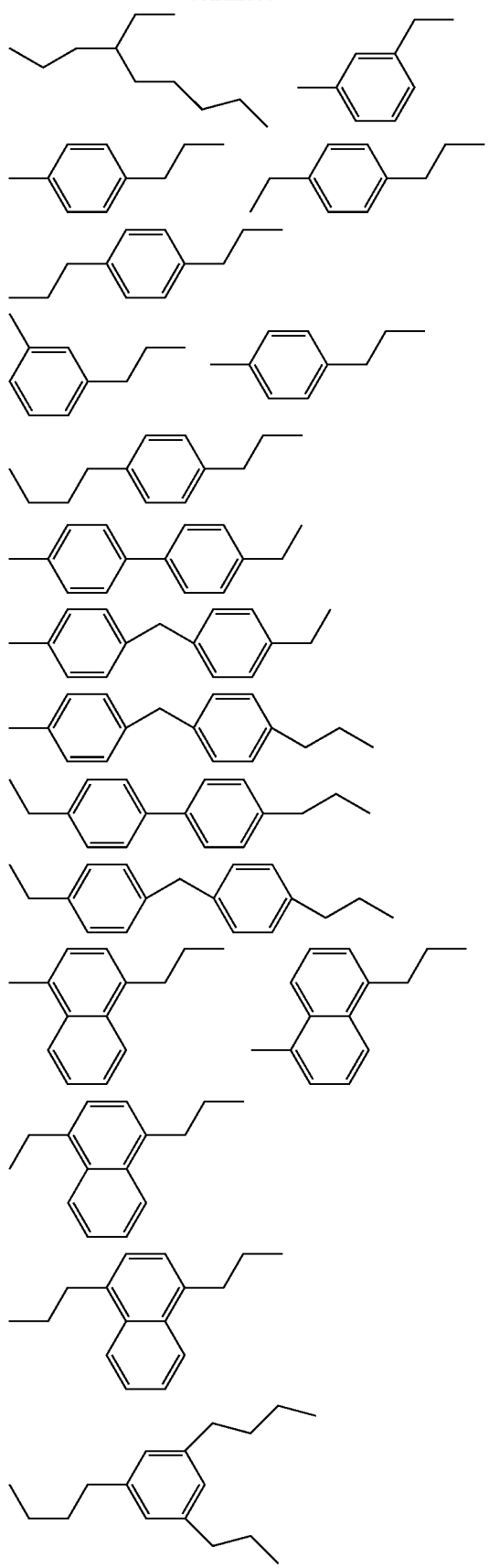

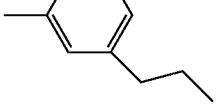

In general formula (I-1) above, q represents 0 or 1. When q is 0, it means that —(C(=O)—O)$_q$— is a single bond.

In the case where the divalent linking group for X does not contain —O—C(=O)—, q is preferably 1, and in the case where the divalent linking group contains —O—C(=O)—, q is preferably 0.

In general formula (I-1) above, R$^2$ represents a single bond, an alkylene group which may have a substituent, or an aromatic group which may have a substituent.

The alkylene group for R$^2$ may be chain-like or cyclic. Specific examples of the alkylene group include the same "linear or branched aliphatic hydrocarbon groups" and "aliphatic hydrocarbon group containing a ring in the structure thereof" as those described above for the "divalent hydrocarbon group which may have a substituent" for X. Among these, as the alkylene group for R$^2$, a linear alkylene group having 1 to 10 carbon atoms is preferable, and a methylene group or an ethylene group is more preferable.

The aromatic group of for R$^2$ which may have a substituent may be either an aromatic hydrocarbon group or an aromatic group which contains an atom other than carbon atoms in the ring structure thereof (i.e., heterocyclic compound).

Examples of the aromatic hydrocarbon group include the same aromatic hydrocarbon groups as those described above in relation to the "divalent hydrocarbon group which may have a substituent" for X. As the aromatic hydrocarbon group for R$^2$, a group in which one or more hydrogen atoms have been removed from a phenyl group or a naphthyl group is particularly desirable. The aromatic hydrocarbon group for R$^2$ may be a group in which part or all of the hydrogen atoms of the aromatic hydrocarbon group have been substituted with an alkyl group of 1 to 5 carbon atoms, a fluorine atom, a fluorinated alkyl group of 1 to 5 carbon atoms, or an oxygen atom (=O), and preferably a group in which part or all of the hydrogen atoms of the aromatic hydrocarbon group have been substituted with a fluorine atom.

As the aromatic group containing an atom other than carbon atom in the ring structure thereof, a group in which two or more hydrogen atoms have been removed from a heterocycle such as quinoline, pyridine, oxole and imidazole is preferably used.

Among these, as R$^2$, a single bond or an aromatic group which may have a substituent is preferable.

In general formula (I-1) above, r represents an integer of 0 to 8. When r is 0, it means that —(CF$_2$)$_r$— is a single bond.

In the case where R$^2$ is a single bond or an alkylene group which may have a substituent, r is preferably an integer of 1 to 8, more preferably an integer of 1 to 4, and still more preferably 1 or 2. In the case where R$^2$ is an aromatic group which may have a substituent, r is preferably 0.

Specific examples of groups preferable as a group represented by general formula (I-1) are shown below.

[Chemical Formula 32]

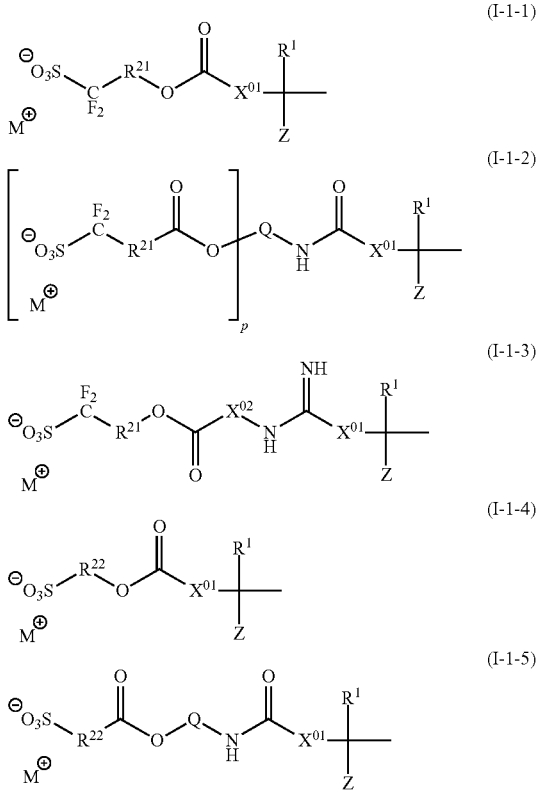

In the formulae, $R^1$, Z, Q, p and $M^+$ are the same as defined above; $X^{01}$ represents a single bond or an alkylene group which may have a substituent; $R^{21}$ represents a single bond or an alkylene group which may have a substituent; $X^{02}$ represents an alkylene group which may have a substituent; and $R^{22}$ represents an aromatic group which may have a substituent.

In the formulae (I-1-1) to (I-1-5), $R^1$, Z, Q, p and $M^+$ are the same as defined for $R^1$, Z, Q, p and $M^+$ in the formula (I-1).

In the formulae (I-1-1) to (I-1-5), $X^{01}$ represents a single bond or an alkylene group which may have a substituent. Specific examples of the alkylene group which may have a substituent include the same "linear or branched aliphatic hydrocarbon groups" and "aliphatic hydrocarbon group containing a ring in the structure thereof" as those described above for the "divalent hydrocarbon group which may have a substituent" for X. As $X^{01}$, a single bond or an ethylene group is particularly desirable.

In the formulae (I-1-1) to (I-1-3), $R^{21}$ represents a single bond or an alkylene group which may have a substituent. The alkylene group for $R^{21}$ which may have a substituent is the same groups as those described above for $R^2$ in the formula (I-1). As $R^{21}$, a single bond or a methylene group is particularly desirable.

In the formula (I-1-3), $X^{02}$ represents an alkylene group which may have a substituent, and specific examples thereof include the same "linear or branched aliphatic hydrocarbon groups" and "aliphatic hydrocarbon group containing a ring in the structure thereof" as those described above for the "divalent hydrocarbon group which may have a substituent" for X in the formula (I-1). As $X^{02}$, an ethylene group is particularly desirable.

In the formulae (I-1-4) and (I-1-5), $R^{22}$ represents an aromatic group which may have a substituent. The aromatic group for $R^{22}$ which may have a substituent is the same groups as those described above for $R^2$ in the formula (I-1). As $R^{22}$, a group in which one or more hydrogen atoms have been removed from a phenyl group or a naphthyl group, or a group in which two or more hydrogen atoms have been removed from quinoline are particularly preferable.

[Structural Units Constituting Polymeric Compound]

The main chain of the polymeric compound (A1) which has an anion moiety on at least one terminal thereof is not particularly limited, and is preferably formed by cleavage of the ethylenic double bond (C=C). The polymeric compound (A1) preferably contains a structural unit derived from a compound having an ethylenic double bond.

In the present description, the expression "structural unit derived from a compound having an ethylenic double bond" refers to a structural unit that is formed by the cleavage of the ethylenic double bond of the compound having an ethylenic double bond.

Examples of the compound having an ethylenic double bond include acrylic acid or an ester thereof which may have the hydrogen atom bonded to the carbon atom on the α-position substituted with a substituent, acrylamide or a derivative thereof in which the hydrogen atom bonded to the carbon atom on the α-position may be substituted with a substituent, styrene or a derivative thereof in which the hydrogen atom bonded to the carbon atom on the α-position may be substituted with a substituent, a vinylnaphthalene or a derivative thereof in which the hydrogen atom bonded to the carbon atom on the α-position may be substituted with a substituent, a cycloolefin or a derivative thereof, and a vinylsulfonate ester.

Among these, acrylic acid or an ester thereof which may have the hydrogen atom bonded to the carbon atom on the α-position substituted with a substituent, acrylamide or a derivative thereof in which the hydrogen atom bonded to the carbon atom on the α-position may be substituted with a substituent, styrene or a derivative thereof in which the hydrogen atom bonded to the carbon atom on the α-position may be substituted with a substituent, and a vinylnaphthalene or a derivative thereof in which the hydrogen atom bonded to the carbon atom on the α-position may be substituted with a substituent are preferable, and an acrylate ester which may have the hydrogen atom bonded to the carbon atom on the α-position substituted with a substituent is more preferable.

An "acrylate ester" refers to a compound in which the terminal hydrogen atom of the carboxy group of acrylic acid ($CH_2$=CH—COOH) has been substituted with an organic group.

In the present specification, an acrylate ester having the hydrogen atom bonded to the carbon atom on the α-position substituted with a substituent is sometimes referred to as "α-substituted acrylate ester". Further, acrylate esters and α-substituted acrylate esters are collectively referred to as "(α-substituted) acrylate ester".

Examples of the substituent bonded to the carbon atom on the α-position of an α-substituted acrylate ester include a halogen atom, an alkyl group of 1 to 5 carbon atoms, a halogenated alkyl group of 1 to 5 carbon atoms and a hydroxyalkyl group. With respect to the "structural unit derived from an acrylate ester", the "α-position (the carbon atom on the α-position)" refers to the carbon atom having the carbonyl group bonded thereto, unless specified otherwise.

Examples of the halogen atom as the substituent on the α-position include a fluorine atom, a chlorine atom, a bromine atom and an iodine atom.

Specific examples of the alkyl group of 1 to 5 carbon atoms for the substituent on the α-position include linear or branched alkyl groups such as a methyl group, an ethyl group, a propyl group, an isopropyl group, an n-butyl group, an isobutyl group, a tert-butyl group, a pentyl group, an isopentyl group, and a neopentyl group.

Specific examples of the halogenated alkyl group of 1 to 5 carbon atoms as a substituent on the α-position include groups in which part or all of the hydrogen atoms of the aforementioned alkyl group of 1 to 5 carbon atoms are substituted with halogen atoms. Examples of the halogen atom include a fluorine atom, a chlorine atom, a bromine atom and an iodine atom, and a fluorine atom is particularly desirable.

Specific examples of the hydroxyalkyl group as a substituent on the α-position include groups in which part or all of the hydrogen atoms of the aforementioned alkyl group of 1 to 5 carbon atoms are substituted with a hydroxy group.

In the present invention, it is preferable that a hydrogen atom, an alkyl group of 1 to 5 carbon atoms or a halogenated alkyl group of 1 to 5 carbon atoms is bonded to the α-position of an (α-substituted) acrylate ester, a hydrogen atom, an alkyl group of 1 to 5 carbon atoms or a fluorinated alkyl group of 1 to 5 carbon atoms is more preferable, and in terms of industrial availability, a hydrogen atom or a methyl group is the most desirable.

The organic group which the (α-substituted) acrylate ester has is not particularly limited, and examples thereof include a characteristic group such as the aforementioned acid dissociable group; an —$SO_2$— containing cyclic group, a lactone-containing cyclic group, a polar group-containing hydrocarbon group, a non-acid-dissociable aliphatic polycyclic group as described later in relation to structural units (a2) to (a4); and a characteristic group-containing group having a characteristic group in the structure thereof. Examples of the characteristic group-containing group include groups in which the aforementioned characteristic group is bonded to a divalent linking group. Examples of the divalent linking group include the same divalent linking groups as those described above for W.

Examples of "acrylamide and derivatives thereof" include acrylamide in which the hydrogen atom bonded to the carbon atom on the α-position may be substituted with a substituent (hereafter, sometimes referred to as (α-substituted) acrylamide), and a compound in which either or both terminal hydrogen atoms on the amino group of α-substituted) acrylamide is substituted with a substituent.

As the substituent to be bonded to the carbon atom on the α-position of acrylamide and derivatives thereof, the same substituents as those described above for the substituent to be bonded to the carbon atom on the α-position of an α-substituted acrylate ester can be mentioned.

As the substituent which substitutes either or both terminal hydrogen atoms on the amino group of (α-substituted) acrylamide, an organic group is preferable. The organic group is not particularly limited, and examples thereof include the same organic groups as those described above for (α-substituted) acrylate ester.

Examples of the compound in which either or both terminal hydrogen atoms on the amino group of (α-substituted) acrylamide is substituted with a substituent include a compound in which —C(=O)—O— bonded to the carbon atom on the α-position of the aforementioned (α-substituted) acrylate ester is replaced by —C(=O)—N($R^b$)— (in the formula, $R^b$ represents a hydrogen atom or an alkyl group of 1 to 5 carbon atoms).

In the formula, the alkyl group for $R^b$ is preferably linear or branched.

Examples of "styrene and derivatives thereof" include styrene which may have the hydrogen atom bonded to the carbon atom on the α-position substituted with a substituent, and a hydrogen atom bonded to the benzene ring substituted with a substituent other than a hydroxy group (hereafter, sometimes referred to as "(α-substituted) styrene"); hydroxystyrene which may have the hydrogen atom bonded to the carbon atom on the α-position substituted with a substituent, and a hydrogen atom bonded to the benzene ring substituted with a substituent other than a hydroxy group (hereafter, sometimes referred to as "(α-substituted) hydroxystyrene"); a compound in which the hydrogen atom within the hydroxy group of (α-substituted) hydroxystyrene is substituted with an organic group; vinylbenzoic acid which may have the hydrogen atom bonded to the carbon atom on the α-position substituted with a substituent, and a hydrogen atom bonded to the benzene ring substituted with a substituent other than a hydroxy group and a carboxy group (hereafter, sometimes referred to as "(α-substituted) vinylbenzoic acid"); and a compound in which the hydrogen atom within the carboxy group of (α-substituted) vinylbenzoic acid is substituted with an organic group.

Hydroxystyrene is a compound which has 1 vinyl group and at least 1 hydroxy group bonded to a benzene ring. The number of hydroxy groups bonded to the benzene ring is preferably 1 to 3, and particularly preferably 1. The bonding position of the hydroxy group on the benzene ring is not particularly limited. When there is 1 hydroxy group, a para-4th position from the bonding position of the vinyl group is preferable. When there are 2 or more hydroxy groups, a desired combination of the bonding positions can be used.

Vinylbenzoic acid is a compound in which one vinyl group is bonded to the benzene ring of benzoic acid.

The bonding position of the vinyl group on the benzene ring is not particularly limited.

As the substituent to be bonded to the carbon atom on the α-position of styrene and derivatives thereof, the same substituents as those described above for the substituent to be bonded to the carbon atom on the α-position of an α-substituted acrylate ester can be mentioned.

The substituent other than a hydroxy group and a carboxy group which may be bonded to the benzene ring of styrene or a derivative thereof is not particularly limited, and examples thereof include a halogen atom, an alkyl group of 1 to 5 carbon atoms, and a halogenated alkyl group of 1 to 5 carbon atoms. Examples of the halogen atom include a fluorine atom, a chlorine atom, a bromine atom and an iodine atom, and a fluorine atom is particularly desirable.

The organic group within the compound in which the hydrogen atom within the hydroxy group of (α-substituted) hydroxystyrene is substituted with an organic group is not particularly limited, and examples thereof include the same organic groups as those described above for the aforementioned (α-substituted) acrylate ester.

The organic group within the compound in which the hydrogen atom within the carboxy group of (α-substituted) vinylbenzoic acid is substituted with an organic group is not particularly limited, and examples thereof include the same organic groups as those described above for the aforementioned (α-substituted) acrylate ester.

Examples of "vinylnaphthalene and derivatives thereof" include vinylnaphthalene which may have the hydrogen atom bonded to the carbon atom on the α-position substituted with a substituent, and a hydrogen atom bonded to the naphthalene ring substituted with a substituent other than a hydroxy group (hereafter, sometimes referred to as "(α-substituted) vinyl-naphthalene"); vinyl(hydroxynaphthalene) which may have the hydrogen atom bonded to the carbon atom on the α-position substituted with a substituent, and a hydrogen atom bonded to the naphthalene ring substituted with a substituent other than a hydroxy group (hereafter, sometimes referred to as "(α-substituted) vinyl(hydroxynaphthalene)"); and a compound in which the hydrogen atom within the hydroxy group of (α-substituted) vinyl(hydroxynaphthalene) is substituted with a substituent.

Vinyl(hydroxynaphthalene) is a compound which has 1 vinyl group and at least 1 hydroxy group bonded to a naphthalene ring. The vinyl group may be bonded to the 1st or 2nd position of the naphthalene ring. The number of hydroxy groups bonded to the naphthalene ring is preferably 1 to 3, and particularly preferably 1. The bonding position of the hydroxy group on the naphthalene ring is not particularly limited. When the vinyl group is bonded to the 1st or 2nd position of the naphthalene ring, the hydroxy group is preferably bonded to either one of the 5th to 8th position of the naphthalene ring. In particular, when the number of hydroxy group is 1, the hydroxy group is preferably bonded to either one of the 5th to 7th position of the naphthalene ring, and more preferably the 5th or 6th position. When there are 2 or more hydroxy groups, a desired combination of the bonding positions can be used.

As the substituent to be bonded to the carbon atom on the α-position of vinylnaphthalene and derivatives thereof, the same substituents as those described above for the substituent to be bonded to the carbon atom on the α-position of an α-substituted acrylate ester can be mentioned.

As the substituent which may be bonded to the naphthalene ring of vinylnaphthalene and derivatives thereof, the same substituents as those described above for the substituent which may be bonded to the benzene ring of the (α-substituted) styrene can be mentioned.

The organic group within the compound in which the hydrogen atom within the hydroxy group of (α-substituted) vinyl(hydroxynaphthalene) is substituted with an organic group is not particularly limited, and examples thereof include the same organic groups as those described above for the aforementioned (α-substituted) acrylate ester.

Specific examples of the structural unit derived from an (α-substituted) acrylic acid or an ester thereof include a structural unit represented by general formula (I) shown below.

Specific examples of the structural unit derived from an (α-substituted) acrylamide or a derivative thereof include a structural unit represented by general formula (II) shown below.

Specific examples of the structural unit derived from an (α-substituted) styrene or a derivative thereof include a structural unit represented by general formula (III) shown below.

Further, specific examples of the structural unit derived from an (α-substituted) vinylnaphthalene or a derivative thereof include a structural unit represented by general formula (IV) shown below.

[Chemical Formula 33]

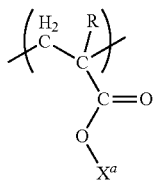

(I)

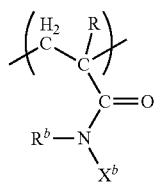

(II)

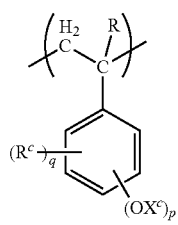

(III)

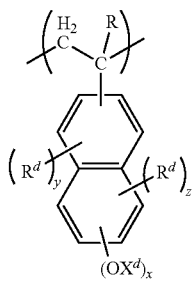

(IV)

In the formulae, R represents a hydrogen atom, an alkyl group of 1 to 5 carbon atoms or a halogenated alkyl group of 1 to 5 carbon atoms; $X^a$ to $X^b$ each independently represents a hydrogen atom or an organic group; $R^b$ represents a hydrogen atom or an alkyl group of 1 to 5 carbon atoms; $R^c$ and $R^d$ each independently represents a halogen atom, —COOX$^e$ (X$^e$ represents a hydrogen atom or an organic group), an alkyl group of 1 to 5 carbon atoms or a halogenated alkyl group of 1 to 5 carbon atoms; p represents an integer of 0 to 3; q represents an integer of 0 to 5; and p+q=0 to 5; provided that, when q is an integer of 2 or more, the plurality of $R^c$ groups may be the same or different from each other; x represents an integer of 0 to 3; y represents an integer of 0 to 3; z represents an integer of 0 to 4, and x+y+z=0 to 7, provided that, when y+z is an integer of 2 or more, the plurality of $R^d$ groups may be the same or different from each other.

As described above, in the resist composition of the present invention, the component (A) is preferably a base component (A0) which exhibits increased polarity by the action of acid. In the base component (A0), the component which exhibits increased polarity by the action of acid may be a polymeric component (A1) or a resin component constituting the base component (A0) other than the polymeric compound (A1).

Among these, the polymeric compound (A1) is preferably a polymeric compound useful for a base component which generates acid upon exposure and exhibits increased polarity by the action of acid. The polymeric compound (A1) has an anion portion which generates acid upon exposure, at the terminal of the main chain thereof. In the case where the polymeric compound (A1) is a polymeric compound which exhibits increased polarity by the action of acid and exhibits changed solubility in a developing solution, anion portions at the terminal of the main chain thereof and portions (e.g., acid decomposable group in a structural unit (a1) described later) of the polymeric compound, which contributes the change in solubility by the action of acid, are uniformly distributed within the resist film. At exposed portions, acid is generated uniformly from the polymeric compound, thereby changing the solubility of the polymeric compound thereof appropriately. As a result, excellent lithography properties can be obtained.

[Component (A1)]

As the structural units constituting the component (A1) which exhibits increased polarity by the action of acid, any of the multitude of conventional structural units used within the resin of resist compositions for ArF excimer lasers or KrF excimer lasers (and particularly for ArF excimer lasers) can be used. Examples of the structural unit include a structural unit (a1) containing an acid decomposable group that exhibits increased polarity by the action of acid, a structural unit (a2) containing a lactone-containing cyclic group or an —$SO_2$— containing cyclic group, a structural unit (a3) containing a polar group, and a structural unit (a4) containing an acid non-dissociable cyclic group.

Among these, the polymeric compound (A1) which exhibits increased polarity by the action of acid preferably contains the structural unit (a1).

[Component (A1')]

As the component (A1'), a polymeric compound having a terminal group (I-1) on at least one terminal of the main chain thereof can be used. As the constitution of portions other than the terminal portion, the same constitutions as those of a resin component (base resin) which is typically used as a base component for a chemically amplified resist composition can be employed.

As the structural units constituting the component (A1'), any of the multitude of conventional structural units used within the resin of resist compositions for ArF excimer lasers or KrF excimer lasers (and particularly for ArF excimer lasers) can be used.

Examples of the structural unit include a structural unit (a1) containing an acid decomposable group that exhibits increased polarity by the action of acid, a structural unit (a2) containing a lactone-containing cyclic group or an —$SO_2$— containing cyclic group, a structural unit (a3) containing a polar group, and a structural unit (a4) containing an acid non-dissociable cyclic group.

The component (A1') preferably contains the structural unit (a1).

In the present invention, the component (A1') preferably has a structural unit derived from an acrylate ester which may have the hydrogen atom bonded to the carbon atom on the α-position substituted with a substituent.

In the resist composition of the present invention, it is particularly desirable that the component (A1') has a structural unit (a11) derived from an acrylate ester which may have the hydrogen atom bonded to the carbon atom on the α-position substituted with a substituent and contains an acid decomposable group which exhibits increased polarity by the action of acid.

It is preferable that the component (A1') include, in addition to the structural unit (a11), at least one structural unit (a2') selected from the group consisting of a structural unit derived from an acrylate ester which may have the hydrogen atom bonded to the carbon atom on the α-position substituted with a substituent and contains an —$SO_2$— containing cyclic group, and a structural unit derived from an acrylate ester which may have the hydrogen atom bonded to the carbon atom on the α-position substituted with a substituent and contains a lactone-containing cyclic group.

In addition to the structural unit (a1') or in addition to the structural units (a1') and (a2'), it is preferable that the component (A1') further include a structural unit (a3-12-21) derived from an acrylate ester containing a polar group-containing aliphatic hydrocarbon group and may have the hydrogen atom bonded to the carbon atom on the α-position substituted with a substituent.

(Structural Unit (a1))

The structural unit (a1) has an acid decomposable group that exhibits increased polarity by the action of acid.

The term "acid decomposable group" refers to a group in which at least a part of the bond within the structure thereof is cleaved by the action of acid generated from the anion portion at the terminal of the main chain, the acid generator component (B) described later, or the acid generator component (C) described later upon exposure.

Examples of acid decomposable groups which exhibit increased polarity by the action of an acid include groups which are decomposed by the action of acid to form a polar group.

Examples of the polar group include a carboxy group, a hydroxy group, an amino group and a sulfo group (—$SO_3H$). Among these, a polar group containing —OH in the structure thereof (hereafter, referred to as "OH-containing polar group") is preferable, a carboxy group or a hydroxy group is more preferable, and a carboxy group is particularly desirable.

More specifically, as an example of an acid decomposable group, a group in which the aforementioned polar group has been protected with an acid dissociable group (such as a group in which the hydrogen atom of the OH-containing polar group has been protected with an acid dissociable group) can be given.

An "acid dissociable group" is a group in which at least the bond between the acid dissociable group and the adjacent carbon atom is cleaved by the action of acid generated from the anion portion at the terminal of the main chain, the acid generator component (B) described later, or the acid generator component (C) described later upon exposure. It is necessary that the acid dissociable group that constitutes the acid decomposable group is a group which exhibits a lower polarity than the polar group generated by the dissociation of the acid dissociable group. Thus, when the acid dissociable group is dissociated by the action of acid, a polar group exhibiting a higher polarity than that of the acid dissociable group is generated, thereby increasing the polarity. As a result, the polarity of the entire polymeric compound is increased. By the increase in the polarity, the solubility in an alkali developing solution changes and, the solubility in an alkali developing solution is relatively increased, whereas the solubility in a developing solution containing an organic solvent (organic developing solution) is relatively decreased.

The acid dissociable group is not particularly limited, and any of the groups that have been conventionally proposed as acid dissociable groups for the base resins of chemically amplified resists can be used. Generally, groups that form either a cyclic or chain-like tertiary alkyl ester with the carboxyl group of the (meth)acrylic acid, and acetal-type acid dissociable groups such as alkoxyalkyl groups are widely known.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(=O)—O—). In this tertiary alkyl ester, the action of acid causes cleavage of the bond between the oxygen atom and the tertiary carbon atom, thereby forming a carboxy group.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable groups".

Examples of tertiary alkyl ester-type acid dissociable groups include aliphatic branched, acid dissociable groups and aliphatic cyclic group-containing acid dissociable groups.

The term "aliphatic branched" refers to a branched structure having no aromaticity. The "aliphatic branched, acid dissociable group" is not limited to be constituted of only carbon atoms and hydrogen atoms (not limited to hydrocarbon groups), but is preferably a hydrocarbon group. Further, the "hydrocarbon group" may be either saturated or unsaturated, but is preferably saturated.

As an example of the aliphatic branched, acid dissociable group, for example, a group represented by the formula —C($R^{71}$)($R^{72}$)($R^{73}$) can be given. In the formula, each of $R^{71}$ to $R^{73}$ independently represents a linear alkyl group of 1 to 5 carbon atoms. The group represented by the formula —C($R^{71}$)($R^{72}$)($R^{73}$) preferably has 4 to 8 carbon atoms, and specific examples include a tert-butyl group, a 2-methyl-2-butyl group, a 2-methyl-2-pentyl group and a 3-methyl-3-pentyl group.

Among these, a tert-butyl group is particularly desirable.

The term "aliphatic cyclic group" refers to a monocyclic group or polycyclic group that has no aromaticity.

In the "aliphatic cyclic group-containing acid dissociable group", the "aliphatic cyclic group" may or may not have a substituent. Examples of the substituent include an alkyl group of 1 to 5 carbon atoms, an alkoxy group of 1 to 5 carbon atoms, a fluorine atom, a fluorinated alkyl group of 1 to 5 carbon atoms, and an oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated.

The aliphatic cyclic group may be either a monocyclic group or a polycyclic group.

The aliphatic cyclic group preferably has 3 to 30 carbon atoms, more preferably 5 to 30, still more preferably 5 to 20, still more preferably 6 to 15, and most preferably 6 to 12. As the monocyclic aliphatic hydrocarbon group, a group in which one or more hydrogen atoms have been removed from a monocycloalkane is preferable. The monocycloalkane preferably has 3 to 6 carbon atoms, and specific examples thereof include cyclobutane, cyclopentane and cyclohexane. As the polycyclic aliphatic hydrocarbon group, a group in which one or more hydrogen atoms have been removed from a polycycloalkane is preferable, and the polycyclic group preferably has 7 to 12 carbon atoms. Examples of the polycycloalkane include adamantane, norbornane, isobornane, tricyclodecane and tetracyclododecane. In these aliphatic cyclic groups, part of the carbon atoms constituting the ring may be replaced with an ethereal oxygen atom (—O—).

Examples of aliphatic cyclic group-containing acid dissociable groups include (i) a monovalent aliphatic cyclic group in which a substituent (a group or an atom other than hydrogen) is bonded to the carbon atom on the ring skeleton to which an atom adjacent to the acid dissociable group (e.g., "—O—" within "—C(=O)—O— group") is bonded to form a tertiary carbon atom; and (ii) a group which has a branched alkylene group containing a tertiary carbon atom, and a monovalent aliphatic cyclic group to which the tertiary carbon atom is bonded.

In the group (i), as the substituent bonded to the carbon atom to which an atom adjacent to the acid dissociable group on the ring skeleton of the aliphatic cyclic group, an alkyl group can be mentioned. Examples of the alkyl group include the same groups as those represented by $R^{14}$ in formulae (1-1) to (1-9) described later. Specific examples include a 2-methyl-2-adamantyl group and a 2-ethyl-2-adamantyl group.

Specific examples of the group (i) include groups represented by general formulas (1-1) to (1-9) shown below. Specific examples thereof include groups having an aliphatic cyclic group such as an adamantyl group, cyclohexyl group, cyclopentyl group, norbornyl group, tricyclodecyl group or tetracyclododecyl group, and a branched alkylene group having a tertiary carbon atom bonded thereto.

Specific examples of the group (ii) include groups represented by general formulas (2-1) to (2-6) shown below.

[Chemical Formula 34]

(1-1)

(1-2)

(1-3)

(1-4)

(1-5)

(1-6)

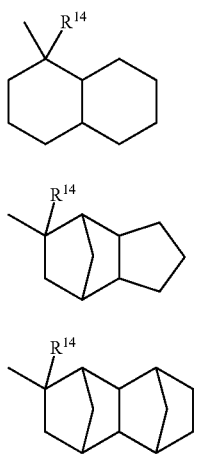

(1-7)

(1-8)

(1-9)

In the formulae above, $R^{14}$ represents an alkyl group; and g represents an integer of 0 to 8.

[Chemical Formula 35]

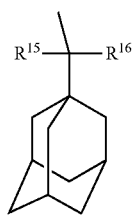 (2-1)

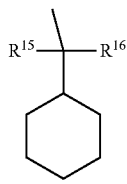 (2-2)

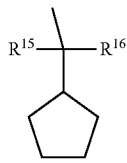 (2-3)

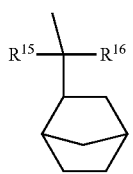 (2-4)

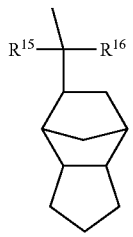 (2-5)

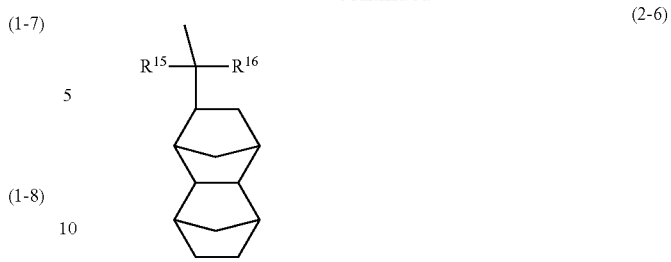

(2-6)

In the formulae, each of $R^{15}$ and $R^{16}$ independently represents an alkyl group.

In formulae (1-1) to (1-9), the alkyl group for $R^{14}$ may be linear, branched or cyclic, and is preferably linear or branched.

The linear alkyl group preferably has 1 to 5 carbon atoms, more preferably 1 to 4, and still more preferably 1 or 2. Specific examples include a methyl group, an ethyl group, an n-propyl group, an n-butyl group and an n-pentyl group. Among these, a methyl group, an ethyl group or an n-butyl group is preferable, and a methyl group or an ethyl group is more preferable.

The branched alkyl group preferably has 3 to 10 carbon atoms, and more preferably 3 to 5. Specific examples of such branched alkyl groups include an isopropyl group, an isobutyl group, a tert-butyl group, an isopentyl group and a neopentyl group, and an isopropyl group is particularly desirable.

g is preferably an integer of 0 to 3, more preferably an integer of 1 to 3, and still more preferably 1 or 2.

In formulae (2-1) to (2-6), as the alkyl group for $R^{15}$ and $R^{16}$, the same alkyl groups as those for $R^{14}$ can be used.

In formulas (1-1) to (1-9) and (2-1) to (2-6), part of the carbon atoms constituting the ring may be replaced with an ethereal oxygen atom (—O—).

Further, in formulas (1-1) to (1-9) and (2-1) to (2-6), one or more of the hydrogen atoms bonded to the carbon atoms constituting the ring may be substituted with a substituent. Examples of the substituent include an alkyl group of 1 to 5 carbon atoms, a fluorine atom and a fluorinated alkyl group.

An "acetal-type acid dissociable group" generally substitutes a hydrogen atom at the terminal of an OH-containing polar group such as a carboxy group or hydroxyl group, so as to be bonded with an oxygen atom. When acid is generated upon exposure, the generated acid acts to break the bond between the acetal-type acid dissociable group and the oxygen atom to which the acetal-type, acid dissociable group is bonded, thereby forming an OH-containing polar group such as a carboxy group or a hydroxy group.

Examples of acetal-type acid dissociable groups include groups represented by general formula (p1) shown below.

[Chemical Formula 36]

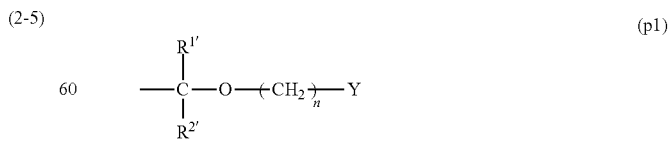

(p1)

In the formula, $R^{1\prime}$ and $R^{2\prime}$ each independently represent a hydrogen atom or an alkyl group of 1 to 5 carbon atoms; n represents an integer of 0 to 3; and Y represents an alkyl group of 1 to 5 carbon atoms or an aliphatic cyclic group.

In general formula (p1), n is preferably an integer of 0 to 2, more preferably 0 or 1, and most preferably 0.

As the alkyl group for $R^{1'}$ and $R^{2'}$, the same alkyl groups as those described above the alkyl groups as the substituent which may be bonded to the carbon atom on the α-position of the aforementioned α-substituted alkylester can be used, although a methyl group or ethyl group is preferable, and a methyl group is particularly desirable.

In the present invention, it is preferable that at least one of $R^{1'}$ and $R^{2'}$ be a hydrogen atom. That is, it is preferable that the acid dissociable group (p1) is a group represented by general formula (p1-1) shown below.

[Chemical Formula 37]

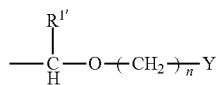

(p1-1)

In the formula, $R^{1'}$, n and Y are the same as defined above.

As the alkyl group for Y, the same alkyl groups as those described above the for the substituent which may be bonded to the carbon atom on the α-position of the aforementioned α-substituted alkylester can be mentioned.

As the aliphatic cyclic group for Y, any of the aliphatic monocyclic/polycyclic groups which have been proposed for conventional ArF resists and the like can be appropriately selected for use. For example, the same aliphatic cyclic groups described above in connection with the "acid dissociable group containing an aliphatic cyclic group" can be used.

Further, as the acetal-type, acid dissociable group, groups represented by general formula (p2) shown below can also be used.

[Chemical Formula 38]

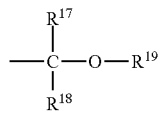

(p2)

In the formula, $R^{17}$ and $R^{18}$ each independently represent a linear or branched alkyl group or a hydrogen atom; and $R^{19}$ represents a linear, branched or cyclic alkyl group; or $R^{17}$ and $R^{19}$ each independently represents a linear or branched alkylene group, and the $R^{17}$ group is bonded to the $R^{19}$ group to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly desirable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, the same groups as those described above for the "aliphatic cyclic group", i.e., groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the $R^{19}$ group may be bonded to the $R^{17}$ group.

In the formula (p2), a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4 to 7-membered ring, and more preferably a 4 to 6-membered ring. Specific examples of the cyclic group include tetrahydropyranyl group and tetrahydrofuranyl group.

With respect to the structural unit (a1), there is not particular limitation to the structure of the other portion, as long as the structural unit has an acid decomposable group. The structural unit is preferably derived from a compound containing an ethylenic double bond (C=C) and contains an acid decomposable group which exhibits increased polarity by the action of acid. Examples thereof include a structural unit (a11) derived from an acrylate ester which may have the hydrogen atom bonded to the carbon atom on the α-position substituted with a substituent and contains an acid decomposable group which exhibits increased polarity by the action of acid; a structural unit (a12) derived from hydroxystyrene or a hydroxystyrene derivative in which at least a part of the hydrogen atom of the hydroxy group is protected with an acid decomposable group or a substituent containing an acid decomposable group; and a structural unit (a13) derived from vinylbenzoic acid or a vinylbenzoic acid derivative in which at least a part of the hydrogen atom within —C(=O)—OH is protected with an acid decomposable group or a substituent containing an acid decomposable group.

As the acid decomposable group and acid dissociable group in the structural units (a11) to (a13), the same groups as those described above can be used.

Among these, as the structural unit (a1), the structural unit (a11) is preferable.

Structural Unit (a11)

Specific examples of the structural unit (a11) include a structural unit represented by general formula (a11-0-1) shown below and a structural unit represented by general formula (a11-0-2) shown below.

[Chemical Formula 39]

(a11-0-1)

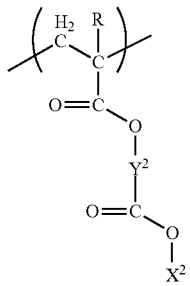

(a11-0-2)

In the formulae, R represents a hydrogen atom, an alkyl group of 1 to 5 carbon atoms or a halogenated alkyl group of 1 to 5 carbon atoms; $X^1$ represents an acid dissociable group; $Y^2$ represents a divalent linking group; and $X^2$ represents an acid dissociable group.

In general formula (a11-0-1), the alkyl group and the halogenated alkyl group for R are respectively the same as defined for the alkyl group and the halogenated alkyl group for the substituent which may be bonded to the carbon atom on the α-position of the aforementioned α-substituted acrylate ester. R is preferably a hydrogen atom, an alkyl group of 1 to 5 carbon atoms or a fluorinated alkyl group of 1 to 5 carbon atoms, and most preferably a hydrogen atom or a methyl group.

$X^1$ is not particularly limited as long as it is an acid dissociable group. Examples thereof include the aforementioned tertiary alkyl ester-type acid dissociable groups and acetal-type acid dissociable groups, and tertiary alkyl ester-type acid dissociable groups are preferable.

In general formula (a11-0-2), R is the same as defined above.

$X^2$ is the same as defined for $X^1$ in general formula (a11-0-1).

The divalent linking group for $Y^2$ is not particularly limited, and preferable examples thereof include a divalent hydrocarbon group which may have a substituent and a divalent linking group containing a hetero atom.

A hydrocarbon "has a substituent" means that part or all of the hydrogen atoms within the hydrocarbon group is substituted with a substituent (a group or an atom other than hydrogen).

The hydrocarbon group may be either an aliphatic hydrocarbon group or an aromatic hydrocarbon group.

An "aliphatic hydrocarbon group" refers to a hydrocarbon group that has no aromaticity.

The divalent aliphatic hydrocarbon group as the divalent hydrocarbon group for $Y^2$ may be either saturated or unsaturated. In general, the divalent aliphatic hydrocarbon group is preferably saturated.

As specific examples of the aliphatic hydrocarbon group, a linear or branched aliphatic hydrocarbon group, and an aliphatic hydrocarbon group containing a ring in the structure thereof can be given.

The linear or branched aliphatic hydrocarbon group preferably has 1 to 10 carbon atoms, more preferably 1 to 6, still more preferably 1 to 4, and most preferably 1 to 3.

As the linear aliphatic hydrocarbon group, a linear alkylene group is preferable, and specific examples thereof include the same linear alkylene group as those exemplified above for W in the formula (c-1-21).

As the branched aliphatic hydrocarbon group, a branched alkylene group is preferable, and specific examples thereof include the same branched alkylene group as those exemplified above for W in the formula (c-1-21).

The linear or branched aliphatic hydrocarbon group may or may not have a substituent. Examples of the substituent include a fluorine atom, a fluorinated alkyl group of 1 to 5 carbon atoms and an oxygen atom (=O).

The aliphatic hydrocarbon group containing a ring in the structure thereof is the same groups as those exemplified above for the "aliphatic hydrocarbon group containing a ring in the structure thereof" in the explanation for W in the formula (c-1-21).

Of these, a group in which two hydrogen atoms have been removed from cyclopentane, cyclohexane, adamantane or norbornane is particularly desirable.

The aromatic hydrocarbon group is a hydrocarbon group having an aromatic ring.

Examples of the aromatic hydrocarbon group as the divalent hydrocarbon group for $Y^2$ include the same divalent aromatic hydrocarbon groups as those described for W in the formula (c-1-21).

With respect to a "divalent linking group containing a hetero atom" for $Y^2$, a hetero atom is an atom other than carbon and hydrogen, and examples thereof include an oxygen atom, a nitrogen atom, a sulfur atom and a halogen atom.

As the divalent linking group containing a hetero atom, the same divalent linking group containing a hetero atom as those described above for W in the formula (c-1-21) can be mentioned, and a group represented by formula —$(CH_2)_{a'}$—C(=O)—O—$(CH_2)_{b'}$— is preferably used. In the formula, a' is an integer of 1 to 10, preferably an integer of 1 to 8, more preferably an integer of 1 to 5, still more preferably 1 or 2, and most preferably 1. b' is an integer of 1 to 10, preferably an integer of 1 to 8, more preferably an integer of 1 to 5, still more preferably 1 or 2, and most preferably 1.

Among the aforementioned examples, as the divalent linking group for $Y^2$, a linear or branched alkylene group, a divalent alicyclic hydrocarbon group or a divalent linking group containing a hetero atom is particularly desirable. Among these, an alkylene group or a divalent linking group containing a hetero atom is more preferable.

Specific examples of the structural unit (a11) include structural units represented by general formulas (a1-1) to (a1-4) shown below.

[Chemical Formula 40]

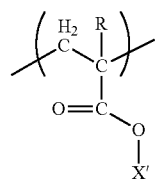

(a1-1)

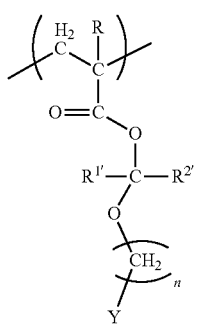
(a1-2)

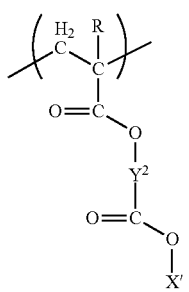
(a1-3)

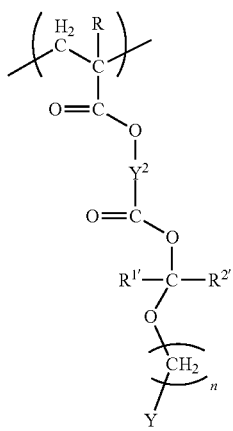
(a1-4)

In the formulas, R, $R^{1'}$, $R^{2'}$, n, Y and $Y^2$ are the same as defined above; and X' represents a tertiary alkyl ester-type acid dissociable group.

In the formulas, the tertiary alkyl ester-type acid dissociable group for X' include the same tertiary alkyl ester-type acid dissociable groups as those described above.

As $R^{1'}$, $R^{2'}$, n and Y are respectively the same as defined for $R^{1'}$, $R^{2'}$, n and Y in general formula (p1) described above in connection with the "acetal-type acid dissociable group".

$Y^2$ is the same as defined for $Y^2$ in general formula (a11-0-2).

Specific examples of structural units represented by general formulae (a1-1) to (a1-4) are shown below.

In the formulas shown below, $R^\alpha$ represents a hydrogen atom, a methyl group or a trifluoromethyl group.

[Chemical Formula 41]

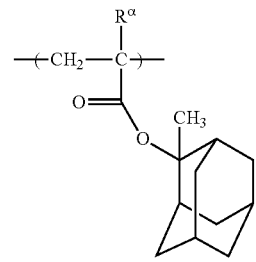
(a1-1-1)

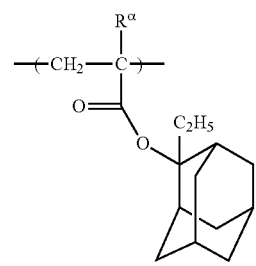
(a1-1-2)

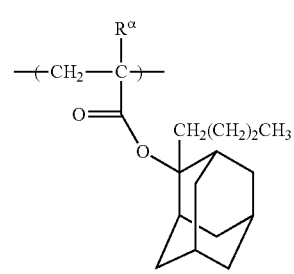
(a1-1-3)

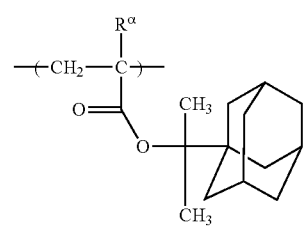
(a1-1-4)

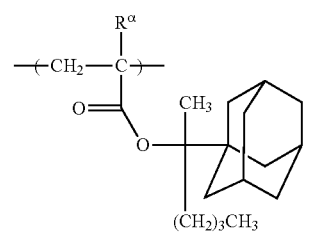
(a1-1-5)

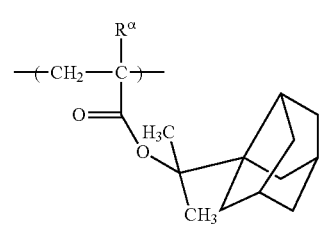
(a1-1-6)

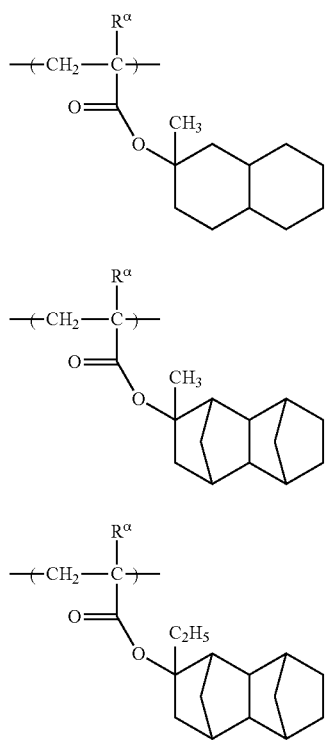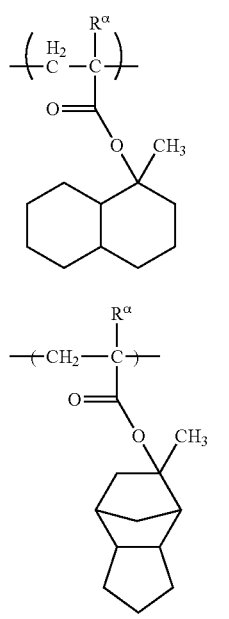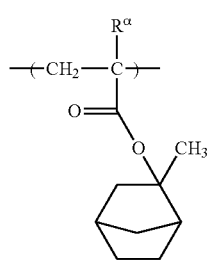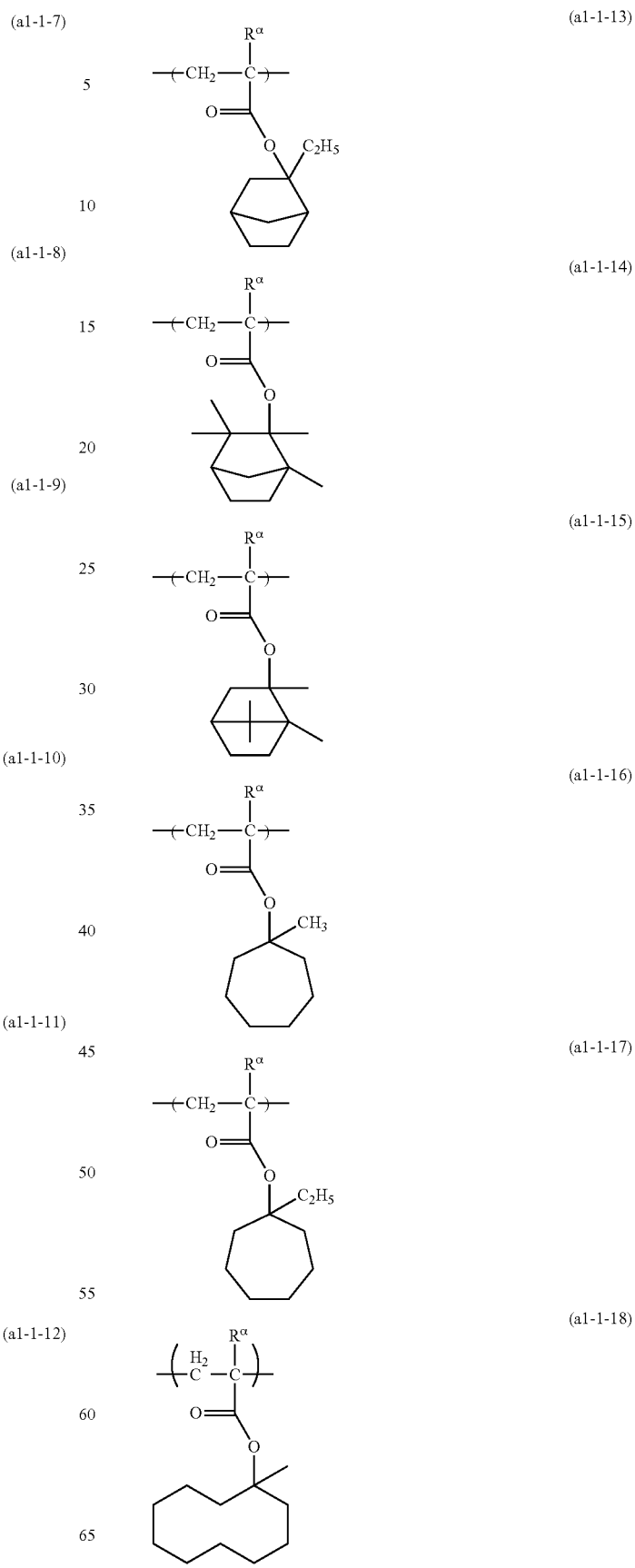

(a1-1-19) 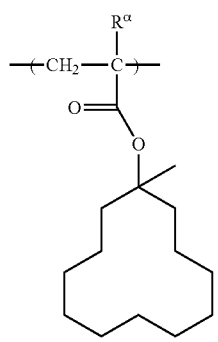
(a1-1-20) 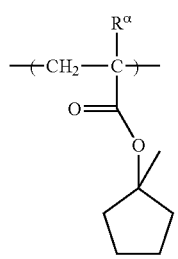
(a1-1-21) 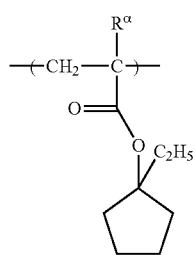
[Chemical Formula 43]
(a1-1-22) 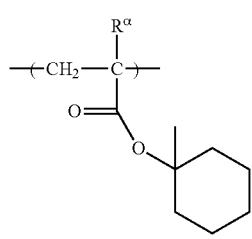
(a1-1-23) 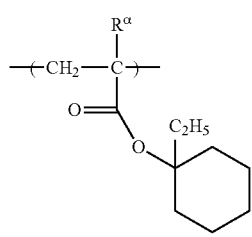
(a1-1-24) 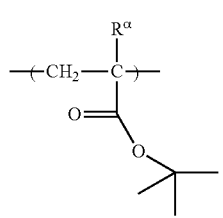
(a1-1-25) 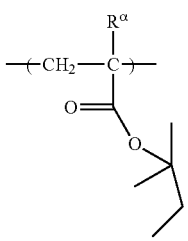
(a1-1-26) 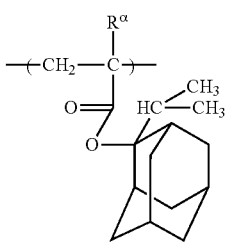
(a1-1-27) 
(a1-1-28) 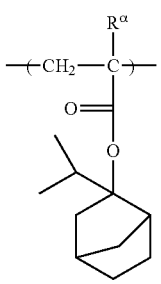
(a1-1-29) 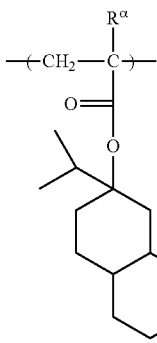

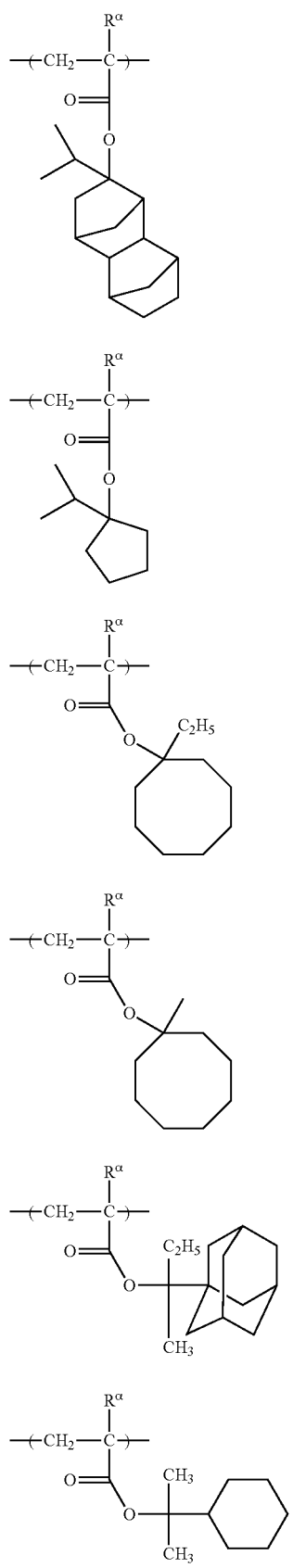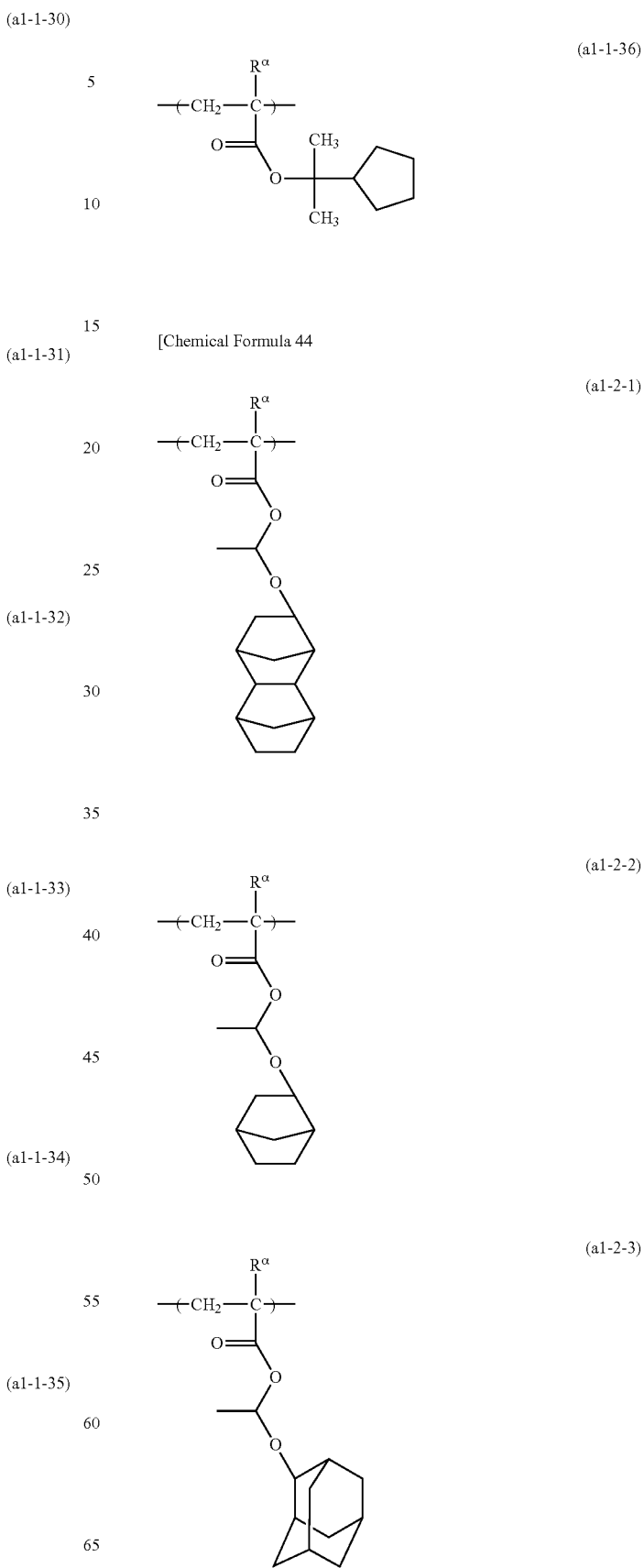

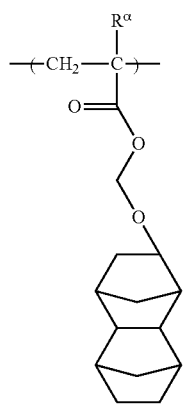
(a1-2-4)
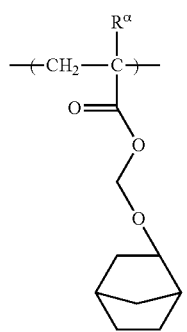
(a1-2-5)
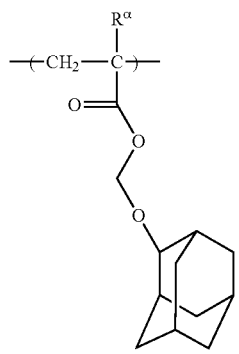
(a1-2-6)
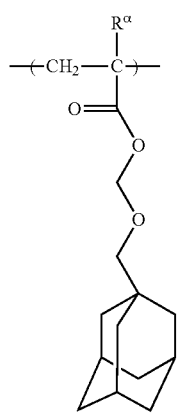
(a1-2-7)
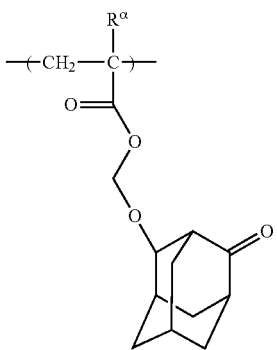
(a1-2-8)
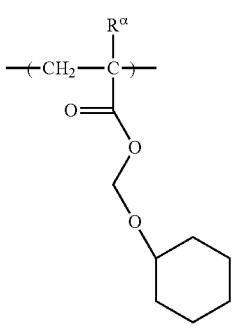
(a1-2-9)
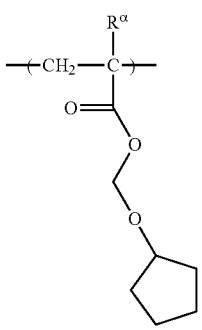
(a1-2-10)
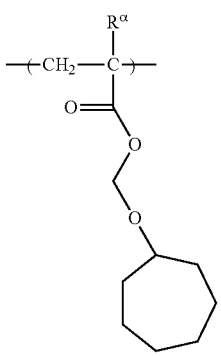
(a1-2-11)

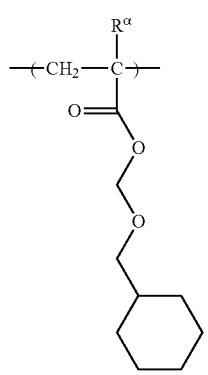 (a1-2-12)
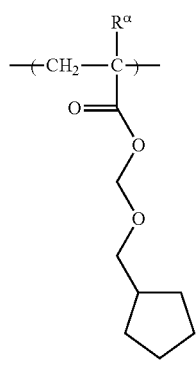 (a1-2-13)
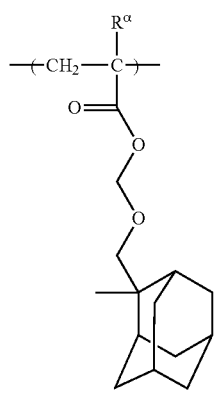 (a1-2-14)
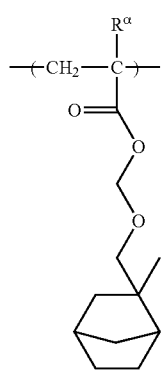 (a1-2-15)
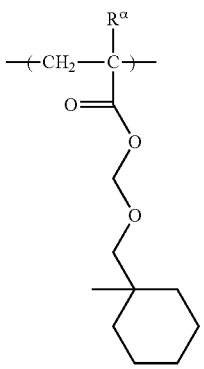 (a1-2-16)
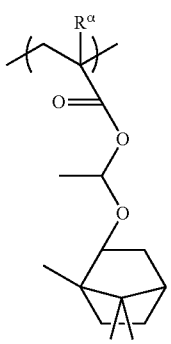 (a1-2-17)
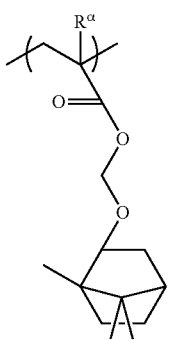 (a1-2-18)
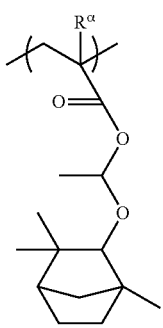 (a1-2-19)

(a1-2-20)
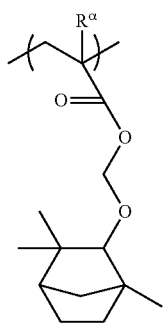
(a1-2-21)
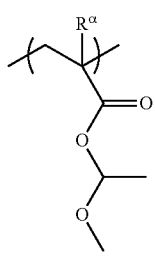
(a1-2-22)
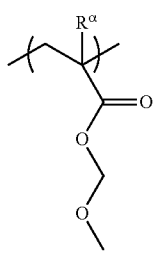
(a1-2-23)
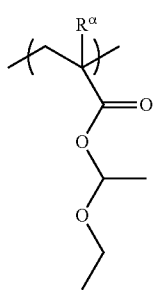
(a1-2-24)
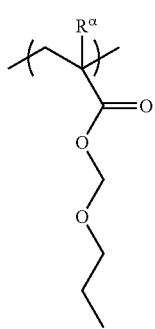
[Chemical Formula 45]
(a1-3-1)
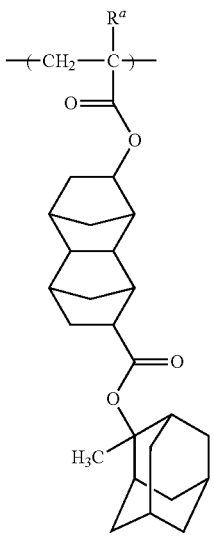
(a1-3-2)
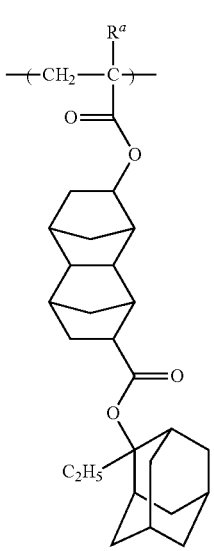
(a1-3-3)
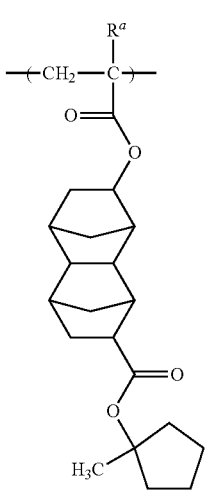

-continued
(a1-3-4)
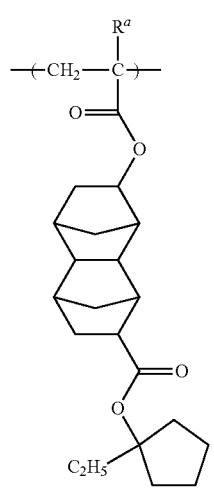
(a1-3-5)
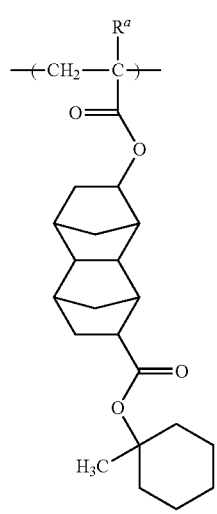
(a1-3-6)
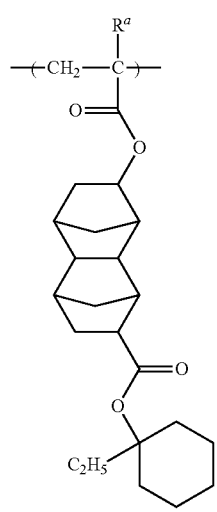
-continued
(a1-3-7)
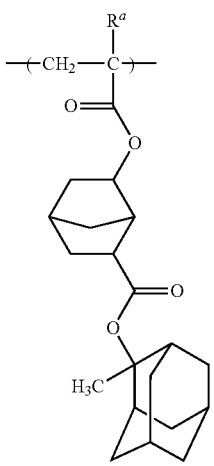
(a1-3-8)
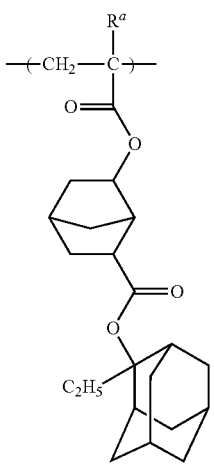
(a1-3-9)
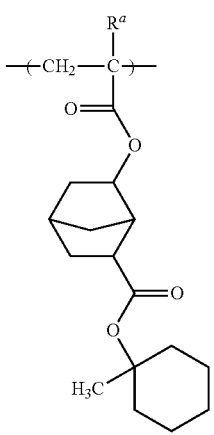

(a1-3-10) 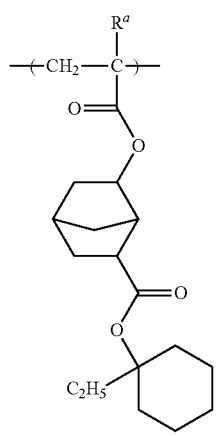
(a1-3-11) 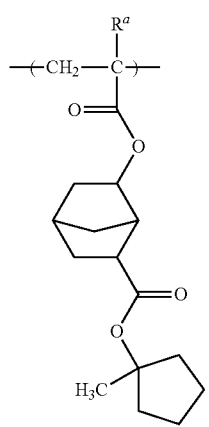
(a1-3-12) 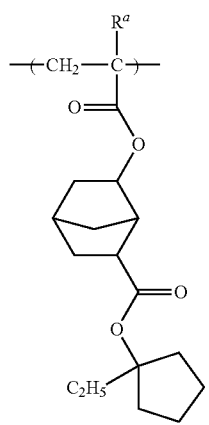
(a1-3-13) 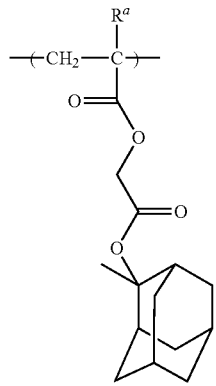
(a1-3-14) 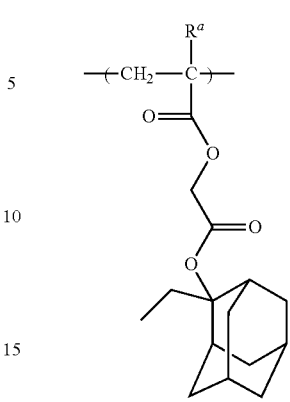
(a1-3-15) 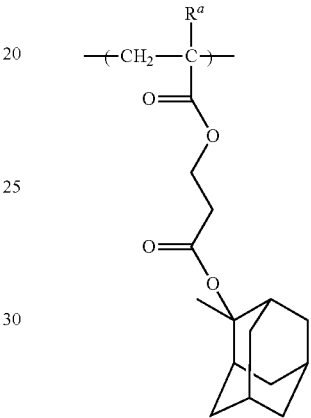
(a1-3-16) 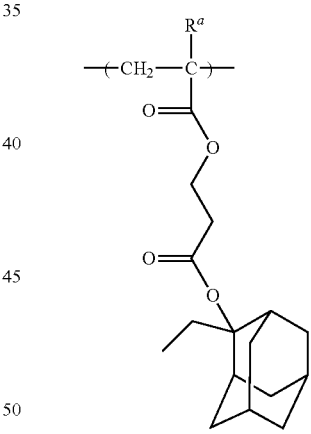
(a1-3-17) 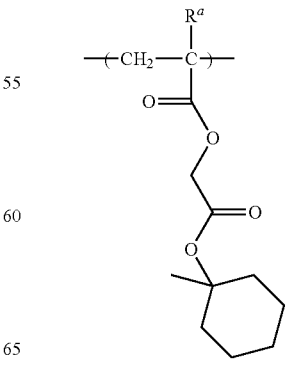

(a1-3-18)
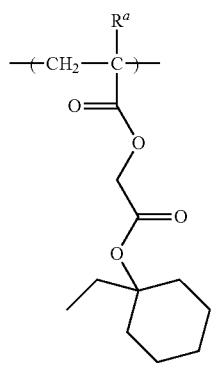
[Chemical Formula 46]
(a1-3-19)
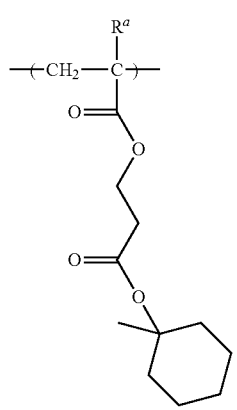
(a1-3-20)
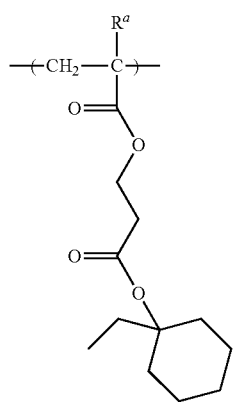
(a1-3-21)
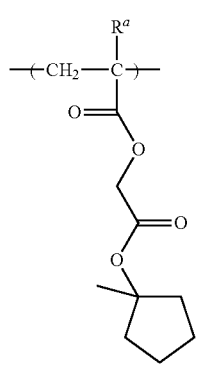
(a1-3-22)
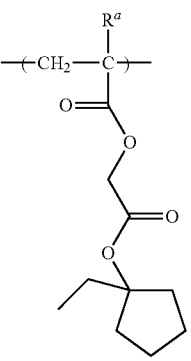
(a1-3-23)
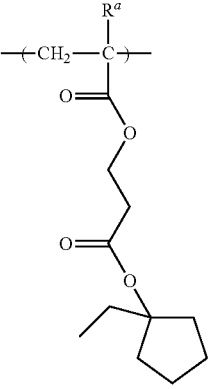
(a1-3-24)

[Chemical Formula 47]
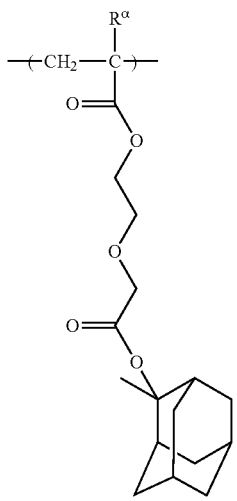
(a1-3-25)
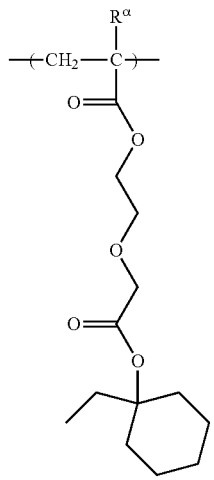
(a1-3-28)
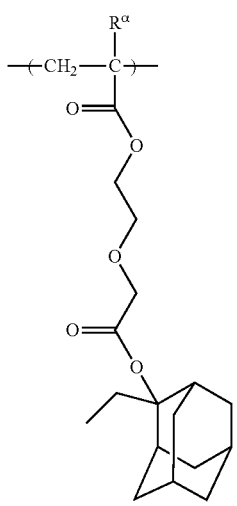
(a1-3-26)
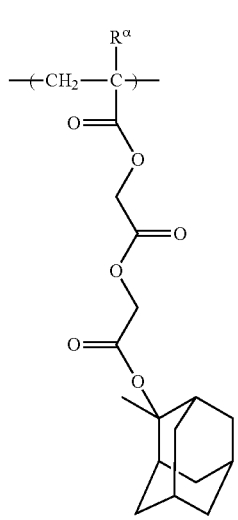
(a1-3-29)
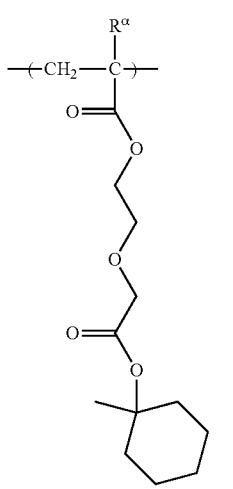
(a1-3-27)
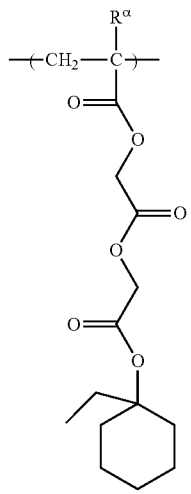
(a1-3-30)

105
-continued
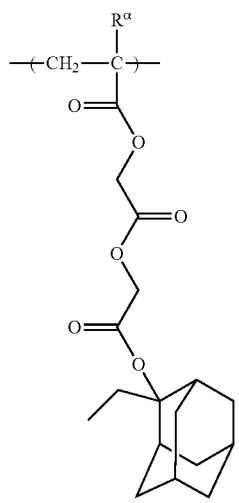
(a1-3-31)
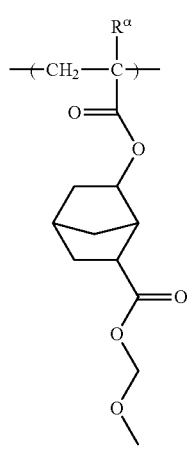
(a1-3-32)
[Chemical Formula 48]
106
-continued
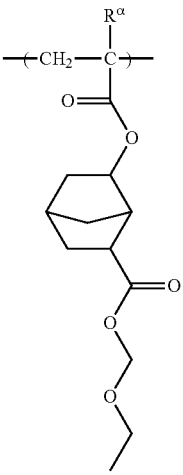
(a1-4-2)
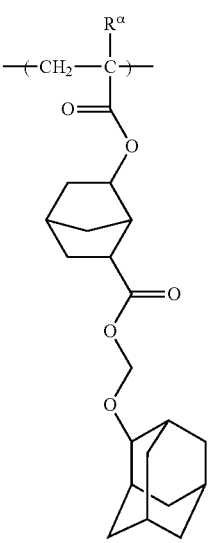
(a1-4-3)
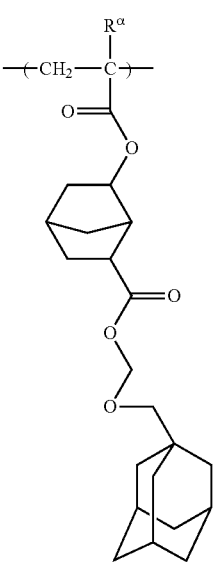
(a1-4-4)

(a1-4-5)
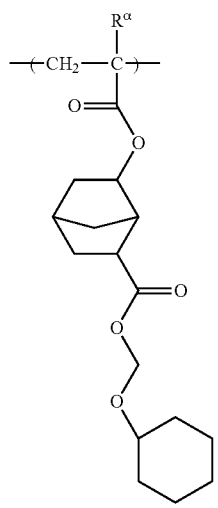
(a1-4-6)
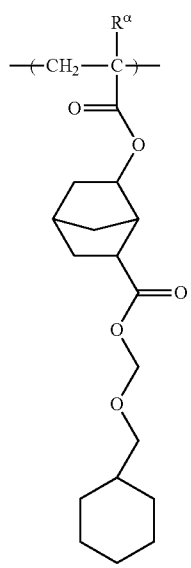
(a1-4-7)
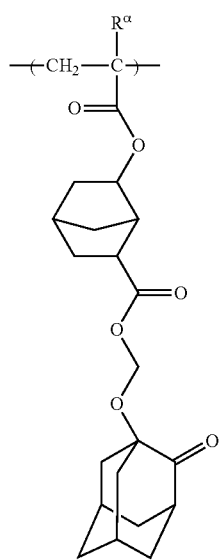
(a1-4-8)
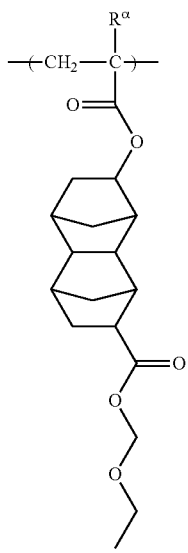
(a1-4-9)
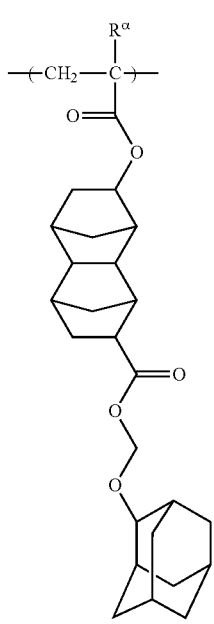

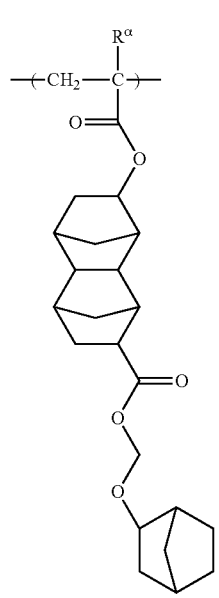
(a1-4-10)
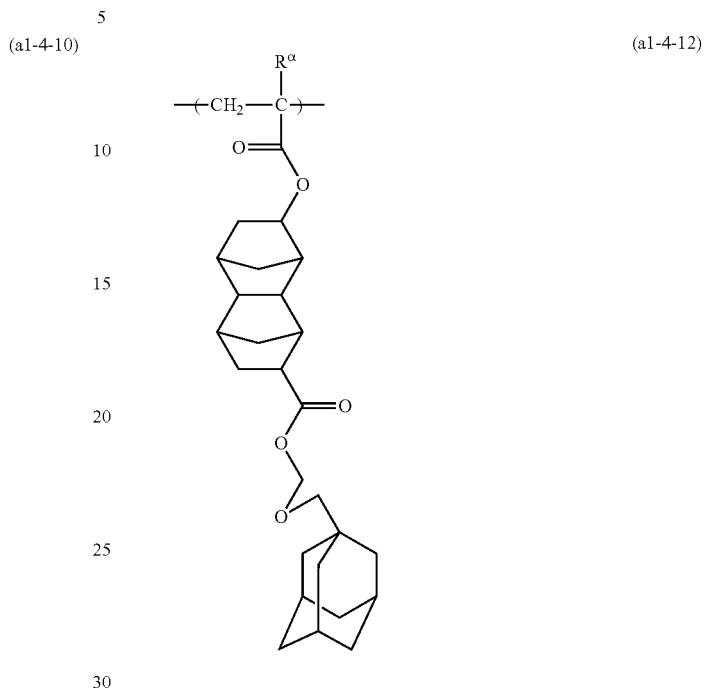
(a1-4-12)
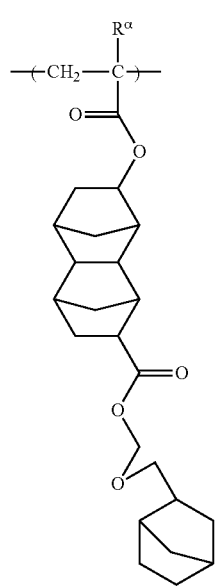
(a1-4-11)
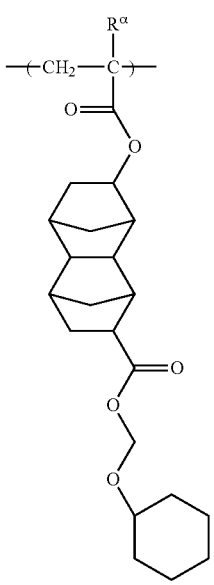
(a1-4-13)

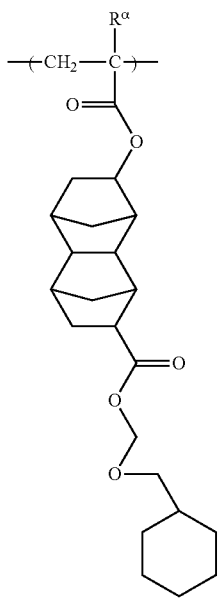
(a1-4-14)

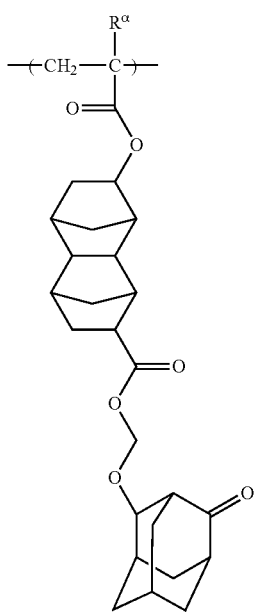
(a1-4-15)

As the structural unit (a1), one type of structural unit may be used alone, or two or more types of structural units may be used in combination.

Among these, structural units represented by general formula (a1-1), (a1-2) or (a1-3) are preferable. More specifically, at least one structural unit selected from the group consisting of structural units represented by formulas (a1-1-1) to (a-1-1-4), (a1-1-20) to (a1-1-23), (a1-2-1) to (a1-2-24) and (a1-3-25) to (a1-3-28) is more preferable.

Further, as the structural unit (a1), structural units represented by general formula (a1-1-01) shown below which include the structural units represented by formulas (a1-1-1) to (a1-1-3) and (a1-1-26), structural units represented by general formula (a1-1-02) shown below which include the structural units represented by formulas (a1-1-16), (a1-1-17), (a1-1-20) to (a1-1-23) and (a1-1-32), structural units represented by general formula (a1-1-03) which include the structural units represented by formulas (a1-1-3), (a1-2-6) and (a1-2-7), structural units represented by general formula (a1-1-04) which include the structural units represented by formulas (a1-2-3), (a1-2-6) and (a1-2-7), structural units represented by general formula (a1-3-01) shown below which include the structural units represented by formulas (a1-3-25) and (a1-3-26), structural units represented by general formula (a1-3-02) shown below which include the structural units represented by formulas (a1-3-27) and (a1-3-28), and structural units represented by general formula (a1-3-03) shown below which include the structural units represented by formulas (a1-3-29) and (a1-3-30) are also preferable.

[Chemical Formula 49]

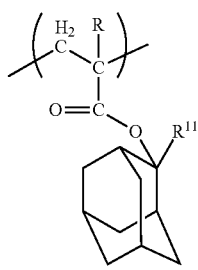
(a1-1-01)

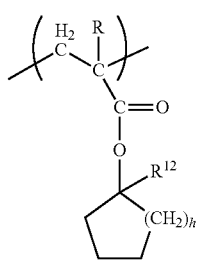
(a1-1-02)

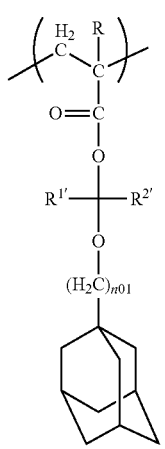
(a1-1-03)

(a1-1-04)

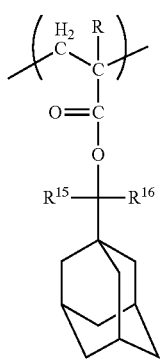

In the formulae, $R^{11}$ represents an alkyl group of 1 to 5 carbon atoms; $R^{12}$ represents an alkyl group of 1 to 7 carbon atoms; and h represents an integer of 1 to 6; and R, $R^{1'}$, $R^{2'}$, n01, $R^{15}$ and $R^{16}$ are the same as defined above.

In general formula (a1-1-01), R is the same as defined above. The alkyl group of 1 to 5 carbon atoms for $R^{11}$ is the same as defined for the alkyl group of 1 to 5 carbon atoms for R, and a methyl group, an ethyl group or an isopropyl group is preferable.

In general formula (a1-1-02), R is the same as defined above. The alkyl group of 1 to 5 carbon atoms for $R^{12}$ is the same as defined for the alkyl group of 1 to 5 carbon atoms for R, and a methyl group, an ethyl group or an isopropyl group is preferable. h is preferably 1 or 2, and most preferably 2.

In general formula (a1-1-03), R, $R^{1'}$, $R^{2'}$ and n01 are the same as defined above.

In general formula (a1-1-04), R, $R^{15}$ and $R^{16}$ are the same as defined above.

In the present invention, as the structural unit (a11), it is preferable to include at least one structural unit selected from the group consisting of a structural unit represented by general formula (a11-0-11) shown below, a structural unit represented by general formula (a11-0-12) shown below, a structural unit represented by general formula (a11-0-13) shown below, a structural unit represented by general formula (a11-0-14) shown below, a structural unit represented by general formula (a11-0-15) shown below and a structural unit represented by general formula (a11-0-2) shown below.

Among these examples, as the structural unit (a11), it is preferable to include at least one structural unit selected from the group consisting of a structural unit represented by general formula (a11-0-11) shown below, a structural unit represented by general formula (a11-0-12) shown below, a structural unit represented by general formula (a11-0-13) shown below, a structural unit represented by general formula (a11-0-14) shown below and a structural unit represented by general formula (a11-0-15) shown below.

[Chemical Formula 50]

(a11-0-11)

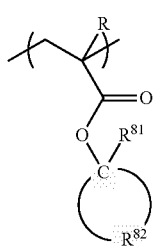

(a11-0-12)

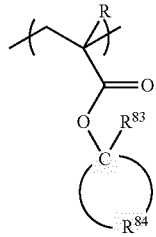

(a11-0-13)

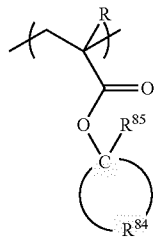

(a11-0-14)

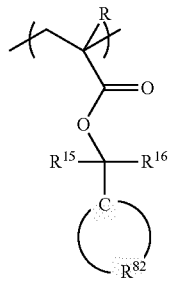

(a11-0-15)

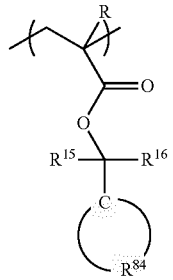

(a11-0-2)

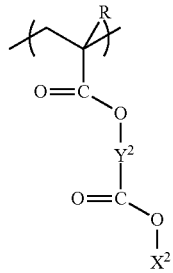

In the formulae, R represents a hydrogen atom, an alkyl group of 1 to 5 carbon atoms or a halogenated alkyl group of 1 to 5 carbon atoms; $R^{81}$ represents an alkyl group; $R^{82}$ represents a group which forms an aliphatic monocyclic group with the carbon atom to which $R^{82}$ is bonded; $R^{83}$ represents a branched alkyl group; $R^{84}$ represents a group which forms an aliphatic polycyclic group with the carbon atom to which $R^{84}$ is bonded; $R^{85}$ represents a linear alkyl group of 1 to 5 carbon atoms; $R^{15}$ and $R^{16}$ each independently represents an alkyl group; $Y^2$ represents a divalent linking group; and $X^2$ represents an acid dissociable group.

In the formulae, R, $Y^2$ and $X^2$ are the same as defined above.

In general formula (a11-0-11), as the alkyl group for $R^{81}$, the same alkyl groups as those described above for $R^{14}$ in formulae (1-1) to (1-9) can be used, preferably a methyl group, an ethyl group or an isopropyl group.

As the aliphatic monocyclic group formed by $R^{82}$ and the carbon atoms to which $R^{82}$ is bonded, the same aliphatic cyclic groups as those described above for the aforementioned tertiary alkyl ester-type acid dissociable group and which are monocyclic can be used. Specific examples include groups in which one or more hydrogen atoms have been removed from a monocycloalkane. The monocycloalkane is preferably a 3- to 11-membered ring, more preferably a 3- to 8-membered ring, still more preferably a 4- to 6-membered ring, and most preferably a 5- or 6-membered ring.

The monocycloalkane may or may not have part of the carbon atoms constituting the ring replaced with an ether bond (—O—).

Further, the monocycloalkane may have a substituent such as an alkyl group of 1 to 5 carbon atoms, a fluorine atom or a fluorinated alkyl group of 1 to 5 carbon atoms.

As an examples of $R^{82}$ constituting such an aliphatic monocyclic group, a linear alkylene group which may have an ether bond (—O—) interposed between the carbon atoms can be given.

Specific examples of structural units represented by general formula (a11-0-11) include structural units represented by the aforementioned formulas (a1-1-16) to (a1-1-23), (a1-1-27) and (a1-1-31). Among these, a structural unit represented by general formula (a11-1-02) shown below which includes the structural units represented by the aforementioned formulas (a1-1-16), (a1-1-17), (a1-1-20) to (a1-1-23), (a1-1-27), (a1-1-31), (a1-1-32) and (a1-1-33) is preferable. Further, a structural unit represented by general formula (a11-1-02') shown below is also preferable.

In the formulas, h represents an integer of 1 to 4, and preferably 1 or 2.

[Chemical Formula 51]

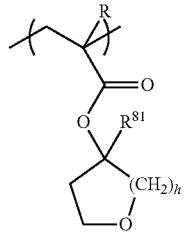

(a11-1-02)

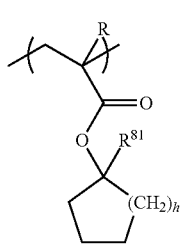

(a11-1-02')

In the formulae, R and $R^{81}$ are the same as defined above; and h represents an integer of 1 to 4.

In general formula (a11-0-12), as the branched alkyl group for $R^{83}$, the same alkyl groups as those described above for $R^{14}$ in formulas (1-1) to (1-9) which are branched can be used, and an isopropyl group is particularly desirable.

As the aliphatic polycyclic group formed by $R^{84}$ and the carbon atoms to which $R^{84}$ is bonded, the same aliphatic cyclic groups as those described above for the aforementioned tertiary alkyl ester-type acid dissociable group and which are polycyclic can be used.

Specific examples of structural units represented by general formula (a11-0-12) include structural units represented by the aforementioned formulas (a1-1-26) and (a1-1-28) to (a1-1-30).

As the structural unit (a11-0-12), a structural unit in which the aliphatic polycyclic group formed by $R^{84}$ and the carbon atom to which $R^{84}$ is bonded is a 2-adamantyl group is preferable, and a structural unit represented by the aforementioned formula (a1-1-26) is particularly desirable.

In general formula (a11-0-13), R and $R^{84}$ are the same as defined above.

As the linear alkyl group for $R^{85}$, the same linear alkyl groups as those described above for $R^{14}$ in the aforementioned formulas (1-1) to (1-9) can be mentioned, and a methyl group or an ethyl group is particularly desirable.

Specific examples of structural units represented by general formula (a11-0-13) include structural units represented by the aforementioned formulas (a1-1-1), (a1-1-2) and (a1-1-7) to (a1-1-15) which were described above as specific examples of the structural unit represented by general formula (a1-1).

As the structural unit (a11-0-13), a structural unit in which the aliphatic polycyclic group formed by $R^{84}$ and the carbon atom to which $R^{84}$ is bonded is a 2-adamantyl group is preferable, and a structural unit represented by the aforementioned formula (a1-1-1) or (a1-1-2) is particularly desirable.

Further, a compound in which the aliphatic polycyclic group formed by $R^{84}$ and the carbon atom to which $R^{84}$ is bonded is a "group in which one or more hydrogen atoms have been removed from tetracyclododecane" is also preferable, and a compound represented by the aforementioned formula (a1-1-8), (a1-1-9) or (a1-1-30) is also preferable.

In general formula (a11-0-14), R and $R^{82}$ are the same as defined above. $R^{15}$ and $R^{16}$ are the same as $R^{15}$ and $R^{16}$ in the aforementioned general formulae (2-1) to (2-6), respectively.

Specific examples of structural units represented by general formula (a11-0-14) include structural units represented by the aforementioned formulae (a1-1-35) and (a1-1-36) which were described above as specific examples of the structural unit represented by general formula (a1-1).

In general formula (a11-0-15), R and $R^{84}$ are the same as defined above. $R^{15}$ and $R^{16}$ are the same as $R^{15}$ and $R^{16}$ in the aforementioned general formulae (2-1) to (2-6), respectively.

Specific examples of structural units represented by general formula (a11-0-15) include structural units represented by the aforementioned formulas (a1-1-4) to (a1-1-6) and (a1-1-34) which were described above as specific examples of the structural unit represented by general formula (a1-1).

Examples of structural units represented by general formula (a11-1-2) include structural units represented by the aforementioned formulas (a1-3) and (a1-4), and a structural unit represented by formula (a1-3) is particularly preferable.

As a structural unit represented by general formula (a11-1-2), those in which $Y^2$ is a group represented by the aforementioned formula —$Y^{21}$—O—$Y^{22}$— or —$Y^{21}$—C(=O)—O—$Y^{22}$— is particularly desirable.

Preferable examples of such structural units include a structural unit represented by general formula (a1-3-01) shown below, a structural unit represented by general formula (a1-3-02) shown below, and a structural unit represented by general formula (a1-3-03) shown below.

[Chemical Formula 52]

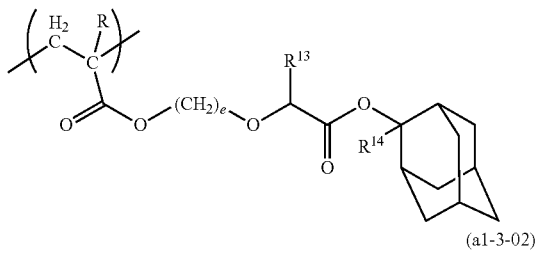

(a1-3-01)

(a1-3-02)

In the formulas, R is the same as defined above; $R^{13}$ represents a hydrogen atom or a methyl group; $R^{14}$ represents an alkyl group; e represents an integer of 1 to 10; and n' represents an integer of 0 to 6.

[Chemical Formula 53]

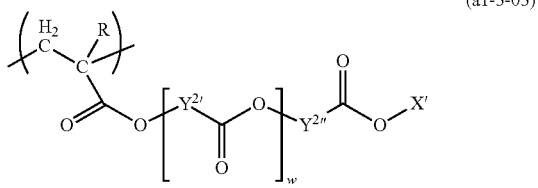

(a1-3-03)

In the formula, R is as defined above; each of $Y^{2'}$ and $Y^{2''}$ independently represents a divalent linking group; X' represents an acid dissociable group; and w represents an integer of 0 to 3.

In general formulas (a1-3-01) and (a1-3-02), $R^{13}$ is preferably a hydrogen atom.

$R^{14}$ is the same as defined for $R^{14}$ in the aforementioned formulas (1-1) to (1-9).

e is preferably an integer of 1 to 8, more preferably 1 to 5, still more preferably 2 to 5, particularly preferably 1 or 2, and most preferably 2.

n' represents an integer of 1 to 6, preferably an integer of 0 to 3, more preferably 1 or 2, and most preferably 2.

Specific examples of structural units represented by general formula (a1-3-01) include structural units represented by the aforementioned formulas (a1-3-25) and (a1-3-26).

Specific examples of structural units represented by general formula (a1-3-02) include structural units represented by the aforementioned formulas (a1-3-27) and (a1-3-28).

In general formula (a1-3-03), as the divalent linking group for $Y^{2'}$ and $Y^{2''}$, the same groups as those described above for $Y^2$ in general formula (a1-3) can be used.

As $Y^{2'}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As $Y^{2''}$, a divalent hydrocarbon group which may have a substituent is preferable, a linear aliphatic hydrocarbon group is more preferable, and a linear alkylene group is still more preferable. Among linear alkylene groups, a linear alkylene group of 1 to 5 carbon atoms is preferable, and a methylene group or an ethylene group is particularly desirable.

As the acid dissociable group for X', the same groups as those described above can be used. X' is preferably a tertiary alkyl ester-type acid dissociable group, more preferably the aforementioned group (i) in which a substituent is bonded to the carbon atom to which an atom adjacent to the acid dissociable group is bonded to on the ring skeleton of a monovalent aliphatic cyclic group to form a tertiary carbon atom. Among these, a group represented by the aforementioned general formula (1-1) is particularly desirable.

w represents an integer of 0 to 3, preferably an integer of 0 to 2, more preferably 0 or 1, and most preferably 1.

As the structural unit represented by general formula (a1-3-03), a structural unit represented by general formula (a1-3-03-1) or (a1-3-03-2) shown below is preferable, and a structural unit represented by general formula (a1-3-03-1) is particularly desirable.

[Chemical Formula 54]

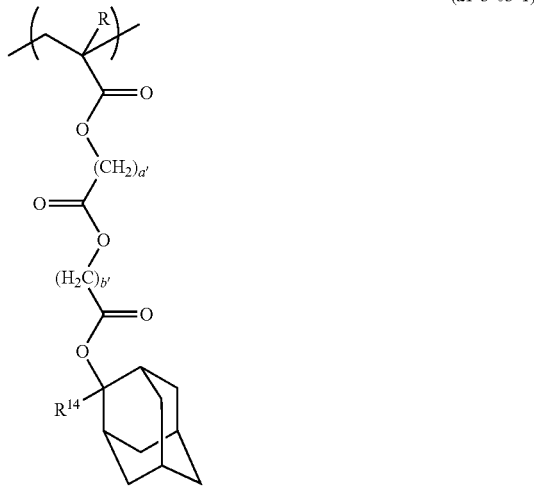

(a1-3-03-1)

-continued

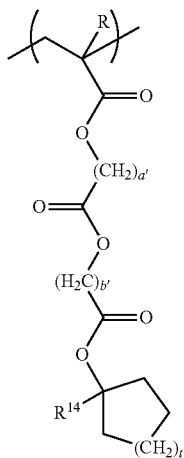

(a1-3-03-2)

In the formulas, R and $R^{14}$ are the same as defined above; a' represents an integer of 1 to 10; b' represents an integer of 1 to 10; and t represents an integer of 0 to 3.

In general formulas (a1-3-03-1) and (a1-3-03-2), a' is the same as defined above, preferably an integer of 1 to 8, more preferably 1 to 5, and most preferably 1 or 2.

b' is the same as defined above, preferably an integer of 1 to 8, more preferably 1 to 5, and most preferably 1 or 2.

t is preferably an integer of 1 to 3, and most preferably 1 or 2.

Specific examples of structural units represented by general formula (a1-3-03-1) or (a1-3-03-2) include structural units represented by the aforementioned formulas (a1-3-29) to (a1-3-32).

Structural Unit (a12) and Structural Unit (a13):

In the present specification, the structural unit (a12) is a structural unit in which at least a part of the hydrogen atom within the phenolic hydroxy group of hydroxystyrene or a derivative thereof is protected with a substituent containing an acid decomposable group.

Further, the structural unit (a13) is a structural unit in which at least a part of the hydrogen atom within —C(=O)—OH of vinylbenzoic acid or a derivative thereof is protected with a substituent containing an acid decomposable group.

In the structural units (a12) and (a13), as the substituent containing an acid decomposable group, the tertiary alkyl ester-type acid dissociable group and the acetal-type acid dissociable group described above for the structural unit (a11) can be given as preferable examples.

As the structural unit (a1) contained in the polymeric compound (A1) or (A1'), 1 type of structural unit may be used, or 2 or more types may be used.

As the structural unit (a1), a structural unit (a11) derived from an acrylate ester which may have the hydrogen atom bonded to the carbon atom on the α-position substituted with a substituent is preferable.

In the polymeric compound (A) or (A1'), the amount of the structural unit (a1) based on the combined total of all structural units constituting the polymeric compound is preferably 5 to 80 mol %, more preferably 10 to 75 mol %, still more preferably 15 to 70 mol %, particularly preferably 15 to 60 mol %, and most preferably 20 to 55 mol %.

When the amount of the structural unit (a1) is at least as large as the lower limit of the above-mentioned range, a pattern can be easily formed using a resist composition prepared from the polymeric compound (A1) or (A1') and various lithography properties such as sensitivity, resolution, LWR and the like are improved. On the other hand, when the amount of the structural unit (a1) is no more than the upper limit of the above-mentioned range, a good balance can be reliably achieved with the other structural units.

(Structural Unit (a2))

By virtue of the structural unit (a2) containing a —$SO_2$— containing cyclic group or a lactone-containing cyclic group, a resist composition containing the polymeric compound (A1) or (A1') including the structural unit (a2) is capable of improving the adhesion of a resist film to a substrate, and increasing the compatibility with the developing solution containing water (especially in the case of alkali developing process), thereby contributing to improvement of lithography properties.

The structural unit (a2) is preferably at least one structural unit (a2') selected from the group consisting of a structural unit derived from an acrylate ester which may have the hydrogen atom bonded to the carbon atom on the α-position substituted with a substituent and contains an —$SO_2$— containing cyclic group (hereafter, referred to as "structural unit (a2$^S$)"), and a structural unit derived from an acrylate ester which may have the hydrogen atom bonded to the carbon atom on the α-position substituted with a substituent and contains a lactone-containing cyclic group (hereafter, referred to as "structural unit (a2$^L$)").

Here, an "—$SO_2$— containing cyclic group" refers to a cyclic group having a ring containing —$SO_2$— within the ring structure thereof, i.e., a cyclic group in which the sulfur atom (S) within —$SO_2$— forms part of the ring skeleton of the cyclic group. The ring containing —$SO_2$— within the ring skeleton thereof is counted as the first ring. A cyclic group in which the only ring structure is the ring that contains —$SO_2$— in the ring skeleton thereof is referred to as a monocyclic group, and a group containing other ring structures is described as a polycyclic group regardless of the structure of the other rings. The —$SO_2$— containing cyclic group may be either a monocyclic group or a polycyclic group.

As the —$SO_2$— containing cyclic group, a cyclic group containing —O—$SO_2$— within the ring skeleton thereof, i.e., a cyclic group containing a sultone ring in which —O—S— within the —O—$SO_2$— group forms part of the ring skeleton thereof is particularly desirable.

The —$SO_2$— containing cyclic group preferably has 3 to 30 carbon atoms, more preferably 4 to 20, still more preferably 4 to 15, and most preferably 4 to 12. Herein, the number of carbon atoms refers to the number of carbon atoms constituting the ring skeleton, excluding the number of carbon atoms within a substituent.

The —$SO_2$— containing cyclic group may be either a —$SO_2$— containing aliphatic cyclic group or a —$SO_2$— containing aromatic cyclic group. A —$SO_2$— containing aliphatic cyclic group is preferable.

Examples of the —$SO_2$— containing aliphatic cyclic group include aliphatic cyclic groups in which part of the carbon atoms constituting the ring skeleton has been substituted with a —$SO_2$— group or a —O—$SO_2$— group and has at least one hydrogen atom removed from the aliphatic hydrocarbon ring. Specific examples include an aliphatic hydrocarbon ring in which a —$CH_2$— group constituting the ring skeleton thereof has been substituted with a —$SO_2$— group and has at least one hydrogen atom removed therefrom; and an aliphatic hydrocarbon ring in which a —$CH_2$—$CH_2$— group constituting the ring skeleton has been substituted with a —O—$SO_2$— group and has at least one hydrogen atom removed therefrom.

The alicyclic hydrocarbon ring preferably has 3 to 20 carbon atoms, and more preferably 3 to 12 carbon atoms.

The alicyclic hydrocarbon ring may be either a monocyclic group or a polycyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The —$SO_2$— containing cyclic group may have a substituent. Examples of substituents include an alkyl group, an alkoxy group, a halogen atom, a halogenated alkyl group, a hydroxy group, an oxygen atom (=O), —COOR", —OC(=O)R", a hydroxyalkyl group and a cyano group.

The alkyl group for the substituent is preferably an alkyl group of 1 to 6 carbon atoms. Further, the alkyl group is preferably a linear alkyl group or a branched alkyl group. Specific examples include a methyl group, an ethyl group, a propyl group, an isopropyl group, an n-butyl group, an isobutyl group, a tert-butyl group, a pentyl group, an isopentyl group, a neopentyl group and a hexyl group. Among these, a methyl group or an ethyl group is preferable, and a methyl group is particularly desirable.

As the alkoxy group for the substituent, an alkoxy group of 1 to 6 carbon atoms is preferable. Further, the alkoxy group is preferably a linear or branched alkoxy group. Specific examples of the alkoxy groups include the aforementioned alkyl groups for the substituent having an oxygen atom (—O—) bonded thereto.

Examples of the halogen atom for the substituent include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

As examples of the halogenated alkyl group for the substituent, groups in which part or all of the hydrogen atoms of the aforementioned alkyl groups for the substituent have been substituted with the aforementioned halogen atoms can be given. As the halogenated alkyl group, a fluorinated alkyl group is preferable, and a perfluoroalkyl group is particularly desirable.

In the —COOR" group and the —OC(=O)R" group, R" represents a hydrogen atom or a linear, branched or cyclic alkyl group of 1 to 15 carbon atoms.

When R" represents a linear or branched alkyl group, it is preferably an alkyl group of 1 to 10 carbon atoms, more preferably an alkyl group of 1 to 5 carbon atoms, and most preferably a methyl group or an ethyl group.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

The hydroxyalkyl group for the substituent preferably has 1 to 6 carbon atoms, and specific examples thereof include the aforementioned alkyl groups for the substituent in which at least one hydrogen atom has been substituted with a hydroxy group.

More specific examples of the —$SO_2$— containing cyclic group include groups represented by general formulas (3-1) to (3-4) shown below.

[Chemical Formula 55]

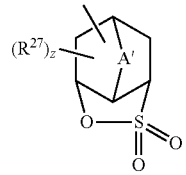

(3-1)

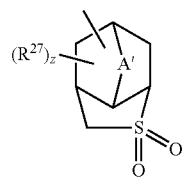

(3-2)

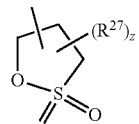

(3-3)

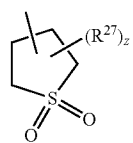

(3-4)

In the formulae, A' represents an oxygen atom, a sulfur atom or an alkylene group of 1 to 5 carbon atoms which may contain an oxygen atom or a sulfur atom; z represents an integer of 0 to 2; and $R^{27}$ represents an alkyl group, an alkoxy group, a halogenated alkyl group, a hydroxyl group, —COOR", —OC(=O)R", a hydroxyalkyl group or a cyano group, wherein R" represents a hydrogen atom or an alkyl group.

In general formulas (3-1) to (3-4) above, A' represents an oxygen atom (—O—), a sulfur atom (—S—) or an alkylene group of 1 to 5 carbon atoms which may contain an oxygen atom or a sulfur atom.

As the alkylene group of 1 to 5 carbon atoms for A', a linear or branched alkylene group is preferable, and examples thereof include a methylene group, an ethylene group, an n-propylene group and an isopropylene group.

Examples of alkylene groups that contain an oxygen atom or a sulfur atom include the aforementioned alkylene groups in which —O— or —S— is bonded to the terminal of the alkylene group or present between the carbon atoms of the alkylene group. Specific examples of such alkylene groups include —O—$CH_2$—, —$CH_2$—O—$CH_2$—, —S—$CH_2$— and —$CH_2$—S—$CH_2$—.

As A', an alkylene group of 1 to 5 carbon atoms or —O— is preferable, more preferably an alkylene group of 1 to 5 carbon atoms, and most preferably a methylene group.

z represents an integer of 0 to 2, and is most preferably 0.

If there are two of the $R^{27}$ group, as indicated by the value z, then the two of the $R^{27}$ group may be the same or different from each other.

As the alkyl group, alkoxy group, halogenated alkyl group, —COOR″, —OC(=O)R″ and hydroxyalkyl group for $R^{27}$, the same alkyl groups, alkoxy groups, halogenated alkyl groups, —COOR″, —OC(=O)R″ and hydroxyalkyl groups as those described above as the substituent for the —$SO_2$— containing cyclic group can be mentioned.

Specific examples of the cyclic groups represented by general formulas (3-1) to (3-4) are shown below. In the formulas shown below, "Ac" represents an acetyl group.

[Chemical Formula 56]

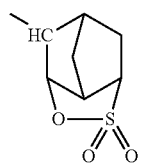 (3-1-1)

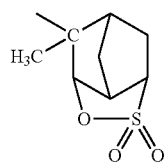 (3-1-2)

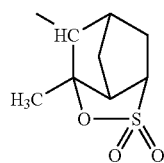 (3-1-3)

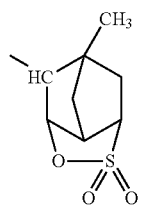 (3-1-4)

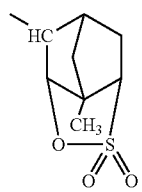 (3-1-5)

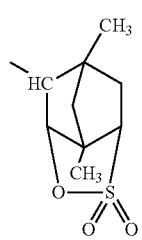 (3-1-6)

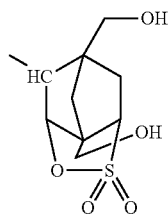 (3-1-7)

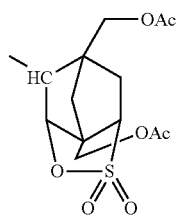 (3-1-8)

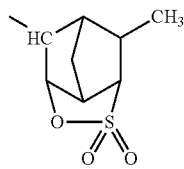 (3-1-9)

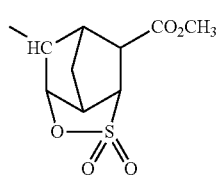 (3-1-10)

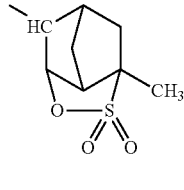 (3-1-11)

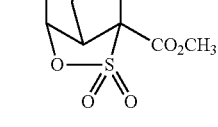 (3-1-12)

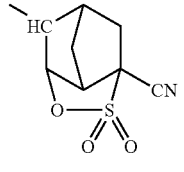 (3-1-13)

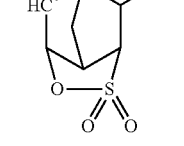 (3-1-14)

-continued
(3-1-15)
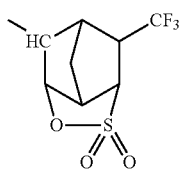
(3-1-16)
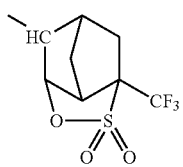
(3-1-17)
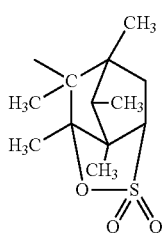
(3-1-18)
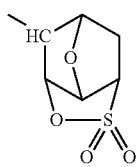
(3-1-19)
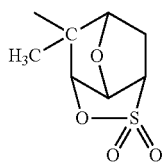
(3-1-20)
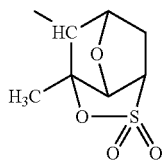
(3-1-21)
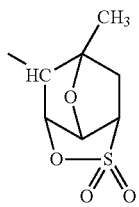
[Chemical Formula 57]
(3-1-22)
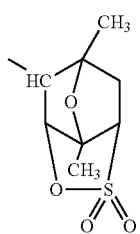
-continued
(3-1-23)
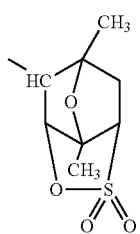
(3-1-24)
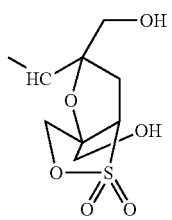
(3-1-25)
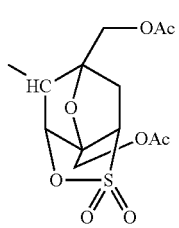
(3-1-26)
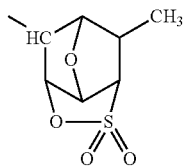
(3-1-27)
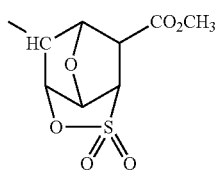
(3-1-28)
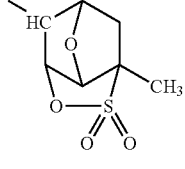
(3-1-29)
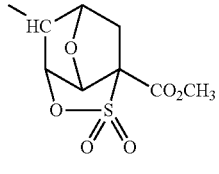
(3-1-30)
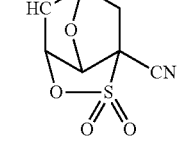

(3-1-31) 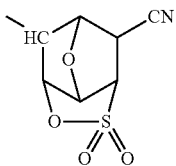

(3-1-32) 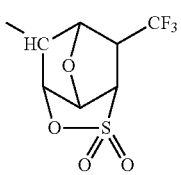

(3-1-33) 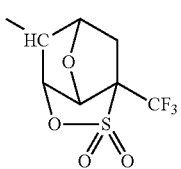

[Chemical Formula 58]

(3-2-1) 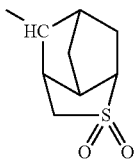

(3-2-2) 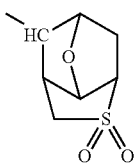

(3-3-1) 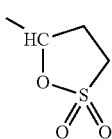

(3-4-1) 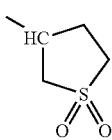

As the —SO$_2$— containing cyclic group, a group represented by the aforementioned general formula (3-1) is preferable, at least one member selected from the group consisting of groups represented by the aforementioned chemical formulas (3-1-1), (3-1-18), (3-3-1) and (3-4-1) is more preferable, and a group represented by chemical formula (3-1-1) is most preferable.

The term "lactone-containing cyclic group" refers to a cyclic group including a ring containing a —O—C(=O)— structure (lactone ring). The term "lactone ring" refers to a single ring containing a —O—C(=O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings. The lactone-containing cyclic group may be either a monocyclic group or a polycyclic group.

The lactone-containing cyclic group for the structural unit (a2$^L$) is not particularly limited, and an arbitrary structural unit may be used. Specific examples of lactone-containing monocyclic groups include a group in which one hydrogen atom has been removed from a 4- to 6-membered lactone ring, such as a group in which one hydrogen atom has been removed from β-propionolactone, a group in which one hydrogen atom has been removed from γ-butyrolactone, and a group in which one hydrogen atom has been removed from δ-valerolactone. Further, specific examples of lactone-containing polycyclic groups include groups in which one hydrogen atom has been removed from a lactone ring-containing bicycloalkane, tricycloalkane or tetracycloalkane.

With respect to the structural unit (a2), there is not particular limitation to the structure of the other portion, as long as the structural unit has a —SO$_2$— containing cyclic group or a lactone-containing cyclic group. The structural unit (a2) is preferably at least one structural unit selected from the group consisting of a structural unit (a2$^S$) derived from an acrylate ester which may have the hydrogen atom bonded to the carbon atom on the α-position substituted with a substituent and contains an —SO$_2$— containing cyclic group, and a structural unit (a2$^L$) derived from an acrylate ester which may have the hydrogen atom bonded to the carbon atom on the α-position substituted with a substituent and contains a lactone-containing cyclic group.

Structural Unit (a2$^S$):

More specific examples of the structural unit (a2$^S$) include structural units represented by general formula (a2-0) shown below.

[Chemical Formula 59]

(a2-0)

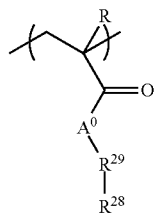

In the formula, R represents a hydrogen atom, an alkyl group of 1 to 5 carbon atoms or a halogenated alkyl group of 1 to 5 carbon atoms; A$^0$ represents —O— or —NH—; R$^{28}$ represents an —SO$_2$— containing cyclic group; and R$^{29}$ represents a single bond or a divalent linking group.

In general formula (a2-0), R is the same as defined above.

$R^{28}$ is the same as defined for the aforementioned —$SO_2$— containing group.

$R^{29}$ may be either a single bond or a divalent linking group. In terms of the effects of the present invention, a divalent linking group is preferable.

The divalent linking group for $R^{29}$ is not particularly limited, and examples thereof include the same divalent linking groups as those described above for W in the aforementioned formula (c-1-21). Among these, an alkylene group or a divalent linking group containing an ester bond (—C(=O)—O—) is preferable.

As the alkylene group, a linear or branched alkylene group is preferable. Specific examples include the same linear alkylene groups and branched alkylene groups as those described above for the aliphatic hydrocarbon group represented by $Y^2$.

As the divalent linking group containing an ester bond, a group represented by general formula: —$R^{30}$—C(=O)—O— (in the formula, $R^{30}$ represents a divalent linking group) is particularly desirable. That is, the structural unit (a2$^S$) is preferably a structural unit represented by general formula (a2-0-1) shown below.

[Chemical Formula 60]

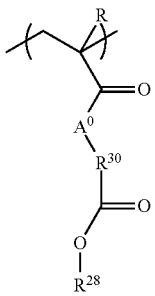

(a2-0-1)

In the formula, R, $A^0$ and $R^{28}$ are the same as defined above; and $R^{30}$ represents a divalent linking group.

$R^{30}$ is not particularly limited, and examples thereof include the same divalent linking groups as those described above for W in the aforementioned formula (c-1-21).

As the divalent linking group for $R^{30}$, a linear or branched alkylene group, an aliphatic hydrocarbon group containing a ring in the structure thereof, or a divalent linking group containing a hetero atom is preferable.

As the linear or branched alkylene group, aliphatic hydrocarbon group containing a ring in the structure thereof, or divalent linking group containing a hetero atom, the same linear or branched alkylene group, aliphatic hydrocarbon group containing a ring in the structure thereof, or divalent linking group containing a hetero atom as those described above as preferable examples of W in the aforementioned formula (c-1-21) can be mentioned.

Among these, a linear or branched alkylene group, or a divalent linking group containing an oxygen atom as a hetero atom is more preferable.

As the linear alkylene group, a methylene group or an ethylene group is preferable, and a methylene group is particularly desirable.

As the branched alkylene group, an alkylmethylene group or an alkylethylene group is preferable, and —CH($CH_3$)—, —C($CH_3$)$_2$— or —C($CH_3$)$_2$CH$_2$— is particularly desirable.

As the divalent linking group containing an oxygen atom, a divalent linking group containing an ether bond or an ester bond is preferable, and a group represented by the aforementioned formula —$Y^{21}$—O—$Y^{22}$—, —[$Y^{21}$—C(=O)—O]$_{m'}$—$Y^{22}$— or —$Y^{21}$—O—C(=O)—$Y^{22}$— is more preferable. Each of $Y^{21}$ and $Y^{22}$ independently represents a divalent hydrocarbon group which may have a substituent; and m' represents an integer of 0 to 3.

Among these, —$Y^{21}$—O—C(=O)—$Y^{22}$— is preferable, and a group represented by the formula —($CH_2$)$_c$—O—C(=O)—($CH_2$)$_d$— is particularly desirable. c represents an integer of 1 to 5, and preferably 1 or 2. d represents an integer of 1 to 5, and preferably 1 or 2.

In particular, as the structural unit (a2$^S$), a structural unit represented by general formula (a2-0-11) or (a2-0-12) shown below is preferable, and a structural unit represented by general formula (a2-0-12) shown below is more preferable.

[Chemical Formula 61]

(a2-0-11)

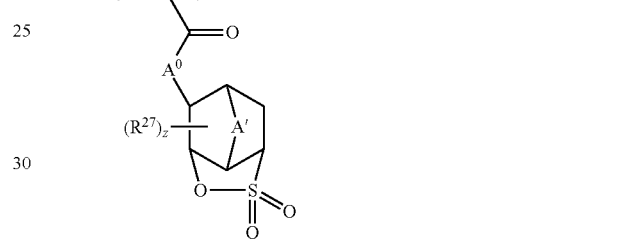

(a2-0-12)

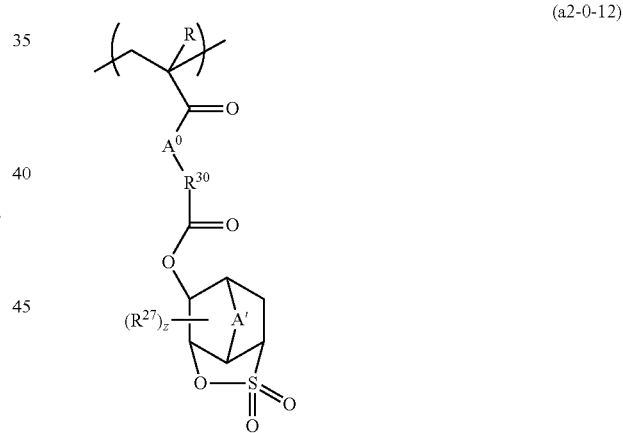

In the formulae, R, $A^0$, A', $R^{27}$, z and $R^{30}$ are the same as defined above.

In general formula (a2-0-11), A' is preferably a methylene group, an oxygen atom (—O—) or a sulfur atom (—S—).

As $R^{30}$, a linear or branched alkylene group or a divalent linking group containing an oxygen atom is preferable. As the linear or branched alkylene group and the divalent linking group containing an oxygen atom represented by $R^{30}$, the same linear or branched alkylene groups and the divalent linking groups containing an oxygen atom as those described above can be mentioned.

As the structural unit represented by general formula (a2-0-12), a structural unit represented by general formula (a2-0-12a) or (a2-0-12b) shown below is particularly desirable.

[Chemical Formula 62]

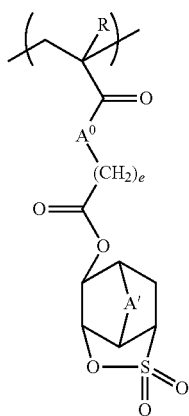
(a2-0-12a)

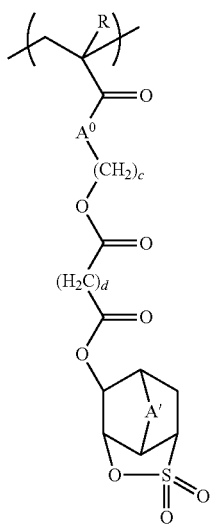
(a2-0-12b)

In the formulas, R, $A^0$ and A' are the same as defined above; and each of c to e independently represents an integer of 1 to 3.

Structural Unit ($a2^L$):

Examples of the structural unit ($a2^L$) include structural units represented by the aforementioned general formula (a2-0) in which the $R^{28}$ group has been substituted with a lactone-containing cyclic group. Specific examples include structural units represented by general formulas (a2-1) to (a2-5) shown below.

[Chemical Formula 63]

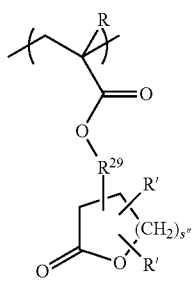
(a2-1)

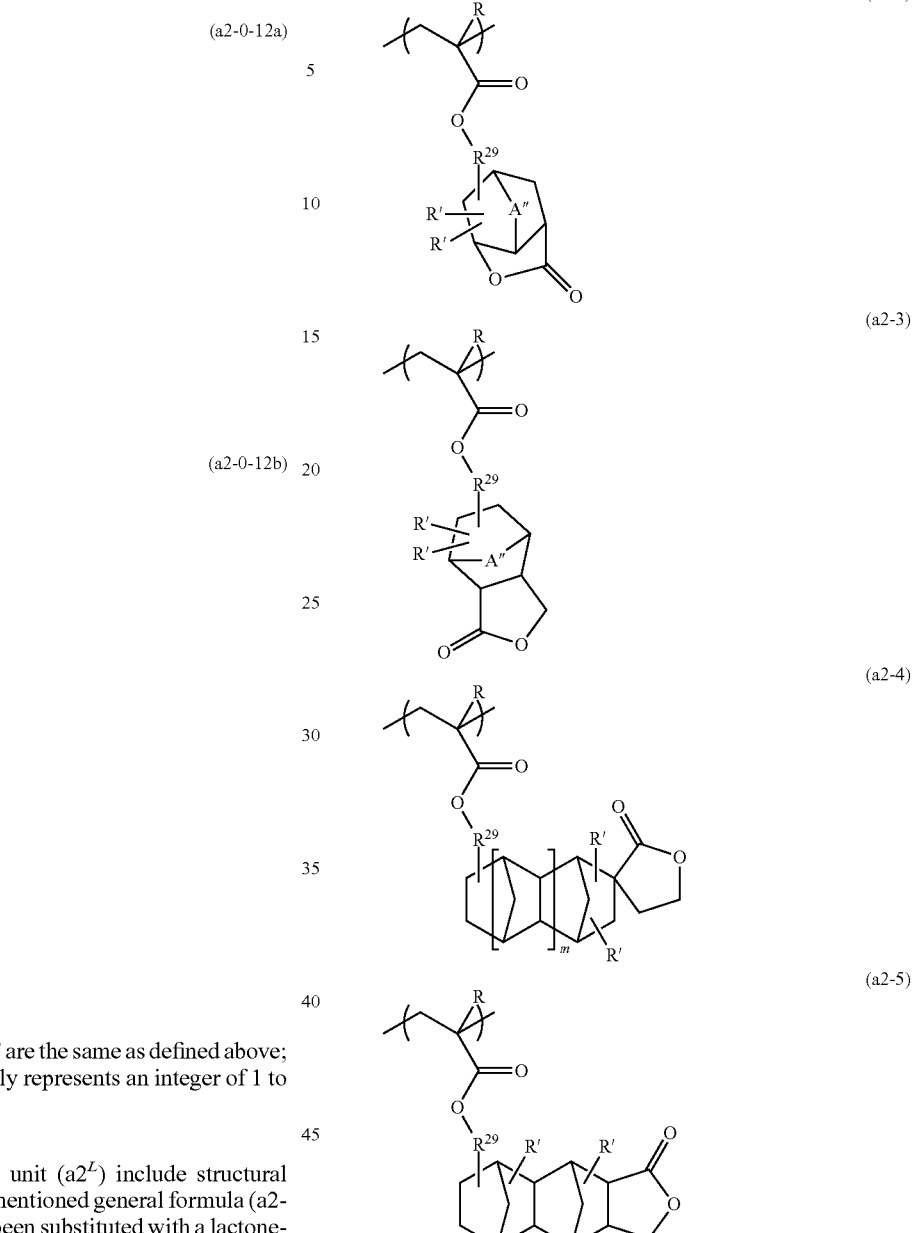

In the formulas, R represents a hydrogen atom, an alkyl group of 1 to 5 carbon atoms or a halogenated alkyl group of 1 to 5 carbon atoms; each R' independently represents a hydrogen atom, an alkyl group, an alkoxy group, a halogen atom, a halogenated alkyl group, a hydroxy group, an oxygen atom (=O), —COOR", OC(=O)R", a hydroxyalkyl group or a cyano group, wherein R" represents a hydrogen atom or an alkyl group; $R^{29}$ represents a single bond or a divalent linking group; s" represents an integer of 0 to 2; A" represents an oxygen atom, a sulfur atom or an alkylene group of 1 to 5 carbon atoms which may contain an oxygen atom or a sulfur atom; and m represents 0 or 1.

In general formulas (a2-1) to (a2-5), R is the same as defined above.

As the alkyl group, alkoxy group, halogen atom, halogenated alkyl group, —COOR", —OC(=O)R" and hydroxyalkyl group for R', the same alkyl groups, alkoxy groups, halogen atoms, halogenated alkyl groups, —COOR", —OC(=O)R" (R" is the same as defined above) and hydroxyalkyl groups as those described above as the substituent for the —SO₂— containing cyclic group can be mentioned.

As the alkyl group for R', an alkyl group of 1 to 5 carbon atoms is preferable, and examples thereof include a methyl group, an ethyl group, a propyl group, an n-butyl group and a tert-butyl group.

As the alkoxy group for R', an alkoxy group of 1 to 5 carbon atoms is preferable, and examples thereof include a methoxy group, an ethoxy group, an n-propoxy group, an iso-propoxy group, an n-butoxy group and a tert-butoxy group In terms of industrial availability, R' is preferably a hydrogen atom.

The alkyl group for R" may be any of linear, branched or cyclic.

When R" is a linear or branched alkyl group, it preferably has 1 to 10 carbon atoms, more preferably 1 to 5 carbon atoms.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

As examples of A", the same groups as those described above for A' in general formula (3-1) can be given. A" is preferably an alkylene group of 1 to 5 carbon atoms, an oxygen atom (—O—) or a sulfur atom (—S—), and more preferably an alkylene group of 1 to 5 carbon atoms or —O—. As the alkylene group of 1 to 5 carbon atoms, a methylene group or a dimethylethylene group is preferable, and a methylene group is particularly desirable.

R²⁹ is the same as defined for R²⁹ in the aforementioned general formula (a2-0).

In formula (a2-1), s" is preferably 1 or 2.

Specific examples of structural units represented by general formulas (a2-1) to (a2-5) are shown below. In the formulas shown below, R^α represents a hydrogen atom, a methyl group or a trifluoromethyl group.

[Chemical Formula 64]

(a2-1-1)

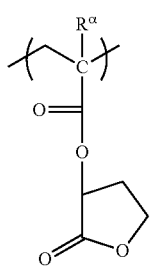

(a2-1-2)

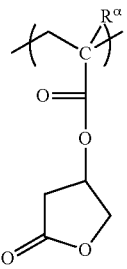

(a2-1-3)

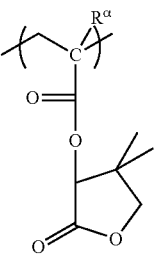

(a2-1-4)

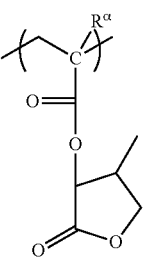

(a2-1-5)

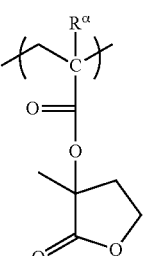

(a2-1-6)

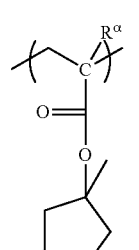

(a2-1-7)

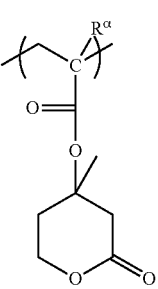

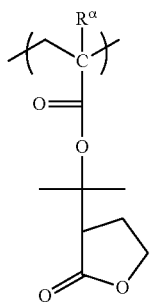 (a2-1-8)
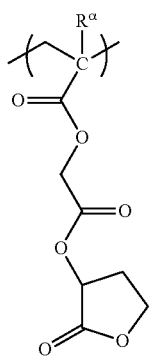 (a2-1-9)
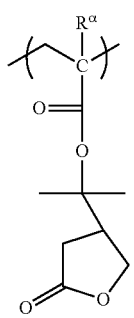 (a2-1-10)
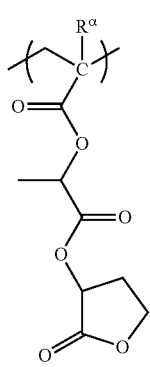 (a2-1-11)
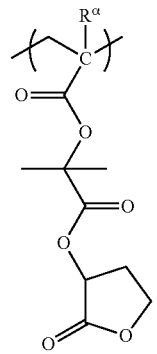 (a2-1-12)
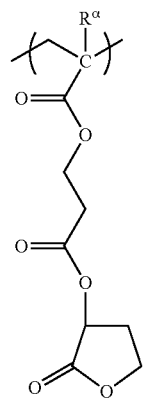 (a2-1-13)
[Chemical Formula 65]
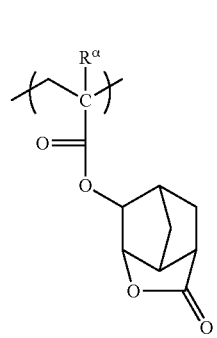 (a2-2-1)
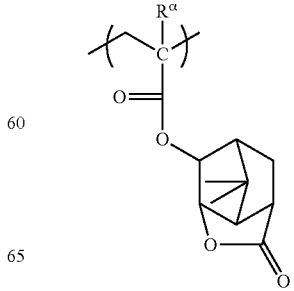 (a2-2-2)

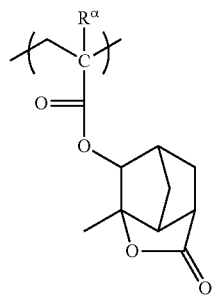
(a2-2-3)
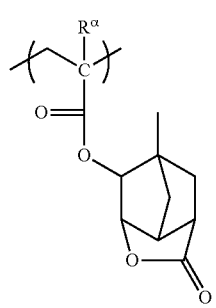
(a2-2-4)
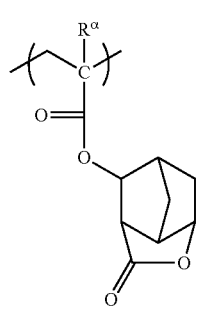
(a2-2-5)
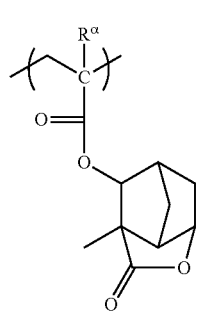
(a2-2-6)
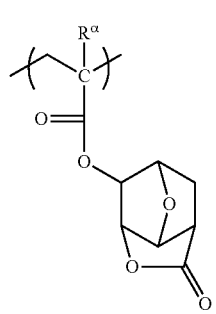
(a2-2-7)
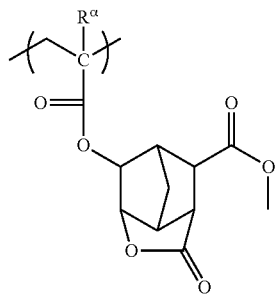
(a2-2-8)
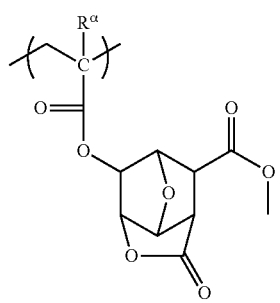
(a2-2-9)
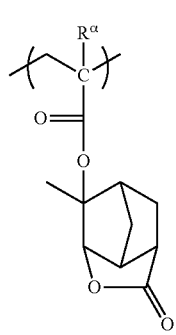
(a2-2-10)
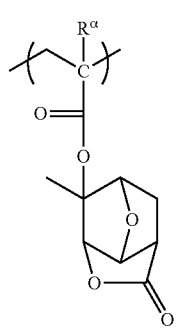
(a2-2-11)
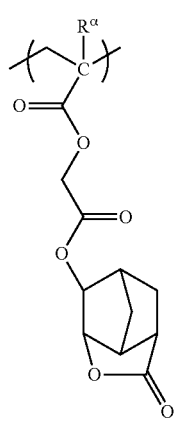
(a2-2-12)

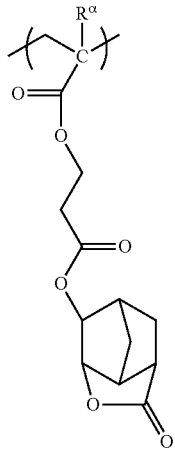
(a2-2-13)
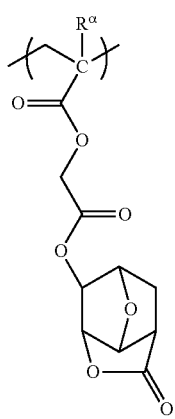
(a2-2-14)
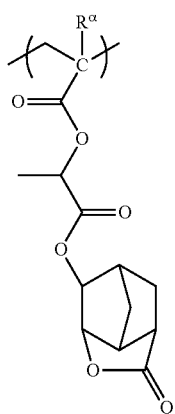
(a2-2-15)
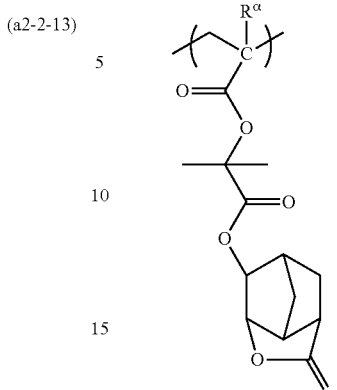
(a2-2-16)
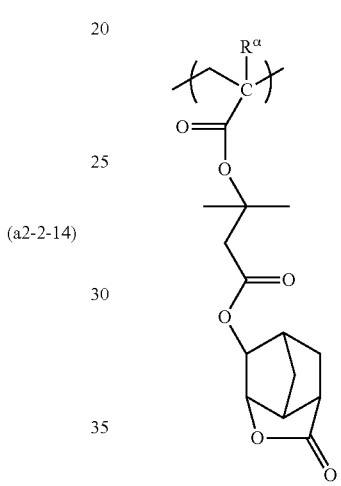
(a2-2-17)
[Chemical Formula 66]
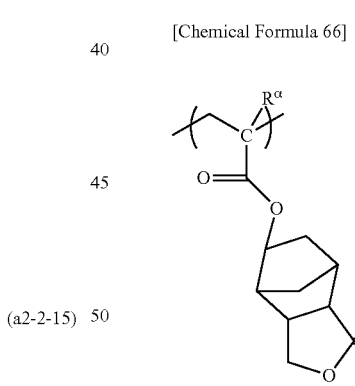
(a2-3-1)
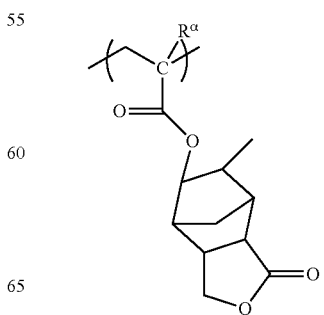
(a2-3-2)

(a2-3-3)
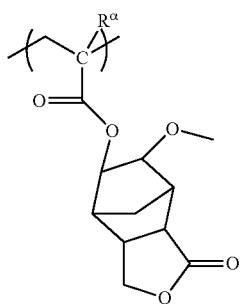
(a2-3-4)
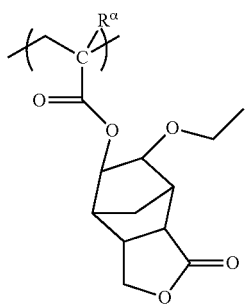
(a2-3-5)
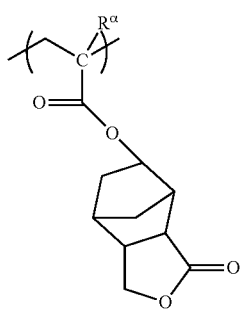
[Chemical Formula 67]
(a2-4-1)
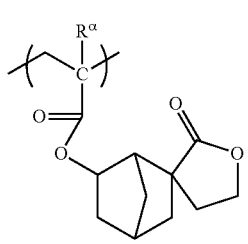
(a2-4-2)
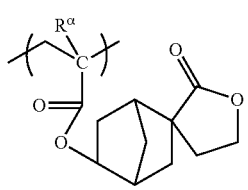
(a2-4-3)
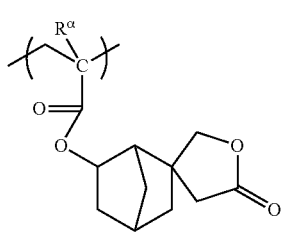
(a2-4-4)
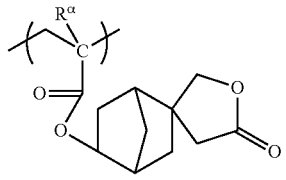
(a2-4-5)
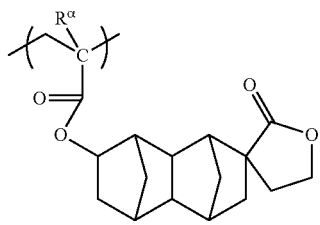
(a2-4-6)
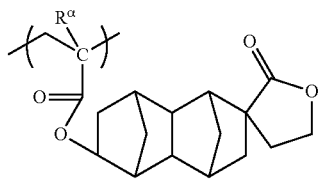
(a2-4-7)
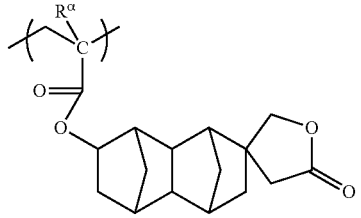
(a2-4-8)
(a2-4-9)
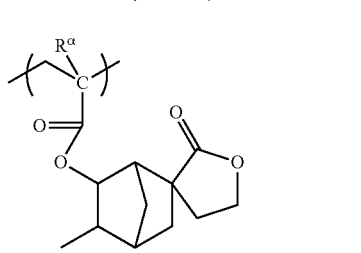
(a2-4-10)
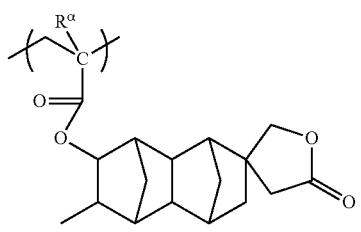

-continued
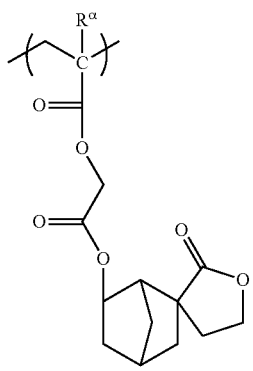
(a2-4-11)
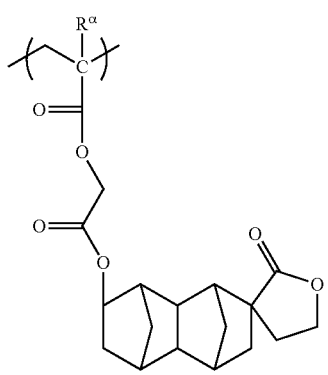
(a2-4-12)
[Chemical Formula 68]
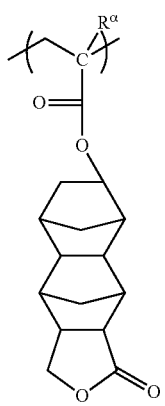
(a2-5-1)
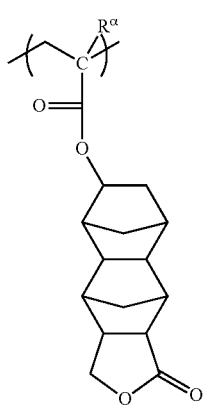
(a2-5-2)
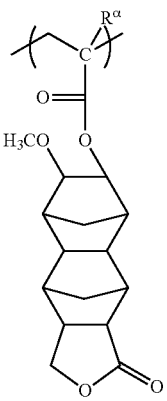
(a2-5-3)
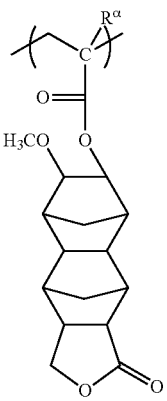
(a2-5-4)
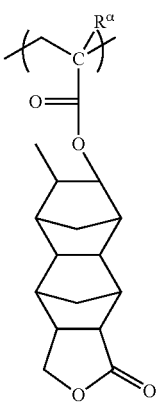
(a2-5-5)
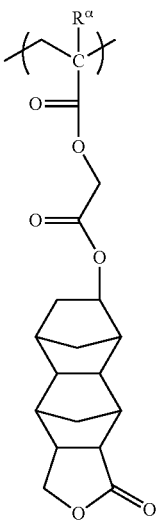

(a2-5-6)

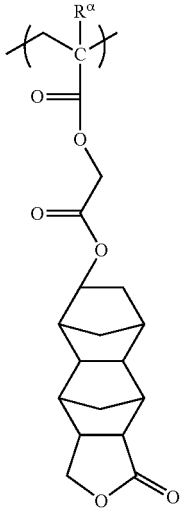

As the structural unit (a2$^L$), it is preferable to use at least one structural unit selected from the group consisting of structural units represented by the aforementioned general formulas (a2-1) to (a2-5), more preferably at least one structural unit selected from the group consisting of structural units represented by the aforementioned general formulas (a2-1) to (a2-3), and most preferably at least one structural unit selected from the group consisting of structural units represented by the aforementioned general formulas (a2-1) and (a2-3).

Specifically, it is preferable to use at least one structural unit selected from the group consisting of formulas (a2-1-1) (a2-1-2) (a2-2-1), (a2-2-7), (a2-2-12), (a2-2-14), (a2-3-1) and (a2-3-5).

Further, as the structural unit (a2$^L$), a structural unit represented by formula (a2-6) or (a2-7) shown below is also preferable.

[Chemical Formula 69]

(a2-6)

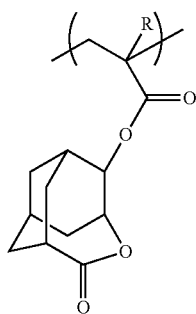

(a2-7)

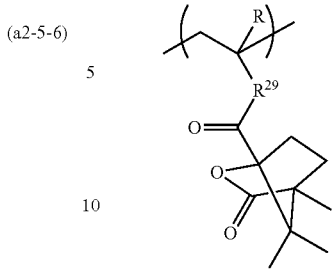

In the formulae, R and R$^{29}$ are the same as defined above.

In the polymeric compounds (A1) and (A1'), as the structural unit (a2), one type of structural unit may be used, or two or more types may be used in combination. For example, as the structural unit (a2), a structural unit (a2$^S$) may be used alone, or a structural unit (a2$^L$), or a combination of these structural units may be used.

Further, as the structural unit (a2$^S$) or the structural unit (a2$^L$), either a single type of structural unit may be used, or two or more types may be used in combination.

In the polymeric compound (A1) or (A1'), the amount of the structural unit (a2) based on the combined total of all structural units constituting the polymeric compound (A1) or (A1') is preferably 1 to 80 mol %, more preferably 10 to 70 mol %, still more preferably 10 to 65 mol %, and most preferably 10 to 60 mol %.

When the amount of the structural unit (a2) is at least as large as the lower limit of the above-mentioned range, the effect of using the structural unit (a2) can be satisfactorily achieved. On the other hand, when the amount of the structural unit (a2) is no more than the upper limit of the above-mentioned range, a good balance can be achieved with the other structural units, and various lithography properties such as DOF and CDU and pattern shape can be improved.

(Structural Unit (a3))

The structural unit (a3) is a structural unit containing a polar group. When the polymeric compound includes the structural unit (a3), the hydrophilicity of the polymeric compound is enhanced, thereby contributing to improvement in resolution.

The structural unit (a3) is preferably a structural unit (a3-12-21) derived from an acrylate ester which may have the hydrogen atom bonded to the carbon atom on the α-position substituted with a substituent and contains a polar group-containing aliphatic hydrocarbon group.

Examples of the polar group include —OH, —COOH, —CN, —SO$_2$NH$_2$, —CONH$_2$ and a hydroxyalkyl group in which part of the hydrogen atoms of an alkyl group have been substituted with fluorine atoms. Of these, —OH is preferable.

The structural unit (a3) is preferably a structural unit containing a hydrocarbon group in which part of the hydrogen atoms has been substituted with a polar group. The hydrocarbon group may be either an aliphatic hydrocarbon group or an aromatic hydrocarbon group. Among these, as the hydrocarbon group, an aliphatic hydrocarbon group is preferable.

Examples of the aliphatic hydrocarbon group as the hydrocarbon group include linear or branched hydrocarbon groups (preferably alkylene groups) of 1 to 10 carbon atoms, and aliphatic cyclic groups (monocyclic groups and polycyclic groups).

These aliphatic cyclic groups (monocyclic groups and polycyclic groups) can be selected appropriately from the multitude of groups that have been proposed for the resins of resist compositions designed for use with ArF excimer lasers. The aliphatic cyclic group preferably has 3 to 30 carbon atoms, more preferably 5 to 30, still more preferably 5 to 20, still more preferably 6 to 15, and most preferably 6 to 12. As the aliphatic cyclic group, a group in which two or more hydrogen atoms have been removed from a monocycloalkane or a polycycloalkane such as a bicycloalkane, tricycloalkane or tetracycloalkane can be used. Specific examples include groups in which two or more hydrogen atoms have been removed from a monocycloalkane such as cyclopentane or cyclohexane; and groups in which two or more hydrogen atoms have been removed from a polycycloalkane such as adamantane, norbornane, isobornane, tricyclodecane or tetracyclododecane. The aliphatic cyclic group may or may not have a substituent. Examples of the substituent include an alkyl group of 1 to 5 carbon atoms, a fluorine atom, and a fluorinated alkyl group of 1 to 5 carbon atoms.

The aromatic hydrocarbon group as the hydrocarbon group is a hydrocarbon group containing an aromatic ring, and preferably has 5 to 30 carbon atoms, more preferably 6 to 20, still more preferably 6 to 15, and most preferably 6 to 10. Here, the number of carbon atoms within a substituent(s) is not included in the number of carbon atoms of the aromatic hydrocarbon group. Examples of the aromatic ring contained in the aromatic hydrocarbon group include aromatic hydrocarbon rings, such as benzene, biphenyl, fluorene, naphthalene, anthracene and phenanthrene.

Specific examples of the aromatic hydrocarbon group include a group in which two or more hydrogen atoms have been removed from the aforementioned aromatic hydrocarbon ring (arylene group); and a group in which one hydrogen atom has been removed from the aforementioned aromatic hydrocarbon ring (aryl group) and one hydrogen atom has been substituted with an alkylene group (e.g., a group in which one hydrogen atom has been removed from an aryl group within an arylalkyl group such as a benzyl group, a phenethyl group, a 1-naphthylmethyl group, a 2-naphthylmethyl group, a 1-naphthylethyl group, or a 2-naphthylethyl group). The alkylene group (alkyl chain within the arylalkyl group) preferably has 1 to 4 carbon atoms, more preferably 1 or 2, and most preferably 1.

The aromatic hydrocarbon group may or may not have a substituent. For example, the hydrogen atom bonded to the aromatic hydrocarbon ring within the aromatic hydrocarbon group may be substituted with a substituent. Examples of substituents include an alkyl group, a halogen atom, and a halogenated alkyl group.

The alkyl group as the substituent is preferably an alkyl group of 1 to 5 carbon atoms, and a methyl group, an ethyl group, a propyl group, an n-butyl group or a tert-butyl group is most desirable.

Examples of the halogen atom as the substituent for the aromatic hydrocarbon group include a fluorine atom, a chlorine atom, a bromine atom and an iodine atom, and a fluorine atom is preferable.

Examples of the halogenated alkyl group for the substituent include groups in which part or all of the hydrogen atoms within the aforementioned alkyl groups has been substituted with the aforementioned halogen atoms.

As the structural unit (a3), a structural unit represented by general formula (a3-1) shown below is preferable.

[Chemical Formula 70]

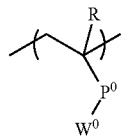

(a3-1)

In the formula, R represents a hydrogen atom, an alkyl group of 1 to 5 carbon atoms or a halogenated alkyl group of 1 to 5 carbon atoms; $P^0$ represents —C(=O)—O—, —C(=O)—NR$^0$—(wherein R$^0$ represents a hydrogen atom or an alkyl group of 1 to 5 carbon atoms) or a single bond; and W$^0$ represents a hydrocarbon group having at least one substituent selected from the group consisting of —OH, —COOH, —CN, —SO$_2$NH$_2$ and —CONH$_2$, provided that the hydrocarbon group may have an oxygen atom or a sulfur atom at an arbitrary position.

In the formula (a3-1), as the alkyl group for R, a linear or branched alkyl group is preferable, and specific examples include a methyl group, an ethyl group, a propyl group, an isopropyl group, an n-butyl group, an isobutyl group, a tert-butyl group, a pentyl group, an isopentyl group and a neopentyl group.

Examples of the halogenated alkyl group for R include groups in which part or all of the hydrogen atoms within the aforementioned alkyl groups has been substituted with a halogen atom. Examples of the halogen atom include a fluorine atom, a chlorine atom, a bromine atom and an iodine atom, and a fluorine atom is particularly desirable.

As R, a hydrogen atom, an alkyl group of 1 to 5 carbon atoms or a fluorinated alkyl group of 1 to 5 carbon atoms is preferable, and a hydrogen atom or a methyl group is particularly desirable.

In the formula (a3-1), $P^0$ represents —C(=O)—O—, —C(=O)—NR$^0$— (wherein R$^0$ represents a hydrogen atom or an alkyl group of 1 to 5 carbon atoms) or a single bond. The alkyl group for R$^0$ is the same as defined for the alkyl group for R.

In the formula (a3-1), W$^0$ represents a hydrocarbon group having at least one substituent selected from the group consisting of —OH, —COOH, —CN, —SO$_2$NH$_2$ and —CONH$_2$, provided that the hydrocarbon group may have an oxygen atom or a sulfur atom at an arbitrary position.

A "hydrocarbon group which has a substituent" refers to a hydrocarbon group in which at least part of the hydrogen atoms bonded to the hydrocarbon group is substituted with a substituent.

The hydrocarbon group for W$^0$ may be either an aliphatic hydrocarbon group, or an aromatic hydrocarbon group.

Preferable examples of the aliphatic hydrocarbon group for W$^0$ include linear or branched hydrocarbon groups of 1 to 10 carbon atoms (preferably alkylene groups) and aliphatic cyclic groups (monocyclic groups and polycyclic groups), and are the same as explained above.

The aromatic hydrocarbon group for W$^0$ is a hydrocarbon group having an aromatic ring, and is the same as explained above.

W$^0$ may have an oxygen atom or a sulfur atom at an arbitrary position. Here, the expression "may have an oxygen atom or a sulfur atom at an arbitrary position" means that part of the carbon atoms constituting the hydrocarbon group or the hydrocarbon group having a substituent (including the carbon atoms of the substituent part) may be substituted with an oxygen atom or a sulfur atom, or a hydrogen atom bonded to the hydrocarbon group may be substituted with an oxygen atom or a sulfur atom.

Examples of $W^0$ which has an oxygen atom (O) at an arbitrary position are shown below.

[Chemical Formula 71]

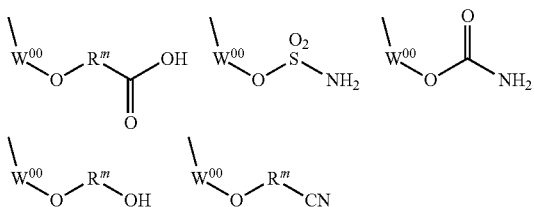

In the formulae, $W^{00}$ represents a hydrocarbon group; and $R^m$ represents an alkylene group of 1 to 5 carbon atoms.

In the formulae above, $W^{00}$ represents a hydrocarbon group, and is the same as defined for $W^0$ in the aforementioned formula (a3-1). $W^{00}$ is preferably an aliphatic hydrocarbon group, and more preferably an aliphatic cyclic group (a monocyclic group or a polycyclic group).

$R^m$ is preferably linear or branched, preferably an alkylene group of 1 to 3 carbon atoms, and more preferably a methylene group or an ethylene group.

Specific examples of preferable structural units as the structural unit (a3) include structural units represented by general formulae (a3-11) to (a3-13) shown below.

[Chemical Formula 72]

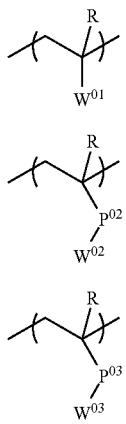

(a3-11)

(a3-12)

(a3-13)

In the formulae, R represents a hydrogen atom, an alkyl group of 1 to 5 carbon atoms or a halogenated alkyl group of 1 to 5 carbon atoms; $W^{01}$ represents an aromatic hydrocarbon group which has at least one substituent selected from the group consisting of —OH, —COOH, —CN, —SO$_2$NH$_2$ and —CONH$_2$; each of $P^{02}$ and $P^{03}$ independently represents —C(=O)—O— or —C(=O)—NR$^0$— (wherein R$^0$ represents a hydrogen atom or an alkyl group of 1 to 5 carbon atoms); $W^{02}$ represents a cyclic hydrocarbon group having at least one substituent selected from the group consisting of —OH, —COOH, —CN, —SO$_2$NH$_2$ and —CONH$_2$, provided that the hydrocarbon group may have an oxygen atom or a sulfur atom at an arbitrary position; and $W^{03}$ represents a linear hydrocarbon group having at least one substituent selected from the group consisting of —OH, —COOH, —CN, —SO$_2$NH$_2$ and —CONH$_2$.

[Structural Unit Represented by General Formula (a3-11)]

In the formula (a3-11), R is the same as defined for R in the aforementioned formula (a3-1).

The aromatic hydrocarbon group for $W^{01}$ is the same as defined for the aromatic hydrocarbon group for $W^0$ in the aforementioned formula (a3-1).

Specific examples of structural units preferable as a structural unit represented by general formula (a3-11) are shown below. In the formulas shown below, $R^\alpha$ represents a hydrogen atom, a methyl group or a trifluoromethyl group.

[Chemical Formula 73]

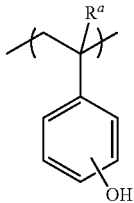

(a3-11-1)

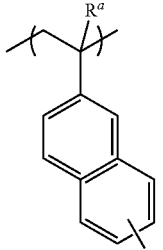

(a3-11-2)

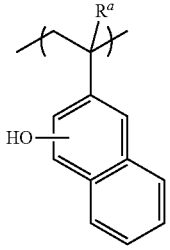

(a3-11-3)

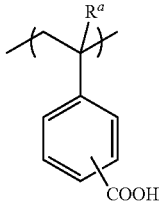

(a3-11-4)

[Structural Unit Represented by General Formula (a3-12)]

In the formula (a3-12), R is the same as defined for R in the aforementioned formula (a3-1).

$P^{02}$ represents —C(=O)—O— or —C(=O)—NR$^0$— (wherein R$^0$ represents a hydrogen atom or an alkyl group of 1 to 5 carbon atoms), and is preferably —C(=O)—O—. The alkyl group for R$^0$ is the same as defined for the alkyl group for R.

The cyclic hydrocarbon group for $W^{02}$ is the same as defined for the aliphatic cyclic groups (monocyclic groups and polycyclic groups) and aromatic hydrocarbon groups explained above for $W^0$ in the aforementioned formula (a3-1).

$W^{02}$ may have an oxygen atom or a sulfur atom at an arbitrary position, and is the same as defined for $W^0$ in the aforementioned formula (a3-1).

Specific examples of structural units preferable as a structural unit represented by general formula (a3-12) are shown below. In the formulas shown below, $R^\alpha$ represents a hydrogen atom, a methyl group or a trifluoromethyl group.

[Chemical Formula 74]

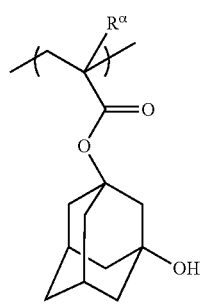
(a3-12-1)

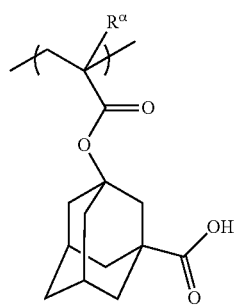
(a3-12-2)

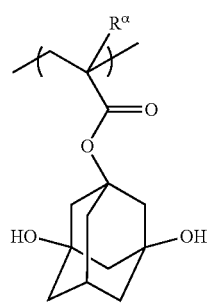
(a3-12-3)

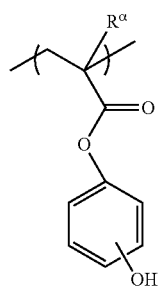
(a3-12-4)

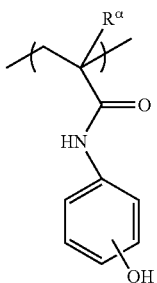
(a3-12-5)

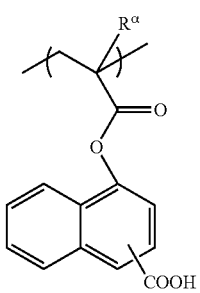
(a3-12-6)

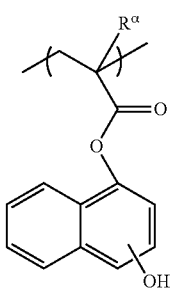
(a3-12-7)

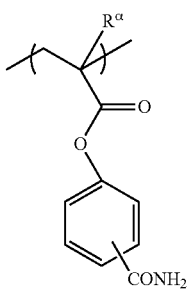
(a3-12-8)

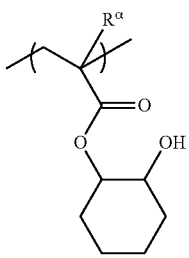
(a3-12-9)

(a3-12-10)
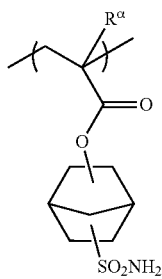

(a3-12-11)
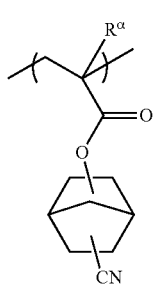

(a3-12-12)
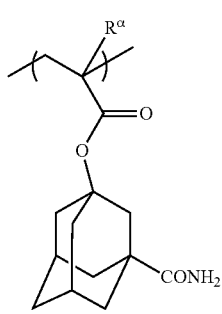

[Chemical Formula 75]

(a3-12-13)
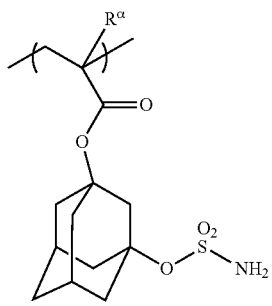

(a3-12-14)
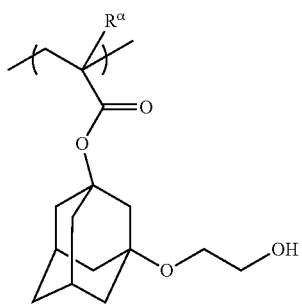

(a3-12-15)
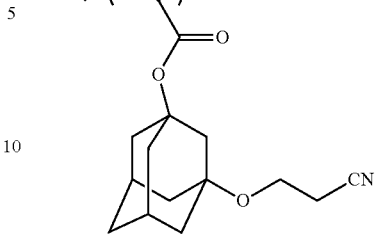

(a3-12-16)
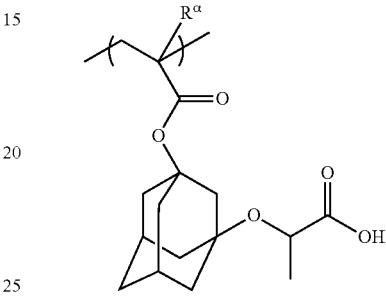

(a3-12-17)
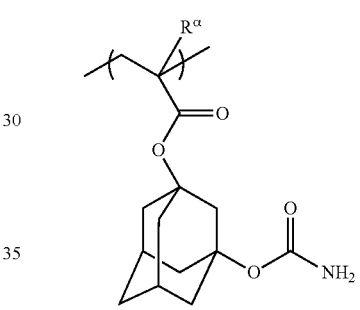

The structural unit represented by general formula (a3-12) is preferably a structural unit (a3-12-21) derived from an acrylate ester which may have the hydrogen atom bonded to the carbon atom on the α-position substituted with a substituent and contains a polar group-containing aliphatic hydrocarbon group.

When the component (A1) includes the structural unit (a3-12-21), the hydrophilicity of the component (A1) is enhanced, thereby contributing to improvement in resolution.

Examples of the polar group include a hydroxyl group, a cyano group, a carboxyl group, or a hydroxyalkyl group in which part of the hydrogen atoms of the alkyl group have been substituted with fluorine atoms, although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups).

These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that includes an aliphatic polycyclic group that contains a hydroxyl group, a cyano group, a carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, a group in which two or more hydrogen atoms have been removed from adamantane, a group in which two or more hydrogen atoms have been removed from norbornane or a group in which two or more hydrogen atoms have been removed from tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3-12-21) is preferably a structural unit derived from a hydroxyethyl ester of acrylic acid. On the other hand, when the hydrocarbon group is a polycyclic group, structural units represented by formulas (a3-12-31), (a3-12-32) and (a3-12-33) shown below are preferable.

[Chemical Formula 76]

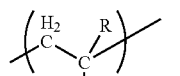
(a3-12-31)

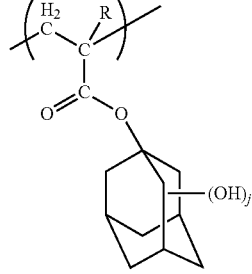
(a3-12-32)

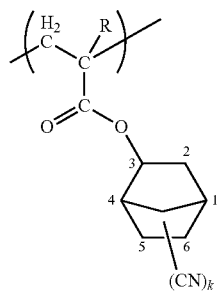
(a3-12-33)

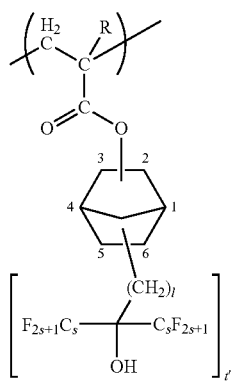

In the formulae, R is as defined above; j is an integer of 1 to 3; k is an integer of 1 to 3; t' is an integer of 1 to 3; l is an integer of 1 to 5; and s is an integer of 1 to 3.

In general formula (a3-12-31), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group.

j is preferably 1, and it is particularly desirable that the hydroxyl group be bonded to the 3rd position of the adamantyl group.

In formula (a3-12-32), k is preferably 1. The cyano group is preferably bonded to the 5th or 6th position of the norbornyl group.

In formula (a3-12-33), t' is preferably 1. l is preferably 1. s is preferably 1. Further, it is preferable that a 2-norbonyl group or 3-norbornyl group be bonded to the terminal of the carboxy group of the acrylic acid. The fluorinated alkylalcohol is preferably bonded to the 5th or 6th position of the norbornyl group.

[Structural Unit Represented by General Formula (a3-13)]

In the formula (a3-13), R is the same as defined for R in the aforementioned formula (a3-1).

$P^{03}$ represents —C(=O)—O— or —C(=O)—NR$^0$— (wherein R$^0$ represents a hydrogen atom or an alkyl group of 1 to 5 carbon atoms), and is preferably —C(=O)—O—. The alkyl group for R$^0$ is the same as defined for the alkyl group for R.

The linear hydrocarbon group for $W^{03}$ preferably has 1 to 10 carbon atoms, more preferably 1 to 5 carbon atoms, and still more preferably 1 to 3 carbon atoms.

The linear hydrocarbon group for $W^{03}$ may have a substituent (a) other than —OH, —COOH, —CN, —SO$_2$NH$_2$ and —CONH$_2$. Examples of the substituent (a) include an alkyl group of 1 to 5 carbon atoms, an aliphatic cyclic group (a monocyclic group or a polycyclic group), a fluorine atom, and a fluorinated alkyl group of 1 to 5 carbon atoms. The aliphatic cyclic group (a monocyclic group or a polycyclic group) for the substituent (a) preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms. As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

Further, as exemplified by a structural unit represented by general formula (a3-13-a) shown below, the linear hydrocarbon group for $W^{03}$ may have a plurality of substituents (a), and the plurality of substituents (a) may be mutually bonded to form a ring.

[Chemical Formula 77]

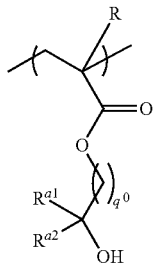

(a3-13-a)

In the formula, R represents a hydrogen atom, an alkyl group of 1 to 5 carbon atoms or a halogenated alkyl group of 1 to 5 carbon atoms; each of $R^{a1}$ and $R^{a2}$ independently represents an alkyl group of 1 to 5 carbon atoms, an aliphatic cyclic group (a monocyclic group or a polycyclic group), a fluorine atom, or a fluorinated alkyl group of 1 to 5 carbon atoms, provided that $R^{a1}$ and $R^{a2}$ may be mutually bonded to form a ring; and $q^0$ represents an integer of 1 to 4 carbon atoms.

In the formula (a3-13-a), R is the same as defined for R in the aforementioned formula (a3-1).

The aliphatic cyclic group (a monocyclic group or a polycyclic group) for $R^{a1}$ and $R^{a2}$ is the same as defined for the aliphatic cyclic group (a monocyclic group or a polycyclic group) for the substituent (a).

Further, $R^{a1}$ and $R^{a2}$ may be mutually bonded to form a ring. In such a case, a cyclic group is formed by $R^{a1}$, $R^{a2}$ and the carbon atom having $R^{a1}$ and $R^{a2}$ bonded thereto. The cyclic group may be a monocyclic group or a polycyclic group, and specific examples thereof include a group in which one or more hydrogen atoms have been removed from the monocycloalkane or polycycloalkane given as examples in the explanation of the aliphatic cyclic group (a monocyclic group or a polycyclic group) for the substituent (a).

$q^0$ is preferably 1 or 2, and more preferably 1.

Specific examples of structural units preferable as a structural unit represented by general formula (a3-13) are shown below. In the formulas shown below, $R^\alpha$ represents a hydrogen atom, a methyl group or a trifluoromethyl group.

[Chemical Formula 78]

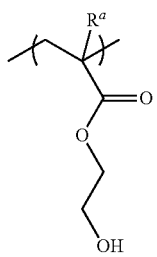

(a3-13-1)

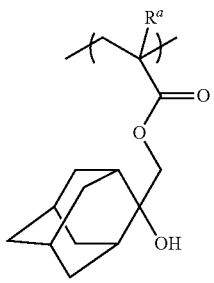

(a3-13-2)

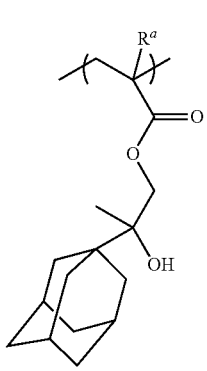

(a3-13-3)

As the structural unit (a3) contained in the polymeric compound (A1) or (A1'), 1 type of structural unit may be used, or 2 or more types may be used.

In the polymeric compound (A1), the amount of the structural unit (a3) based on the combined total of all structural units constituting the polymeric compound is preferably 0 to 40 mol %, more preferably 0 to 35 mol %, still more preferably 0 to 30 mol %, and particularly preferably 0 to 25 mol %.

When the amount of the structural unit (a3) is at least as large as the lower limit of the above-mentioned range, the effect of using the structural unit (a3) (effect of improving resolution, lithography properties and pattern shape) can be satisfactorily achieved. On the other hand, when the amount of the structural unit (a3) is no more than the upper limit of the above-mentioned range, a good balance can be achieved with the other structural units.

When the component (A1') contains the structural unit (a3), the amount of the structural unit (a3) based on the combined total of all structural units constituting the component (A1') is preferably 1 to 50 mol %, more preferably 3 to 45 mol %, and still more preferably 5 to 40 mol %. When the amount of the structural unit (a3) is at least as large as the lower limit of the above-mentioned range, the effect of using the structural unit (a3) can be satisfactorily achieved. On the other hand, when the amount of the structural unit (a3) is no more than the upper limit of the above-mentioned range, a good balance can be achieved with the other structural units.

(Other Structural Units)

The component (A1) or (A1') may also have a structural unit (a4) which is other than the above-mentioned structural units (a1)) to (a3), as long as the effects of the present invention are not impaired.

The structural unit (a4) is a structural unit containing an acid non-dissociable cyclic group. By including the structural unit (a4), dry etching resistance of the resist pattern to be formed is improved. Further, the hydrophobicity of the polymeric compound is further improved. Increase in the hydrophobicity contributes to improvement in terms of resolution, shape of the resist pattern and the like, particularly in an organic solvent developing process.

As the structural unit (a4), any other structural unit which cannot be classified as one of the above structural units (a1) to (a3) can be used without any particular limitation, and any of the multitude of conventional structural units used within resist resins for ArF excimer lasers or KrF excimer lasers (and particularly for ArF excimer lasers) can be used.

Preferable examples of the structural unit (a4) include a structural unit derived from an acrylate ester which contains a non-acid-dissociable aliphatic polycyclic group and may have the hydrogen atom bonded to the carbon atom on the α-position substituted with a substituent, a structural unit derived from a styrene monomer and a structural unit derived from a vinylnaphthalene monomer. Examples of this polycyclic group include the same groups as those described above in relation to the aforementioned structural unit (a1).

An "acid non-dissociable cyclic group" in the structural unit (a4) refers to a cyclic group which is not dissociated by the action of the acid which is generated from either the anion portion at the terminal of the main chain or the component (B) described later upon exposure, and remains in the structural unit. The cyclic group may be either an aliphatic cyclic group or an aromatic cyclic group, and is preferably an aliphatic cyclic group. The aliphatic cyclic group may be either a monocyclic group or a polycyclic group. In terms of the aforementioned effects, a polycyclic group is preferable.

Examples of the acid non-dissociable polycyclic group include a non-acid-dissociable aliphatic polycyclic group, and a group in which at least one group selected from $R^{15}$ and $R^{16}$ in formulae (2-1) to (2-6) explained in relation to the structural unit (a1) is replaced by a hydrogen atom.

Examples of the acid non-dissociable aliphatic polycyclic group include monovalent aliphatic polycyclic groups in which the carbon atom having an atom adjacent to the aliphatic polycyclic group (e.g., —O— within —C(=O)—O—) bonded thereto has no substituent (a group or an atom other than hydrogen). The aliphatic cyclic group is not particularly limited as long as it is acid non-dissociable, and any of the multitude of conventional polycyclic groups used within the resin component of resist compositions for ArF excimer lasers or KrF excimer lasers (and particularly for ArF excimer lasers) can be used. The aliphatic cyclic group may be either saturated or unsaturated, preferably saturated.

Specific examples include groups in which one hydrogen atom has been removed from the cycloalkanes (such as monocycloalkanes and polycycloalkanes) described above in the explanation of the aliphatic cyclic group for the structural unit (a1).

The aliphatic cyclic group may be either a monocyclic group or a polycyclic group. In terms of the aforementioned effects, a polycyclic group is preferable. In particular, a bi-, tri- or tetracyclic group is preferable. In consideration of industrial availability and the like, at least one polycyclic group selected from amongst a tricyclodecyl group, an adamantyl group, a tetracyclododecyl group, an isobornyl group and a norbornyl group is particularly desirable.

Specific examples of the acid non-dissociable aliphatic cyclic group include monovalent aliphatic cyclic groups in which the carbon atom having an atom adjacent to the aliphatic cyclic group (e.g., —O— within —C(=O)—O—) bonded thereto has no substituent (a group or an atom other than hydrogen). More specific examples include groups represented by general formulas (1-1) to (1-9) explained above in relation to the structural unit (a1) in which the $R^{14}$ group has been substituted with a hydrogen atom; and a cycloalkane having a tertiary carbon atom constituting the ring skeleton and having one hydrogen atom removed from.

The aliphatic cyclic group may have a substituent. Examples of the substituent include an alkyl group of 1 to 5 carbon atoms, a fluorine atom and a fluorinated alkyl group.

As the structural unit (a4), a structural unit in which an acid dissociable group in a structural unit (a1) is replaced by an acid non-dissociable cyclic group can be mentioned. Among these, a structural unit derived from an acrylate ester which may have the hydrogen atom bonded to the carbon atom on the α-position substituted with a substituent and contains an acid non-dissociable cyclic group, that is, a structural unit represented by general formula (a4-0) shown below is preferable, and structural units represented by general formulae (a4-1) to (a4-5) shown below are particularly preferable.

[Chemical Formula 79]

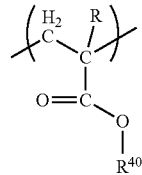

(a4-0)

In the formula, R is the same as defined above; and $R^{40}$ represents an acid non-dissociable cyclic group.

Specific examples of the structural unit (a4) include units with structures represented by general formulas (a4-1) to (a4-5) shown below.

[Chemical Formula 80]

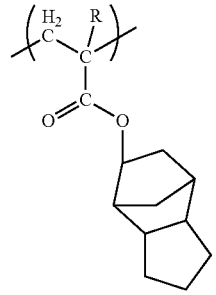

(a4-1)

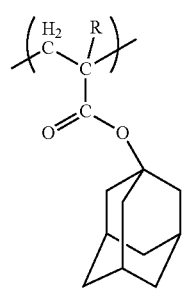

(a4-2)

-continued

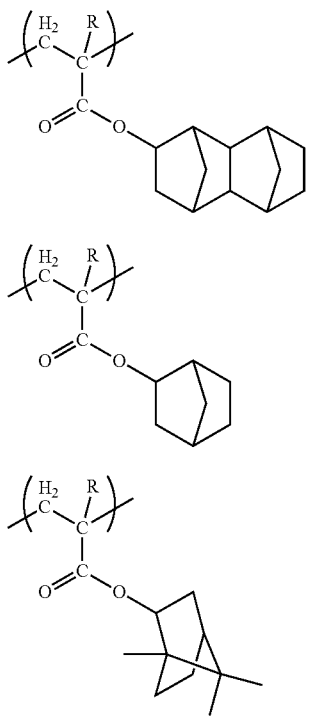

(a4-3)

(a4-4)

(a4-5)

In the formulas, R is the same as defined above.

As the structural unit (a4), one type of structural unit may be used, or two or more types may be used in combination.

When the structural unit (a4) is included in the component (A1) or (A1'), the amount of the structural unit (a4) based on the combined total of all structural units constituting the component (A1) or (A1') is preferably 0 to 30 mol %, more preferably 0 to 20 mol %, still more preferably 1 to 20 mol %, particularly preferably 1 to 15 mol %, and most preferably 1 to 10 mol %.

In the fifth aspect of the present invention, the polymeric compound (A1') is preferably a copolymer containing the structural unit (a1), and more preferably a copolymer containing the structural units (a1) and (a2).

Examples of such copolymers include a copolymer consisting of the structural units (a1) and (a2), a copolymer consisting of the structural units (a1) and (a3), and a copolymer consisting of the structural units (a1), (a2) and (a3).

In the seventh aspect of the present invention, the polymeric compound (A1) is preferably a polymeric compound having at least the structural unit (a1).

The polymeric compound may further contains the structural units (a2), (a3) and (a4), and particularly preferably contains at least one structural unit selected from structural units (a2) and (a3).

As the polymeric compound (A1)
a polymeric compound containing structural units (a1) and (a2) which constitute the polymeric compound;
a polymeric compound containing structural units (a1) and (a3) which constitute the polymeric compound; and
a polymeric compound containing structural units (a1), (a2) and (a3) which constitute the polymeric compound,
can be given as preferable examples.

In the fifth aspect of the present invention, as the component (A1'), a copolymer that includes a combination of structural units represented by formulae (A1'-11) to (A1'-23) shown below is particularly desirable. In general formulas shown below, R, $R^{11}$ to $R^{16}$, $R^{29}$, s", $R^{1'}$, $R^{2'}$, n01, j, e, A', a and h are the same as defined above, and the plurality of R may be the same or different.

[Chemical Formula 81]

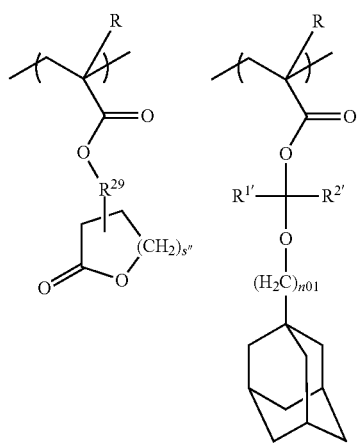

(A1'-11)

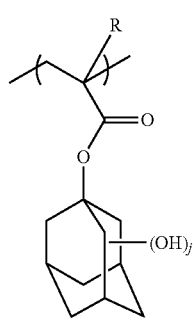

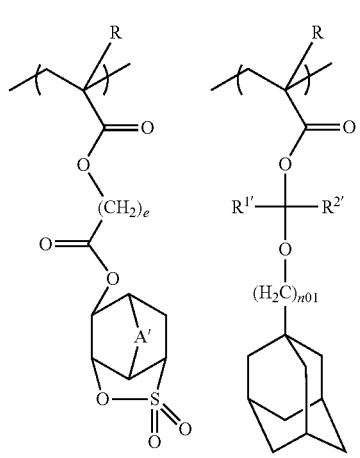

(A1'-12)

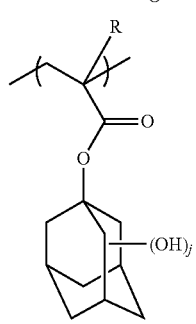

(A1'-13)
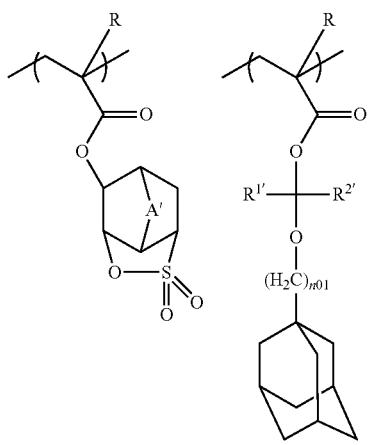
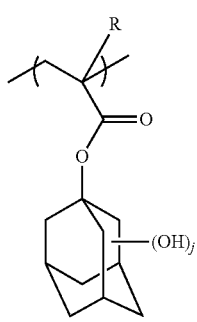
[Chemical Formula 82]
(A1'-14)
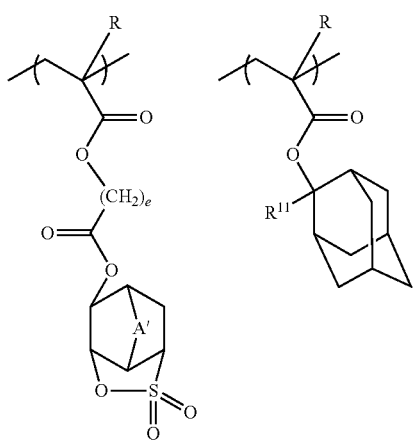
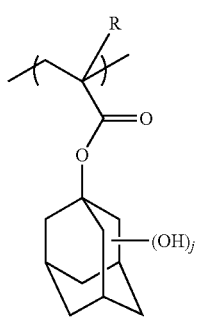
(A1'-15)
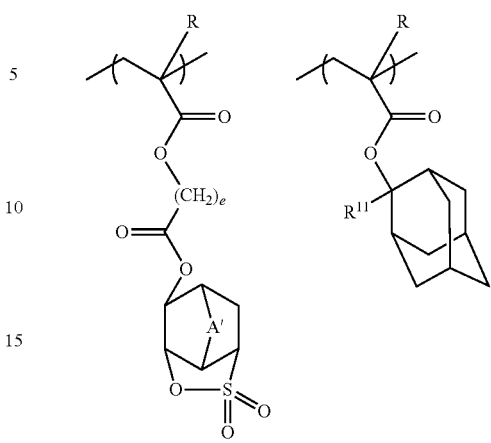
(A1'-16)
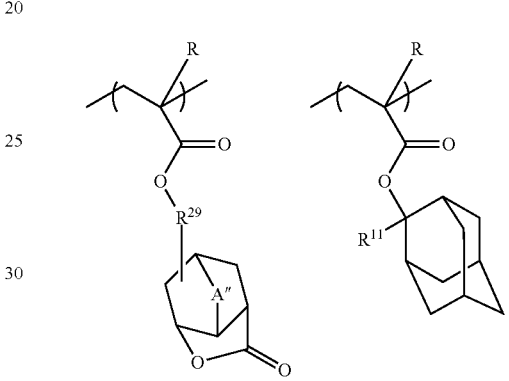
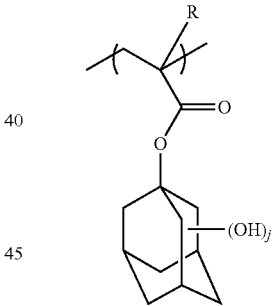
[Chemical Formula 83]
(A1'-17)
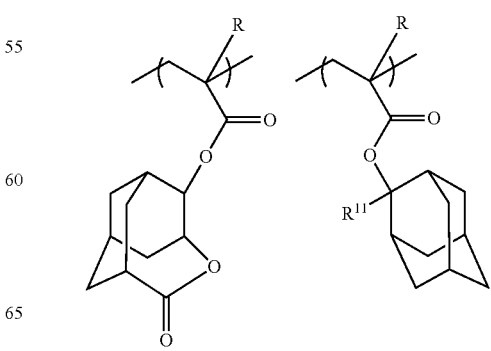

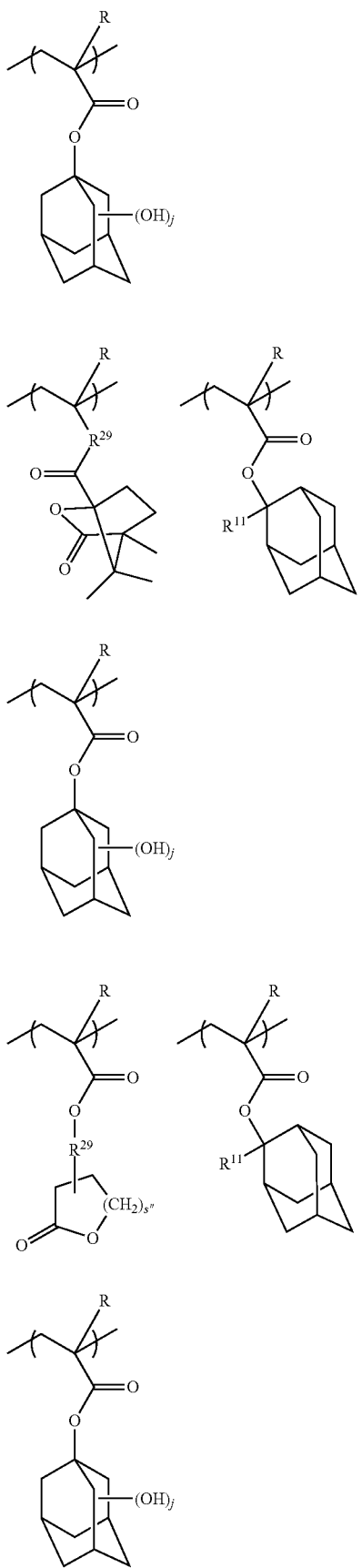
(A1'-18)
(A1'-19)
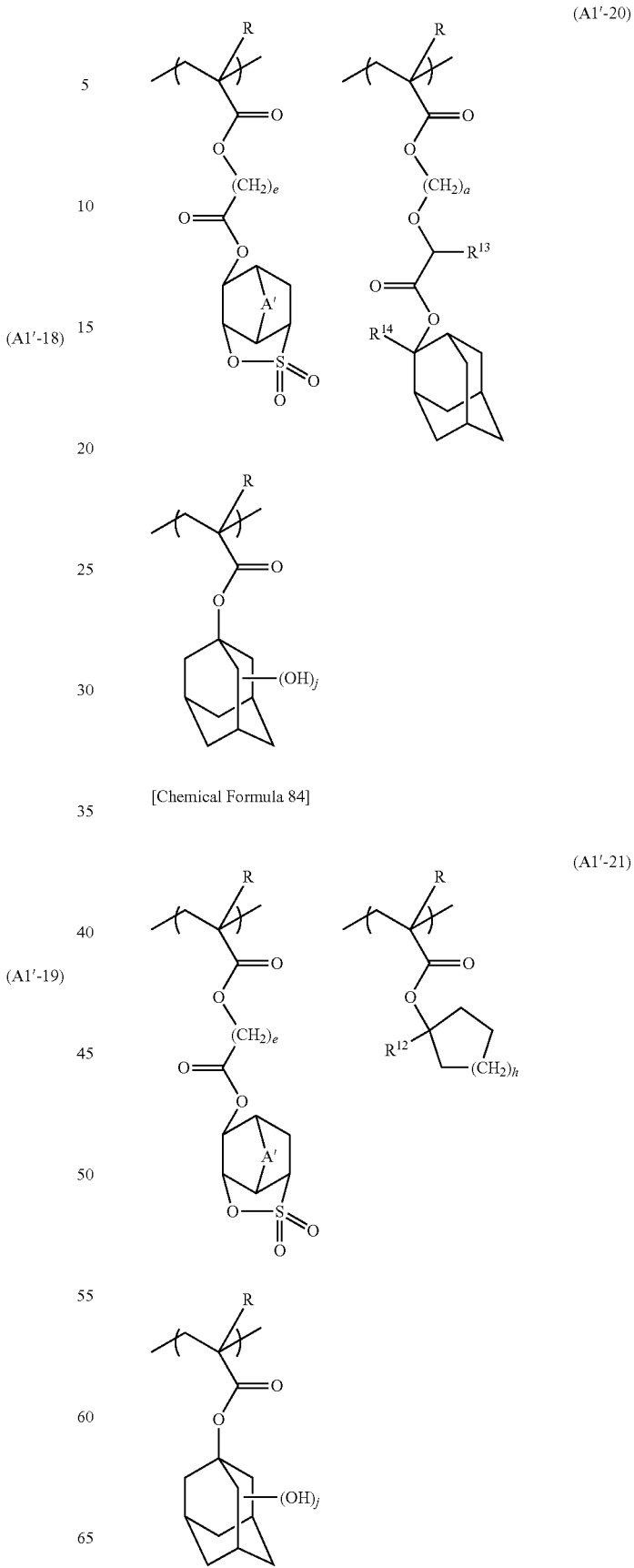
(A1'-20)
[Chemical Formula 84]
(A1'-21)

(A1'-22)

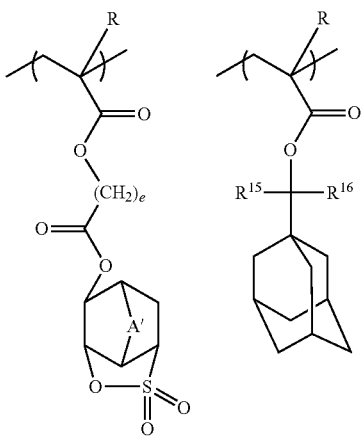

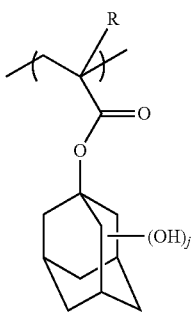

(A1'-23)

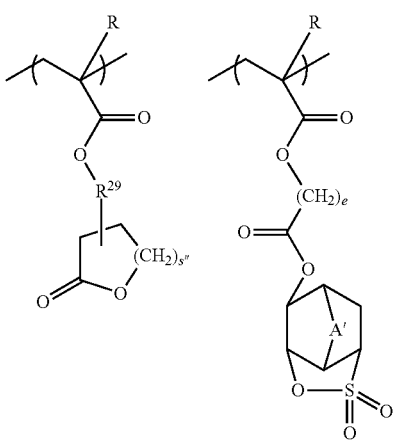

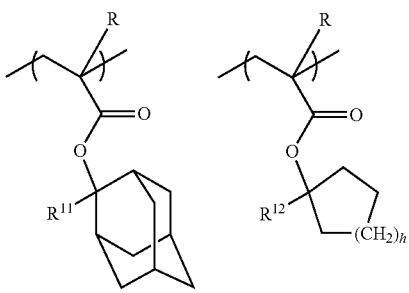

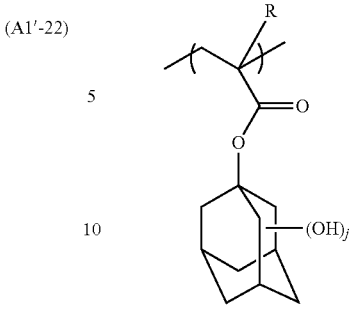

The weight average molecular weight (Mw) (the polystyrene equivalent value determined by gel permeation chromatography) of the polymeric compound contained in the component (A1) or (A1') is not particularly limited, but is preferably 1,000 to 50,000, more preferably 1,500 to 40,000, and most preferably 2,500 to 30,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) of the polymeric compound contained in the component (A1) or (A1') is not particularly limited, but is preferably 1.0 to 5.0, more preferably 1.0 to 3.0, particularly preferably 1.0 to 2.5, and most preferably 1.2 to 2.5. Here, Mn is the number average molecular weight.

In the component (A), as the component (A1'), one type may be used, or two or more types may be used in combination.

In the component (A), the amount of the component (A1') based on the total weight of the component (A) is preferably 25% by weight or more, more preferably 50% by weight or more, still more preferably 75% by weight or more, and may be even 100% by weight. When the amount of the component (A1') is 25% by weight or more, various lithography properties are improved.

The component (A1) can be produced, for example, by a radical polymerization of the monomers corresponding with each of the structural units that constitute the component (A1), using the aforementioned radical polymerization initiator of the present invention. As the monomers which yield the corresponding structural units, commercially available monomers may be used.

[Component (A2)]

In the resist composition of the present invention, the component (A) may contain "a base component which exhibits changed solubility in a developing solution under action of acid" other than the component (A1) and (A1') (hereafter, referred to as "component (A2)").

As the component (A2), it is preferable to use a compound that has a molecular weight of at least 500 and less than 2,500, contains a hydrophilic group, and also contains an acid dissociable group described above in connection with the component (A1).

Specific examples include compounds containing a plurality of phenol skeletons in which a part of the hydrogen atoms within hydroxyl groups have been substituted with the aforementioned acid dissociable groups.

Examples of the component (A2) include low molecular weight phenolic compounds in which a portion of the hydrogen atoms within hydroxyl groups have been substituted with an aforementioned acid dissociable group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers, tetramers, pentamers and hexamers of formalin condensation products of phenols such as phenol, m-cresol, p-cresol and xylenol. Needless to say, the low molecular weight phenol compound is not limited to these examples. In particular, a phenol compound having 2 to 6 triphenylmethane skeletons is preferable in terms of resolution and LWR.

Also, there are no particular limitations on the acid dissociable group, and suitable examples include the groups described above.

As the component (A2), a resin component other than the component (A1) is preferably used. Examples of the resin component other than the component (A1) include a polymeric compound other than the polymeric compound of the fourth aspect of the present invention, such as a polymeric compound produced using a conventional radical polymerization initiator instead of the radical polymerization initiator of the second aspect of the present invention. There are no particular limitations on the composition of the polymeric compound. It is preferable that the polymeric compound includes the structural units (a1) to (a3).

As the component (A2), one type of base component may be used, or two or more types of base components may be used in combination.

In the resist composition of the present invention, as the component (A), one type may be used, or two or more types may be used in combination.

In the resist composition of the present invention, the amount of the component (A) can be appropriately adjusted depending on the thickness of the resist film to be formed, and the like.

<Component (C)>

In the case where the resist composition of the fifth aspect of the present invention includes the component (B) in addition to the component (A), it is preferable that the resist composition further includes the component (C). When a resist pattern is formed using a resist composition containing the component (C), the contrast between exposed portions and unexposed portions is improved.

The resist composition of the seventh aspect of the present invention includes the components (A), (B), and (C).

The component (C) is an acid generator component which generates acid having a pKa of at least 0 upon exposure.

In the present invention, pKa refers to an acid dissociation constant which is generally used as a parameter which shows the acid strength of an objective substance. The pKa value of the acid generated from the component (B1) can be determined by a conventional method. Alternatively, the pKa value can be estimated by calculation using a conventional software such as "ACD/Labs" (trade name; manufactured by Advanced Chemistry Development, Inc.).

In the resist composition of the present invention, pKa of acid generated from the component (C) upon exposure is at least 0, preferably 0 to 15, more preferably 0.2 to 10, and still more preferably 0.5 to 8. The acid having a pKa within the aforementioned range becomes relatively weak compared to the acid generated from an acid generator (for example, component (B) described later) which is typically used as an acid generator of conventional chemically amplified resist compositions. Therefore, the component (C) functions as a quencher which traps the acid generated from either the terminal of the main chain of the component (A) or the component (B) described later, by salt exchange.

The structure of the component (C) is not particularly limited, as long as acid generated from the component (C) is within the range of pKa above, and specific examples thereof include at least one compound selected from the group consisting of a compound (C1) represented by general formula (c-1) shown below, a compound (C2) represented by general formula (c2) shown below and a compound (C3) represented by general formula (c3) shown below.

[Chemical Formula 85]

(c1)

(c2)

(c3)

In the formulae, $R^3$ represents a hydrocarbon group which may have a substituent; $Z^{2c}$ represents a hydrocarbon group of 1 to 30 carbon atoms which may have a substituent, provided that the carbon adjacent to S has no fluorine atom as a substituent; $R^4$ represents an organic group; $Y^3$ represents a linear, branched or cyclic alkylene group or an arylene group; $Rf_0$ represents a hydrocarbon group; and each $Z^+$ independently represents a sulfonium or iodonium cation.

(Component (C1))
Anion Moiety

In formula (c1), $R^3$ represents a hydrocarbon group which may have a substituent.

The hydrocarbon group of for $R^3$ which may have a substituent may be either an aromatic hydrocarbon group or an aliphatic hydrocarbon group.

The aromatic hydrocarbon group is a hydrocarbon group having an aromatic ring. The aromatic hydrocarbon group preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2, and most preferably 1.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned hetero atom can be used.

In the latter example, as the substituent for the aromatic hydrocarbon group, an alkyl group, an alkoxy group, a halogen atom, a halogenated alkyl group, a hydroxyl group, an oxygen atom (=O) or the like can be used.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Example of the halogenated alkyl group as the substituent for the aromatic hydrocarbon group includes a group in which part or all of the hydrogen atoms within the aforementioned alkyl group have been substituted with the aforementioned halogen atoms.

The aliphatic hydrocarbon group for $R^3$ may be either a saturated aliphatic hydrocarbon group, or an unsaturated aliphatic hydrocarbon group. Further, the aliphatic hydrocarbon group may be linear, branched or cyclic.

In the aliphatic hydrocarbon group for $R^3$, part of the carbon atoms constituting the aliphatic hydrocarbon group may be substituted with a substituent group containing a hetero atom, or part or all of the hydrogen atoms constituting the aliphatic hydrocarbon group may be substituted with a substituent group containing a hetero atom.

As the "hetero atom" for $R^3$, there is no particular limitation as long as it is an atom other than carbon and hydrogen. Examples of hetero atoms include a halogen atom, an oxygen atom, a sulfur atom and a nitrogen atom.

Examples of the halogen atom include a fluorine atom, a chlorine atom, an iodine atom and a bromine atom.

The substituent group containing a hetero atom may consist of a hetero atom, or may be a group containing a group or atom other than a hetero atom.

Specific examples of the substituent group for substituting a part of the carbon atoms include —O—, —C(=O)—O—, —C(=O)—, —O—C(=O)—O—, —C(=O)—NH—, —NH— (the H may be substituted with a substituent such as an alkyl group or an acyl group), —S—, —S(=O)$_2$— and —S(=O)$_2$—O—. When the aliphatic hydrocarbon group is cyclic, the aliphatic hydrocarbon group may contain any of these substituent groups in the ring structure.

Examples of the substituent group for substituting part or all of the hydrogen atoms include an alkoxy group, a halogen atom, a halogenated alkyl group, a hydroxyl group, an oxygen atom (=O) and a cyano group.

The aforementioned alkoxy group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5, still more preferably 2 to 4, and particularly preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, particularly preferably 6 to 15, and most preferably 6 to 12.

As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L6) and (S1) to (S4) shown below.

[Chemical Formula 86]

(L1)

(L2)

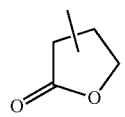

(L3)

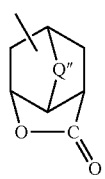

(L4)

(L5)

(L6)

(S1)

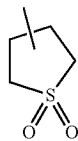

(S2)

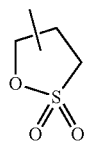

(S3)

(S4)

In the formulas, Q″ represents an alkylene group of 1 to 5 carbon atoms, —O—, —S—, —O—R$^{94}$— or —S—R$^{95}$— (R$^{94}$ and R$^{95}$ each independently represent an alkylene group of 1 to 5 carbon atoms); and m represents an integer of 0 or 1.

In the formulae, as the alkylene group for Q″, R$^{94}$ and R$^{95}$, the same alkylene groups as those described above for R$^{91}$ to R$^{93}$ can be used.

In these aliphatic cyclic groups, part of the hydrogen atoms bonded to the carbon atoms constituting the ring structure may be substituted with a substituent. Examples of substituents include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the substituent groups for substituting part or all of the hydrogen atoms can be used.

In the present invention, among these, as the hydrocarbon group for R$^3$ which may have a substituent, an aromatic hydrocarbon group which may have a substituent or an aliphatic cyclic group which may have a substituent is preferable, and a phenyl group or a naphthyl group which may have a substituent, or a group in which one or more hydrogen atoms have been removed from a polycycloalkane such as adamantane, norbornane, isobornane, tricyclodecane or tetracyclododecane is more preferable.

As the hydrocarbon group for R$^3$ which may have a substituent, a linear or branched alkyl group or a fluorinated alkyl group is also preferable.

As the linear or branched alkyl group for R$^3$, the same alkyl groups as those described above can be mentioned.

The fluorinated alkyl group for R$^3$ may be either chain-like or cyclic, but is preferably linear or branched.

The fluorinated alkyl group preferably has 1 to 11 carbon atoms, more preferably 1 to 8, and still more preferably 1 to 4.

Specific examples include a group in which part or all of the hydrogen atoms constituting a linear alkyl group (such as a methyl group, an ethyl group, a propyl group, a butyl group, a pentyl group, a hexyl group, a heptyl group, an octyl group, a nonyl group or a decyl group) have been substituted with fluorine atom(s), and a group in which part or all of the hydrogen atoms constituting a branched alkyl group (such as a 1-methylethyl group, a 1-methylpropyl group, a 2-methylpropyl group, a 1-methylbutyl group, a 2-methylbutyl group or a 3-methylbutyl group) have been substituted with fluorine atom(s).

The fluorinated alkyl group for $R^3$ may contain an atom other than fluorine. Examples of the atom other than fluorine include an oxygen atom, a carbon atom, a hydrogen atom, an oxygen atom, a sulfur atom and a nitrogen atom.

Among these, as the fluorinated alkyl group for $R^3$, a group in which part or all of the hydrogen atoms constituting a linear alkyl group have been substituted with fluorine atom(s) is preferable, and a group in which all of the hydrogen atoms constituting a linear alkyl group have been substituted with fluorine atoms (i.e., a perfluoroalkyl group) is more preferable.

Specific examples of preferable anion moieties for the component (C1) are shown below.

[Chemical Formula 87]

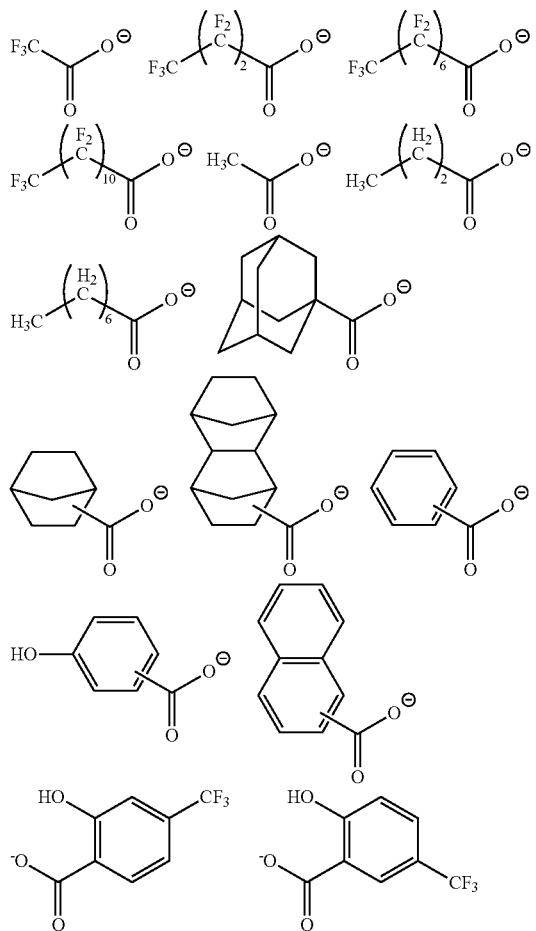

Cation Moiety

In formula (C1), $Z^+$ represents a sulfonium or an iodonium cation.

The sulfonium or an iodonium cation for $Z^+$ is not particularly limited, and examples thereof include the same cation moieties as those of compounds represented by the aforementioned formula (c-1), (c-2) or (c-3).

As the component (C1), one type of compound may be used, or two or more types of compounds may be used in combination.

(Component (C2))

Anion Moiety

In formula (c2), $Z^{2c}$ represents a hydrocarbon group of 1 to 30 carbon atoms which may have a substituent.

The hydrocarbon group of 1 to 30 carbon atoms for $Z^{2c}$ which may have a substituent may be either an aliphatic hydrocarbon group or an aromatic hydrocarbon group, and the same aliphatic hydrocarbon groups and aromatic hydrocarbon groups as those described above for the aforementioned $R^3$ can be used.

Among these, as the hydrocarbon group for $Z^{2c}$ which may have a substituent, an aliphatic cyclic group which may have a substituent is preferable, and a group in which one or more hydrogen atoms have been removed from adamantane, norbornane, isobornane, tricyclodecane, tetracyclododecane or camphor (which may have a substituent) is more preferable.

The hydrocarbon group for $Z^{2c}$ may have a substituent, and the same substituents as those described above for $R^3$ can be used. However, in $Z^{2c}$, the carbon adjacent to the S atom within $SO_3^-$ has no fluorine atom as a substituent. By virtue of $SO_3^-$ having no fluorine atom adjacent thereto, the anion of the component (C2) becomes an appropriately weak acid anion, thereby improving the quenching ability of the component (C).

Specific examples of preferable anion moieties for the component (C2) are shown below.

[Chemical Formula 88]

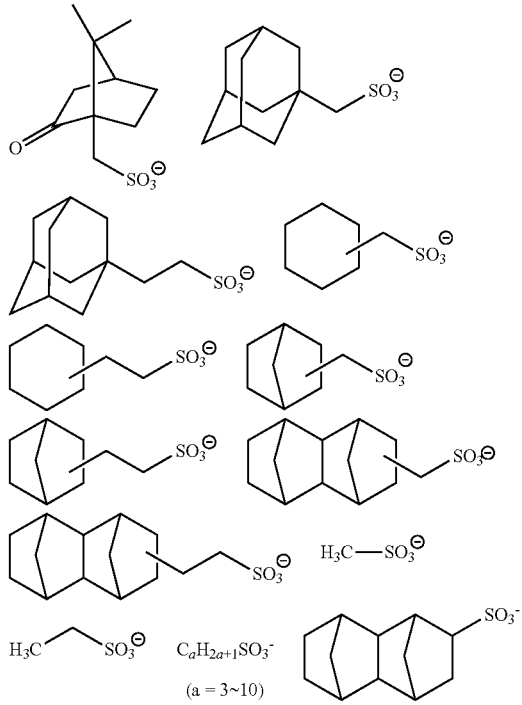

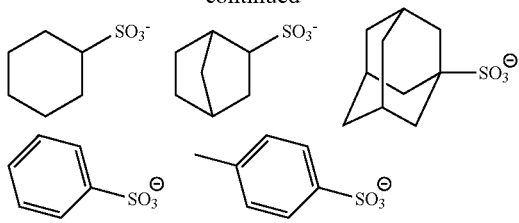

Cation Moiety

In formula (c2), $Z^+$ is the same as defined for $Z^+$ in the aforementioned formula (c1).

As the component (C2), one type of compound may be used, or two or more types of compounds may be used in combination.

(Component (C3))
Anion Moiety

In formula (c3), $R^4$ represents an organic group.

The organic group for $R^4$ is not particularly limited, and examples thereof include an alkyl group, an alkoxy group, —O—C(=O)—C($R^{C2}$)=CH$_2$ ($R^{C2}$ represents a hydrogen atom, an alkyl group of 1 to 5 carbon atoms or a halogenated alkyl group of 1 to 5 carbon atoms) and —O—C(=O)—$R^{C3}$ ($R^{C3}$ represents a hydrocarbon group).

The alkyl group for $R^4$ is preferably a linear or branched alkyl group of 1 to 5 carbon atoms, and specific examples include a methyl group, an ethyl group, a propyl group, an isopropyl group, an n-butyl group, an isobutyl group, a tert-butyl group, a pentyl group, an isopentyl group, and a neopentyl group. Part of the hydrogen atoms within the alkyl group for $R^4$ may be substituted with a hydroxy group, a cyano group or the like.

The alkoxy group for $R^4$ is preferably an alkoxy group of 1 to 5 carbon atoms, and specific examples thereof include a methoxy group, an ethoxy group, an n-propoxy group, an iso-propoxy group, an n-butoxy group and a tert-butoxy group. Among these, a methoxy group and an ethoxy group are particularly desirable.

When $R^4$ is —O—C(=O)—C($R^{C2}$)=CH$_2$, $R^{C2}$ represents a hydrogen atom, an alkyl group of 1 to 5 carbon atoms or a halogenated alkyl group of 1 to 5 carbon atoms.

The alkyl group of 1 to 5 carbon atoms for $R^{C2}$ is preferably a linear or branched alkyl group of 1 to 5 carbon atoms, and specific examples thereof include a methyl group, an ethyl group, a propyl group, an isopropyl group, an n-butyl group, an isobutyl group, a tert-butyl group, a pentyl group, an isopentyl group and a neopentyl group.

The halogenated alkyl group for $R^{C2}$ is a group in which part or all of the hydrogen atoms of the aforementioned alkyl group of 1 to 5 carbon atoms has been substituted with halogen atoms. Examples of the halogen atom include a fluorine atom, a chlorine atom, a bromine atom and an iodine atom, and a fluorine atom is particularly desirable.

As $R^{C2}$, a hydrogen atom, an alkyl group of 1 to 3 carbon atoms or a fluorinated alkyl group of 1 to 3 carbon atoms is preferable, and a hydrogen atom or a methyl group is particularly desirable in terms of industrial availability.

When $R^4$ is —O—C(=O)—$R^{C3}$, $R^{C3}$ represents a hydrocarbon group.

The hydrocarbon group for $R^{C3}$ may be either an aromatic hydrocarbon group or an aliphatic hydrocarbon group. Specific examples of the hydrocarbon group for $R^{C3}$ include the same hydrocarbon groups as those described for $R^3$.

Among these, as the hydrocarbon group for $R^{C3}$, an alicyclic group (e.g., a group in which one or more hydrogen atoms have been removed from a cycloalkane such as cyclopentane, cyclohexane, adamantane, norbornane, isobornane, tricyclodecane or tetracyclododecane) or an aromatic group (e.g., a phenyl group or a naphthyl group) is preferable. When $R^{C3}$ is an alicyclic group, the resist composition can be satisfactorily dissolved in an organic solvent, thereby improving the lithography properties. Alternatively, when $R^{C3}$ is an aromatic group, the resist composition exhibits an excellent photoabsorption efficiency in a lithography process using EUV or the like as the exposure source, thereby resulting in the improvement of the sensitivity and the lithography properties.

Among these, as $R^4$, —O—C(=O)—C($R^{C2'}$)=CH$_2$($R^{C2'}$ represents a hydrogen atom or a methyl group) or —O—C(=O)—$R^{C3'}$($R^{C3'}$ represents an aliphatic cyclic group) is preferable.

In formula (c3), $Y^3$ represents a linear, branched or cyclic alkylene group or an arylene group.

Examples of the linear, branched or cyclic alkylene group or the arylene group for $Y^3$ include the "linear or branched aliphatic hydrocarbon group", "cyclic aliphatic hydrocarbon group" and "aromatic hydrocarbon group" described above as the divalent linking group for W in the aforementioned formula (c-1-21).

Among these, as $Y^3$, an alkylene group is preferable, a linear or branched alkylene group is more preferable, and a methylene group or an ethylene group is still more preferable.

In formula (c3), $Rf_0$ represents a hydrocarbon group.

The hydrocarbon group represented by $Rf_0$ is the same as defined for the hydrocarbon group represented by $R^3$. As $Rf_0$, a hydrocarbon group containing a fluorine atom is preferable, and a fluorinated alkyl group is more preferable, and the same fluorinated alkyl groups as those described above for $R^3$ are still more preferable.

Specific examples of preferable anion moieties for the component (C3) are shown below.

[Chemical Formula 89]

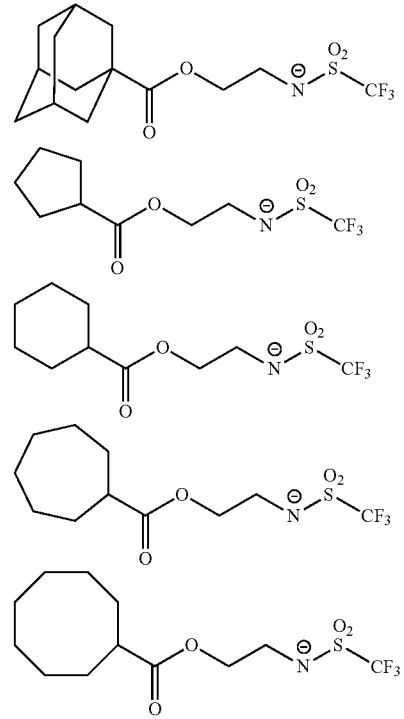

-continued
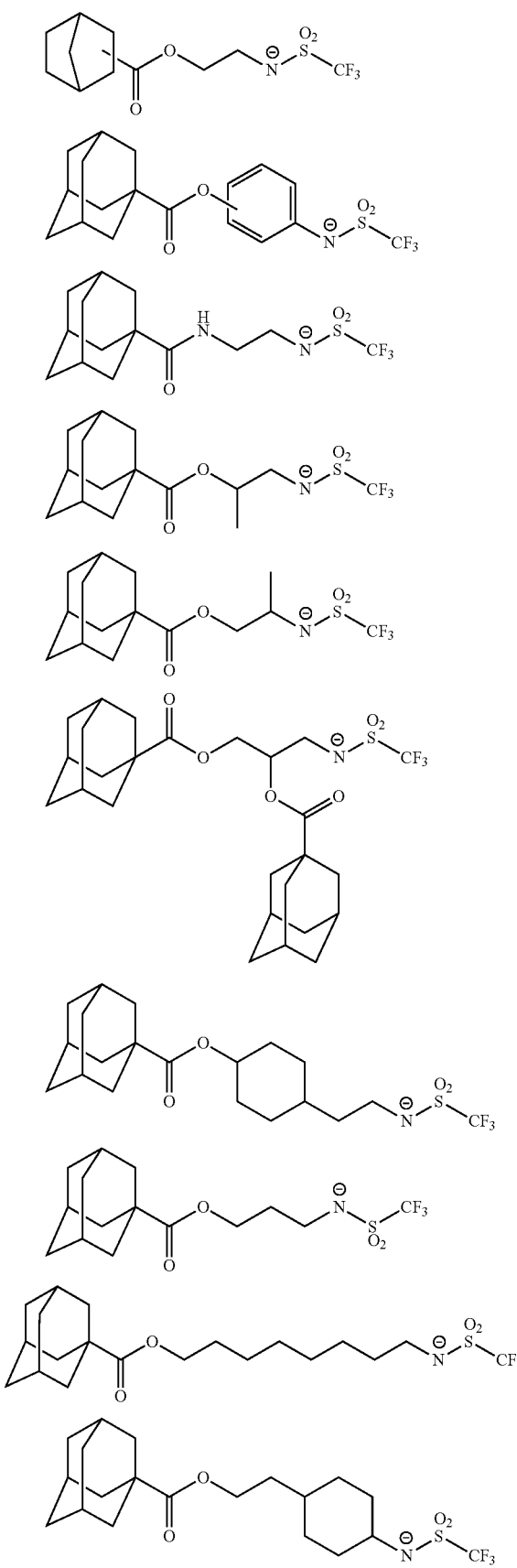
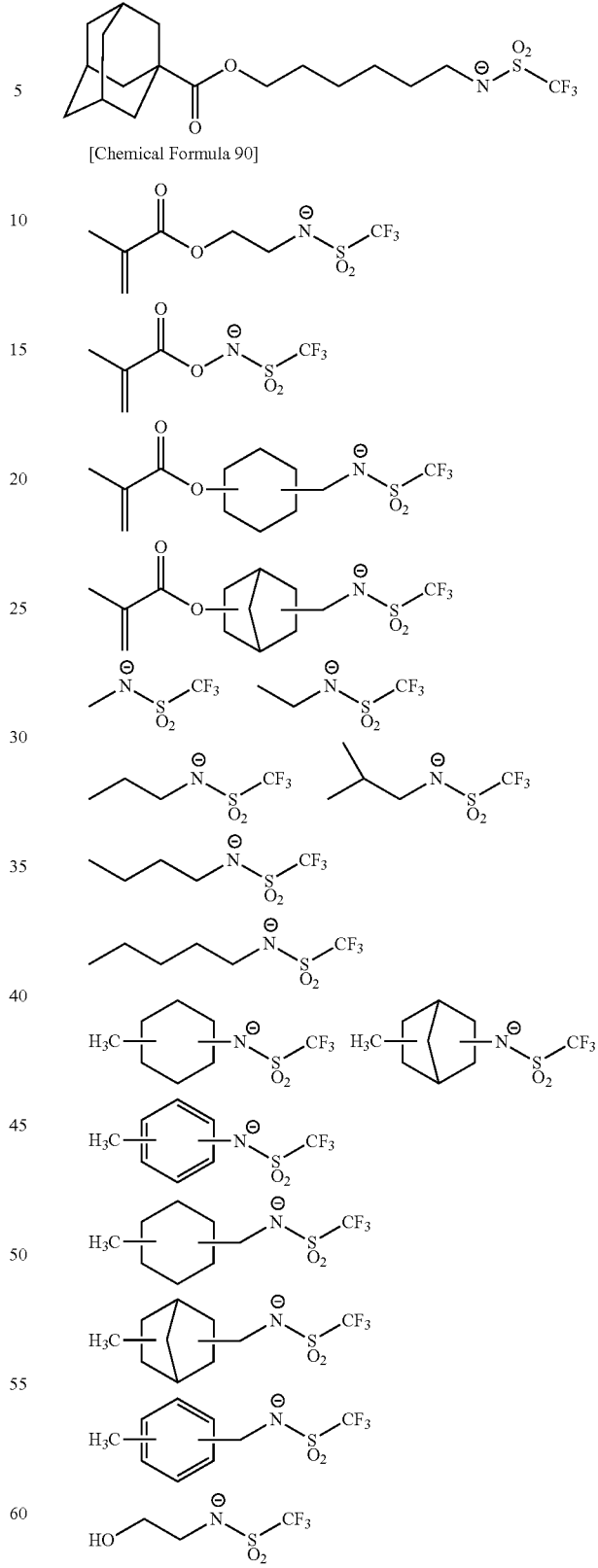
[Chemical Formula 90]
Cation Moiety
In formula (c3), $Z^+$ is the same as defined for $Z^+$ in the aforementioned formula (c1).

As the component (C3), one type of compound may be used, or two or more types of compounds may be used in combination.

The component (C1) may contain one of the aforementioned components (C1) to (C3), or at least two of the aforementioned components (C1) to (C3).

The total amount of the components (C1) to (C3) relative to 100 parts by weight of the component (A) is preferably within a range from 0.3 to 20.0 parts by weight, more preferably from 0.5 to 15 parts by weight, still more preferably from 1.0 to 13 parts by weight, and particularly preferably from 1.0 to 10 parts by weight. When the amount is at least as large as the lower limit of the above-mentioned range, excellent lithography properties and excellent resist pattern shape can be obtained. On the other hand, when the amount is no more than the upper limit of the above-mentioned range, sensitivity can be maintained at a satisfactory level, and throughput becomes excellent.

[Production Method of Components (C1) to (C3)]

In the present invention, the production methods of the components (C1) and (C2) are not particularly limited, and the components (C1) and (C2) can be produced by conventional methods.

Further, the production method of the component (C3) is not particularly limited. For example, in the case where $R^4$ in the formula (c3) has an oxygen atom on the terminal bonded to $Y^3$, a compound (i-1) represented by general formula (i-1) shown below can be reacted with a compound (i-2) represented by general formula (i-2) shown below to obtain a compound (i-3) represented by general formula (i-3) shown below, and the compound (i-3) can be reacted with a compound (i-4) having a desired cation $Z^+$ ($Q^-Z^+$), thereby producing a compound (C3) represented by general formula (c3).

[Chemical Formula 91]

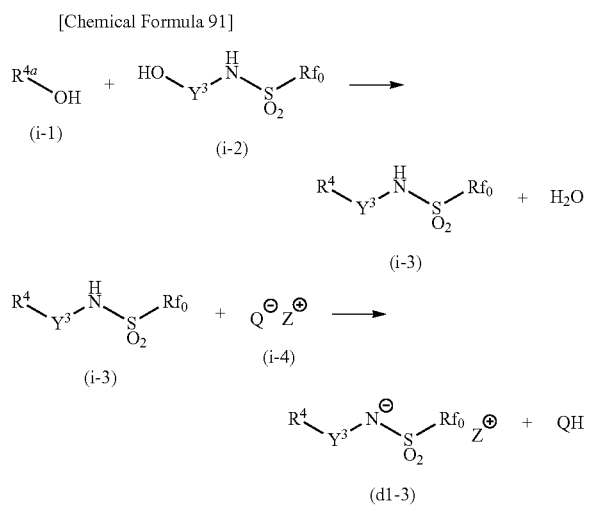

In the formulae, $R^4$, $Y^3$, $Rf_0$ and $Z^+$ are respectively the same as defined for $R^4$, $Y^3$, $Rf_0$ and $Z^+$ in the general formula (c3); $R^{4a}$ represents a group in which the terminal oxygen atom has been removed from $R^4$; and $Q^-$ represents a counteranion.

Firstly, the compound (i-1) is reacted with the compound (i-2), thereby obtaining the compound (i-3).

In formula (i-1), $R^{4a}$ represents a group in which the terminal oxygen atom has been removed from $R^4$. In formula (i-2), $Y^3$ and $Rf_0$ are the same as defined above.

As the compound (i-1) and the compound (i-2), commercially available compounds may be used, or the compounds may be synthesized.

The method for reacting the compound (i-1) with the compound (i-2) to obtain the compound (i-3) is not particularly limited, but can be performed, for example, by reacting the compound (i-1) with the compound (i-2) in an organic solvent in the presence of an appropriate acidic catalyst, followed by washing and recovering the reaction mixture.

The acidic catalyst used in the above reaction is not particularly limited, and examples thereof include toluenesulfonic acid and the like. The amount of the acidic catalyst is preferably 0.05 to 5 moles, per 1 mole of the compound (i-2).

As the organic solvent used in the above reaction, any organic solvent which is capable of dissolving the raw materials, i.e., the compound (i-1) and the compound (i-2) can be used, and specific examples thereof include toluene and the like. The amount of the organic solvent is preferably 0.5 to 100 parts by weight, more preferably 0.5 to 20 parts by weight, relative to the amount of the compound (i-1). As the solvent, one type may be used alone, or two or more types may be used in combination.

In general, the amount of the compound (i-2) used in the above reaction is preferably 0.5 to 5 moles per 1 mole of the compound (i-1), and more preferably 0.8 to 4 moles per 1 mole of the compound (i-1).

The reaction time depends on the reactivity of the compounds (i-1) and (i-2), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

Next, the obtained compound (i-3) is reacted with the compound (i-4), thereby obtaining the compound (d1-3).

In formula (i-4), $Z^+$ is the same as defined above, and $Q^-$ represents a counteranion.

The method for reacting the compound (i-3) with the compound (i-4) to obtain the compound (C3) is not particularly limited, but can be performed, for example, by dissolving the compound (i-3) in an appropriate organic solvent and water in the presence of an appropriate alkali metal hydroxide, followed by addition of the compound (i-4) and reacting while stirring.

The alkali metal hydroxide used in the above reaction is not particularly limited, and examples thereof include sodium hydroxide, potassium hydroxide and the like. The amount of the alkali metal hydroxide is preferably 0.3 to 3 moles, per 1 mole of the compound (i-3).

Examples of the organic solvent used in the above reaction include dichloromethane, chloroform, ethyl acetate and the like. The amount of the organic solvent is preferably 0.5 to 100 parts by weight, and more preferably 0.5 to 20 parts by weight, relative to the amount of the compound (i-3). As the solvent, one type may be used alone, or two or more types may be used in combination.

In general, the amount of the compound (i-4) used in the above reaction is preferably 0.5 to 5 moles per 1 mole of the compound (i-3), and more preferably 0.8 to 4 moles per 1 mole of the compound (i-3).

The reaction time depends on the reactivity of the compounds (i-3) and (i-4), the reaction temperature or the like. However, in general, the reaction time is preferably 1 to 80 hours, and more preferably 3 to 60 hours.

The reaction temperature in the above reaction is preferably 20 to 200° C., and more preferably 20 to 150° C.

After the reaction, the compound (C3) contained in the reaction mixture may be separated and purified. The separation and purification can be conducted by a conventional method. For example, any one of concentration, solvent extraction, distillation, crystallization, recrystallization and chromatography can be used alone, or two or more of these methods may be used in combination.

The structure of the compound (C3) obtained in the above-described manner can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

<Component (B)>

The resist composition of the fifth aspect of the present invention may further include an acid generator component (B) (hereafter, referred to as "component (B)") which generates acid upon irradiation of radial rays. That is, the component (B) in the fifth aspect of the present invention is an optional component.

In the seventh aspect of the present invention, the component (B) is an acid generator and does not fall under the definition of the component (C). That is, the component (B) in the seventh aspect of the present invention is an acid generator component which generates acid having a pKa of lower than 0 upon exposure. When the resist composition of the fifth aspect of the present invention includes the component (B), as the component (B), there is no particular limitation, and any of the known acid generators used in conventional chemically amplified resist compositions can be used.

In the resist composition of the fifth aspect or seventh aspect of the present invention, pKa of acid generated from the component (B) is lower than 0, preferably −0.5 to −15, more preferably −1.0 to −13, and still more preferably −1.5 to −11.

When pKa is within the above-mentioned range, the acid strength to change the solubility of the component (A) in a developing solution can be obtained.

In the seventh aspect of the present invention, as the structure of the component (B), there is no particular limitation, as long as the generated acid fulfills the pKa above, and any of the known acid generators used in conventional chemically amplified resist compositions can be used.

Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As an onium salt acid generator, a compound represented by general formula (b-1) or (b-2) shown below can be used.

[Chemical Formula 92]

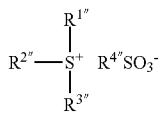
(b-1)

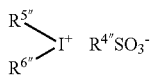
(b-2)

In the formulas above, $R^{1''}$ to $R^{3''}$, $R^{5''}$ and $R^{6''}$ each independently represent an aryl group or alkyl group, wherein two of $R^{1''}$ to $R^{3''}$ in the formula (b-1) may be bonded to each other to form a ring with the sulfur atom; and $R^{4''}$ represents an alkyl group, a halogenated alkyl group, an aryl group or an alkenyl group which may have a substituent, provided that at least one of $R^{1''}$ to $R^{3''}$ represents an aryl group, and at least one of $R^{5''}$ and $R^{6''}$ represents an aryl group.

In the resist composition according to the seventh aspect of the present invention, in $R^{4''}$, the carbon adjacent to the S atom has a fluorine atom as a substituent.

$R^{1''}$ to $R^{3''}$ in general formula (b-1) and $R^{5''}$ to $R^{6''}$ in general formula (b-2) are respectively the same as defined for $R^{1''}$ to $R^{3''}$ in general formula (c-1) above and $R^{5''}$ to $R^{6''}$ in general formula (c-2) above.

In formulas (b-1) and (b-2), $R^{4''}$ represents an alkyl group, a halogenated alkyl group, an aryl group or an alkenyl group which may have a substituent.

The alkyl group for $R^{4''}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms.

As an example of the halogenated alkyl group for $R^{4''}$, a group in which part of or all of the hydrogen atoms of the aforementioned linear, branched or cyclic alkyl group have been substituted with halogen atoms can be given. Examples of the aforementioned halogen atom include a fluorine atom, a chlorine atom, a bromine atom and an iodine atom, and a fluorine atom is preferable.

In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%. Higher halogenation ratio is preferable because the acid strength increases.

The aryl group for $R^{4''}$ is preferably an aryl group of 6 to 20 carbon atoms.

The alkenyl group for $R^{4''}$ is preferably an alkenyl group of 2 to 10 carbon atoms.

With respect to $R^{4''}$, the expression "may have a substituent" means that part of or all of the hydrogen atoms within the aforementioned linear, branched or cyclic alkyl group, halogenated alkyl group, aryl group or alkenyl group may be substituted with substituents (atoms other than hydrogen atoms, or groups).

However, in the resist composition according to the seventh aspect of the present invention, in $R^{4''}$, the carbon adjacent to the S atom within $SO_3$— has a fluorine atom as a substituent.

By virtue of $SO_3$— having a fluorine atom adjacent thereto, the anion of the component (B) becomes an appropriately strong acid anion, thereby the change of the solubility of the component (A) in a developing solution satisfactorily proceeds.

$R^{4''}$ may have one substituent, or two or more substituents.

Examples of the substituent include a halogen atom, a hetero atom, an alkyl group, a group represented by the formula $X^3$-$Q^1$- (wherein, $Q^1$ represents a divalent linking group containing an oxygen atom; and $X^3$ represents a hydrocarbon group of 3 to 30 carbon atoms which may have a substituent), and a group represented by the formula $X^c$-$Q^1$-$Y^1$— (wherein, $Q^1$ is the same as defined above; $X^c$ represents a hydrocarbon group of 3 to 30 carbon atoms which may have a substituent; and $Y^1$ represents an alkylene group of 1 to 4 carbon atoms which may have a substituent or a fluorinated alkylene group of 1 to 4 carbon atoms which may have a substituent).

Examples of halogen atoms and alkyl groups as substituents include the same halogen atoms and alkyl groups as those described above with respect to the halogenated alkyl group for $R^{4''}$.

Examples of hetero atoms include an oxygen atom, a nitrogen atom, and a sulfur atom.

In the group represented by formula $X^3$-$Q^1$-, $Q^1$ represents a divalent linking group containing an oxygen atom.

In the group represented by the formula $X^c$-$Q^1$-$Y^1$—, $Q^1$ represents a divalent linking group containing an oxygen atom.

$Q^1$ may contain an atom other than an oxygen atom. Examples of atoms other than oxygen include a carbon atom, a hydrogen atom, a sulfur atom and a nitrogen atom.

Examples of divalent linking groups containing an oxygen atom include non-hydrocarbon, oxygen atom-containing linkage groups such as an oxygen atom (an ether bond; —O—), an ester bond (—C(=O)—O—), an amido bond (—C(=O)—NH—), a carbonyl group (—C(=O)—) and a carbonate group (—O—C(=O)—O—); and a combination of any of the aforementioned non-hydrocarbon, oxygen atom-containing linkage groups with an alkylene group.

Specific examples of the combinations of the aforementioned non-hydrocarbon, oxygen atom-containing linkage groups with anlkylene groups include —$R^{91}$—O—, —$R^{92}$—O—C(=O)— and —C(=O)—O—$R^{93}$—O—C(=O)— (in the formulas, $R^{91}$ to $R^{93}$ each independently represent an alkylene group.)

The alkylene group for $R^{91}$ to $R^{93}$ is preferably a linear or branched alkylene group, and preferably has 1 to 12 carbon atoms, more preferably 1 to 5, and particularly preferably 1 to 3.

Specific examples of the alkylene group include a methylene group [—CH$_2$—]; alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$—; an ethylene group [—CH$_2$CH$_2$—]; alkylethylene groups such as —CH(CH$_3$)CH$_2$—, —CH(CH$_3$)CH(CH$_3$)—, —C(CH$_3$)$_2$CH$_2$— and —CH(CH$_2$CH$_3$)CH$_2$—; a trimethylene group (n-propylene group) [—CH$_2$CH$_2$CH$_2$—]; alkyltrimethylene groups such as —CH(CH$_3$)CH$_2$CH$_2$— and —CH$_2$CH(CH$_3$)CH$_2$—; a tetramethylene group [—CH$_2$CH$_2$CH$_2$CH$_2$—]; alkyltetramethylene groups such as —CH(CH$_3$)CH$_2$CH$_2$CH$_2$— and —CH$_2$CH(CH$_3$)CH$_2$CH$_2$—; and a pentamethylene group [—CH$_2$CH$_2$CH$_2$CH$_2$CH$_2$—].

As $Q^1$, a divalent linking group containing an ester bond or an ether bond is preferable, and —$R^{91}$—O—, —$R^{92}$—O—C(=O)— or —C(=O)—O—$R^{93}$—O—C(=O)— is more preferable.

In the group represented by the formula $X^3$-$Q^1$-, the hydrocarbon group for $X^3$ may be either an aromatic hydrocarbon group or an aliphatic hydrocarbon group.

In the group represented by the formula $X^c$-$Q^1$-, the hydrocarbon group for $X^c$ may be either an aromatic hydrocarbon group or an aliphatic hydrocarbon group.

The aromatic hydrocarbon group is a hydrocarbon group having an aromatic ring. The aromatic hydrocarbon group preferably has 3 to 30 carbon atoms, more preferably 5 to 30, still more preferably 5 to 20, still more preferably 6 to 15, and most preferably 6 to 12. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an alkylaryl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atom, more preferably 1 or 2, and most preferably 1.

The aromatic hydrocarbon group may have a substituent. For example, part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which part of the carbon atoms constituting the ring within the aforementioned aryl group has been substituted with a hetero atom such as an oxygen atom, a sulfur atom or a nitrogen atom, and a heteroarylalkyl group in which part of the carbon atoms constituting the aromatic hydrocarbon ring within the aforementioned arylalkyl group has been substituted with the aforementioned hetero atom can be used.

In the latter example, as the substituent for the aromatic hydrocarbon group, an alkyl group, an alkoxy group, a halogen atom, a halogenated alkyl group, a hydroxyl group, an oxygen atom (=O) or the like can be used.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Example of the halogenated alkyl group as the substituent for the aromatic hydrocarbon group includes a group in which part or all of the hydrogen atoms within the aforementioned alkyl group have been substituted with the aforementioned halogen atoms.

The aliphatic hydrocarbon group for $X^3$ may be either a saturated aliphatic hydrocarbon group, or an unsaturated aliphatic hydrocarbon group. Further, the aliphatic hydrocarbon group may be linear, branched or cyclic.

In the aliphatic hydrocarbon group for $X^3$, part of the carbon atoms constituting the aliphatic hydrocarbon group may be substituted with a substituent group containing a hetero atom, or part or all of the hydrogen atoms constituting the aliphatic hydrocarbon group may be substituted with a substituent group containing a hetero atom.

As the "hetero atom" for $X^3$, there is no particular limitation as long as it is an atom other than carbon and hydrogen. Examples of hetero atoms include a halogen atom, an oxygen atom, a sulfur atom and a nitrogen atom.

Examples of the halogen atom include a fluorine atom, a chlorine atom, an iodine atom and a bromine atom.

The substituent group containing a hetero atom may consist of a hetero atom, or may be a group containing a group or atom other than a hetero atom.

Specific examples of the substituent group for substituting a part of the carbon atoms include —O—, —C(=O)—O—, —C(=O)—, —O—C(=O)—O—, —C(=O)—NH—, —NH— (the H may be substituted with a substituent such as an alkyl group or an acyl group), —S—, —S(=O)₂— and —S(=O)₂—O—. When the aliphatic hydrocarbon group is cyclic, the aliphatic hydrocarbon group may contain any of these substituent groups in the ring structure.

Examples of the substituent group for substituting part or all of the hydrogen atoms include an alkoxy group, a halogen atom, a halogenated alkyl group, a hydroxyl group, an oxygen atom (=O) and a cyano group.

The aforementioned alkoxy group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the aforementioned halogen atom include a fluorine atom, a chlorine atom, a bromine atom and an iodine atom, and a fluorine atom is preferable.

Example of the aforementioned halogenated alkyl group includes a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, or a cyclic aliphatic hydrocarbon group (aliphatic cyclic group) is preferable.

The linear saturated hydrocarbon group (alkyl group) preferably has 1 to 20 carbon atoms, more preferably 1 to 15, and most preferably 1 to 10. Specific examples include a methyl group, an ethyl group, a propyl group, a butyl group, a pentyl group, a hexyl group, a heptyl group, an octyl group, a nonyl group, a decyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15, and most preferably 3 to 10. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5, still more preferably 2 to 4, and particularly preferably 3. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30, still more preferably 5 to 20, particularly preferably 6 to 15, and most preferably 6 to 12.

As the aliphatic cyclic group, a group in which one or more hydrogen atoms have been removed from a monocycloalkane or a polycycloalkane such as a bicycloalkane, tricycloalkane or tetracycloalkane can be used. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)₂— or —S(=O)₂—O—. Specific examples of such aliphatic cyclic groups include groups represented by formulas (L1) to (L6) and (S1) to (S4) shown below.

[Chemical Formula 93]

(L1)

(L2)

(L3)

(L4)

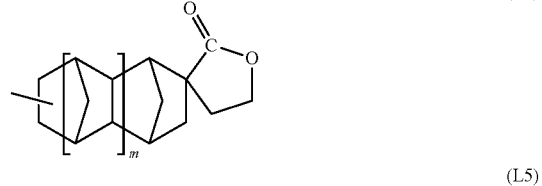

(L5)

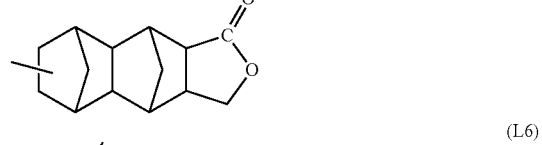

(L6)

(S1)

(S2)

(S3)

(S4)

In the formulas, Q" represents an alkylene group of 1 to 5 carbon atoms, —O—, —S—, —O—$R^{94}$— or —S—$R^{95}$— ($R^{94}$ and $R^{95}$ each independently represent an alkylene group of 1 to 5 carbon atoms); and m represents an integer of 0 or 1.

In the formulae, as the alkylene group for Q", $R^{94}$ and $R^{95}$, the same alkylene groups as those described above for $R^{91}$ to $R^{93}$ can be used.

In these aliphatic cyclic groups, part of the hydrogen atoms bonded to the carbon atoms constituting the ring structure may be substituted with a substituent. Examples of substituents include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the substituent groups for substituting part or all of the hydrogen atoms can be used.

In the present invention, as $X^3$, a cyclic group which may have a substituent is preferable. The cyclic group may be either an aromatic hydrocarbon group which may have a substituent, or an aliphatic cyclic group which may have a substituent, and an aliphatic cyclic group which may have a substituent is preferable.

As the aromatic hydrocarbon group, a naphthyl group which may have a substituent, or a phenyl group which may have a substituent is preferable.

As the aliphatic cyclic group which may have a substituent, an aliphatic polycyclic group which may have a substituent is preferable. As the aliphatic polycyclic group, the aforementioned group in which one or more hydrogen atoms have been removed from a polycycloalkane, and groups represented by the aforementioned formulas (L2) to (L6), (S3) and (S4) are preferable.

In the present invention, $R^{4'''}$ preferably has $X^3$-$Q^1$- as a substituent. In such a case, $R^{4'''}$ is preferably a group represented by the formula $X^3$-$Q^1$-$Y^{10}$— (in the formula, $Q^1$ and $X^3$ are the same as defined above; and $Y^{10}$ represents an alkylene group of 1 to 4 carbon atoms which may have a substituent, or a fluorinated alkylene group of 1 to 4 carbon atoms which may have a substituent).

In the group represented by the formula $X^3$-$Q^1$-$Y^{10}$—, as the alkylene group for $Y^{10}$, the same alkylene group as those described above for $Q^1$ in which the number of carbon atoms is 1 to 4 can be used.

In the group represented by the formula $X^c$-$Q^1$-$Y^{10}$—, as the alkylene group for $Y^{10}$, the same alkylene group as those described above for $Q^1$ in which the number of carbon atoms is 1 to 4 can be used.

As the fluorinated alkylene group, the aforementioned alkylene group in which part or all of the hydrogen atoms has been substituted with fluorine atoms can be used.

Specific examples of $Y^{10}$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

As $Y^{10}$, a fluorinated alkylene group is preferable, and a fluorinated alkylene group in which the carbon atom bonded to the adjacent sulfur atom is fluorinated is particularly desirable. Specific examples for the fluorinated alkylene group include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—; —$CH_2CF_2$—, —$CH_2CH_2CF_2$—, —$CH_2CF_2CF_2$—; —$CH_2CH_2CH_2CF_2$—, —$CH_2CH_2CF_2CF_2$—, and —$CH_2CF_2CF_2CF_2$—.

Among these, —$CF_2$—, —$CF_2CF_2$—, —$CF_2CF_2CF_2$—, or $CH_2CF_2CF_2$— is preferable, —$CF_2$—, —$CF_2CF_2$— or —$CF_2CF_2CF_2$— is more preferable, and —$CF_2$— is particularly preferable.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group has been substituted with groups other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxyl group.

In the seventh aspect of the present invention, $R^{4'''}$ preferably has $X^c$-$Q^1$-$Y^{10}$— as a substituent.

Specific examples of suitable onium salt acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyptetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts is replaced by an alkyl sulfonate, such as methanesulfonate, n-propanesulfonate, n-butanesulfonate, n-octanesulfonate, 1-adamantanesulfonate, 2-norbornanesulfonate or d-camphor-10-sulfonate; or replaced by an aromatic sulfonate, such as benzenesulfonate, perfluorobenzenesulfonate or p-toluenesulfonate.

Furthermore, onium salts in which the anion moiety of these onium salts are replaced by an anion moiety represented by any one of formulas (b1) to (b9) shown below can be used.

[Chemical Formula 94]

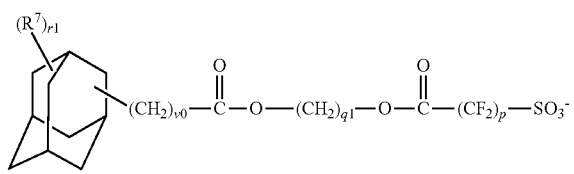
(b1)

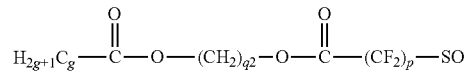
(b2)

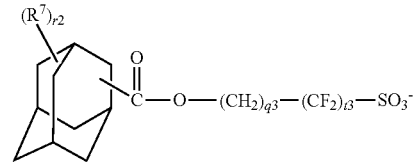
(b3)

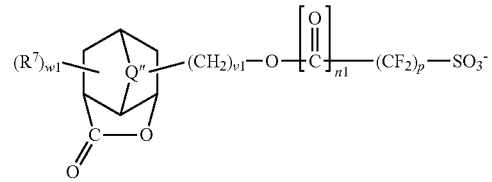
(b4)

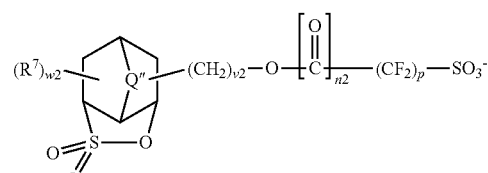
(b5)

[Chemical Formula 95]

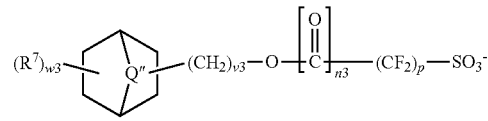
(b6)

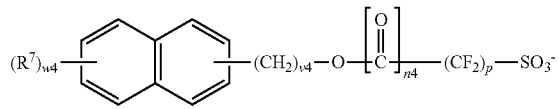
(b7)

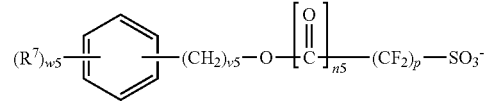
(b8)

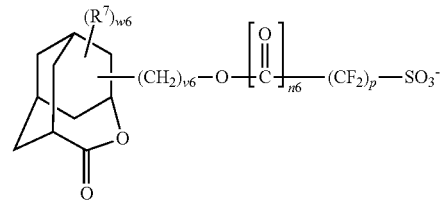
(b9)

In the formulas, p represents an integer of 1 to 3; each of q1 and q2 independently represents an integer of 1 to 5; q3 represents an integer of 1 to 12; t3 represents an integer of 1 to 3; each of r1 and r2 independently represents an integer of 0 to 3; g represents an integer of 1 to 20; $R^7$ represents a substituent; each of n1 to n6 independently represents 0 or 1; each of v0 to v6 independently represents an integer of 0 to 3; each of w1 to w6 independently represents an integer of 0 to 3; and Q" is the same as defined above.

As the substituent for $R^7$, the same groups as those which the aforementioned hydrocarbon group for $R^3$ in the formula (c1) may have as a substituent can be used.

If there are two or more of the $R^7$ group, as indicated by the values r1, r2, and w1 to w6, then the two or more of the $R^7$ groups may be the same or different from each other.

Further, onium salt-based acid generators in which the anion moiety in general formula (b-1) or (b-2) is replaced by an anion moiety represented by general formula (b-3) or (b-4) shown below (the cation moiety is the same as that of (b-1) or (b-2)) may be used.

[Chemical Formula 96]

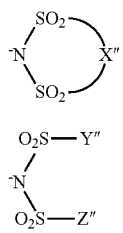
(b-3)

(b-4)

In the formulas, X" represents an alkylene group of 2 to 6 carbon atoms in which at least one hydrogen atom has been substituted with a fluorine atom; and Y" and Z" each independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and it is preferable that the number of hydrogen atoms substituted with fluorine atoms is as large as possible because the acid strength increases and the transparency to high energy radiation of 200 nm or less or electron beam is improved.

The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

Furthermore, as an onium salt-based acid generator, a sulfonium salt having a cation moiety represented by the general formula (c-3) may be used. The anion moiety of the sulfonium salt having a cation moiety represented by the general formula (c-3) is not particularly limited, and the same anion moieties for onium salt-based acid generators which have been proposed may be used. Examples of such anion moieties include fluorinated alkylsulfonic acid ions such as anion moieties ($R^{4''}SO_3^-$) for onium salt-based acid generators represented by general formula (b-1) or (b-2) shown above; and anion moieties represented by general formula (b-3) or (b-4) shown above.

In the present description, an oxime sulfonate-based acid generator is a compound having at least one group represented by general formula (B-1) shown below, and has a feature of generating acid by irradiation. Such oxime sulfonate-based acid generators are widely used for a chemically amplified resist composition, and can be appropriately selected.

[Chemical Formula 97]

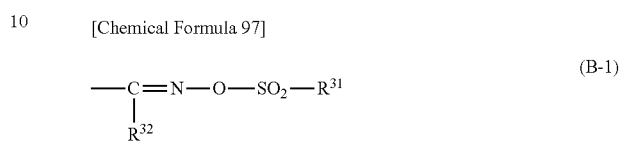
(B-1)

In the formula (B-1), $R^{31}$ and $R^{32}$ each independently represent an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The alkyl group or the aryl group "has a substituent" means that part or all of the hydrogen atoms of the alkyl group or the aryl group is substituted with a substituent.

The alkyl group preferably has 1 to 20 carbon atoms, more preferably 1 to 10 carbon atoms, still more preferably 1 to 8 carbon atoms, particularly preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of halogen atoms include fluorine atoms, chlorine atoms, bromine atoms and iodine atoms, and fluorine atoms are particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms and the "completely halogenated aryl group" refers to an aryl group in which all of hydrogen atoms are substituted with halogen atoms.

As $R^{31}$, an alkyl group of 1 to 4 carbon atoms having no substituent or a fluorinated alkyl group of 1 to 4 carbon atoms is particularly desirable.

As the organic group for $R^{32}$, a linear, branched, or cyclic alkyl group, aryl group, or cyano group is preferable. As the alkyl group or the aryl group for $R^{32}$, the same alkyl groups or aryl groups as those described above for $R^{31}$ can be used.

As $R^{32}$, a cyano group, an alkyl group of 1 to 8 carbon atoms having no substituent or a fluorinated alkyl group of 1 to 8 carbon atoms is particularly desirable.

Preferable examples of the oxime sulfonate-based acid generator include compounds represented by general formula (B-2) or (B-3) shown below.

[Chemical Formula 98]

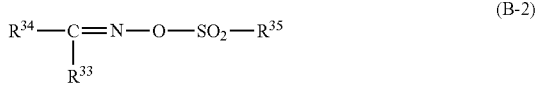

(B-2)

In the formula (B-2), $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 99]

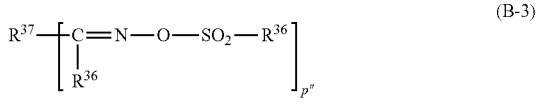

(B-3)

In the formula (B-3), $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (B-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenantryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (B-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propyl sulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methyl sulfonyl oxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 86) may be preferably used.

Furthermore, as preferable examples, the following can be used.

[Chemical Formula 100]

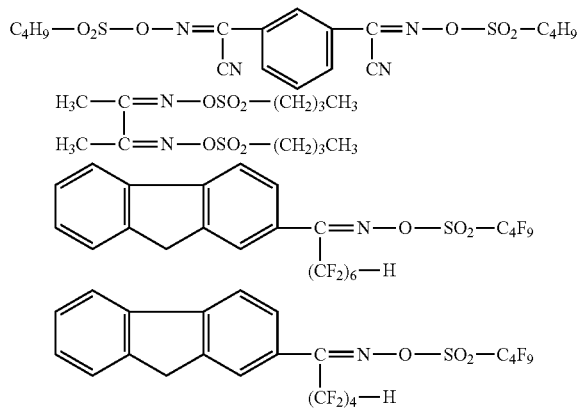

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be mentioned.

As the component (B), one type of acid generator may be used, or two or more types of acid generators may be used in combination.

When the resist composition of the present invention contains a component (B), as the component (B), it is preferable to use an onium salt having a fluorinated alkylsulfonic acid ion as the anion moiety.

When the resist composition of the present invention contains the component (B), the amount of the component (B) relative to 100 parts by weight of the component (A) is preferably 0.5 to 50 parts by weight, and more preferably 1 to 40 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

<Component (D)>

It is preferable that the resist composition of the present invention further includes a nitrogen-containing organic compound (D) which does not fall under the category of the components (A) to (C) (hereafter referred to as the component (D)), as an optional component.

As the component (D), there is no particular limitation as long as it functions as an acid diffusion control agent, i.e., a quencher which traps the acid generated from the component (A1), component (A1'), and component (B) upon exposure. A multitude of these components (D) have already been proposed, and any of these known compounds may be used. Among these, an aliphatic amine, particularly a secondary aliphatic amine or tertiary aliphatic amine is preferable.

An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkyl amines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decylamine, and tri-n-dodecylamine; and alkylalcoholamines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine and tri-n-octylamine are particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine and triethanolamine triacetate, and triethanolamine triacetate is preferable.

Further, as the component (D), an aromatic amine may be used.

Examples of aromatic amines include aniline, pyridine, 4-dimethylaminopyridine, pyrrole, indole, pyrazole, imidazole and derivatives thereof, as well as diphenylamine, triphenylamine, tribenzylamine, 2,6-diisopropylaniline and N-tert-butoxycarbonylpyrrolidine.

As the component (D), one type of compound may be used alone, or two or more types may be used in combination.

The component (D) is typically used in an amount within a range from 0.01 to 5.0 parts by weight, relative to 100 parts by weight of the component (A). When the amount of the component (D) is within the above-mentioned range, the shape of the resist pattern and the post exposure stability of the latent image formed by the pattern-wise exposure of the resist layer are improved.

<Component (E)>

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of phosphorous oxo acid derivatives include esters in which a hydrogen atom within the above-mentioned phosphorous oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenyl phosphonate, diphenyl phosphonate and dibenzyl phosphonate.

Examples of phosphinic acid derivatives include phenylphosphinic acid and phosphinic acid esters.

As the component (E), salicylic acid is particularly desirable.

As the component (E), one type may be used alone, or two or more types may be used in combination.

The component (E) is typically used in an amount within a range from 0.01 to 5.0 parts by weight, relative to 100 parts by weight of the component (A).

<Component (F)>

The resist composition may further include a fluorine additive (hereafter, referred to as "component (F)") for imparting water repellency to the resist film. As the component (F), for example, a fluorine-containing polymeric compound described in Japanese Unexamined Patent Application, First Publication No. 2010-002870.

Specific examples of the component (F) include polymers having a structural unit (f1) represented by general formula (f1-1) shown below. As such polymer, a polymer (homopolymer) consisting of a structural unit (f1); a copolymer of a structural unit represented by formula (f1-1) shown below and the aforementioned structural unit (a1); and a copolymer of a structural unit represented by the formula (f1-1) shown below, a structural unit derived from acrylic acid or methacrylic acid and the aforementioned structural unit (a1) are preferable. As the structural unit (a1) to be copolymerized with a structural unit represented by formula (f1-1) shown below, a structural unit represented by the aforementioned formula (a1-1) is preferable, and a structural unit represented by the aforementioned formula (a1-1-32) is particularly desirable.

[Chemical Formula 101]

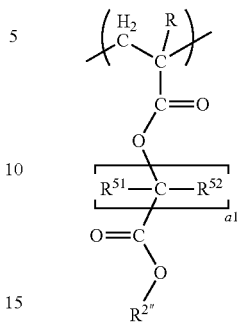

(f1-1)

In the formula, R is the same as defined above; $R^{51}$ and $R^{52}$ each independently represents a hydrogen atom, a halogen atom, an alkyl group of 1 to 5 carbon atoms or a halogenated alkyl group of 1 to 5 carbon atoms, provided that the plurality of $R^{51}$ and $R^{52}$ may be the same or different; a1 represents an integer of 1 to 5; and $R^{2'''}$ represents an organic group containing a fluorine atom.

In formula (f1-1), R is the same as defined above. As R, a hydrogen atom or a methyl group is preferable.

In formula (f1-1), examples of the halogen atom for $R^{51}$ and $R^{52}$ include a fluorine atom, a chlorine atom, a bromine atom and an iodine atom, and a fluorine atom is particularly desirable. Examples of the alkyl group of 1 to 5 carbon atoms for $R^{51}$ and $R^{52}$ include the same alkyl group of 1 to 5 carbon atoms for R defined above, and a methyl group or an ethyl group is preferable. Specific examples of the halogenated alkyl group of 1 to 5 carbon atoms represented by $R^{51}$ and $R^{52}$ include groups in which part or all of the hydrogen atoms of the aforementioned alkyl groups of 1 to 5 carbon atoms have been substituted with halogen atoms. Examples of the halogen atom include a fluorine atom, a chlorine atom, a bromine atom and an iodine atom, and a fluorine atom is particularly desirable. Among these, as $R^{51}$ and $R^{52}$, a hydrogen atom, a fluorine atom or an alkyl group of 1 to 5 carbon atoms is preferable, and a hydrogen atom, a fluorine atom, a methyl group or an ethyl group is more preferable.

In formula (f1-1), a1 represents an integer of 1 to 5, preferably an integer of 1 to 3, and more preferably 1 or 2.

In formula (f1-1), $R^{2'''}$ represents an organic group containing a fluorine atom, and is preferably a hydrocarbon group containing a fluorine atom.

The hydrocarbon group containing a fluorine atom may be linear, branched or cyclic, and preferably has 1 to 20 carbon atoms, more preferably 1 to 15 carbon atoms, and most preferably 1 to 10 carbon atoms.

It is preferable that the hydrocarbon group having a fluorine atom has 25% or more of the hydrogen atoms within the hydrocarbon group fluorinated, more preferably 50% or more, and most preferably 60% or more, as the hydrophobicity of the resist film during immersion exposure is enhanced.

Among these, as $R^{2'''}$, a fluorinated hydrocarbon group of 1 to 5 carbon atoms is particularly preferable, and a methyl group, $—CH_2—CF_3$, $—CH_2—CF_2—CF_3$, $—CH(CF_3)_2$, $—CH_2—CH_2—CF_3$, and $—CH_2—CH_2—CF_2—CF_2—CF_2—CF_3$ are most preferable.

When the component (F) is a fluorine-containing polymeric compound (polymeric compound), the weight average molecular weight (Mw) (the polystyrene equivalent value determined by gel permeation chromatography) of the component (F) is not particularly limited, but is preferably 1,000 to 50,000, more preferably 5,000 to 40,000, and most preferably 10,000 to 30,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, when the component (F) is a fluorine-containing polymeric compound, the dispersity (Mw/Mn) of the component (F) is not particularly limited, but is preferably 1.0 to 5.0, more preferably 1.0 to 3.0, and most preferably 1.2 to 2.5.

Here, Mn is the number average molecular weight.

When the component (F) is a fluorine-containing polymeric compound, the component (F) can be obtained, for example, by a conventional radical polymerization or the like of the monomers corresponding with each of the structural units, using a radical polymerization initiator such as dimethyl-2,2-azobis(2-methylpropionate) (V-601) or azobisisobutyronitrile (AIBN). By using a chain transfer agent such as HS—$CH_2$—$CH_2$—$CH_2$—$C(CF_3)_2$—OH in polymerization reaction, a —$C(CF_3)_2$—OH group can be introduced at the terminals of the component (F). Such a copolymer having introduced a hydroxyalkyl group in which some of the hydrogen atoms of the alkyl group are substituted with fluorine atoms is effective in reducing defects and LER (line edge roughness: unevenness of the side walls of a line pattern).

As the monomers which yield the corresponding structural units, commercially available monomers may be used, or the monomers may be synthesized by a conventional method.

As the component (F), one type may be used alone, or two or more types may be used in combination.

The component (F) is typically used in an amount within a range from 0.5 to 10 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

<Component (S)>

The resist composition of the present invention can be prepared by dissolving the materials for the resist composition in an organic solvent (hereafter, frequently referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethylsulfoxide (DMSO).

These solvents can be used individually, or in combination as a mixed solvent.

Among these, propylene glycol monomethyl ether acetate (PGMEA), propylene glycol monomethyl ether (PGME), cyclohexanone and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

Furthermore, as the component (S), a mixed solvent of PGMEA and cyclohexanone, or a mixed solvent of PGMEA, PGME and cyclohexanone is also preferable. In such a case, the mixing ratio of the former in terms of weight ratio is preferably PGMEA:cyclohexanone=95 to 5:10 to 90, and the mixing ratio of the latter in terms of weight ratio is preferably PGMEA:PGME:cyclohexanone=35 to 55:20 to 40:15 to 35.

The amount of the component (S) is not particularly limited, and is appropriately adjusted to a concentration which enables coating of a resist solution to a substrate. In general, the organic solvent is used in an amount such that the solid content of the resist composition becomes within the range from 1 to 20% by weight, and preferably from 2 to 15% by weight.

According to the present invention, a resist composition which exhibits excellent lithography properties such as sensitivity, EL margin (exposure latitude), MEF (mask reproducibility) and LWR (reduced roughness), and excellent shape can be obtained.

The reason why these effects can be achieved has not been elucidated yet, but the polymeric compound contained in the resist composition of the fifth aspect of the present invention has a terminal group (I-1) which generates acid upon exposure. Therefore, it is presumed that, acid is generated from the terminal of the polymeric compound at exposed portions, and sensitivity can be improved. Further, it is presumed that, in the case where the polymeric compound has a group which exhibits a function of generating acid, the excess diffusion of acid generated can be suppressed, as compared to the case where the acid generator of low-molecular compound as exemplified above as a component (B) is used alone, and hence, these effects as described above can be obtained.

The polymeric compound (A1) contained in the resist composition of the seventh aspect of the present invention has an anion portion which generates acid upon exposure, on at least one terminal of the main chain thereof, and hence, exhibits a function of generating acid upon exposure.

For example, the group represented by the general formula (an1) and the terminal group (I-1) have a sulfonium salt portion at the terminal thereof, thereby generating sulfonic acid upon exposure.

Therefore, it is presumed that, acid is generated from the terminal of the polymeric compound at exposed portions, and sensitivity can be improved.

Further, it is presumed that, in the case where the polymeric compound has a group which exhibits a function of generating acid, the excess diffusion of acid generated can be suppressed, as compared to the case where the acid generator of low-molecular compound as exemplified above as a component (B) is used alone.

The anion portions at the terminal of the main chain, which generate acid upon exposure, is uniformly distributed within the resist film, and at exposed portions, acid is generated uniformly from the anion portions. As a result, at exposed portions, the acid decomposable group in the polymeric compound (A1) is likely to be decomposed uniformly.

In the case where the polymeric compound contained in the resist composition of the fifth aspect of the present invention is the component (A1') which exhibits changed solubility in a developing solution by the action of acid, the terminal group (I-1) which generates acid upon exposure is uniformly distributed within the resist film together with the component (A1'). It is presumed that acid is uniformly generated from the terminal group (I-1) at exposed portions, so that the acid decomposable groups within the component (A1') is uniformly cleaved at exposed portions, thereby achieving the aforementioned effects. The component (A1') has a group (I-1) which generates acid upon exposure, and the acid decomposable group and acid generated are present in relatively close. It is presumed that a decomposition reaction by the action of acid is likely to proceed, thereby improving the aforementioned effect.

In the case where the polymeric compound contained in the resist composition of the seventh aspect of the present invention is the component (A1) which exhibits increased polarity by the action of acid, the acid decomposable group and acid generated from the anion portion are present in relatively close. As a result, a decomposition reaction of the acid decomposable group is likely to proceed by the action of acid, Furthermore, the polymeric compound contained in the resist composition of the seventh aspect of the present invention includes the component (C) which functions as a quencher, in addition to the polymeric compound (A1). It is presumed that the component (C) lose the function as a quencher at exposed portions, thereby making a large contrast of concentration of acid between the exposed portions and the unexposed portions, and enabling formation of a pattern with excellent shape and lithography properties.

<<Method of Forming a Resist Pattern>>

The method of forming a resist pattern according to the sixth aspect and eighth aspect of the present invention includes: forming a resist film on a substrate using a resist composition of the fifth aspect of the present invention; conducting exposure of the resist film; and developing the resist film to form a resist pattern.

The method for forming a resist pattern according to the present invention can be performed, for example, as follows.

Firstly, a resist composition is applied onto a substrate using a spinner or the like, and a prebake (post applied bake (PAB)) is conducted under temperature conditions of 80 to 150° C. for 40 to 120 seconds, preferably 60 to 90 seconds to form a resist film. Then, for example, either by exposure with an ArF excimer laser or an electron beam (EB) through a desired mask pattern using an ArF exposure apparatus or an electron beam lithography apparatus, or by patterning via direct irradiation with an electron beam without using a mask pattern, followed by post exposure bake (PEB) under temperature conditions of 80 to 150° C. for 40 to 120 seconds, preferably 60 to 90 seconds. Subsequently, the resist film is subjected to a developing process.

In the case of an alkali developing process, an alkali developing solution such as a 0.1 to 10% by weight aqueous solution of tetramethylammonium hydroxide (TMAH) is used to perform an alkali developing treatment.

Alternatively, in the case of a solvent developing process, an organic solvent is used to perform a developing treatment. As the organic solvent, any of the conventional organic solvents can be used which are capable of dissolving the component (A) (prior to exposure). Specific examples of the organic solvent include polar solvents such as ketone solvents, ester solvents, alcohol solvents, amide solvents and ether solvents, and hydrocarbon solvents. Among these, ester solvents are preferable. As an ester solvent, butyl acetate is preferable.

After the developing treatment, it is preferable to conduct a rinse treatment. In the case of an alkali developing process, it is preferable to conduct a water rinse using pure water. In the case of a solvent developing process, it is preferable to use a rinse liquid containing the aforementioned organic solvent.

In the case of a solvent developing process, after the developing treatment or the rinsing, the developing solution or the rinse liquid remaining on the pattern can be removed by a treatment using a supercritical fluid.

Thereafter, drying is conducted. If desired, bake treatment (post bake) can be conducted following the developing. In this manner, a resist pattern that is faithful to the mask pattern can be obtained.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic anti-reflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio.

More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film is formed (triple-layer resist method).

The wavelength to be used for exposure is not particularly limited and the exposure can be conducted using radiations such as ArF excimer laser, KrF excimer laser, $F_2$ excimer laser, extreme ultraviolet rays (EUV), vacuum ultraviolet rays (VUV), electron beam (EB), X-rays, and soft X-rays.

The resist composition of the present invention is effective to KrF excimer laser, ArF excimer laser, EB and EUV, and particularly effective to ArF excimer laser.

The exposure of the resist film can be either a general exposure (dry exposure) conducted in air or an inert gas such as nitrogen, or immersion exposure (immersion lithography).

In immersion lithography, exposure (immersion exposure) is conducted in a state where the region between the lens and the resist layer formed on a wafer (which was conventionally filled with air or an inert gas such as nitrogen) is filled with a solvent (an immersion medium) that has a larger refractive index than the refractive index of air.

More specifically, in immersion lithography, the region between the resist film formed in the above-described manner and lens at the lowermost portion of the exposure apparatus is filled with a solvent (an immersion medium) that has a larger refractive index than the refractive index of air, and in this state, the resist film is subjected to exposure (immersion exposure) through a desired mask pattern.

The immersion medium preferably exhibits a refractive index larger than the refractive index of air but smaller than the refractive index of the resist film to be subjected to immersion exposure. The refractive index of the immersion medium is not particularly limited as long as it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which preferably have a boiling point within a range from 70 to 180° C. and more preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

As the immersion medium, water is preferable in terms of cost, safety, environment and versatility.

As an example of the alkali developing solution used in an alkali developing process, a 0.1 to 10% by weight aqueous solution of tetramethylammonium hydroxide (TMAH) can be given.

As the organic solvent contained in the organic developing solution used in a solvent developing process, any of the conventional organic solvents can be used, which are capable of dissolving the component (A) (prior to exposure).

Specific examples of the organic solvent include polar solvents such as ketone solvents, ester solvents, alcohol solvents, amide solvents and ether solvents, and hydrocarbon solvents.

If desired, the organic developing solution may have a conventional additive blended.

Examples of the additive include surfactants.

The surfactant is not particularly limited, and for example, an ionic or non-ionic fluorine and/or silicon surfactant can be used.

When a surfactant is added, the amount thereof based on the total amount of the organic developing solution is generally 0.001 to 5% by weight, preferably 0.005 to 2% by weight, and more preferably 0.01 to 0.5% by weight.

The developing treatment can be performed by a conventional developing method. Examples thereof include a method in which the substrate is immersed in the developing solution for a predetermined time (a dip method), a method in which the developing solution is cast up on the surface of the substrate by surface tension and maintained for a predetermined period (a puddle method), a method in which the developing solution is sprayed onto the surface of the substrate (spray method), and a method in which the developing solution is continuously ejected from a developing solution ejecting nozzle while scanning at a constant rate to apply the developing solution to the substrate while rotating the substrate at a constant rate (dynamic dispense method).

As the organic solvent contained in the rinse liquid used in the rinse treatment after the developing treatment in the case of a solvent developing process, any of the aforementioned organic solvents contained in the organic developing solution can be used which hardly dissolves the resist pattern.

In general, at least one solvent selected from the group consisting of hydrocarbon solvents, ketone solvents, ester solvents, alcohol solvents, amide solvents and ether solvents is used.

Among these, at least one solvent selected from the group consisting of hydrocarbon solvents, ketone solvents, ester solvents, alcohol solvents and amide solvents is preferable, more preferably at least one solvent selected from the group consisting of alcohol solvents and ester solvents, and an alcohol solvent is particularly desirable.

The rinse treatment using a rinse liquid (washing treatment) can be conducted by a conventional rinse method.

Examples of the rinse method include a method in which the rinse liquid is continuously applied to the substrate while rotating it at a constant rate (rotational coating method), a method in which the substrate is immersed in the rinse liquid for a predetermined time (dip method), and a method in which the rinse liquid is sprayed onto the surface of the substrate (spray method).

EXAMPLES

As follows is a description of examples of the present invention, although the scope of the present invention is by no way limited by these examples.

In the NMR analysis, the internal standard for $^1$H-NMR and $^{13}$C-NMR was tetramethylsilane (TMS). The internal standard for $^{19}$F-NMR was hexafluorobenzene (provided that the peak of hexafluorobenzene was regarded as −160 ppm).

Synthesis Example 1

Synthesis of Compound Anion-A

In a nitrogen atmosphere, 28.0 g of ACVA and 36.8 g of Anion-a were added to 280 g of dichloromethane, followed by stirring at room temperature. Then, 27.8 g of diisopropylcarbodiimide was added thereto, followed by stirring for 10 minutes. Then, 2.44 g dimethylaminopyridine as a catalyst was added thereto, and a reaction was effected at 30° C. for 24 hours. 1400 g of t-butyl methyl ether was added to the suspended reaction solution, followed by stirring for 30 minutes. Then, the precipitated object was separated by filtration, followed by drying, thereby obtaining 20.8 g of Anion-A.

The obtained compound was analyzed by NMR, and the structure thereof was identified by the following results.

$^1$H-NMR (400 MHz, DMSO-d6): δ(ppm)=4.61 (dt, 4H, CH2CF2), 2.40-2.65 (m, 8H, CH2CH2), 1.72 (s, 6H, CH3), 1.66 (s, 6H, CH3).

$^{19}$F-NMR (376 MHz, DMSO-d6): δ(ppm)=−111.4.

From the results shown above, it was confirmed that the compound Anion-A had a structure shown below.

[Chemical Formula 102]

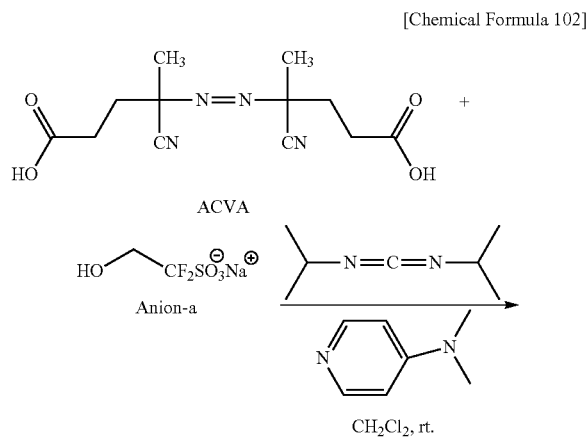

Synthesis Example 2

Synthesis of Compound (I-A)

10.50 g of TPS-Br, 8.70 g of Anion-A, 155.0 g of dichloromethane, and 78.0 g of pure water were added to a beaker, followed by stirring at room temperature for 1 hour. Then, the dichloromethane phase was separated, and washed with 78.0 g of pure water repeatedly, followed by distillation of the organic phase under reduced pressure, thereby obtaining 13.80 g of compound (I-A) in the form of a white solid.

The obtained compound was analyzed by NMR, and the structure thereof was identified by the following results.

$^1$H-NMR (400 MHz, DMSO-d6): δ(ppm)=7.78-7.90 (m, 30H, ArH), 4.61 (dt, 4H, CH2CF2), 2.40-2.65 (m, 8H, CH2CH2), 1.72 (s, 6H, CH3), 1.66 (s, 6H, CH3).

$^{19}$F-NMR (376 MHz, DMSO-d6): δ(ppm)=−111.4.

From the results shown above, it was confirmed that the compound (I-A) had a structure shown below.

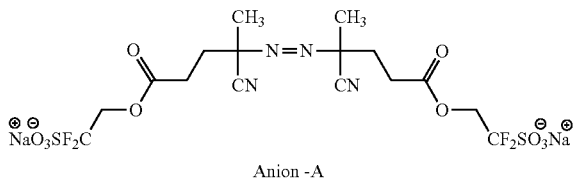

[Chemical Formula 103]

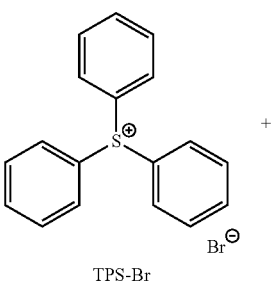

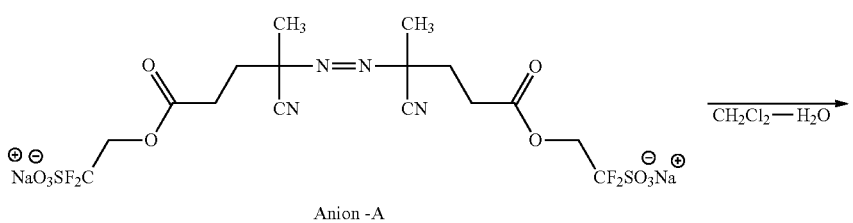

-continued

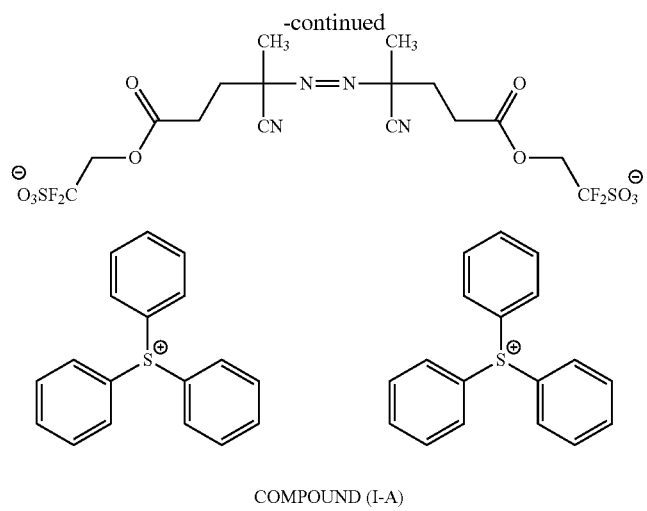

COMPOUND (I-A)

Synthesis Examples 3 to 55

Synthesis of compounds (I-B) to (I-BB)

The same procedure as in Synthesis Example 2 was performed, except that the TPS-Br (cation) was changed to a compound shown in Tables 1 to 18 (equimolar amount). In this manner, compounds (I-B) to (I-BB) shown in Tables 1 to 18 were obtained.

Each of the obtained compounds was analyzed by NMR. The results are shown in Tables 1 to 18.

TABLE 1

| COMPOUND | NMR | CATION | PRODUCT |
|---|---|---|---|
| I-B | 1H-NMR (400 MHz, DMSO-d6): δ (ppm) = 8.50 (d, 4H, ArH), 8.37 (d, 4H, ArH), 7.93 (t, 4H, ArH), 7.55-7.75 (m, 14H, ArH), 4.61 (dt, 4H, CH2CF2), 2.40-2.65 (m, 8H, CH2CH2), 1.72 (s, 6H, CH3), 1.66 (s, 6H, CH3). 19F-NMR (376 MHz, DMSO-d6): δ (ppm) = −111.4. | | |
| I-C | 1H-NMR (400 MHz, DMSO-d6): δ (ppm) = 7.72-7.84 (m, 24H, ArH), 7.56 (d, 4H, ArH), 4.61 (dt, 4H, CH2CF2), 3.35 (s, 6M, ArCH3), 2.40-2.65 (m, 8H, CH2CH2), 1.72 (s, 6H, CH3), 1.66 (s, 6H, CH3). 19F-NMR (376 MHz, DMSO-d6): δ (ppm) = −111.4. | | |
| I-D | 1H-NMR (400 MHz, DMSO-d6): δ (ppm) = 7.75-7.86 (m, 20H, ArH), 7.61 (s, 4H, ArH), 4.65 (s, 4H, CH2O), 4.61 (dt, 4H, CH2CF2), 2.40-2.65 (m, 8H, CH2CH2), 2.31 (s, 12H, ArCH3), 1.49-1.97 (m, 36H, Adamantane + CH3). 19F-NMR (376 MHz, DMSO-d6): δ (ppm) = −111.4. | | |

TABLE 2

| COMPOUND | CATION | PRODUCT | NMR |
|---|---|---|---|
| I-E | [sulfonium cation with ethyl-cyclopentyl ester, dimethylphenyl, diphenyl sulfonium] | [azo bis(cyanopropyl) diester with CF2SO3− counterion, paired with sulfonium cation] | 1H-NMR (400 MHz, DMSO-d6): δ (ppm) = 7.76-7.82 (m, 20H, ArH), 7.59 (s, 4H, ArH), 4.61 (dt, 4H, CH2CF2), 4.55 (s, 4H, OCH2), 2.40-2.65 (m, 8H, CH2CH2), 2.29 (m, 12H, ArCH3), 1.90-1.93 (m, 8H, CH2CH3, cyclopentyl), 1.48-1.75 (m, 24H, CH3 + cyclopentyl), 0.77-0.81 (t, 6H, CH2CH3). 19F-NMR (376 MHz, DMSO-d6): δ (ppm) = −111.4. |
| I-F | [sulfonium cation with methyl-cyclopentyl ester, dimethylphenyl, diphenyl sulfonium] | [azo bis(cyanopropyl) diester with CF2SO3− counterion, paired with sulfonium cation] | 1H-NMR (400 MHz, DMSO-d6): δ (ppm) = 7.76-7.82 (m, 20H, ArH), 7.59 (s, 4H, ArH), 4.61 (dt, 4H, CH2CF2), 4.55 (s, 4H, OCH2), 2.40-2.65 (m, 8H, CH2CH2), 2.29 (m, 12H, ArCH3), 1.90-2.08 (m, 4H, cyclopentyl), 1.48-1.75 (m, 30H, Cp-CH3 + cyclopentyl + CH3). 19F-NMR (376 MHz, DMSO-d6): δ (ppm) = −111.4. |
| I-G | [4-hydroxy-3,5-dimethylphenyl diphenyl sulfonium] | [azo bis(cyanopropyl) diester with CF2SO3− counterion, paired with sulfonium cation] | 1H-NMR (400 MHz, DMSO-d6): δ (ppm) = 10.05 (s, 2H, OH), 7.64-7.87 (m, 20H, ArH), 7.56 (s, 4H, ArH), 4.61 (dt, 4H, CH2CF2), 2.40-2.65 (m, 8H, CH2CH2), 2.22 (m, 12H, ArCH3), 1.72 (s, 6H, CH3), 1.66 (s, 6H, CH3). 19F-NMR (376 MHz, DMSO-d6): δ (ppm) = −111.4. |

TABLE 3

| COMPOUND | CATION | PRODUCT | NMR |
|---|---|---|---|
| I-H | [diphenylsulfonium cation with 2,6-dimethyl-4-(carboxymethoxy)phenyl group] | [bis(2,2-difluoro-2-sulfonatoethyl) 4,4'-azobis(4-cyanopentanoate) paired with two diphenylsulfonium cations bearing 2,6-dimethyl-4-(carboxymethoxy)phenyl groups] | 1H-NMR (400 MHz, DMSO-d6): δ (ppm) = 7.71-7.89 (m, 20H, ArH), 7.59 (s, 4H, ArH), 4.61 (dt, 4H, CH2CF2), 4.53 (s, 4H, OCH2), 2.40-2.65 (m, 8H, CH2CH2), 2.30 (s, 12H, ArCH3), 1.72 (s, 6H, CH3), 1.66 (s, 6H, CH3). 19F-NMR (376 MHz, DMSO-d6): δ (ppm) = −111.4. |
| I-I | [diphenylsulfonium cation with 2,6-dimethyl-4-(tert-butoxycarbonylmethoxy)phenyl group] | [bis(2,2-difluoro-2-sulfonatoethyl) 4,4'-azobis(4-cyanopentanoate) paired with two diphenylsulfonium cations bearing 2,6-dimethyl-4-(tert-butoxycarbonylmethoxy)phenyl groups] | 1H-NMR (400 MHz, DMSO-d6): δ (ppm) = 7.75-7.86 (m, 20H, ArH), 7.63 (s, 4H, ArH), 4.61 (dt, 4H, CH2CF2), 4.55 (s, 4H, OCH2), 2.40-2.65 (m, 8H, CH2CH2), 2.30 (s, 12H, ArCH3), 1.72 (s, 6H, CH3), 1.66 (s, 6H, CH3), 1.43 (s, 18H, t-Butyl). 19F-NMR (376 MHz, DMSO-d6): δ (ppm) = −111.4. |

TABLE 3-continued

| COMPOUND | NMR | CATION | PRODUCT |
|---|---|---|---|
| I-J | 1H-NMR (400 MHz, DMSO-d6): δ (ppm) = 7.75-7.87 (m, 20H, ArH), 7.63 (s, 4H, ArH), 4.94 (t, 4H, OCH2CF2), 4.84 (s, 4H, OCH2), 4.61 (dt, 4H, CH2CF2), 2.40-2.65 (m, 8H, CH2CH2), 2.37 (s, 12H, ArCH3), 1.72 (s, 6H, CH3), 1.66 (s, 6H, CH3). 19F-NMR (376 MHz, DMSO-d6): δ (ppm) = −80.4, −111.4, −119.7. | | |

TABLE 4

| COMPOUND | CATION | PRODUCT | NMR |
|---|---|---|---|
| I-K | 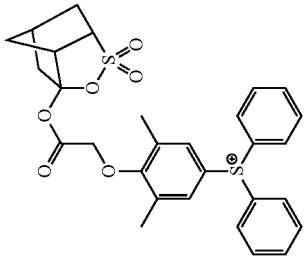 | 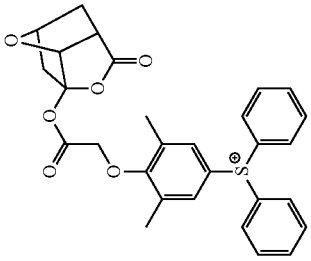 | 1H-NMR (400 MHz, DMSO-d6): δ (ppm) = 7.72-7.83 (m, 20H, ArH), 7.59 (s, 4H, ArH), 4.90 (m, 2H, sultone), 4.63-4.68 (m, 6H, CH2O + sultone), 4.61 (dt, 4H, CH2CF2), 3.83-3.89 (m, 2H, sultone), 3.43 (m, 2H, sultone), 1.75-2.65 (m, 30H, CH2CH2 + sultone + ArCH3), 1.72 (s, 6H, CH3), 1.66 (s, 6H, CH3). 19F-NMR (376 MHz, DMSO-d6): δ (ppm) = −111.4. |
| I-L | 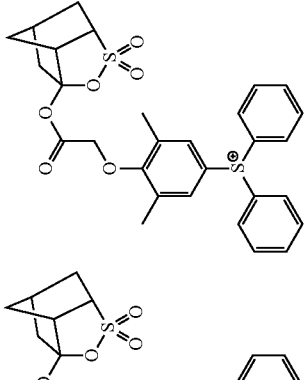 | 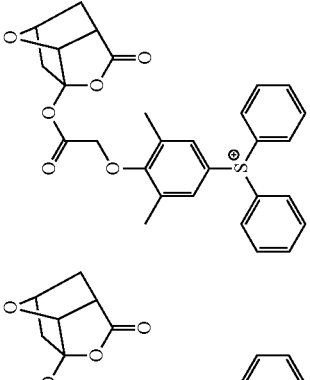 | 1H-NMR (400 MHz, DMSO-d6): δ (ppm) = 7.74-7.84 (m, 20H, ArH), 7.61 (s, 4H, ArH), 5.42 (t, 2H, oxo-norbornane), 4.97 (s, 2H, oxo-norbornane), 4.67-4.71 (m, 8H, OCH2 + oxo-norbornane), 2.40-2.65 (m, 8H, CH2CH2), 2.32 (s, 12H, ArCH3), 2.06-2.16 (m, 4H, oxo-norbornane), 1.72 (s, 6H, CH3), 1.66 (s, 6H, CH3). 19F-NMR (376 MHz, DMSO-d6): δ (ppm) = −111.4. |
| I-M | 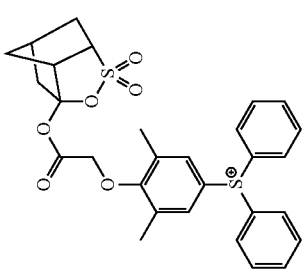 | 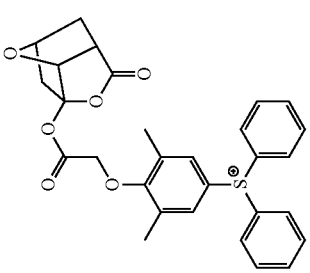 | 1H-NMR (400 MHz, DMSO-d6): δ (ppm) = 7.73-7.85 (m, 20H, ArH), 7.59 (S, 4H, ArH), 4.61 (dt, 4H, CH2CF2), 3.83 (t, 4H, OCH2), 2.40-2.65 (m, 8H, CH2CH2), 2.33 (s, 12H, ArCH3), 1.72 (s, 6H, CH3), 1.66 (s, 6H, CH3), 1.45 (m, 8H, CH2 in n-hexyl), 1.29 (m, 8H, CH2 in n-hexyl), 0.87 (t, 6H, CH3 in n-hexyl). 19F-NMR (376 MHz, DMSO-d6): δ (ppm) = −111.4. |

TABLE 5

| COMPOUND | NMR | CATION | PRODUCT |
|---|---|---|---|
| I-N | 1H-NMR (400 MHz, DMSO-d6): δ (ppm) = 8.53 (d, 4H, ArH), 8.27 (d, 4H, ArH), 7.95 (t, 4H, ArH), 7.74 (t, 4H, ArH), 7.20 (s, 2H, ArH), 6.38 (s, 2H, ArH), 4.61 (dt, 4H, CH2CF2), 4.05 (t, 4H, OCH2), 2.40-2.65 (m, 8H, CH2CH2), 1.84 (s, 12H, ArCH3), 1.72 (s, 6H, CH3), 1.69 (quin, 4H, CH2 in n-hexyl), 1.66 (s, 6H, CH3), 1.37 (quin, 4H, CH2 in n-hexyl), 1.24-1.26 (m, 8H, CH2 in n-hexyl), 0.82 (t, 6H, CH3 in n-hexyl). 19F-NMR (376 MHz, DMSO-d6): δ (ppm) = −111.4. | | |
| I-O | 1H-NMR (400 MHz, DMSO-d6): δ (ppm) = 7.99-8.01 (d, 4H, ArH), 7.73-7.76 (t, 2H, ArH), 7.58-7.61 (t, 4H, ArH), 5.31 (s, 4H, SCH2C=O), 4.61 (dt, 4H, CH2CF2), 3.49-3.62 (m, 8H, CH2 in tetramethylenesulfide), 2.18-2.65 (m, 16H, CH2S+CH2CH2), 1.72 (s, 6H, CH3), 1.66 (s, 6H, CH3). 19F-NMR (376 MHz, DMSO-d6): δ (ppm) = −111.4. | | |
| I-P | 1H-NMR (400 MHz, DMSO-d6): δ (ppm) = 8.02-8.05 (m, 4H, ArH), 7.61-7.73 (m, 6H, ArH), 4.61 (dt, 4H, CH2CF2), 3.76-3.86 (m, 8H, SCH2), 2.40-2.65 (m, 8H, CH2CH2), 2.09-2.12 (m, 4H, CH2 in pentamethylenesulfide), 1.84-1.93 (m, 4H, CH2 in pentamethylenesulfide), 1.61-1.72 (m, 16H, CH3 + CH2 in pentamethylenesulfide). 19F-NMR (376 MHz, DMSO-d6): δ (ppm) = −111.4. | | |

TABLE 6

| COMPOUND | NMR | CATION | PRODUCT |
|---|---|---|---|
| I-Q | 1H-NMR (400 MHz, DMSO-d6): δ (ppm) = 8.04-8.09 (m, 4H, ArH), 7.69-7.79 (m, 6H, ArH), 4.61 (dt, 4H, CH2CF2), 3.29 (s, 12H, SCH3), 2.40-2.65 (m, 8H, CH2CH2), 1.72 (s, 6H, CH3), 1.66 (s, 6H, CH3). 19F-NMR (376 MHz, DMSO-d6): δ (ppm) = −111.4. | dimethyl(phenyl)sulfonium | dimethyl(phenyl)sulfonium salt with bis(CF2SO3−) azo-linked diester |
| I-R | 1H-NMR (400 MHz, DMSO-d6): δ (ppm) = 8.07 (d, 4H, ArH), 7.81 (d, 4H, ArH), 4.61 (dt, 4H, CH2CF2), 4.10 (t, 4H, CH2 in pentamethylenesulfide), 3.59 (d, 4H, CH2 in pentamethylenesulfide), 2.40-2.65 (m, 8H, CH2CH2), 2.20 (d, 4H, CH2 in pentamethylenesulfide), 1.71-2.19 (m, 14H, CH3 + CH2 in pentamethylenesulfide), 1.66 (s, 6H, CH3), 1.23 (s, 18H, t-Bu). 19F-NMR (376 MHz, DMSO-d6): δ (ppm) = −111.4. | 1-(4-tert-butylphenyl)tetrahydro-2H-thiopyran-1-ium | corresponding sulfonium salt |
| I-S | 1H-NMR (400 MHz, DMSO-d6): δ (ppm) = 7.77-7.89 (m, 20H, ArH), 7.70 (s, 4H, ArH), 5.10 (s, 4H, CH2O), 4.61 (dt, 4H, CH2CF2), 2.40-2.65 (m, 8H, CH2CH2), 2.07-2.19 (m, 18H, CH3O + ArCH3), 1.72 (s, 6H, CH3), 1.66 (s, 6H, CH3). 19F-NMR (376 MHz, DMSO-d6): δ (ppm) = −111.4. | triphenylsulfonium-containing aryl acetate | corresponding sulfonium salt |

TABLE 7

| COMPOUND | CATION | PRODUCT | NMR |
|---|---|---|---|
| I-T | tris(4-tert-butylphenyl)sulfonium | tris(4-tert-butylphenyl)sulfonium salt of bis(2-(trifluoromethylsulfonato)ethyl) 4,4'-azobis(4-cyanopentanoate) | 1H-NMR (400 MHz, DMSO-d6); δ (ppm) = 7.84 (d, 12H, ArH), 7.78 (d, 12H, ArH), 4.61 (dt, 4H, CH2CF2), 2.40–2.65 (m, 8H, CH2CH2), 1.72 (s, 6H, CH3), 1.66 (s, 6H, CH3), 1.33 (s, 54H, tBu). 19F-NMR (376 MHz, DMSO-d6); δ (ppm) = –111.4. |
| I-U | (4-trifluoromethylsulfonyloxy-3,5-dimethylphenyl)diphenylsulfonium | corresponding sulfonium salt of bis(2-(trifluoromethylsulfonato)ethyl) 4,4'-azobis(4-cyanopentanoate) | 1H-NMR (400 MHz, DMSO-d6); δ (ppm) = 7.73–7.89 (m, 24H, ArH), 4.61 (dt, 4H, CH2CF2), 2.40–2.65 (m, 8H, CH2CH2), 2.38 (s, 12H, ArCH3), 1.72 (s, 6H, CH3), 1.66 (s, 6H, CH3). 19F-NMR (376 MHz, DMSO-d6); δ (ppm) = –70.2, –111.4. |
| I-V | (4-(2-adamantyloxycarbonylmethoxy)-3,5-dimethylphenyl)diphenylsulfonium | corresponding sulfonium salt of bis(2-(trifluoromethylsulfonato)ethyl) 4,4'-azobis(4-cyanopentanoate) | 1H-NMR (400 MHz, DMSO-d6); δ (ppm) = 7.69–7.85 (m, 20H, ArH), 7.56 (s, 4H, ArH), 4.75 (s, 8H, OCH2), 4.61 (dt, 4H, CH2CF2), 2.40–2.65 (m, 8H, CH2CH2), 2.31 (s, 12H, ArCH3), 2.19 (m, 4H, Adamantane), 1.47–1.98 (m, 42H, CH3 + Adamantane). 19F-NMR (376 MHz, DMSO-d6); δ (ppm) = –111.4. |

TABLE 8

| COMPOUND | CATION | PRODUCT | NMR |
|---|---|---|---|
| I-W | (adamantanone-OC(O)CH2O-dimethylphenyl-S+Ph2 structure) | (bis-triflate ester of azo-dinitrile with two adamantanone-OC(O)CH2O-dimethylphenyl-S+Ph2 cations) | 1H-NMR (400 MHz, DMSO-d6): δ (ppm) = 7.72–7.84 (m, 20H, ArH), 7.59 (s, 4H, ArH), 4.61 (dt, 4H, CH2CF2), 4.56 (s, 4H, OCH2), 2.40–2.65 (m, 12H, CH2CH2 + Adamantane), 2.27–2.34 (m, 26H, ArCH3 + Adamantane), 1.94–1.97 (m, 4H, Adamantane), 1.74–1.79 (m, 4H, Adamantane), 1.72 (s, 6H, CH3), 1.66 (s, 6H, CH3). 19F-NMR (376 MHz, DMSO-d6): δ (ppm) = −111.4. |
| I-X | (methoxycarbonylmethoxy-dimethylphenyl-S+Ph2 structure) | (bis-triflate ester of azo-dinitrile with two methoxycarbonylmethoxy-dimethylphenyl-S+Ph2 cations) | 1H-NMR (400 MHz, DMSO-d6): δ (ppm) = 7.72–7.84 (m, 20H, ArH), 7.59 (s, 4H, ArH), 4.64 (s, 4H, OCH2), 4.61 (dt, 4H, CH2CF2), 3.70 (s, 6H, OCH3), 2.40–2.65 (m, 8H, CH2CH2), 2.29 (s, 12H, ArCH3), 1.72 (s, 6H, CH3), 1.66 (s, 6H, CH3). 19F-NMR (376 MHz, DMSO-d6): δ (ppm) = −111.4. |
| I-Y | (methoxy-dimethylphenyl-S+Ph2 structure) | (bis-triflate ester of azo-dinitrile with two methoxy-dimethylphenyl-S+Ph2 cations) | 1H-NMR (400 MHz, DMSO-d6): δ (ppm) = 7.78–7.89 (m, 20H, ArH), 7.64 (s, 4H, ArH), 4.61 (dt, 4H, CH2CF2), 3.79 (s, 6H, OCH3), 2.40–2.65 (m, 8H, CH2CH2), 2.32 (s, 12H, ArCH3), 1.72 (s, 6H, CH3), 1.66 (s, 6H, CH3). 19F-NMR (376 MHz, DMSO-d6): δ (ppm) = −111.4. |

TABLE 9

| COMPOUND | NMR | CATION | PRODUCT |
|---|---|---|---|
| I-Z | 1H-NMR (400 MHz, DMSO-d6): δ (ppm) = 7.76-7.87 (m, 20H, ArH), 7.69 (s, 4H, ArH), 4.61 (dt, 4H, CH2CF2), 2.40-2.65 (m, 8H, CH2CH2), 2.13 (s, 12H, ArCH3), 1.66-2.03 (m, 42H, CH3 + Adamantane). 19F-NMR (376 MHz, DMSO-d6): δ (ppm) = −111.4. | | |
| AA | 1H-NMR (400 MHz, DMSO-d6): δ (ppm) = 7.79-7.93 (m, 24H, ArH), 4.61 (dt, 4H, CH2CF2), 2.73 (t, 4H, COCH2), 2.40-2.65 (m, 8H, CH2CH2), 2.19 (s, 12H, ArCH3), 1.65-1.72 (m, 16H, CH3 + CH2 in decanyl), 1.25-1.38 (m, 28H, CH2 in decanyl), 0.85 (t, 6H, CH3 in decanyl). 19F-NMR (376 MHz, DMSO-d6): δ (ppm) = −111.4. | | |

TABLE 9-continued
| COMPOUND | NMR | CATION | PRODUCT |
|---|---|---|---|
| I-AB | 1H-NMR (400 MHz, DMSO-d6): δ (ppm) = 8.76 (s, 2H, ArH), 8.59-8.64 (m, 2H, ArH), 8.42 (t, 4H, ArH), 8.03-8.19 (m, 10H, ArH), 7.81 (t, 2H, ArH), 7.69 (t, 4H, ArH), 4.61 (dt, 4H, CH2CF2), 2.40-2.65 (m, 8H, CH2CH2), 1.72 (s, 6H, CH3), 1.66 (s, 6H, CH3). 19F-NMR (376 MHz, DMSO-d6): δ (ppm) = −62.1, −111.4. | 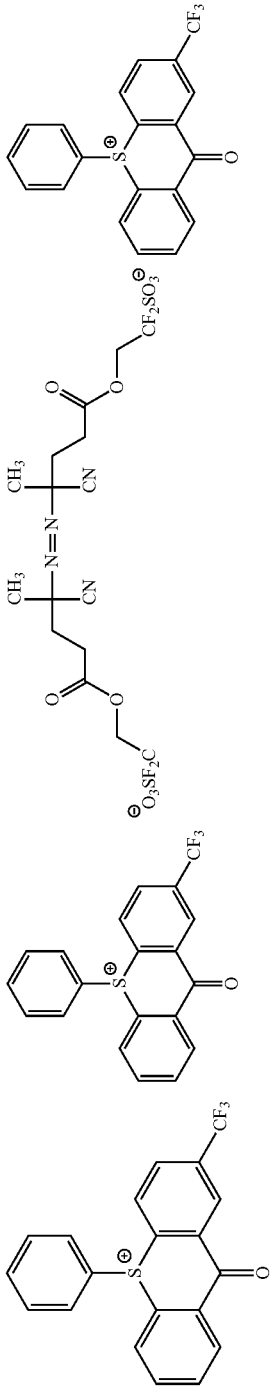 | 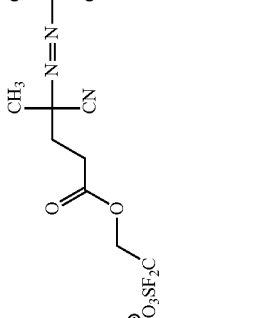 |

TABLE 10

| COMPOUND | NMR | CATION | PRODUCT |
|---|---|---|---|
| I-AC | 1H-NMR (400 MHz, DMSO-d6): δ (ppm) = 4.61 (dt, 4H, CH2CF2), 3.36 (t, 12H, CH2 in n-butyl), 2.40-2.65 (m, 8H, CH2CH2), 1.72 (s, 6H, CH3), 1.68 (quintet, 12H, CH2 in n-butyl), 1.66 (s, 6H, CH3), 1.35-1.44 (m, 12H, CH2 in n-butyl), 0.81-0.93 (m, 18H, CH3 in n-butyl). 19F-NMR (376 MHz, DMSO-d6): δ (ppm) = −111.4. | tributylsulfonium cation | bis(trifluoroethyl sulfonate) diester of azobis(cyanovaleric acid) with tributylsulfonium cation |
| I-AD | 1H-NMR (400 MHz, DMSO-d6): δ (ppm) = 8.29 (d, 8H, ArH), 7.93-8.09 (m, 12H, ArH), 4.61 (dt, 4H, CH2CF2), 2.40-2.65 (m, 8H, CH2CH2), 1.72 (s, 6H, CH3), 1.66 (s, 6H, CH3). 19F-NMR (376 MHz, DMSO-d6): δ (ppm) = −47.9, −111.4. | (trifluoromethyl)diphenylsulfonium cation | product with (trifluoromethyl)diphenylsulfonium cation |
| I-AE | 1H-NMR (400 MHz, DMSO-d6): δ (ppm) = 7.90-8.24 (m, 14H, ArH), 4.61 (dt, 4H, CH2CF2), 3.85 (s, 6H, OCH3), 2.42 (s, 12H, ArCH3) 2.40-2.65 (m, 8H, CH2CH2), 1.72 (s, 6H, CH3), 1.66 (s, 6H, CH3). 19F-NMR (376 MHz, DMSO-d6): δ (ppm) = −48.8, −111.4. | (trifluoromethyl)(phenyl)(4-methoxy-3,5-dimethylphenyl)sulfonium cation | product with (trifluoromethyl)(phenyl)(4-methoxy-3,5-dimethylphenyl)sulfonium cation |

TABLE 11

| COM-POUND | CATION | PRODUCT | NMR |
|---|---|---|---|
| I-AF | | | 1H-NMR (400 MHz, DMSO-d6): δ (ppm) = 10.12 (s, 2H, OH), 7.90-8.24 (m, 14H, ArH), 4.61 (dt, 4H, CH2CF2), 2.42 (s, 12H, ArCH3), 2.40-2.65 (m, 8H, CH2CH2), 1.72 (s, 6H, CH3), 1.66 (s, 6H, CH3). 19F-NMR (376 MHz, DMSO-d6): δ (ppm) = −48.2, −111.4. |
| I-AG | | | 1H-NMR (400 MHz, DMSO-d6): δ (ppm) = 8.49 (d, 4H, ArH), 8.30 (d, 4H, ArH), 7.93 (t, 4H, ArH), 7.73 (t, 4H, ArH), 7.30 (s, 4H, ArH), 4.61 (dt, 4H, CH2CF2), 4.52 (s, 4H, OCH2), 2.40-2.65 (m, 8H, CH2CH2), 2.16-2.24 (m, 16H, ArCH3 + Adamantane), 1.44-1.92 (m, 42H, Adamantane + CH3). 19F-NMR (376 MHz, DMSO-d6): δ (ppm) = −111.4. |
| I-AH | | | 1H-NMR (400 MHz, DMSO-d6): δ (ppm) = 9.73 (br s, 2H, OH), 8.47 (d, 4H, ArH), 8.24 (d, 4H, ArH), 7.91 (t, 4H, ArH), 7.71 (t, 4H, ArH), 7.18 (s, 4H, ArH), 4.61 (dt, 4H, CH2CF2), 2.40-2.65 (m, 8H, CH2CH2), 2.10 (s, 12H, ArCH3), 1.72 (s, 6H, CH3), 1.66 (s, 6H, CH3). 19F-NMR (376 MHz, DMSO-d6): δ (ppm) = −111.4. |

TABLE 12

| COMPOUND | NMR | CATION | PRODUCT |
|---|---|---|---|
| I-AI | 1H-NMR (400 MHz, DMSO-d6); δ (ppm) = 7.75-7.87 (m, 20H, ArH), 7.62 (s, 4H, ArH), 4.61 (dt, 4H, CH2CF2), 3.97 (t, 4H, OCH2), 2.03-2.65 (m, 28H, CH2CH2 + CH2CH2CF2 + ArCH3), 1.72 (s, 6H, CH3), 1.66 (s, 6H, CH3). 19F-NMR (376 MHz, DMSO-d6): δ (ppm) = −78.3, −111.4, −111.6, −121.8, −123.5. | | |
| I-AJ | 1H-NMR (400 MHz, DMSO-d6); δ (ppm) = 7.75-7.86 (m, 20H, ArH), 7.60 (s, 4H, ArH), 4.61 (dt, 4H, CH2CF2), 3.87 (t, 4H, OCH2), 2.40-2.65 (m, 12H, CH2CH2 + CH2 in cation), 2.20 (s, 12H, ArCH3), 2.12 (s, 12H, NCH3), 1.86 (t, 4H, NCH2), 1.72 (s, 6H, CH3), 1.66 (s, 6H, CH3). 19F-NMR (376 MHz, DMSO-d6): δ (ppm) = −111.4. | | |

TABLE 12-continued

| COMPOUND | NMR | CATION | PRODUCT |
|---|---|---|---|
| I-AK | 1H-NMR (400 MHz, DMSO-d6): δ (ppm) = 7.77-7.89 (m, 20H, ArH), 7.71 (s, 4H, ArH), 4.61 (dt, 4H, CH2CF2), 2.40-2.65 (m, 12H, CH2CH2 + CH2 – Ad), 2.20 (s, 12H, ArCH3), 1.97 (s, 6H, Adamantane), 1.62-1.73 (m, 36H, CH3 + Adamantane). 19F-NMR (376 MHz, DMSO-d6): δ (ppm) = –111.4. | | |

TABLE 13

| COMPOUND | NMR | CATION | PRODUCT |
|---|---|---|---|
| I-AL | 1H-NMR (400 MHz, DMSO-d6): δ (ppm) = 7.74-7.84 (m, 20H, ArH), 7.61 (s, 4H, ArH), 4.49-4.66 (m, 12H, CH2CF2 + norbornane + OCH2), 3.24 (m, 2H, CH2CF2 + norbornane), 2.40-2.65 (m, 12H, CH2CH2 + norbornane), 2.37 (s, 12H, ArCH3), 1.91-2.06 (m, 4H, norbornane), 1.72 (s, 6H, CH3), 1.57-1.67 (m, 10H, CH3 + norbornane). 19F-NMR (376 MHz, DMSO-d6): δ (ppm) = −111.4. | | |
| I-AM | 1H-NMR (400 MHz, DMSO-d6): δ (ppm) = 7.80-7.92 (m, 20H, ArH), 7.67 (s, 4H, ArH), 4.66 (s, 4H, OCH2), 4.61 (dt, 4H, CH2CF2), 2.40-2.65 (m, 8H, CH2CH2), 2.37 (s, 12H, ArCH3), 2.13-2.16 (m, 4H, cyclohexyl), 1.93 (q, 4H, CH2 in ethyl), 1.72 (s, 6H CH3), 1.66 (s, 6H, CH3), 1.14-1.57 (m, 16H, cyclohexyl), 0.84 (t, 6H, CH3 in ethyl). 19F-NMR (376 MHz, DMSO-d6): δ (ppm) = −111.4. | | |
| I-AN | 1H-NMR (400 MHz, DMSO-d6): δ (ppm) = 8.44 (d, 2H, ArH), 8.22 (m, 4H, ArH), 7.73-7.89 (m, 26H, ArH), 7.50 (d, 2H, ArH), 4.61 (dt, 4H, CH2CF2), 2.40-2.65 (m, 8H, CH2CH2), 1.72 (s, 6H, CH3), 1.66 (s, 6H, CH3). 19F-NMR (376 MHz, DMSO-d6): δ (ppm) = −111.4. | | |

TABLE 14

| COMPOUND | NMR | CATION | PRODUCT |
|---|---|---|---|
| I-AO | 1H-NMR (400 MHz, DMSO-d6): δ (ppm) = 8.24 (d, 8H, ArH), 7.59 (t, 4H, ArH), 7.47 (t, 8H, ArH), 4.61 (dt, 4H, CH2CF2), 2.40-2.65 (m, 8H, CH2CH2), 1.72 (s, 6H, CH3), 1.66 (s, 6H, CH3). 19F-NMR (376 MHz, DMSO-d6): δ (ppm) = −111.4. | diphenyliodonium cation | product with two $CF_2SO_3^\ominus$ groups |
| I-AP | 1H-NMR (400 MHz, DMSO-d6): δ (ppm) = 8.55 (d, 4H, ArH), 8.38 (d, 4H, ArH), 8.32 (d, 4H, ArH), 8.03 (d, 4H, ArH), 7.93-7.97 (m, 2H, ArH), 7.82-7.88 (m, 16H, ArH), 7.55 (d, 4H, ArH), 4.61 (dt, 4H, CH2CF2), 2.40-2.65 (m, 8H, CH2CH2), 1.72 (s, 6H, CH3), 1.66 (s, 6H, CH3). 19F-NMR (376 MHz, DMSO-d6): δ (ppm) = −111.4. | di(naphthyl)phenylsulfonium cation | product |
| I-AQ | 1H-NMR (400 MHz, DMSO-d6): δ (ppm) = 4.61 (dt, 4H, CH2CF2), 4.46 (s, 4H, CH2(C=O)), 3.38-3.58 (m, 8H, CH2SCH2), 2.40-2.65 (m, 8H, CH2CH2), 1.56-2.33 (m, 54H, CH3 + Adamantane + CH2CH2 in tetramethylenesulfide). 19F-NMR (376 MHz, DMSO-d6): δ (ppm) = −111.4. | tetrahydrothiophenium adamantyl ester cation | product |

TABLE 15

| COM-POUND | CATION | PRODUCT | NMR |
|---|---|---|---|
| I-AR | (adamantane-carboxylate-dimethylphenyl-tetramethylenesulfonium cation) | (bis-cation with azo-dinitrile-diester linker, two $CF_2SO_3^{\ominus}$ counterions) | 1H-NMR (400 MHz, DMSO-d6); δ (ppm) = 7.75 (s, 4H, Ar), 4.61 (dt, 4H, CH2CF2), 3.91-3.96 (m, 4H, CH2 in tetramethylenesulfide), 3.72-3.79 (m, 4H, CH2 in tetramethylenesulfide), 2.40-2.65 (m, 8H, CH2CH2), 2.29-2.39 (m, 8H, CH2 in tetramethylenesulfide), 1.75-2.19 (m, 42H, ArCH3 + Adamantane), 1.72 (s, 6H, CH3), 1.66 (s, 6H, CH3). 19F-NMR (376 MHz, DMSO-d6); δ (ppm) = −111.4. |
| I-AS | (adamantane-carboxylate-dimethylphenyl-pentamethylenesulfonium cation) | (bis-cation with azo-dinitrile-diester linker, two $CF_2SO_3^{\ominus}$ counterions) | 1H-NMR (400 MHz, DMSO-d6); δ (ppm) = 7.82 (m, 4H, ArH), 4.61 (dt, 4H, CH2CF2), 3.73-3.91 (m, 8H CH2 in pentamethylenesulfide), 2.41-2.65 (m, 8H, CH2CH2), 1.56-2.40 (m, 66H, CH3 + ArCH3 + CH2 in pentamethylenesulfide + Adamantane). 19F-NMR (376 MHz, DMSO-d6); δ (ppm) = −111.4. |

TABLE 15-continued

| COMPOUND | NMR | CATION | PRODUCT |
|---|---|---|---|
| I-AT | 1H-NMR (400 MHz, DMSO-d6); δ (ppm) = 8.23 (d, 8H, ArH), 7.98 (d, 8H, ArH), 4.61 (dt, 4H, CH2CF2), 2.40-2.65 (m, 8H, CH2CH2), 1.72 (s, 6H, CH3), 1.66 (s, 6H, CH3), 1.37 (s, 36H, t-Butyl). 19F-NMR (376 MHz, DMSO-d6); δ (ppm) = −48.5, −111.4. | bis(4-tert-butylphenyl)(trifluoromethyl)sulfonium with CF$_2$SO$_3^\ominus$ counterion | Azo diester with two bis(4-tert-butylphenyl)(trifluoromethyl)sulfonium CF$_2$SO$_3^\ominus$ groups |

TABLE 16

| COMPOUND | CATION | PRODUCT | NMR |
|---|---|---|---|
| I-AU | (adamantyl ester dimethylphenyl diphenylsulfonium) | (bis-adamantyl/triflate product) | 1H-NMR (400 MHz, DMSO-d6): δ (ppm) = 7.77–7.98 (m, 20H, ArH), 7.64 (s, 4H, ArH), 4.61 (dt, 4H, CH2CF2), 4.57 (s, 4H, CH2O), 2.42 (s, 12H, ArCH3), 2.40–2.65 (m, 8H, CH2CH2), 2.02–2.26 (m, 18H, Adamantane), 1.76 (br, 12H, Adamantane), 1.72 (s, 6H, CH3), 1.66 (s, 6H, CH3). 19F-NMR (376 MHz, DMSO-d6): δ (ppm) = −111.4. |
| I-AV | (GBL ester dimethylphenyl diphenylsulfonium) | (bis-GBL/triflate product) | 1H-NMR (400 MHz, DMSO-d6): δ (ppm) = 7.77–7.89 (m, 20H, ArH), 7.64 (s, 4H, ArH), 4.82 (s, 4H, OCH2), 5.70 (t, 2H, CH in GBL), 4.61 (dt, 4H, CH2CF2), 4.46–4.30 (m, 4H, GBL), 2.71–2.64 (m, 2H, GBL), 2.40–2.65 (m, 8H, CH2HC2), 2.33–2.24 (m, 14H, ArCH3 + GBL), 1.72 (s, 6H, CH3), 1.66 (s, 6H, CH3). 19F-NMR (376 MHz, DMSO-d6): δ (ppm) = −111.4. |
| I-AW | (phenyl benzothiophenium) | (bis-triflate azo product) | 1H-NMR (400 MHz, DMSO-d6): δ (ppm) = 8.28 (d, 4H, ArH), 8.11 (d, 2H, ArH), 7.86 (t, 2H, ArH), 7.63–7.81 (m, 14H, ArH), 4.61 (dt, 4H, CH2CF2), 2.40–2.65 (m, 8H, CH2CH2), 1.72 (s, 6H, CH3), 1.66 (s, 6H, CH3). 19F-NMR (376 MHz, DMSO-d6): δ (ppm) = −111.4. |

TABLE 17

| COMPOUND | NMR | CATION | PRODUCT |
|---|---|---|---|
| I-AX | 1H-NMR (400 MHz, DMSO-d6); δ (ppm) = 8.05 (d, 4H, ArH), 7.74 (d, 4H, ArH), 4.61 (dt, 4H, CH2CF2), 3.85 (s, 6H, SCH3), 2.40-2.65 (m, 8H, CH2CH2), 1.72 (s, 6H, CH3), 1.66 (s, 6H, CH3), 1.30 (s, 36H, t-Bu). 19F-NMR (376 MHz, DMSO-d6); δ (ppm) = −111.4. | | |
| I-AY | 1H-NMR (400 MHz, DMSO-d6); δ (ppm) = 8.41 (m, 4H, ArH), 8.12 (d, 2H, ArH, 7.73-7.93 (m, 4H, ArH), 7.19 (dr 2H, ArH), 5.23 (s, 4H, OCH2), 4.95 (m, 2H, Adamantane), 4.61 (dt, 4H, CH2CF2), 4.03 (m, 4H, CH2S), 3.75 (m, 4H, CH2S), 2.27-2.65 (m, 16H, CH2CH2 + SCH2CH2), 1.42-1.99 (m, 40H, CH3 + Adamantane). 19F-NMR (376 MHz, DMSO-d6); δ (ppm) = −111.4. | | |

TABLE 17-continued

| COMPOUND | NMR | CATION | PRODUCT |
|---|---|---|---|
| I-AZ | 1H-NMR (400 MHz, DMSO-d6); δ (ppm) = 8.42 (m, 4H, ArH), 8.17 (d, 2H, ArH), 7.78-7.91 (m, 4H, ArH), 7.23 (d, 2H, ArH), 5.26 (s, 4H, CH2), 4.61 (dt, 4H, CH2CF2), 3.75-4.19 (m, 14H, SCH2 + OCH3), 2.29-2.65 (m, 16H, CH2CH2 + SCH2CH2), 1.72 (s, 6H, CH3), 1.66 (s, 6H, CH3). 19F-NMR (376 MHz, DMSO-d6); δ (ppm) = −111.4. | | |

TABLE 18

| COMPOUND | NMR | CATION | PRODUCT |
|---|---|---|---|
| I-BA | 1H-NMR (400 MHz, DMSO-d6): δ (ppm) = 8.28 (d, 4H, ArH), 8.12 (d, 2H, ArH), 7.88 (t, 2H, ArH), 7.80 (d, 2H, ArH), 7.62-7.74 (m, 10H, ArH), 4.61 (dt, 4H, CH2CF2), 2.40-2.65 (m, 8H, CH2CH2), 1.72 (s, 6H, CH3), 1.66 (s, 6H, CH3), 1.27 (s, 18H, t-Butyl). 19F-NMR (376 MHz, DMSO-d6): δ (ppm) = −111.4. | | |
| I-BB | 1H-NMR (400 MHz, DMSO-d6): δ (ppm) = 7.76-7.90 (m, 24H, ArH), 4.61 (dt, 4H, CH2CF2), 2.40-2.69 (m, 10H, CH2CH2 + camphane), 2.08-2.26 (m, 16H, ArCH3 + camphane), 1.65-1.72 (m, 14H, CH3 + camphane), 1.19 (s, 6H, CH3 in camphane), 1.09 (s, 6H, CH3 in camphane), 1.04 (s, 6H, CH3 in camphane). 19F-NMR (376 MHz, DMSO-d6): δ (ppm) = −111.4. | | |

Polymer Synthesis Example 1

Synthesis of Polymeric Compound 1

11.2 g of γ-butyrolactone was added to a flask equipped with a thermometer, a reflux tube, a stirrer and a nitrogen inlet tube under a nitrogen atmosphere, and the internal temperature was raised to 85° C. while stirring.

Separately from the above, 3.0 g (17.6 mmol) of monomer (1), 4.4 g (17.6 mmol) of monomer (2) and 2.1 g (8.8 mmol) of monomer (3) were dissolved in 50.0 g of γ-butyrolactone. Then, 0.71 g of the compound (I-A) as a radical polymerization initiator was added and dissolved in the obtained solution.

The mixed solution was added to the flask in a dropwise manner at a constant rate over 4 hours, and then heated while stirring for 1 hour, and the reacting solution was cooled to room temperature.

The obtained reaction polymer solution was added to an excess amount of a methanol/water mixed solution in a dropwise manner so as to deposit a polymer. Thereafter, the precipitated white powder was separated by filtration, followed by washing with a methanol/water mixed solution and drying under reduced pressure, thereby obtaining 6.5 g of a polymeric compound 1 as an objective compound.

With respect to the polymeric compound, the weight average molecular weight (Mw) and the dispersity (Mw/Mn) were determined by the polystyrene equivalent value as measured by gel permeation chromatography (GPC). As a result, it was found that the weight average molecular weight was 10,150, and the dispersity was 1.78.

Further, as a result of an analysis by $^{13}$C-NMR, it was found that the copolymer compositional ratio (ratio (molar ratio) of the respective structural units within the structural formula) was l/m/n=36/40/24.

[Chemical Formula 104]

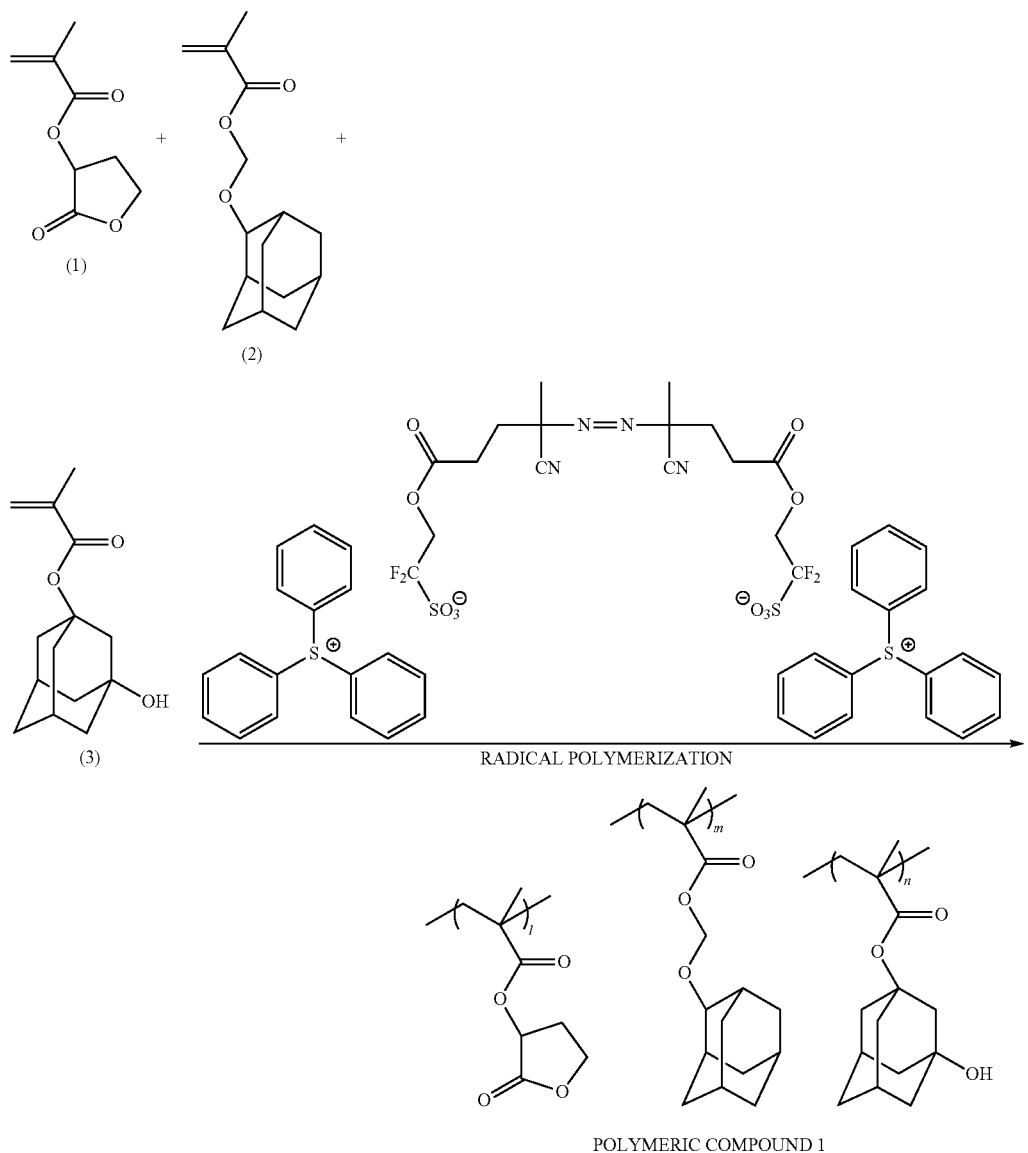

POLYMERIC COMPOUND 1

Polymer Synthesis Examples 2 to 38

Synthesis of Polymeric Compounds 2 to 38

Polymeric compounds 2 to 38 were produced in the same manner as in Polymer Synthesis Example 1, except that the following monomers (1) to (17) which derived the structural units constituting each polymeric compound were used with a molar ratio indicated in Tables 19 to 22, and the radical polymerization initiators indicated in Tables 19 to 22 were used with an equimolar amount of the radical polymerization initiator used in Polymer Synthesis Example 1. The structures of the radical polymerization initiators V-601 and ACVA are shown below.

The weight average molecular weight (Mw) and the molecular weight distribution (Mw/Mn) of the obtained polymeric compounds 2 to 38 are shown in Tables 19 to 22.

[Chemical Formula 105]

(1)

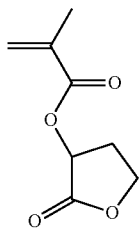

(2)

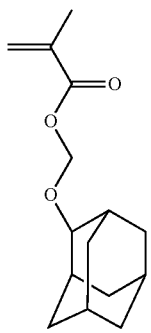

(3)

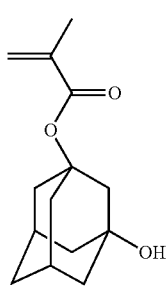

(4)

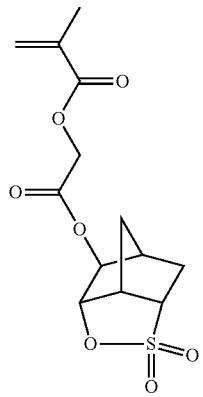

(5)

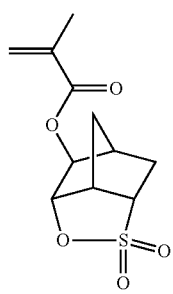

(6)

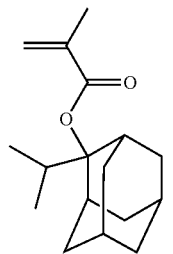

(7)

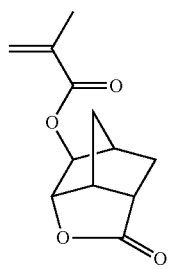

(8)

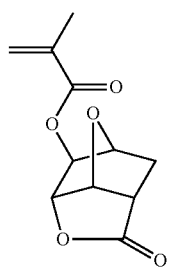

(9)
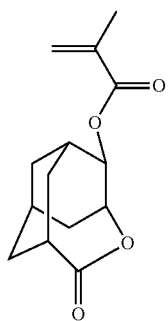
(10)
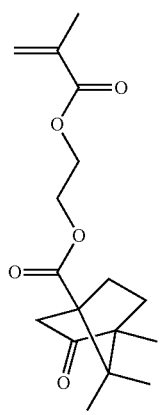
(11)
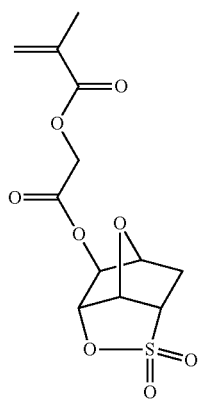
(12)
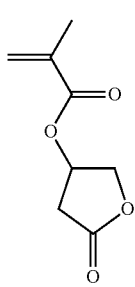
(13)
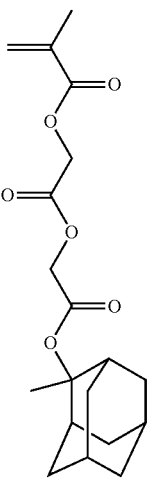
(14)
(15)
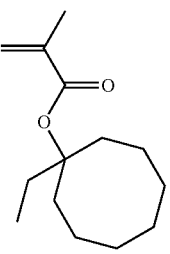
(16)
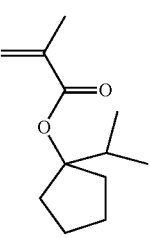
(17)
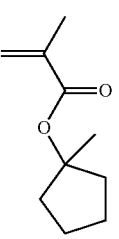

[Chemical Formula 106]
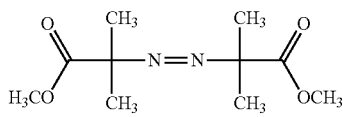
V-601
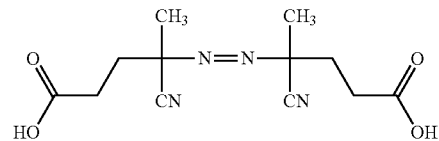
ACVA
TABLE 19
|  |  | POLYMERIC COMPOUND | | | | | | | | | |
|---|---|---|---|---|---|---|---|---|---|---|
|  |  | 1 | 2 | 3 | 4 | 5 | 6 | 7 | 8 | 9 | 10 |
| MONOMER | (1) | 36 | 35 | 34 | 37 | 34 | 35 | 38 |  |  |  |
|  | (2) | 40 | 41 | 42 | 41 | 41 | 40 | 39 | 40 | 42 |  |
|  | (3) | 24 | 24 | 24 | 22 | 25 | 25 | 23 | 20 | 19 |  |
|  | (4) |  |  |  |  |  |  |  | 40 |  | 53 |
|  | (5) |  |  |  |  |  |  |  |  | 39 |  |
|  | (6) |  |  |  |  |  |  |  |  |  | 47 |
|  | (7) |  |  |  |  |  |  |  |  |  |  |
|  | (8) |  |  |  |  |  |  |  |  |  |  |
|  | (9) |  |  |  |  |  |  |  |  |  |  |
|  | (10) |  |  |  |  |  |  |  |  |  |  |
|  | (11) |  |  |  |  |  |  |  |  |  |  |
|  | (12) |  |  |  |  |  |  |  |  |  |  |
|  | (13) |  |  |  |  |  |  |  |  |  |  |
|  | (14) |  |  |  |  |  |  |  |  |  |  |
|  | (15) |  |  |  |  |  |  |  |  |  |  |
|  | (16) |  |  |  |  |  |  |  |  |  |  |
|  | (17) |  |  |  |  |  |  |  |  |  |  |
| POLYMERIZATION INITIATOR |  | I-A | I-C | I-D | I-Z | I-AQ | I-K | I-BA | I-A | I-A | I-A |
| Mw |  | 10150 | 11000 | 11200 | 10100 | 9800 | 9900 | 10000 | 9400 | 9900 | 8100 |
| Mw/Mn |  | 1.78 | 1.90 | 1.77 | 1.78 | 1.77 | 1.75 | 1.87 | 1.91 | 1.67 | 1.7 |
TABLE 20
|  |  | POLYMERIC COMPOUND | | | | | | | | | |
|---|---|---|---|---|---|---|---|---|---|---|
|  |  | 11 | 12 | 13 | 14 | 15 | 16 | 17 | 18 | 19 | 20 |
| MONOMER | (1) |  |  |  |  |  | 45 |  |  |  |  |
|  | (2) |  |  |  |  |  |  |  |  |  |  |
|  | (3) | 20 | 20 | 20 | 20 | 20 | 20 | 20 | 20 | 20 | 20 |
|  | (4) | 44 |  |  |  |  |  |  |  | 45 | 45 |
|  | (5) |  |  |  |  |  |  |  |  |  |  |
|  | (6) | 36 | 35 | 35 | 35 | 35 | 35 | 35 | 35 |  |  |
|  | (7) |  | 45 |  |  |  |  |  |  |  |  |
|  | (8) |  |  | 45 |  |  |  |  |  |  |  |
|  | (9) |  |  |  | 45 |  |  |  |  |  |  |
|  | (10) |  |  |  |  | 45 |  |  |  |  |  |
|  | (11) |  |  |  |  |  |  | 45 |  |  |  |
|  | (12) |  |  |  |  |  |  |  | 45 |  |  |
|  | (13) |  |  |  |  |  |  |  |  | 35 |  |
|  | (14) |  |  |  |  |  |  |  |  |  | 35 |
|  | (15) |  |  |  |  |  |  |  |  |  |  |
|  | (16) |  |  |  |  |  |  |  |  |  |  |
|  | (17) |  |  |  |  |  |  |  |  |  |  |
| POLYMERIZATION INITIATOR |  | I-A | I-A | I-A | I-A | I-A | I-A | I-A | I-A | I-A | I-A |
| Mw |  | 7600 | 7600 | 7600 | 7600 | 7600 | 7500 | 7200 | 7600 | 7500 | 7700 |
| Mw/Mn |  | 1.80 | 1.80 | 1.80 | 1.80 | 1.80 | 1.75 | 1.74 | 1.80 | 1.77 | 1.91 |
TABLE 21
|  |  | POLYMERIC COMPOUND | | | | | | | | | |
|---|---|---|---|---|---|---|---|---|---|---|
|  |  | 21 | 22 | 23 | 24 | 25 | 26 | 27 | 28 | 29 | 30 |
| MONOMER | (1) |  |  | 35 | 36 | 38 |  |  |  |  |  |
|  | (2) |  |  |  | 40 | 39 |  |  |  |  |  |
|  | (3) | 20 | 20 | 12 | 24 | 23 | 20 | 20 | 20 | 20 | 20 |

TABLE 21-continued

| | | POLYMERIC COMPOUND | | | | | | | | |
|---|---|---|---|---|---|---|---|---|---|---|
| | | 21 | 22 | 23 | 24 | 25 | 26 | 27 | 28 | 29 | 30 |
| | (4) | 45 | 45 | 24 | | | 44 | | | | |
| | (5) | | | | | | | | | | |
| | (6) | | | 16 | | | 36 | 35 | 35 | 35 | 35 |
| | (7) | | | | | | | 45 | | | |
| | (8) | | | | | | | | 45 | | |
| | (9) | | | | | | | | | 45 | |
| | (10) | | | | | | | | | | 45 |
| | (11) | | | | | | | | | | |
| | (12) | | | | | | | | | | |
| | (13) | | | | | | | | | | |
| | (14) | | | | | | | | | | |
| | (15) | 35 | | | | | | | | | |
| | (16) | | 35 | | | | | | | | |
| | (17) | | | 13 | | | | | | | |
| POLYMERIZATION INITIATOR | | I-A | I-A | I-A | V601 | ACVA | V601 | V601 | V601 | V601 | V601 |
| Mw | | 7900 | 6900 | 7100 | 10200 | 10100 | 7600 | 7600 | 7600 | 7600 | 7600 |
| Mw/Mn | | 1.89 | 1.61 | 1.94 | 1.71 | 1.69 | 1.80 | 1.80 | 1.80 | 1.80 | 1.80 |

TABLE 22

| | | POLYMERIC COMPOUND | | | | | | | |
|---|---|---|---|---|---|---|---|---|---|
| | | 31 | 32 | 33 | 34 | 35 | 36 | 37 | 38 |
| MONOMER | (1) | 45 | | | | | | | 33 |
| | (2) | | | | | | | | |
| | (3) | 20 | 20 | 20 | 20 | 20 | 20 | 20 | 12 |
| | (4) | | | | 45 | 45 | 45 | 45 | 25 |
| | (5) | | | | | | | | |
| | (6) | 35 | 35 | 35 | | | | | 17 |
| | (7) | | | | | | | | |
| | (8) | | | | | | | | |
| | (9) | | | | | | | | |
| | (10) | | | | | | | | |
| | (11) | | 45 | | | | | | |
| | (12) | | | 45 | | | | | |
| | (13) | | | | 35 | | | | |
| | (14) | | | | | 35 | | | |
| | (15) | | | | | | 35 | | |
| | (16) | | | | | | | 35 | |
| | (17) | | | | | | | | 13 |
| POLYMERIZATION INITIATOR | | V601 | V601 | V601 | V601 | V601 | V601 | V601 | V601 |
| Mw | | 7500 | 7200 | 7600 | 7600 | 7500 | 7500 | 8100 | 7000 |
| Mw/Mn | | 1.75 | 1.74 | 1.80 | 1.85 | 1.77 | 1.83 | 1.89 | 1.77 |

Polymer Synthesis Example 39

Synthesis of Polymeric Compound (39)

13.2 g of γ-butyrolactone (GBL) was added to a flask equipped with a thermometer, a reflux tube, a stirrer and a nitrogen inlet tube under a nitrogen atmosphere, and the internal temperature was raised to 85° C. while stirring.

Separately from the above, 5.0 g (15.8 mmol) of monomer (18), 4.6 g (19.5 mmol) of monomer (19), and 1.9 g (8.2 mmol) of monomer (20) were dissolved in 79.6 g of γ-butyrolactone (GBL). Then, 3.43 g of the compound (I-A) as a radical polymerization initiator was added and dissolved in the obtained solution.

The mixed solution was added to the flask in a dropwise manner at a constant rate over 4 hours, and then heated while stirring for 1 hour, and the reacting solution was cooled to room temperature.

The obtained reaction polymer solution was added to an excess amount of a methanol/water mixed solution in a dropwise manner so as to deposit a polymer. Thereafter, the precipitated white powder was separated by filtration, followed by washing with a methanol/water mixed solution and drying under reduced pressure, thereby obtaining 5.7 g of a polymeric compound (39) as an objective compound.

With respect to the polymeric compound, the weight average molecular weight (Mw) and the dispersity (Mw/Mn) were determined by the polystyrene equivalent value as measured by gel permeation chromatography (GPC). As a result, it was found that the weight average molecular weight was 7,500, and the dispersity was 1.71.

Further, as a result of an analysis by $^{13}C$-NMR, it was found that the copolymer compositional ratio (ratio (molar ratio) of the respective structural units within the structural formula) was l/m/n=40/40/20.

[Chemical Formula 107]

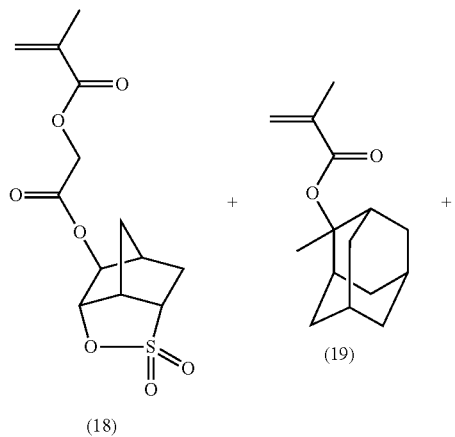

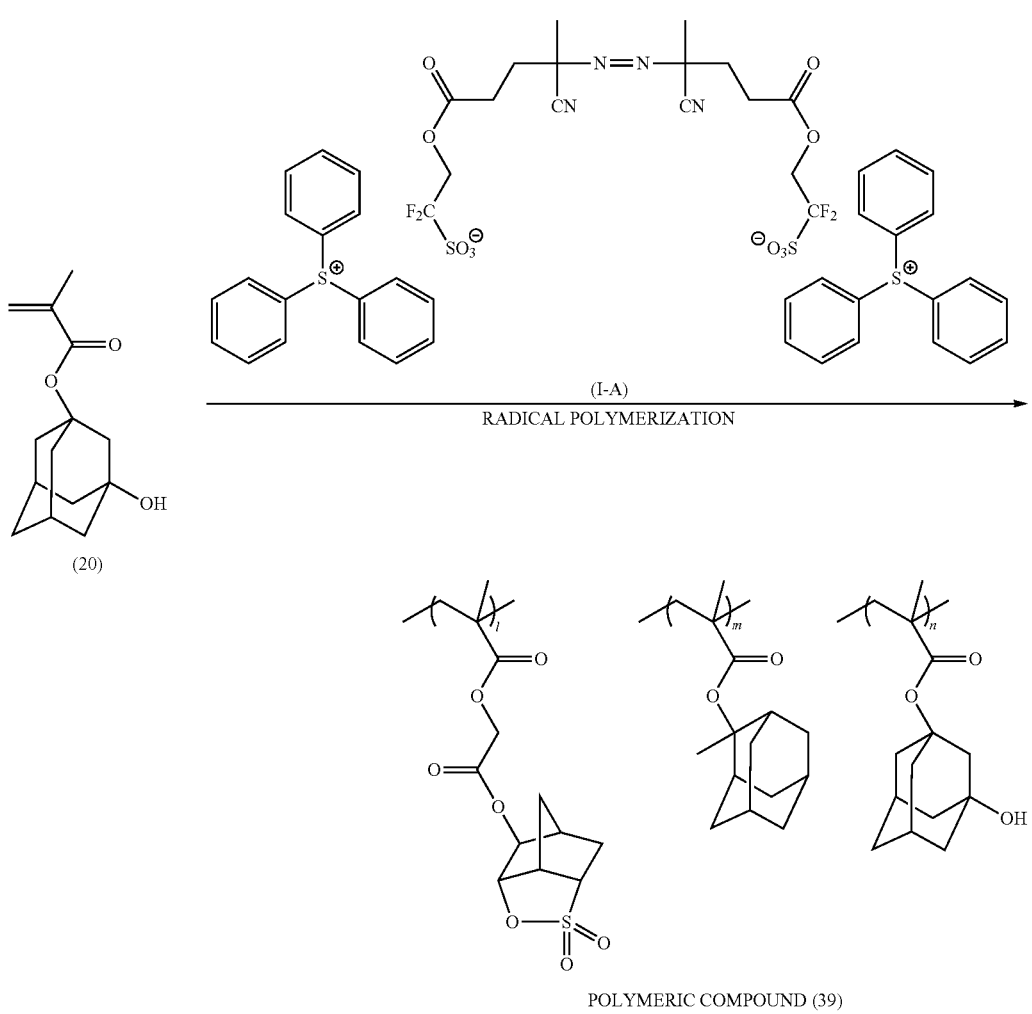

Polymer Synthesis Examples 40 to 46

Synthesis of Polymeric Compounds (40) to (46)

Polymeric compounds (40) to (46) were produced in the same manner as in Polymer Synthesis Example 39, except that the following monomers (18) to (29) which derived the structural units constituting each polymeric compound were used with a molar ratio indicated in Table 23.

The weight average molecular weight (Mw) and the molecular weight distribution (Mw/Mn) of the obtained polymeric compounds (40) to (46) are shown in Table 23.

Comparative Polymer Synthesis Example 1

Synthesis of Polymeric Compound (47)

13.2 g of γ-butyrolactone (GBL) was added to a flask equipped with a thermometer, a reflux tube, a stirrer and a nitrogen inlet tube under a nitrogen atmosphere, and the internal temperature was raised to 85° C. while stirring.

Separately from the above, 5.0 g (15.8 mmol) of monomer (18), 4.6 g (19.5 mmol) of monomer (19), and 1.9 g (8.2 mmol) of monomer (20) were dissolved in 79.6 g of γ-butyrolactone (GBL). Then, 0.72 g of dimethyl 2,2'-azobis(isobutyrate) (product name: V-601, manufactured by Wako Pure Chemical Industries, Ltd.) as a radical polymerization initiator was added and dissolved in the obtained solution.

The mixed solution was added to the flask in a dropwise manner at a constant rate over 4 hours, and then heated while stirring for 1 hour, and the reacting solution was cooled to room temperature.

The obtained reaction polymer solution was added to an excess amount of a methanol/water mixed solution in a dropwise manner so as to deposit a polymer. Thereafter, the precipitated white powder was separated by filtration, followed by washing with a methanol/water mixed solution and drying under reduced pressure, thereby obtaining 8.1 g of a polymeric compound (47) as an objective compound.

With respect to the polymeric compound, the weight average molecular weight (Mw) and the dispersity (Mw/Mn) were determined by the polystyrene equivalent value as measured by gel permeation chromatography (GPC). As a result, it was found that the weight average molecular weight was 6,900, and the dispersity was 1.73.

Further, as a result of an analysis by $^{13}$C-NMR, it was found that the copolymer compositional ratio (ratio (molar ratio) of the respective structural units within the structural formula) was l/m/n=40/40/20.

[Chemical Formula 108]

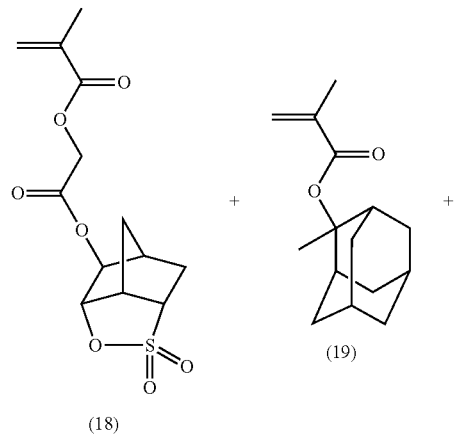

(18)

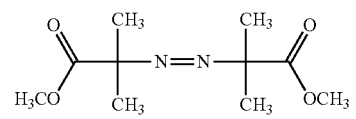

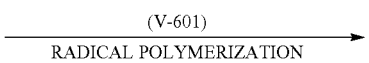

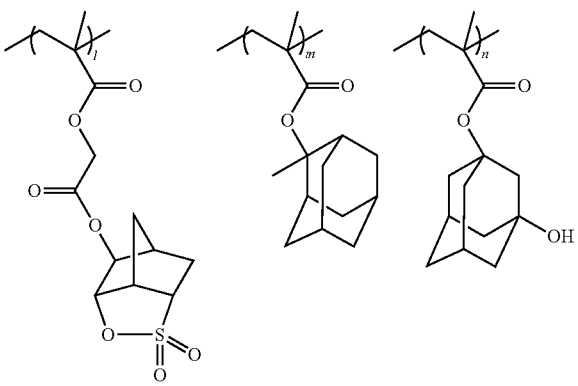

POLYMERIC COMPOUND (47)

Comparative Polymer Synthesis Examples 2 to 9

Synthesis of Polymeric Compounds (48) to (54)

Polymeric compounds (48) to (54) were produced in the same manner as in Comparative Polymer Synthesis Example 1, except that the following monomers (18) to (29) which derived the structural units constituting each polymeric compound were used with a molar ratio indicated in Table 24.

The weight average molecular weight (Mw) and the molecular weight distribution (Mw/Mn) of the obtained polymeric compounds (48) to (54) are shown in Table 24.

[Chemical Formula 109]

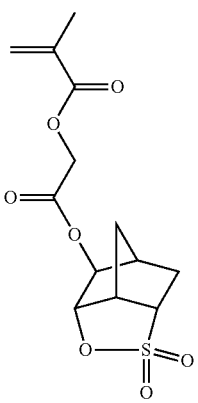

(18)

(19) 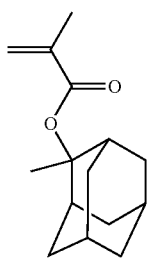
(20) 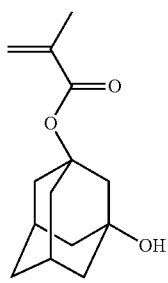
(21) 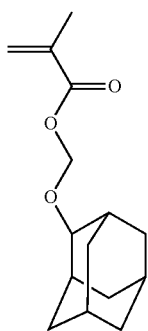
(22) 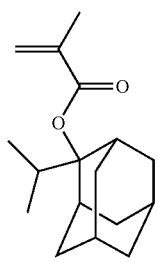
(23) 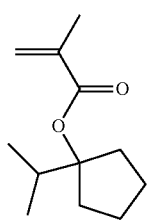
(24) 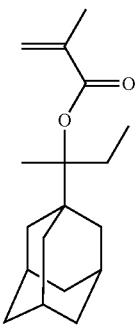
(25) 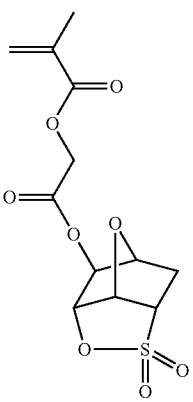
(26) 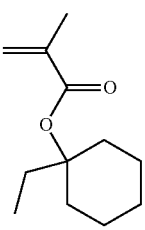
(27) 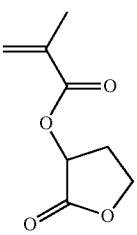
(28) 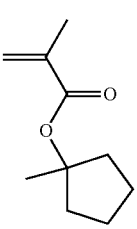

-continued
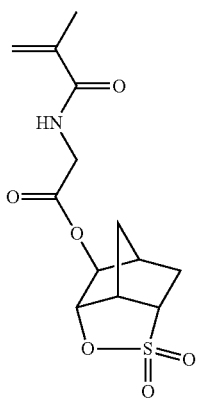
(29)
TABLE 23
| | | POLYMERIC COMPOUND | | | | | | | |
|---|---|---|---|---|---|---|---|---|---|
| | | (39) | (40) | (41) | (42) | (43) | (44) | (45) | (46) |
| MONOMER | (18) | 40 | 40 | 40 | 40 | 40 | | | |
| | (19) | 40 | | | | | | | |
| | (20) | 20 | 20 | 20 | 20 | 20 | | 12 | 12 |
| | (21) | | 40 | | | | | | |
| | (22) | | | 40 | | | | 16 | 16 |
| | (23) | | | | 40 | | | | |
| | (24) | | | | | 40 | | | |
| | (25) | | | | | | 52 | 24 | |
| | (26) | | | | | | 48 | | |
| | (27) | | | | | | | 35 | 35 |
| | (28) | | | | | | | 13 | 13 |
| | (29) | | | | | | | | 24 |
| POLYMERIZATION INITIATOR | | I-A | I-A | I-A | I-A | I-A | I-A | I-A | I-A |
| Mw | | 7500 | 7700 | 6900 | 7200 | 7300 | 7100 | 7300 | 7700 |
| Mw/Mn | | 1.71 | 1.70 | 1.68 | 1.82 | 1.79 | 1.66 | 1.73 | 1.75 |
TABLE 24
| | | POLYMERIC COMPOUND | | | | | | | |
|---|---|---|---|---|---|---|---|---|---|
| | | (47) | (48) | (49) | (50) | (51) | (52) | (53) | (54) |
| MONOMER | (18) | 40 | 40 | 40 | 40 | 40 | | | |
| | (19) | 40 | | | | | | | |
| | (20) | 20 | 20 | 20 | 20 | 20 | | 12 | 12 |
| | (21) | | 40 | | | | | | |
| | (22) | | | 40 | | | | 16 | 16 |
| | (23) | | | | 40 | | | | |
| | (24) | | | | | 40 | | | |
| | (25) | | | | | | 52 | 24 | |
| | (26) | | | | | | 48 | | |
| | (27) | | | | | | | 35 | 35 |
| | (28) | | | | | | | 13 | 13 |
| | (29) | | | | | | | | 24 |
| POLYMERIZATION INITIATOR | | V-601 | V-601 | V-601 | V-601 | V-601 | V-601 | V-601 | V-601 |
| Mw | | 6900 | 6600 | 7000 | 6800 | 7100 | 6900 | 6600 | 6800 |
| Mw/Mn | | 1.73 | 1.66 | 1.82 | 1.79 | 1.70 | 1.68 | 1.73 | 1.68 |
Examples 1 to 28
Comparative Examples 1 to 17
The components shown in Tables 25 to 27 were mixed together and dissolved to obtain positive resist compositions.

TABLE 25

|  | COMPONENT (A) | COMPONENT (B) | COMPONENT (D) | COMPONENT (E) | COMPONENT (S) |
|---|---|---|---|---|---|
| EXAMPLE 1 | (A)-1 [100] | (B)-1 [14.0] | (D)-1 [1.2] | (E)-1 [0.5] | (S)-1 [3000] |
| EXAMPLE 2 | (A)-2 [100] | (B)-1 [14.0] | (D)-1 [1.2] | (E)-1 [0.5] | (S)-1 [3000] |
| EXAMPLE 3 | (A)-3 [100] | (B)-1 [14.0] | (D)-1 [1.2] | (E)-1 [0.5] | (S)-1 [3000] |
| EXAMPLE 4 | (A)-4 [100] | (B)-1 [14.0] | (D)-1 [1.2] | (E)-1 [0.5] | (S)-1 [3000] |
| EXAMPLE 5 | (A)-5 [100] | (B)-1 [14.0] | (D)-1 [1.2] | (E)-1 [0.5] | (S)-1 [3000] |
| EXAMPLE 6 | (A)-6 [100] | (B)-1 [14.0] | (D)-1 [1.2] | (E)-1 [0.5] | (S)-1 [3000] |
| EXAMPLE 7 | (A)-7 [100] | (B)-1 [14.0] | (D)-1 [1.2] | (E)-1 [0.5] | (S)-1 [3000] |
| EXAMPLE 8 | (A)-8 [100] | (B)-1 [14.0] | (D)-1 [1.2] | (E)-1 [0.5] | (S)-1 [3000] |
| EXAMPLE 9 | (A)-9 [100] | (B)-1 [14.0] | (D)-1 [1.2] | (E)-1 [0.5] | (S)-1 [3000] |
| EXAMPLE 10 | (A)-10 [100] | (B)-1 [14.0] | (D)-1 [1.2] | (E)-1 [0.5] | (S)-1 [3000] |
| EXAMPLE 11 | (A)-11 [100] | (B)-1 [14.0] | (D)-1 [1.2] | (E)-1 [0.5] | (S)-1 [3000] |
| EXAMPLE 12 | (A)-12 [100] | (B)-1 [14.0] | (D)-1 [1.2] | (E)-1 [0.5] | (S)-1 [3000] |
| EXAMPLE 13 | (A)-13 [100] | (B)-1 [14.0] | (D)-1 [1.2] | (E)-1 [0.5] | (S)-1 [3000] |
| EXAMPLE 14 | (A)-14 [100] | (B)-1 [14.0] | (D)-1 [1.2] | (E)-1 [0.5] | (S)-1 [3000] |

TABLE 26

|  | COMPONENT (A) | | COMPONENT (B) | COMPONENT (D) | COMPONENT (E) | COMPONENT (F) | COMPONENT (S) |
|---|---|---|---|---|---|---|---|
| EXAMPLE 15 | (A)-15 [100] | | (B)-1 [14.0] | (D)-1 [1.2] | (E)-1 [0.5] | | (S)-1 [3000] |
| EXAMPLE 16 | (A)-16 [100] | | (B)-1 [14.0] | (D)-1 [1.2] | (E)-1 [0.5] | | (S)-1 [3000] |
| EXAMPLE 17 | (A)-17 [100] | | (B)-1 [14.0] | (D)-1 [1.2] | (E)-1 [0.5] | | (S)-1 [3000] |
| EXAMPLE 18 | (A)-18 [100] | | (B)-1 [14.0] | (D)-1 [1.2] | (E)-1 [0.5] | | (S)-1 [3000] |
| EXAMPLE 19 | (A)-19 [100] | | (B)-1 [14.0] | (D)-1 [1.2] | (E)-1 [0.5] | | (S)-1 [3000] |
| EXAMPLE 20 | (A)-20 [100] | | (B)-1 [14.0] | (D)-1 [1.2] | (E)-1 [0.5] | | (S)-1 [3000] |
| EXAMPLE 21 | (A)-21 [100] | | (B)-1 [14.0] | (D)-1 [1.2] | (E)-1 [0.5] | | (S)-1 [3000] |
| EXAMPLE 22 | (A)-22 [100] | | (B)-1 [14.0] | (D)-1 [1.2] | (E)-1 [0.5] | | (S)-1 [3000] |
| EXAMPLE 23 | (A)-23 [100] | | (B)-1 [14.0] | (D)-1 [1.2] | (E)-1 [0.5] | | (S)-1 [3000] |
| EXAMPLE 24 | (A)-1 [100] | | (B)-1 [14.0] | (D)-1 [1.2] | (E)-1 [0.5] | | (S)-1 [3000] |
| EXAMPLE 24 | (A)-1 [100] | | (B)-1 [14.0] | (D)-1 [1.2] | (E)-1 [0.5] | (F)-1 [1.5] | (S)-1 [3000] |
| EXAMPLE 25 | (A)-1 [100] | | (B)-1 [14.0] | (D)-1 [1.21] | (E)-1 [0.5] | (F)-2 [1.5] | (S)-1 [3000] |
| EXAMPLE 26 | (A)-1 [100] | | | (D)-1 [1.2] | (E)-1 [0.5] | | (S)-1 [3000] |
| EXAMPLE 27 | (A)-1 [75.0] | (A)-24 [25.0] | (B)-1 [14.0] | (D)-1 [1.2] | (E)-1 [0.5] | | (S)-1 [3000] |
| EXAMPLE 28 | (A)-1 [100] | | (B)-2 [15.2] | (D)-1 [1.2] | (E)-1 [0.5] | | (S)-1 [3000] |

TABLE 27

|  | COMPONENT (A) | COMPONENT (B) | COMPONENT (D) | COMPONENT (E) | COMPONENT (S) |
|---|---|---|---|---|---|
| COMPARATIVE EXAMPLE 1 | (A)-24 [100] | (B)-1 [14.0] | (D)-1 [1.2] | (E)-1 [0.5] | (S)-1 [3000] |

TABLE 27-continued

| | COMPONENT (A) | COMPONENT (B) | COMPONENT (D) | COMPONENT (E) | COMPONENT (S) |
|---|---|---|---|---|---|
| COMPARATIVE EXAMPLE 2 | (A)-25 [100] | (B)-1 [14.0] | (D)-1 [1.2] | (E)-1 [0.5] | (S)-1 [3000] |
| COMPARATIVE EXAMPLE 3 | (A)-26 [100] | (B)-1 [14.0] | (D)-1 [1.2] | (E)-1 [0.5] | (S)-1 [3000] |
| COMPARATIVE EXAMPLE 4 | (A)-27 [100] | (B)-1 [14.0] | (D)-1 [1.2] | (E)-1 [0.5] | (S)-1 [3000] |
| COMPARATIVE EXAMPLE 5 | (A)-28 [100] | (B)-1 [14.0] | (D)-1 [1.2] | (E)-1 [0.5] | (S)-1 [3000] |
| COMPARATIVE EXAMPLE 6 | (A)-29 [100] | (B)-1 [14.0] | (D)-1 [1.2] | (E)-1 [0.5] | (S)-1 [3000] |
| COMPARATIVE EXAMPLE 7 | (A)-30 [100] | (B)-1 [14.0] | (D)-1 [1.2] | (E)-1 [0.5] | (S)-1 [3000] |
| COMPARATIVE EXAMPLE 8 | (A)-31 [100] | (B)-1 [14.0] | (D)-1 [1.2] | (E)-1 [0.5] | (S)-1 [3000] |
| COMPARATIVE EXAMPLE 9 | (A)-32 [100] | (B)-1 [14.0] | (D)-1 [1.2] | (E)-1 [0.5] | (S)-1 [3000] |
| COMPARATIVE EXAMPLE 10 | (A)-33 [100] | (B)-1 [14.0] | (D)-1 [1.2] | (E)-1 [0.5] | (S)-1 [3000] |
| COMPARATIVE EXAMPLE 11 | (A)-34 [100] | (B)-1 [14.0] | (D)-1 [1.2] | (E)-1 [0.5] | (S)-1 [3000] |
| COMPARATIVE EXAMPLE 12 | (A)-35 [100] | (B)-1 [14.0] | (D)-1 [1.2] | (E)-1 [0.5] | (S)-1 [3000] |
| COMPARATIVE EXAMPLE 13 | (A)-36 [100] | (B)-1 [14.0] | (D)-1 [1.2] | (E)-1 [0.5] | (S)-1 [3000] |
| COMPARATIVE EXAMPLE 14 | (A)-37 [100] | (B)-1 [14.0] | (D)-1 [1-2] | (E)-1 [0.5] | (S)-1 [3000] |
| COMPARATIVE EXAMPLE 15 | (A)-38 [100] | (B)-1 [14.0] | (D)-1 [1.2] | (E)-1 [0.5] | (S)-1 [3000] |
| COMPARATIVE EXAMPLE 16 | (A)-24 [100] | | (D)-1 [1.2] | (E)-1 [0.5] | (S)-1 [3000] |
| COMPARATIVE EXAMPLE 17 | (A)-24 [100] | (B)-2 [15.2] | (D)-1 [1.2] | (E)-1 [0.5] | (S)-1 [3000] |

In Tables 25 to 27, the reference characters indicate the following. Further, the values in brackets [ ] indicate the amount (in terms of parts by weight) of the component added.

(A)-1 to (A)-38: the aforementioned polymeric compounds 1 to 38

(B)-1: compound (B)-1 shown below (B)-2: compound (B)-2 shown below (D)-1: tri-n-octylamine (E)-1: salicylic acid (F)-1: polymeric compound (F)-1 shown below [l/m=77/23 (molar ratio), Mw=23,000, Mw/Mn=1.61, polymeric compound produced by radical polymerization using the radical polymerization initiator V-601]

(F)-2: polymeric compound (F)-2 shown below [l=100 (molar ratio), Mw=22,000, Mw/Mn=1.58, polymeric compound produced by radical polymerization using the radical polymerization initiator V-601]

(S)-1: a mixed solvent of PGMEA/PGME/cyclohexanone=45/30/25 (weight ratio)

[Chemical Formula 110]

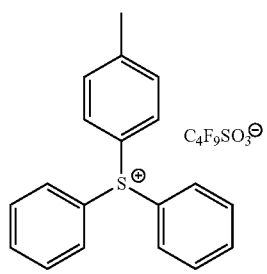

(B)-1

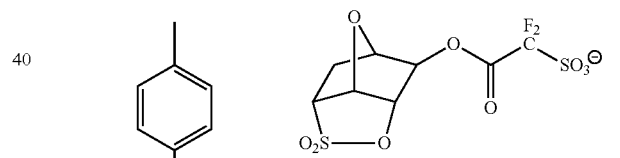

(B)-2

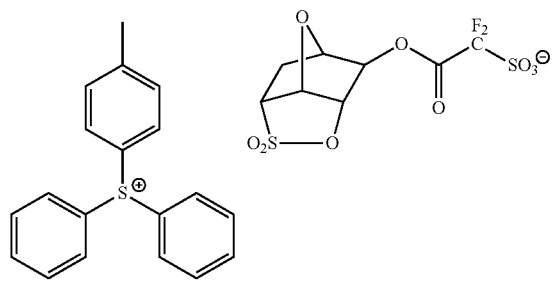

-continued

(F)-1

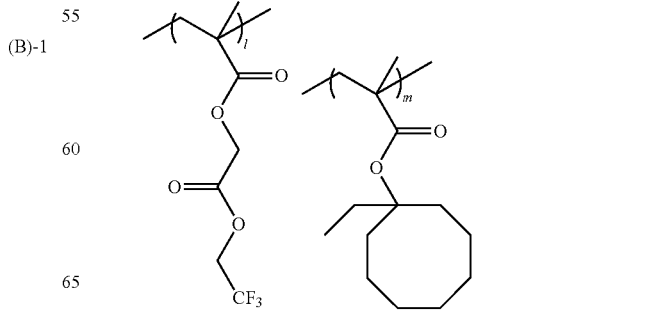

-continued

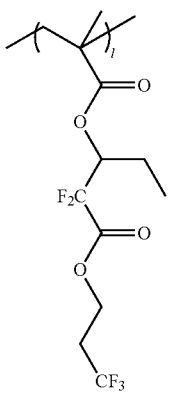

(F)-2

Examples 29 to 38

Comparative Examples 18 to 25

Production of Resist Composition

The components shown in Table 28 were mixed together and dissolved to obtain resist compositions.

In Table 28, the reference characters indicate the following. Further, the values in brackets [ ] indicate the amount (in terms of parts by weight) of the component added.

(A)-39 to (A)-54: the aforementioned polymeric compounds 39 to 54

(B)-2: compound (B)-2 shown below [pKa of generated acid=−3.4]

(C)-1: compound (C)-1 shown below [pKa of generated acid=7.4]

(C)-2: compound (C)-2 shown below [pKa of generated acid=3.0]

(C)-3: compound (C)-3 shown below [pKa of generated acid=4.8]

(F)-2: polymeric compound (F)-2 shown below [l=100 (molar ratio), Mw=22,000, Mw/Mn=1.58, polymeric compound produced by radical polymerization using the radical polymerization initiator V-601]

(E)-1: salicylic acid (S)-1: a mixed solvent of PGMEA/PGME/cyclohexanone=45/30/25 (weight ratio)

TABLE 28

| | COMPONENT (A) | COMPONENT (B) | COMPONENT (C) | COMPONENT (F) | COMPONENT (E) | COMPONENT (S) |
|---|---|---|---|---|---|---|
| EXAMPLE 29 | (A)-39 [100] | (B)-2 [15.0] | (C)-1 [2.10] | (F)-1 [1.50] | (E)-1 [0.50] | (S)-1 [3000] |
| EXAMPLE 30 | (A)-40 [100] | (B)-2 [15.0] | (C)-1 [2.10] | (F)-1 [1.50] | (E)-1 [0.50] | (S)-1 [3000] |
| EXAMPLE 31 | (A)-41 [100] | (B)-2 [15.0] | (C)-1 [2.10] | (F)-1 [1.50] | (E)-1 [0.50] | (S)-1 [3000] |
| EXAMPLE 32 | (A)-42 [100] | (B)-2 [15.0] | (C)-1 [2.10] | (F)-1 [1.50] | (E)-1 [0.50] | (S)-1 [3000] |
| EXAMPLE 33 | (A)-43 [100] | (B)-2 [15.0] | (C)-1 [2.10] | (F)-1 [1.50] | (E)-1 [0.50] | (S)-1 [3000] |
| EXAMPLE 34 | (A)-44 [100] | (B)-2 [15.0] | (C)-1 [2.10] | (F)-1 [1.50] | (E)-1 [0.50] | (S)-1 [3000] |
| EXAMPLE 35 | (A)-45 [100] | (B)-2 [15.0] | (C)-1 [2.10] | (F)-1 [1.50] | (E)-1 [0.50] | (S)-1 [3000] |
| EXAMPLE 36 | (A)-46 [100] | (B)-2 [15.0] | (C)-1 [2.10] | (F)-1 [1.50] | (E)-1 [0.50] | (S)-1 [3000] |
| EXAMPLE 37 | (A)-45 [100] | (B)-2 [15.0] | (C)-2 [1.36] | (F)-1 [1.50] | (E)-1 [0.50] | (S)-1 [3000] |
| EXAMPLE 38 | (A)-45 [100] | (B)-2 [15.0] | (C)-3 [1.50] | (F)-1 [1.50] | (E)-1 [0.50] | (S)-1 [3000] |
| COMPARATIVE EXAMPLE 18 | (A)-47 [100] | (B)-2 [15.0] | (C)-1 [2.10] | (F)-1 [1.50] | (E)-1 [0.50] | (S)-1 [3000] |
| COMPARATIVE EXAMPLE 19 | (A)-48 [100] | (B)-2 [15.0] | (C)-1 [2.10] | (F)-1 [1.50] | (E)-1 [0.50] | (S)-1 [3000] |
| COMPARATIVE EXAMPLE 20 | (A)-49 [100] | (B)-2 [15.0] | (C)-1 [2.10] | (F)-1 [1.50] | (E)-1 [0.50] | (S)-1 [3000] |
| COMPARATIVE EXAMPLE 21 | (A)-50 [100] | (B)-2 [15.0] | (C)-1 [2.10] | (F)-1 [1.50] | (E)-1 [0.50] | (S)-1 [3000] |
| COMPARATIVE EXAMPLE 22 | (A)-51 [100] | (B)-2 [15.0] | (C)-1 [2.10] | (F)-1 [1.50] | (E)-1 [0.50] | (S)-1 [3000] |
| COMPARATIVE EXAMPLE 23 | (A)-52 [100] | (B)-2 [15.0] | (C)-1 [2.10] | (F)-1 [1.50] | (E)-1 [0.50] | (S)-1 [3000] |
| COMPARATIVE EXAMPLE 24 | (A)-53 [100] | (B)-2 [15.0] | (C)-1 [2.10] | (F)-1 [1.50] | (E)-1 [0.50] | (S)-1 [3000] |
| COMPARATIVE EXAMPLE 25 | (A)-54 [100] | (B)-2 [15.0] | (C)-1 [2.10] | (F)-1 [1.50] | (E)-1 [0.50] | (S)-1 [3000] |

[Chemical Formula 111]

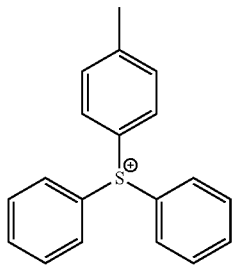
(B)-2

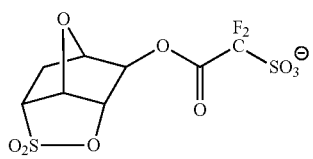
(F)-2

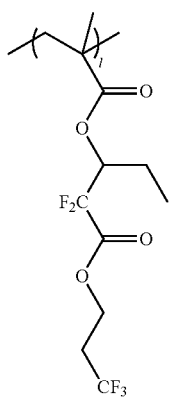
(C)-1

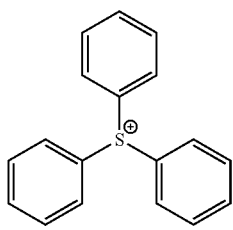
(C)-2

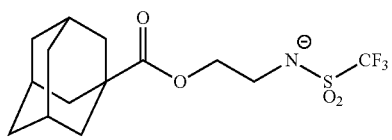

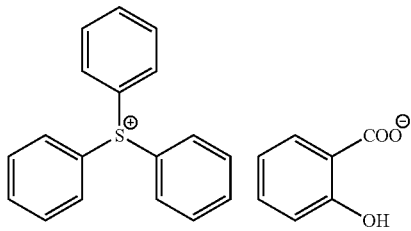

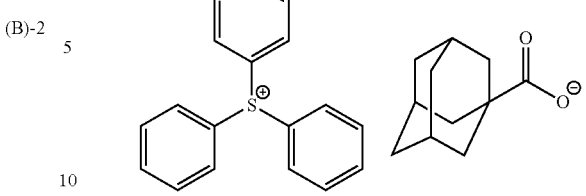
(C)-3

[Formation of Resist Pattern 1]

An organic anti-reflection film composition (product name: ARC95, manufactured by Brewer Science Ltd.) was applied to a 12-inch silicon wafer using a spinner, and the composition was then baked at 205° C. for 90 seconds on a hotplate and dried, thereby forming an organic anti-reflection film having a film thickness of 90 nm.

Then, each positive resist composition obtained in the examples was applied to the organic anti-reflection film using a spinner, and was then prebaked (PAB) on a hotplate at a temperature indicated in Tables 26 and 27 for 60 seconds and dried, thereby forming a resist film having a film thickness of 100 nm.

Subsequently, the resist film was selectively irradiated with an ArF excimer laser (193 nm) through a mask pattern, using an ArF immersion exposure apparatus NSR-S609B (manufactured by Nikon Corporation, NA (numerical aperture)= 1.07, Dipole (in/out=0.78/0.97), w/POLANO).

Next, a PEB treatment was conducted at a temperature indicated in Tables 29 to 31 for 60 seconds, followed by alkali development for 10 seconds at 23° C. in a 2.38% by weight aqueous tetramethylammonium hydroxide (TMAH) solution (product name: NMD-3; manufactured by Tokyo Ohka Kogyo Co., Ltd.). Then, the resist was washed for 15 seconds with pure water, followed by drying by shaking.

Further, a post bake was conducted on a hot plate at 100° C. for 45 seconds.

As a result, in each of the examples except Comparative Example 16, a 1:1 line and space pattern (LS pattern) having a line width of 50 nm and a pitch of 100 nm was formed. (In Comparative Example 16, a pattern was not formed.)

The optimum exposure dose Eop (mJ/cm$^2$; sensitivity) with which the LS pattern was formed was determined. The results are shown in Tables 29 to 31.

[Evaluation of Exposure Latitude (EL Margin)]

With respect to the above Eop, the exposure dose with which an LS pattern having a dimension of the target dimension (line width: 50 nm)±5% (i.e., 47.5 nm to 52.5 nm) was determined, and the EL margin (unit: %) was determined by the following formula. The results are shown in Tables 29 to 31.

EL margin (%)=(|E1−E2|/Eop)×100

In the formula, E1 represents the exposure dose (mJ/cm$^2$) for forming an LS pattern having a line width of 47.5 nm, and E2 represents the exposure dose (mJ/cm$^2$) for forming an LS pattern having a line width of 52.5 nm.

The larger the value of the "EL margin", the smaller the change in the pattern size by the variation of the exposure dose.

[Evaluation of Mask Error Factor (MEF)]

In the same manner as described above, with the above Eop, LS patterns were formed using a mask pattern targeting a line width of 50 nm and a pitch of 100 nm, and a mask pattern targeting a line width of 55 nm and a pitch of 100 nm, and the MEF value was calculated by the following formula. The results are shown in Tables 29 to 31.

MEF=|CD55−CD50|/|MD55−MD50|

In the formula, CD50 and CD55 represent the respective line widths (nm) of the actual LS patterns respectively formed using the mask pattern targeting a line width of 50 nm and the mask pattern targeting a line width of 55 nm. MD50 and MD55 represent the respective target line widths (nm), meaning MD50=50 nm, and MD55=55 nm.

A MEF value closer to 1 indicates that a resist pattern faithful to the mask pattern was formed.

[Evaluation of Line Width Roughness (LWR)]

With respect to each of the LS patterns formed with the above Eop and having a line width of 50 nm and a pitch of 100 nm, the space width at 400 points in the lengthwise direction of the space were measured using a measuring scanning electron microscope (SEM) (acceleration voltage: 300V, product name: S-9380, manufactured by Hitachi High-Technologies Corporation). From the results, the value of 3 times the standard deviation s (i.e., 3s) was determined, and the average of the 3s values at 400 points was calculated as a yardstick of LWR. The results are shown in Tables 29 to 31.

The smaller this 3s value is, the lower the level of roughness of the line width, indicating that a LS pattern with a uniform width was obtained.

[Evaluation of Pattern Shape]

With respect to each pattern formed with the above Eop, the cross-sectional shape was observed using a scanning electron microscope (product name: SU-8000, manufactured by Hitachi High-Technologies Corporation), and the cross-sectional shape was evaluated with the following criteria. The results are shown in Tables 29 to 31.

A: high rectangularity and excellent shape
B: slightly-T-top shaped
C: vertical shape and low rectangularity

TABLE 29

| | PAB (° C.) | PEB (° C.) | Eop (mJ/cm²) | 5% EL (%) | MEF | LWR (nm) | SHAPE |
|---|---|---|---|---|---|---|---|
| EXAMPLE 1 | 100 | 90 | 24.2 | 7.93 | 2.82 | 5.44 | A |
| EXAMPLE 2 | 100 | 90 | 24.7 | 7.88 | 2.84 | 5.51 | A |
| EXAMPLE 3 | 100 | 90 | 25.2 | 8.01 | 2.73 | 5.36 | A |
| EXAMPLE 4 | 100 | 90 | 24.9 | 7.90 | 2.77 | 5.26 | A |
| EXAMPLE 5 | 100 | 90 | 27.5 | 8.33 | 2.62 | 5.15 | A |
| EXAMPLE 6 | 100 | 90 | 25.3 | 8.11 | 2.69 | 5.31 | A |
| EXAMPLE 7 | 100 | 90 | 25.6 | 8.10 | 2.79 | 5.48 | A |
| EXAMPLE 8 | 100 | 90 | 25.7 | 8.57 | 2.45 | 5.11 | A |
| EXAMPLE 9 | 100 | 95 | 26.1 | 8.44 | 2.51 | 5.17 | A |
| EXAMPLE 10 | 90 | 80 | 23.2 | 8.12 | 2.64 | 4.82 | A |
| EXAMPLE 11 | 90 | 85 | 26.9 | 9.01 | 2.41 | 4.88 | A |
| EXAMPLE 12 | 100 | 90 | 27.1 | 8.24 | 2.58 | 5.18 | A |
| EXAMPLE 13 | 100 | 90 | 26.8 | 8.33 | 2.53 | 5.15 | A |
| EXAMPLE 14 | 100 | 95 | 25.5 | 8.11 | 2.49 | 5.48 | A |
| EXAMPLE 15 | 90 | 85 | 24.1 | 7.85 | 2.61 | 5.30 | A |

TABLE 29-continued

| | PAB (° C.) | PEB (° C.) | Eop (mJ/cm²) | 5% EL (%) | MEF | LWR (nm) | SHAPE |
|---|---|---|---|---|---|---|---|
| EXAMPLE 16 | 90 | 85 | 25.8 | 7.89 | 2.55 | 5.27 | A |
| EXAMPLE 17 | 90 | 85 | 27.3 | 9.08 | 2.35 | 4.96 | A |
| EXAMPLE 18 | 90 | 85 | 25.1 | 7.76 | 2.49 | 5.16 | A |
| EXAMPLE 19 | 90 | 85 | 28.5 | 8.42 | 2.61 | 5.32 | A |
| EXAMPLE 20 | 90 | 80 | 23.1 | 7.99 | 2.71 | 4.82 | A |
| EXAMPLE 21 | 90 | 80 | 23.3 | 8.04 | 2.64 | 4.74 | A |
| EXAMPLE 22 | 90 | 80 | 24.0 | 7.75 | 2.81 | 5.01 | A |
| EXAMPLE 23 | 90 | 80 | 28.1 | 9.25 | 2.31 | 4.72 | A |
| EXAMPLE 24 | 100 | 90 | 24.4 | 7.84 | 2.84 | 5.31 | A |
| EXAMPLE 25 | 100 | 90 | 24.7 | 7.90 | 2.88 | 5.29 | A |
| EXAMPLE 26 | 130 | 120 | 21.5 | 7.18 | 2.91 | 5.48 | B |
| EXAMPLE 27 | 100 | 90 | 24.9 | 7.79 | 2.86 | 5.61 | A |
| EXAMPLE 28 | 100 | 90 | 26.8 | 8.83 | 2.42 | 4.88 | A |

TABLE 30

| | PAB (° C.) | PEB (° C.) | Eop (mJ/cm²) | 5% EL (%) | MEF | LWR (nm) | SHAPE |
|---|---|---|---|---|---|---|---|
| COMPARATIVE EXAMPLE 1 | 100 | 90 | 28.2 | 7.58 | 2.85 | 6.02 | B |
| COMPARATIVE EXAMPLE 2 | 100 | 90 | 28.0 | 7.49 | 2.91 | 6.10 | B |
| COMPARATIVE EXAMPLE 3 | 100 | 90 | 30.9 | 8.72 | 2.58 | 5.47 | B |
| COMPARATIVE EXAMPLE 4 | 100 | 90 | 31.2 | 7.98 | 2.76 | 5.80 | B |
| COMPARATIVE EXAMPLE 5 | 100 | 90 | 30.8 | 8.06 | 2.71 | 5.77 | B |
| COMPARATIVE EXAMPLE 6 | 100 | 95 | 29.3 | 7.85 | 2.66 | 6.14 | B |
| COMPARATIVE EXAMPLE 7 | 90 | 85 | 27.7 | 7.60 | 2.79 | 5.94 | B |
| COMPARATIVE EXAMPLE 8 | 90 | 85 | 29.7 | 7.64 | 2.73 | 5.90 | B |
| COMPARATIVE EXAMPLE 9 | 90 | 85 | 31.4 | 8.79 | 2.51 | 5.56 | B |
| COMPARATIVE EXAMPLE 10 | 90 | 85 | 28.9 | 7.51 | 2.66 | 5.78 | B |
| COMPARATIVE EXAMPLE 11 | 90 | 85 | 32.8 | 8.15 | 2.79 | 5.96 | B |
| COMPARATIVE EXAMPLE 12 | 90 | 80 | 26.6 | 7.73 | 2.90 | 5.40 | B |
| COMPARATIVE EXAMPLE 13 | 90 | 80 | 26.8 | 7.78 | 2.82 | 5.31 | B |
| COMPARATIVE EXAMPLE 14 | 90 | 80 | 27.6 | 7.50 | 3.01 | 5.61 | B |
| COMPARATIVE EXAMPLE 15 | 90 | 80 | 32.3 | 8.95 | 2.47 | 5.29 | B |
| COMPARATIVE EXAMPLE 16 | 130 | 120 | — | — | — | — | — |
| COMPARATIVE EXAMPLE 17 | 100 | 90 | 30.82 | 8.54 | 2.57 | 5.42 | B |

TABLE 31

| | PAB (°C.) | PEB (°C.) | Eop (mJ/cm²) | 5% EL (%) | MEF | LWR (nm) | SHAPE |
|---|---|---|---|---|---|---|---|
| EXAMPLE 29 | 110 | 105 | 34.8 | 7.91 | 2.38 | 4.34 | A |
| EXAMPLE 30 | 105 | 100 | 29.7 | 8.02 | 2.21 | 4.28 | A |
| EXAMPLE 31 | 90 | 80 | 24.8 | 7.99 | 2.28 | 4.15 | A |
| EXAMPLE 32 | 90 | 80 | 23.5 | 7.79 | 2.15 | 4.41 | A |
| EXAMPLE 33 | 90 | 80 | 26.3 | 7.58 | 2.21 | 4.03 | A |
| EXAMPLE 34 | 90 | 85 | 26.8 | 8.03 | 2.22 | 4.25 | A |
| EXAMPLE 35 | 90 | 80 | 28.2 | 7.92 | 2.32 | 4.37 | A |
| EXAMPLE 36 | 90 | 80 | 29.1 | 8.18 | 2.42 | 4.44 | A |
| EXAMPLE 37 | 90 | 80 | 27.8 | 8.11 | 2.15 | 4.08 | A |
| EXAMPLE 38 | 90 | 80 | 28.0 | 8.13 | 2.17 | 4.13 | A |
| COMPARATIVE EXAMPLE 18 | 110 | 105 | 38.4 | 6.95 | 2.60 | 4.99 | B |
| COMPARATIVE EXAMPLE 19 | 105 | 100 | 32.8 | 7.05 | 2.41 | 4.92 | B |
| COMPARATIVE EXAMPLE 20 | 90 | 80 | 27.4 | 7.02 | 2.49 | 4.77 | B |
| COMPARATIVE EXAMPLE 21 | 90 | 80 | 25.9 | 6.85 | 2.34 | 5.07 | B |
| COMPARATIVE EXAMPLE 22 | 90 | 80 | 29.0 | 6.66 | 2.41 | 4.63 | B |
| COMPARATIVE EXAMPLE 23 | 90 | 85 | 29.6 | 7.06 | 2.75 | 4.89 | B |
| COMPARATIVE EXAMPLE 24 | 90 | 80 | 31.1 | 6.96 | 2.53 | 5.03 | B |
| COMPARATIVE EXAMPLE 25 | 90 | 80 | 32.1 | 7.19 | 2.64 | 5.11 | B |

From the results shown in Tables 29 and 30 above, it was confirmed that the resist compositions of Examples 1 to 28 according to the present invention exhibited high sensitivity, excellent lithography properties (EL margin, MEF and LWR) and excellent pattern shape as compared to the resist compositions of Comparative Examples 1 to 17.

From the results shown in Table 31 above, it was confirmed that the resist compositions of Examples 29 to 38 according to the present invention exhibited excellent lithography properties (EL margin, MEF, and LWR) and pattern shape as compared to the resist compositions of Comparative Examples 18 to 25.

Example 39

Comparative Examples 26 and 27

The components shown in Table 32 were mixed together and dissolved to obtain positive resist compositions.

TABLE 32

| | COMPONENT (A) | COMPONENT (B) | COMPONENT (D) | COMPONENT (E) | COMPONENT (S) |
|---|---|---|---|---|---|
| EXAMPLE 39 | (A)-1 [100] | (B)-3 [35.0] | (D)-1 [1.2] | (E)-1 [0.5] | (S)-1 [4000] |
| COMPARATIVE EXAMPLE 26 | (A)-24 [100] | (B)-3 [35.0] | (D)-1 [1.2] | (E)-1 [0.5] | (S)-1 [4000] |
| COMPARATIVE EXAMPLE 27 | (A)-25 [100] | (B)-3 [35.0] | (D)-1 [1.2] | (E)-1 [0.5] | (S)-1 [4000] |

In Table 32, reference characters (A)-1, (A)-24, (A)-25, (D)-1, (E)-1 and (S)-1 are the same as defined above, and (B)-3 indicates a compound (B)-3 shown below.

Further, the values in brackets [ ] indicate the amount (in terms of parts by weight) of the component added.

[Chemical Formula 112]

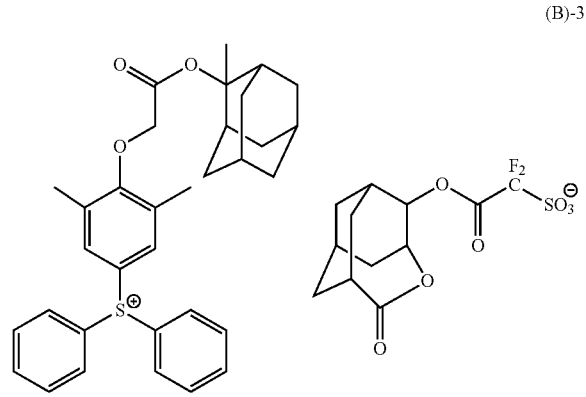

(B)-3

[Formation of Resist Pattern 2]

Using a spinner, each positive resist composition was applied to an 8-inch silicon wafer that had been treated with hexamethyldisilazane (HMDS) at 90° C. for 36 seconds, and was then prebaked (PAB) on a hotplate at a temperature indicated in Table 29 for 60 seconds and dried, thereby forming a resist film having a film thickness of 60 nm.

Subsequently, the resist film was subjected to exposure using an electron beam lithography apparatus HL-800D (VSB) (manufactured by Hitachi, Ltd.) at an acceleration voltage of 70 kV, followed by a bake treatment (PEB) at a temperature indicated in Table 29 for 60 seconds. Then, alkali development was conducted with a 2.38 wt % aqueous TMAH solution (product name: NMD-3; manufactured by Tokyo Ohka Kogyo Co., Ltd.) at 23° C. for 60 seconds, followed by rinsing for 15 seconds with pure water and drying by shaking.

Further, a post bake was conducted on a hot plate at 100° C. for 60 seconds.

As a result, in each of the examples, a 1:1 LS pattern having a line width of 100 nm and a pitch of 200 nm was formed.

The optimum exposure dose Eop ($\mu C/cm^2$; sensitivity) with which the LS pattern was formed was determined, and EL margin (10%), LWR and shape with the above Eop were evaluated in the same manner as described above.

The results are shown in Table 33.

TABLE 33

| | PAB (° C.) | PEB (° C.) | Eop (µC/cm²) | 10% EL (%) | LWR (nm) | SHAPE |
|---|---|---|---|---|---|---|
| EXAMPLE 39 | 100 | 90 | 48.1 | 27.70 | 7.49 | A |
| COMPARATIVE EXAMPLE 26 | 100 | 90 | 56.8 | 25.45 | 7.53 | B |
| COMPARATIVE EXAMPLE 27 | 100 | 90 | 53.5 | 25.19 | 7.64 | B |

From the results shown in Table 33 above, it was confirmed that the resist compositions of Example 39 according to the present invention exhibited high sensitivity, excellent lithography properties (EL margin and LER) and excellent pattern shape as compared to the resist compositions of Comparative Examples 26 and 27.

INDUSTRIAL APPLICABILITY

According to the present invention, there are provided a resist composition which exhibits excellent lithography properties and pattern shape, a new polymeric compound useful for the resist composition, a new compound useful as a radical polymerization initiator which is used in production of the polymeric compound, a method of producing the compound, a radical polymerization initiator containing the compound, and a method of forming a resist pattern using the resist composition.

What is claimed is:

1. A resist composition comprising: a base component (A) which generates acid upon exposure to irradiation with radiation and exhibits changed solubility in a developing solution by the action of acid;
  an acid generator component (B) which generates acid upon exposure to irradiation with radiation, provided that the base component (A) is excluded from the acid generator component (B);
  and an acid generator component (C) that generates acid having a pKa of at least 0 upon exposure to irradiation with radiation, provided that the base component (A) and the acid generator component (B) are excluded from the acid generator component (C),
  wherein the base component (A) comprises a polymeric compound comprising a group represented by general formula (I-1) shown below on at least one terminal of a main chain thereof:

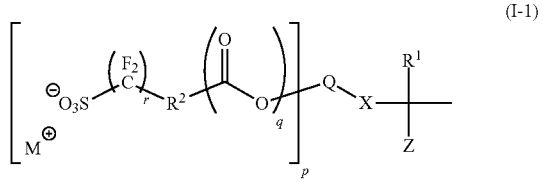
(I-1)

wherein $R^1$ represents a hydrocarbon group of 1 to 10 carbon atoms; Z represents a hydrocarbon group of 1 to 10 carbon atoms or a cyano group; provided that $R^1$ and Z may be mutually bonded to form a ring; X represents a divalent linking group having any one selected from —O—C(=O)—, —NH—C(=O)— and —NH—C(=NH)— on a terminal that comes into contact with Q; p represents an integer of 1 to 3; Q represents a hydrocarbon group having a valency of (p+1), provided that, when p is 1, Q may be a single bond; $R^2$ represents a single bond, an alkylene group which may have a substituent or an aromatic group which may have a substituent; q represents 0 or 1; r represents an integer of 0 to 8; and $M^+$ represents an organic cation.

2. The resist composition according to claim 1, wherein the polymeric compound exhibits increased polarity by the action of acid.

3. The resist composition according to claim 2, wherein the polymeric compound comprises a structural unit (a1) containing an acid decomposable group that exhibits increased polarity by the action of acid.

4. The resist composition according to claim 1, wherein the acid generator component (C) comprises at least one compound selected from the group consisting of a compound (C1) represented by general formula (c1) shown below, a compound (C2) represented by general formula (c2) shown below and a compound (C3) represented by general formula (c3) shown below:

(c1)

(c2)

(c3)

wherein $R^3$ represents a hydrocarbon group which may have a substituent; $Z^{2c}$ represents a hydrocarbon group of 1 to 30 carbon atoms which may have a substituent, provided that the carbon adjacent to S has no fluorine atom as a substituent; $R^4$ represents an organic group; $Y^3$ represents a linear, branched or cyclic alkylene group or an arylene group; $Rf_0$ represents a hydrocarbon group; and each $Z^+$ independently represents a sulfonium or iodonium cation.

* * * * *